United States Patent
Keller et al.

(10) Patent No.: US 9,631,241 B2
(45) Date of Patent: Apr. 25, 2017

(54) COMPLEX SETS OF MIRNAS AS NON-INVASIVE BIOMARKERS FOR COLON CANCER

(71) Applicant: Comprehensive Biomarker Center GmbH, Heidelberg, DE (US)

(72) Inventors: Andreas Keller, Püttlingen (DE); Markus Beier, Weinheim (DE); Eckart Meese, Hütschenhausen (DE); Petra Leidinger, Wadern-Nunkirchen (DE); Anke Wendschlag, Mannheim (DE)

(73) Assignee: Comprehensive Biomarker Center GmbH, Heidelberg (DE)

( * ) Notice: Subject to any disclaimer, the term of this patent is extended or adjusted under 35 U.S.C. 154(b) by 0 days.

(21) Appl. No.: 15/002,725

(22) Filed: Jan. 21, 2016

(65) Prior Publication Data

US 2016/0138117 A1    May 19, 2016

Related U.S. Application Data

(62) Division of application No. 14/239,264, filed as application No. PCT/EP2012/065278 on Aug. 3, 2012, now Pat. No. 9,249,469.

(30) Foreign Application Priority Data

Aug. 19, 2011 (EP) .................................. 11178155

(51) Int. Cl.
*C12Q 1/68* (2006.01)
(52) U.S. Cl.
CPC ...... *C12Q 1/6886* (2013.01); *C12Q 2600/112* (2013.01); *C12Q 2600/118* (2013.01); *C12Q 2600/158* (2013.01); *C12Q 2600/16* (2013.01); *C12Q 2600/178* (2013.01)
(58) Field of Classification Search
CPC ...................................................... C12Q 1/68
See application file for complete search history.

(56) References Cited

U.S. PATENT DOCUMENTS

| 2007/0050146 A1* | 3/2007 | Bentwich | C12N 15/111 |
| | | | 702/19 |
| 2007/0161004 A1* | 7/2007 | Brown | C12N 15/111 |
| | | | 435/6.14 |
| 2009/0181390 A1* | 7/2009 | Li | C12Q 1/6837 |
| | | | 435/6.14 |

OTHER PUBLICATIONS

Chen et al (Cell Research, vol. 18, pp. 997-1006, Sep. 2, 2008, including Supplementary Tables 1-5; see the entire reference).*

* cited by examiner

*Primary Examiner* — Kimberly Chong
(74) *Attorney, Agent, or Firm* — MacMillan, Sobanski & Todd, LLC

(57) ABSTRACT

Described herein are non-invasive methods, kits and means for diagnosing and/or prognosing of colon cancer a body fluid sample from a subject. Further described herein are sets of polynucleotides or sets of primer pairs for detecting sets of miRNAs for diagnosing and/or prognosing of colon cancer in a body fluid sample from a subject. In addition, described herein are sets of miRNAs for diagnosing and/or prognosing of colon cancer in a body fluid sample from a subject.

6 Claims, 57 Drawing Sheets

Figure 1

| SEQ ID NO | miRNA | median g1 | median g2 | qmedian | loggmedian | wmw_rawp | wmw_adjp | ttest_rawp | ttest_adjp | AUC |
|---|---|---|---|---|---|---|---|---|---|---|
| 1 | hsa-miR-1251 | 181 | 43 | 4.25 | 1.45 | 2.72E-09 | 2.57E-07 | 5.52E-13 | 4.68E-10 | 0.98 |
| 2 | hsa-miR-151-3p | 535 | 1349 | 0.40 | -0.93 | 1.54E-09 | 2.17E-07 | 4.07E-12 | 1.53E-09 | 0.01 |
| 3 | hsa-miR-19b | 12067 | 18880 | 0.64 | -0.45 | 6.25E-09 | 4.42E-07 | 5.42E-12 | 1.53E-09 | 0.03 |
| 4 | hsa-miR-361-5p | 523 | 1201 | 0.44 | -0.83 | 1.33E-08 | 7.03E-07 | 1.37E-11 | 2.87E-09 | 0.04 |
| 5 | hsa-miR-106a | 14536 | 3737 | 3.89 | 1.36 | 1.67E-08 | 7.86E-07 | 1.69E-11 | 2.87E-09 | 0.96 |
| 6 | hsa-miR-640 | 139 | 28 | 4.92 | 1.59 | 1.37E-09 | 2.17E-07 | 2.10E-11 | 2.96E-09 | 0.99 |
| 7 | hsa-miR-20b | 6224 | 1250 | 4.98 | 1.60 | 7.25E-10 | 2.17E-07 | 5.75E-11 | 6.97E-09 | 1.00 |
| 8 | hsa-miR-28-3p | 148 | 347 | 0.43 | -0.85 | 4.27E-08 | 1.36E-06 | 1.01E-10 | 1.08E-08 | 0.06 |
| 9 | hsa-miR-208b | 105 | 26 | 4.00 | 1.39 | 3.45E-08 | 1.22E-06 | 1.27E-10 | 1.19E-08 | 0.95 |
| 10 | hsa-miR-145 | 139 | 481 | 0.29 | -1.24 | 5.81E-08 | 1.67E-06 | 2.57E-10 | 2.18E-08 | 0.06 |
| 11 | hsa-let-7d* | 61 | 375 | 0.16 | -1.82 | 7.35E-10 | 2.17E-07 | 3.32E-10 | 2.47E-08 | 0.00 |
| 12 | hsa-miR-934 | 117 | 8 | 13.93 | 2.63 | 3.40E-09 | 2.89E-07 | 3.49E-10 | 2.47E-08 | 0.98 |
| 13 | hsa-miR-17 | 11356 | 4431 | 2.56 | 0.94 | 2.91E-08 | 1.14E-06 | 5.74E-10 | 3.74E-08 | 0.95 |
| 14 | hsa-miR-596 | 94 | 36 | 2.64 | 0.97 | 2.61E-07 | 4.26E-06 | 7.08E-10 | 4.29E-08 | 0.92 |
| 15 | hsa-miR-1180 | 63 | 197 | 0.32 | -1.14 | 1.07E-07 | 2.33E-06 | 7.79E-10 | 4.38E-08 | 0.07 |
| 16 | hsa-miR-664 | 238 | 695 | 0.34 | -1.07 | 4.04E-08 | 1.36E-06 | 8.27E-10 | 4.38E-08 | 0.05 |
| 17 | hsa-miR-20a | 8150 | 1280 | 6.37 | 1.85 | 1.15E-09 | 2.17E-07 | 1.44E-09 | 7.20E-08 | 0.99 |
| 18 | hsa-miR-224 | 29 | 100 | 0.29 | -1.24 | 2.26E-08 | 9.60E-07 | 2.04E-09 | 9.59E-08 | 0.05 |
| 19 | hsa-miR-523 | 121 | 37 | 3.25 | 1.18 | 3.30E-07 | 4.91E-06 | 2.21E-09 | 9.87E-08 | 0.91 |
| 20 | hsa-miR-183* | 114 | 236 | 0.48 | -0.72 | 1.60E-07 | 3.08E-06 | 3.97E-09 | 1.68E-07 | 0.07 |
| 21 | hsa-miR-499-3p | 129 | 49 | 2.64 | 0.97 | 8.56E-09 | 5.58E-07 | 5.37E-09 | 2.17E-07 | 0.97 |
| 22 | hsa-miR-1260 | 2312 | 4854 | 0.48 | -0.74 | 9.95E-08 | 2.22E-06 | 8.73E-09 | 3.37E-07 | 0.07 |
| 23 | hsa-miR-496 | 112 | 44 | 2.53 | 0.93 | 6.82E-07 | 8.19E-06 | 1.52E-08 | 5.61E-07 | 0.90 |
| 24 | hsa-miR-144* | 1009 | 399 | 2.53 | 0.93 | 2.95E-08 | 1.14E-06 | 2.42E-08 | 8.40E-07 | 0.95 |
| 25 | hsa-miR-613 | 1 | 58 | 0.02 | -4.07 | 2.07E-07 | 3.58E-06 | 2.48E-08 | 8.40E-07 | 0.08 |
| 26 | hsa-miR-564 | 198 | 91 | 2.16 | 0.77 | 1.38E-07 | 2.78E-06 | 2.73E-08 | 8.90E-07 | 0.93 |
| 27 | hsa-miR-17* | 1038 | 595 | 1.75 | 0.56 | 1.75E-07 | 3.23E-06 | 4.59E-08 | 1.41E-06 | 0.92 |
| 28 | hsa-miR-607 | 121 | 52 | 2.32 | 0.84 | 5.15E-07 | 6.52E-06 | 4.66E-08 | 1.41E-06 | 0.91 |
| 29 | hsa-miR-1208 | 117 | 49 | 2.37 | 0.86 | 3.19E-07 | 4.82E-06 | 6.01E-08 | 1.76E-06 | 0.92 |
| 30 | hsa-miR-106b | 20755 | 11066 | 1.88 | 0.63 | 4.49E-08 | 1.36E-06 | 7.48E-08 | 2.11E-06 | 0.94 |
| 31 | hsa-miR-26b* | 18 | 76 | 0.23 | -1.45 | 1.36E-06 | 1.28E-05 | 7.97E-08 | 2.12E-06 | 0.11 |
| 32 | hsa-miR-450b-5p | 86 | 35 | 2.43 | 0.89 | 1.06E-06 | 1.13E-05 | 7.99E-08 | 2.12E-06 | 0.90 |
| 33 | hsa-miR-183 | 433 | 967 | 0.45 | -0.80 | 9.07E-07 | 9.86E-06 | 8.25E-08 | 2.12E-06 | 0.10 |
| 34 | hsa-miR-650 | 152 | 78 | 1.94 | 0.66 | 4.69E-07 | 6.11E-06 | 1.40E-07 | 3.48E-06 | 0.91 |
| 35 | hsa-miR-197 | 615 | 2115 | 0.29 | -1.24 | 3.66E-07 | 5.08E-06 | 1.48E-07 | 3.59E-06 | 0.09 |
| 36 | hsa-miR-628-3p | 166 | 321 | 0.52 | -0.66 | 2.08E-06 | 1.82E-05 | 1.61E-07 | 3.79E-06 | 0.11 |
| 37 | hsa-miR-548m | 1 | 67 | 0.01 | -4.20 | 2.73E-07 | 4.37E-06 | 1.84E-07 | 4.21E-06 | 0.09 |
| 38 | hsa-miR-146a | 212 | 437 | 0.49 | -0.72 | 2.85E-06 | 2.30E-05 | 1.95E-07 | 4.36E-06 | 0.12 |
| 39 | hsa-miR-373 | 1 | 48 | 0.02 | -3.86 | 1.43E-08 | 7.12E-07 | 2.34E-07 | 4.85E-06 | 0.05 |
| 40 | hsa-miR-340 | 210 | 337 | 0.62 | -0.47 | 6.54E-07 | 8.03E-06 | 2.35E-07 | 4.85E-06 | 0.10 |

| | | | | | | | | | | |
|---|---|---|---|---|---|---|---|---|---|---|
| 41 | hsa-miR-1247 | 68 | 27 | 2.48 | 0.91 | 1.12E-06 | 1.15E-05 | 2.36E-07 | 4.85E-06 | 0.90 |
| 42 | hsa-miR-505 | 31 | 88 | 0.35 | -1.04 | 1.73E-06 | 1.58E-05 | 2.40E-07 | 4.85E-06 | 0.11 |
| 43 | hsa-miR-34a* | 124 | 1 | 124.45 | 4.82 | 1.19E-09 | 2.17E-07 | 2.50E-07 | 4.94E-06 | 0.99 |
| 44 | hsa-miR-214* | 76 | 19 | 4.03 | 1.39 | 7.21E-07 | 8.49E-06 | 2.58E-07 | 4.98E-06 | 0.90 |
| 45 | hsa-miR-1227 | 69 | 146 | 0.48 | -0.74 | 2.28E-06 | 1.97E-05 | 2.75E-07 | 5.19E-06 | 0.12 |
| 46 | hsa-miR-1246 | 1 | 72 | 0.01 | -4.28 | 1.02E-08 | 5.75E-07 | 2.86E-07 | 5.28E-06 | 0.04 |
| 47 | hsa-miR-635 | 152 | 74 | 2.06 | 0.72 | 1.80E-07 | 3.25E-06 | 3.03E-07 | 5.42E-06 | 0.89 |
| 48 | hsa-miR-487b | 81 | 40 | 2.02 | 0.70 | 1.09E-06 | 1.14E-05 | 3.07E-07 | 5.42E-06 | 0.90 |
| 49 | hsa-miR-28-5p | 369 | 630 | 0.59 | -0.54 | 8.67E-07 | 9.68E-06 | 3.52E-07 | 6.09E-06 | 0.10 |
| 50 | hsa-miR-720 | 4731 | 11356 | 0.42 | -0.88 | 3.76E-06 | 2.90E-05 | 4.01E-07 | 6.80E-06 | 0.13 |
| 51 | hsa-miR-490-3p | 101 | 53 | 1.92 | 0.65 | 1.42E-05 | 8.35E-05 | 4.49E-07 | 7.37E-06 | 0.85 |
| 52 | hsa-miR-23b | 4128 | 5488 | 0.75 | -0.28 | 9.06E-07 | 9.86E-06 | 4.52E-07 | 7.37E-06 | 0.10 |
| 53 | hsa-miR-93 | 7078 | 2703 | 2.62 | 0.96 | 9.44E-08 | 2.22E-06 | 5.13E-07 | 8.21E-06 | 0.93 |
| 54 | hsa-miR-218-1* | 114 | 48 | 2.39 | 0.87 | 6.86E-07 | 8.19E-06 | 5.47E-07 | 8.59E-06 | 0.90 |
| 55 | hsa-miR-483-3p | 20 | 144 | 0.14 | -2.00 | 3.61E-07 | 5.08E-06 | 6.45E-07 | 9.95E-06 | 0.09 |
| 56 | hsa-miR-125a-3p | 37 | 105 | 0.35 | -1.04 | 2.38E-06 | 2.02E-05 | 6.70E-07 | 1.00E-05 | 0.12 |
| 57 | hsa-miR-1225-5p | 88 | 177 | 0.50 | -0.70 | 1.24E-05 | 7.65E-05 | 6.73E-07 | 1.00E-05 | 0.15 |
| 58 | hsa-miR-101 | 956 | 586 | 1.63 | 0.49 | 5.01E-06 | 3.73E-05 | 7.49E-07 | 1.09E-05 | 0.87 |
| 59 | hsa-miR-658 | 36 | 164 | 0.22 | -1.52 | 2.47E-09 | 2.57E-07 | 7.60E-07 | 1.09E-05 | 0.07 |
| 60 | hsa-miR-200a* | 108 | 51 | 2.11 | 0.75 | 3.41E-06 | 2.68E-05 | 8.27E-07 | 1.17E-05 | 0.88 |
| 61 | hsa-miR-296-5p | 208 | 471 | 0.44 | -0.82 | 1.90E-06 | 1.70E-05 | 8.82E-07 | 1.23E-05 | 0.11 |
| 62 | hsa-miR-654-5p | 239 | 120 | 1.99 | 0.69 | 6.24E-07 | 7.78E-06 | 9.20E-07 | 1.24E-05 | 0.90 |
| 63 | hsa-miR-135a | 1 | 45 | 0.02 | -3.81 | 1.82E-06 | 1.64E-05 | 9.23E-07 | 1.24E-05 | 0.13 |
| 64 | hsa-miR-488 | 1 | 51 | 0.02 | -3.93 | 8.10E-07 | 9.16E-06 | 9.52E-07 | 1.26E-05 | 0.10 |
| 65 | hsa-miR-328 | 54 | 208 | 0.26 | -1.35 | 1.30E-05 | 7.84E-05 | 1.05E-06 | 1.37E-05 | 0.15 |
| 66 | hsa-miR-556-5p | 169 | 76 | 2.23 | 0.80 | 9.07E-08 | 2.20E-06 | 1.16E-06 | 1.49E-05 | 0.90 |
| 67 | hsa-miR-144 | 4028 | 1519 | 2.65 | 0.97 | 1.19E-06 | 1.19E-05 | 1.21E-06 | 1.53E-05 | 0.89 |
| 68 | hsa-miR-367* | 100 | 21 | 4.72 | 1.55 | 5.48E-06 | 4.00E-05 | 1.36E-06 | 1.70E-05 | 0.87 |
| 69 | hsa-miR-593* | 410 | 144 | 2.84 | 1.04 | 9.68E-09 | 5.75E-07 | 1.46E-06 | 1.79E-05 | 0.97 |
| 70 | hsa-miR-132* | 1 | 50 | 0.02 | -3.91 | 2.35E-06 | 2.01E-05 | 1.52E-06 | 1.82E-05 | 0.14 |
| 71 | hsa-miR-216a | 240 | 110 | 2.19 | 0.78 | 3.19E-07 | 4.82E-06 | 1.53E-06 | 1.82E-05 | 0.92 |
| 72 | hsa-miR-936 | 53 | 143 | 0.37 | -0.99 | 7.19E-06 | 4.95E-05 | 1.63E-06 | 1.91E-05 | 0.14 |
| 73 | hsa-miR-216b | 222 | 62 | 3.57 | 1.27 | 1.84E-08 | 8.23E-07 | 1.71E-06 | 1.99E-05 | 0.96 |
| 74 | hsa-miR-194 | 7616 | 9240 | 0.82 | -0.19 | 2.60E-06 | 2.16E-05 | 1.82E-06 | 2.08E-05 | 0.12 |
| 75 | hsa-miR-1274a | 174 | 343 | 0.51 | -0.68 | 9.26E-06 | 6.20E-05 | 1.84E-06 | 2.08E-05 | 0.14 |
| 76 | hsa-miR-153 | 134 | 46 | 2.89 | 1.06 | 2.50E-06 | 2.10E-05 | 1.87E-06 | 2.09E-05 | 0.88 |
| 77 | hsa-miR-342-5p | 137 | 234 | 0.59 | -0.53 | 1.20E-05 | 7.51E-05 | 1.92E-06 | 2.11E-05 | 0.14 |
| 78 | hsa-miR-653 | 50 | 100 | 0.51 | -0.68 | 6.04E-06 | 4.27E-05 | 2.18E-06 | 2.37E-05 | 0.13 |
| 79 | hsa-miR-18a | 2434 | 687 | 3.54 | 1.26 | 2.41E-09 | 2.57E-07 | 2.24E-06 | 2.40E-05 | 0.98 |
| 80 | hsa-miR-454 | 246 | 113 | 2.18 | 0.78 | 2.99E-06 | 2.37E-05 | 2.30E-06 | 2.42E-05 | 0.88 |
| 81 | hsa-miR-188-5p | 150 | 88 | 1.70 | 0.53 | 1.20E-06 | 1.19E-05 | 2.32E-06 | 2.42E-05 | 0.87 |
| 82 | hsa-miR-1270 | 37 | 125 | 0.30 | -1.22 | 4.77E-05 | 2.15E-04 | 2.36E-06 | 2.44E-05 | 0.17 |
| 83 | hsa-miR-483-5p | 159 | 325 | 0.49 | -0.72 | 1.54E-05 | 8.89E-05 | 2.66E-06 | 2.72E-05 | 0.15 |

FIG. 1 cont.

| | | | | | | | | | |
|---|---|---|---|---|---|---|---|---|---|
| 84 | hsa-miR-130b | 1209 | 2588 | 0.47 | -0.76 | 7.87E-05 | 3.33E-04 | 2.84E-06 | 2.87E-05 | 0.18 |
| 85 | hsa-miR-143* | 156 | 89 | 1.76 | 0.57 | 7.89E-07 | 9.05E-06 | 2.92E-06 | 2.91E-05 | 0.90 |
| 86 | hsa-miR-1321 | 1 | 60 | 0.02 | -4.09 | 3.40E-07 | 4.97E-06 | 3.22E-06 | 3.17E-05 | 0.09 |
| 87 | hsa-miR-374a | 448 | 154 | 2.91 | 1.07 | 9.07E-08 | 2.20E-06 | 3.33E-06 | 3.25E-05 | 0.90 |
| 88 | hsa-miR-571 | 67 | 29 | 2.33 | 0.84 | 2.13E-05 | 1.16E-04 | 3.69E-06 | 3.53E-05 | 0.85 |
| 89 | hsa-miR-1538 | 86 | 148 | 0.58 | -0.54 | 7.54E-07 | 8.75E-06 | 3.73E-06 | 3.53E-05 | 0.10 |
| 90 | hsa-miR-92a-2* | 1 | 60 | 0.02 | -4.09 | 8.35E-06 | 5.66E-05 | 3.74E-06 | 3.53E-05 | 0.14 |
| 91 | hsa-miR-621 | 518 | 200 | 2.59 | 0.95 | 7.13E-08 | 1.89E-06 | 3.87E-06 | 3.57E-05 | 0.94 |
| 92 | hsa-miR-182 | 4980 | 7787 | 0.64 | -0.45 | 2.10E-05 | 1.16E-04 | 3.89E-06 | 3.57E-05 | 0.15 |
| 93 | hsa-miR-492 | 101 | 55 | 1.83 | 0.61 | 1.30E-05 | 7.84E-05 | 3.92E-06 | 3.57E-05 | 0.85 |
| 94 | hsa-miR-219-2-3p | 5 | 72 | 0.07 | -2.61 | 1.91E-07 | 3.37E-06 | 3.98E-06 | 3.59E-05 | 0.08 |
| 95 | hsa-miR-1261 | 1 | 51 | 0.02 | -3.94 | 1.26E-06 | 1.21E-05 | 4.05E-06 | 3.62E-05 | 0.12 |
| 96 | hsa-miR-597 | 97 | 19 | 4.99 | 1.61 | 2.95E-05 | 1.53E-04 | 4.89E-06 | 4.32E-05 | 0.84 |
| 97 | hsa-miR-551a | 52 | 88 | 0.60 | -0.52 | 1.82E-05 | 1.02E-04 | 5.19E-06 | 4.53E-05 | 0.15 |
| 98 | hsa-miR-891b | 112 | 33 | 3.37 | 1.21 | 1.37E-07 | 2.78E-06 | 5.38E-06 | 4.63E-05 | 0.89 |
| 99 | hsa-miR-1825 | 41 | 111 | 0.37 | -1.00 | 4.77E-05 | 2.15E-04 | 5.42E-06 | 4.63E-05 | 0.17 |
| 100 | hsa-miR-1275 | 74 | 183 | 0.40 | -0.90 | 1.54E-05 | 8.89E-05 | 5.46E-06 | 4.63E-05 | 0.15 |
| 101 | hsa-miR-1908 | 1102 | 2976 | 0.37 | -0.99 | 1.04E-06 | 1.12E-05 | 5.70E-06 | 4.78E-05 | 0.10 |
| 102 | hsa-miR-554 | 122 | 52 | 2.35 | 0.85 | 6.04E-06 | 4.27E-05 | 5.84E-06 | 4.83E-05 | 0.87 |
| 103 | hsa-miR-1301 | 269 | 175 | 1.54 | 0.43 | 1.67E-05 | 9.46E-05 | 5.97E-06 | 4.83E-05 | 0.85 |
| 104 | hsa-miR-96 | 250 | 92 | 2.71 | 1.00 | 1.01E-05 | 6.65E-05 | 5.98E-06 | 4.83E-05 | 0.86 |
| 105 | hsa-miR-646 | 363 | 122 | 2.98 | 1.09 | 5.01E-09 | 3.86E-07 | 5.98E-06 | 4.83E-05 | 0.97 |
| 106 | hsa-miR-376b | 95 | 35 | 2.69 | 0.99 | 2.29E-05 | 1.25E-04 | 6.10E-06 | 4.88E-05 | 0.84 |
| 107 | hsa-miR-1272 | 163 | 77 | 2.11 | 0.75 | 1.59E-06 | 1.46E-05 | 6.36E-06 | 5.04E-05 | 0.89 |
| 108 | hsa-miR-199b-5p | 16 | 58 | 0.29 | -1.25 | 1.28E-05 | 7.84E-05 | 6.55E-06 | 5.13E-05 | 0.15 |
| 109 | hsa-miR-33a | 141 | 77 | 1.84 | 0.61 | 1.26E-06 | 1.21E-05 | 6.59E-06 | 5.13E-05 | 0.89 |
| 110 | hsa-miR-221* | 139 | 57 | 2.42 | 0.88 | 9.28E-06 | 6.20E-05 | 6.87E-06 | 5.30E-05 | 0.86 |
| 111 | hsa-miR-1324 | 131 | 57 | 2.28 | 0.83 | 1.31E-07 | 2.77E-06 | 7.07E-06 | 5.39E-05 | 0.93 |
| 112 | hsa-miR-193a-5p | 95 | 198 | 0.48 | -0.74 | 1.35E-06 | 1.28E-05 | 7.11E-06 | 5.39E-05 | 0.13 |
| 113 | hsa-miR-1226 | 79 | 152 | 0.52 | -0.66 | 5.82E-05 | 2.56E-04 | 7.36E-06 | 5.53E-05 | 0.17 |
| 114 | hsa-miR-193b* | 34 | 120 | 0.28 | -1.27 | 4.39E-05 | 2.05E-04 | 7.97E-06 | 5.93E-05 | 0.17 |
| 115 | hsa-miR-632 | 37 | 75 | 0.50 | -0.69 | 3.48E-05 | 1.74E-04 | 8.29E-06 | 6.11E-05 | 0.16 |
| 116 | hsa-miR-96* | 234 | 109 | 2.14 | 0.76 | 3.51E-07 | 5.04E-06 | 8.66E-06 | 6.33E-05 | 0.91 |
| 117 | hsa-miR-25* | 63 | 139 | 0.46 | -0.79 | 7.93E-05 | 3.33E-04 | 9.30E-06 | 6.74E-05 | 0.18 |
| 118 | hsa-miR-629 | 35 | 314 | 0.11 | -2.18 | 2.99E-05 | 1.54E-04 | 9.46E-06 | 6.76E-05 | 0.16 |
| 119 | hsa-miR-382 | 17 | 71 | 0.24 | -1.41 | 3.84E-05 | 1.88E-04 | 9.49E-06 | 6.76E-05 | 0.17 |
| 120 | hsa-miR-380* | 114 | 44 | 2.58 | 0.95 | 2.74E-05 | 1.43E-04 | 1.10E-05 | 7.80E-05 | 0.84 |
| 121 | hsa-miR-423-5p | 3373 | 8341 | 0.40 | -0.91 | 1.13E-05 | 7.29E-05 | 1.13E-05 | 7.89E-05 | 0.14 |
| 122 | hsa-miR-1267 | 44 | 88 | 0.50 | -0.70 | 1.67E-05 | 9.46E-05 | 1.15E-05 | 8.01E-05 | 0.15 |
| 123 | hsa-miR-1268 | 245 | 522 | 0.47 | -0.76 | 5.59E-05 | 2.47E-04 | 1.17E-05 | 8.10E-05 | 0.17 |
| 124 | hsa-miR-431 | 233 | 103 | 2.25 | 0.81 | 8.24E-05 | 3.41E-04 | 1.25E-05 | 8.55E-05 | 0.82 |
| 125 | hsa-miR-103 | 10775 | 5775 | 1.87 | 0.62 | 1.65E-05 | 9.43E-05 | 1.26E-05 | 8.55E-05 | 0.85 |
| 126 | hsa-miR-92b* | 134 | 282 | 0.48 | -0.74 | 2.08E-06 | 1.82E-05 | 1.27E-05 | 8.55E-05 | 0.11 |
| 127 | hsa-miR-490-5p | 157 | 107 | 1.47 | 0.39 | 1.54E-05 | 8.89E-05 | 1.29E-05 | 8.61E-05 | 0.85 |
| 128 | hsa-miR-1289 | 120 | 58 | 2.07 | 0.73 | 1.16E-04 | 4.55E-04 | 1.30E-05 | 8.61E-05 | 0.81 |

FIG. 1 cont.

| 129 | hsa-miR-137 | 115 | 52 | 2.21 | 0.79 | 3.62E-05 | 1.79E-04 | 1.34E-05 | 8.78E-05 | 0.84 |
|---|---|---|---|---|---|---|---|---|---|---|
| 130 | hsa-miR-125b-2* | 44 | 104 | 0.42 | -0.87 | 1.01E-05 | 6.65E-05 | 1.36E-05 | 8.85E-05 | 0.14 |
| 131 | hsa-miR-606 | 115 | 49 | 2.34 | 0.85 | 1.39E-06 | 1.29E-05 | 1.37E-05 | 8.85E-05 | 0.89 |
| 132 | hsa-miR-31* | 224 | 81 | 2.76 | 1.01 | 1.60E-07 | 3.08E-06 | 1.53E-05 | 9.78E-05 | 0.93 |
| 133 | hsa-miR-92b | 321 | 507 | 0.63 | -0.46 | 8.21E-05 | 3.41E-04 | 1.53E-05 | 9.78E-05 | 0.18 |
| 134 | hsa-miR-633 | 117 | 32 | 3.65 | 1.30 | 2.48E-07 | 4.13E-06 | 1.55E-05 | 9.80E-05 | 0.92 |
| 135 | hsa-miR-941 | 126 | 179 | 0.70 | -0.35 | 6.05E-06 | 4.27E-05 | 1.56E-05 | 9.80E-05 | 0.13 |
| 136 | hsa-miR-33b | 191 | 83 | 2.29 | 0.83 | 2.89E-07 | 4.54E-06 | 1.59E-05 | 9.92E-05 | 0.92 |
| 137 | hsa-miR-330-5p | 26 | 84 | 0.31 | -1.17 | 7.34E-05 | 3.13E-04 | 1.62E-05 | 1.00E-04 | 0.18 |
| 138 | hsa-miR-202 | 8 | 69 | 0.11 | -2.17 | 3.99E-05 | 1.92E-04 | 1.71E-05 | 1.05E-04 | 0.17 |
| 139 | hsa-miR-767-5p | 258 | 124 | 2.08 | 0.73 | 5.08E-06 | 3.74E-05 | 1.78E-05 | 1.08E-04 | 0.87 |
| 140 | hsa-miR-135a* | 14 | 65 | 0.21 | -1.54 | 1.21E-05 | 7.51E-05 | 1.79E-05 | 1.08E-04 | 0.15 |
| 141 | hsa-miR-539 | 11 | 50 | 0.22 | -1.51 | 4.23E-05 | 1.99E-04 | 1.80E-05 | 1.08E-04 | 0.17 |
| 142 | hsa-miR-188-3p | 177 | 100 | 1.77 | 0.57 | 3.87E-07 | 5.29E-06 | 1.81E-05 | 1.08E-04 | 0.91 |
| 143 | hsa-miR-1207-5p | 382 | 1349 | 0.28 | -1.26 | 1.26E-06 | 1.21E-05 | 1.82E-05 | 1.08E-04 | 0.11 |
| 144 | hsa-miR-181d | 24 | 78 | 0.30 | -1.20 | 4.39E-05 | 2.05E-04 | 1.99E-05 | 1.17E-04 | 0.17 |
| 145 | hsa-miR-20b* | 100 | 61 | 1.65 | 0.50 | 3.09E-05 | 1.58E-04 | 2.04E-05 | 1.20E-04 | 0.84 |
| 146 | hsa-miR-181a-2* | 89 | 174 | 0.51 | -0.67 | 1.20E-04 | 4.63E-04 | 2.09E-05 | 1.21E-04 | 0.19 |
| 147 | hsa-miR-186 | 48 | 129 | 0.37 | -0.99 | 1.09E-05 | 7.10E-05 | 2.11E-05 | 1.21E-04 | 0.16 |
| 148 | hsa-miR-425 | 12678 | 20755 | 0.61 | -0.49 | 2.06E-05 | 1.14E-04 | 2.11E-05 | 1.21E-04 | 0.16 |
| 149 | hsa-miR-491-5p | 109 | 201 | 0.54 | -0.61 | 6.76E-05 | 2.92E-04 | 2.26E-05 | 1.29E-04 | 0.19 |
| 150 | hsa-miR-1233 | 130 | 69 | 1.88 | 0.63 | 5.38E-05 | 2.41E-04 | 2.39E-05 | 1.35E-04 | 0.83 |
| 151 | hsa-miR-631 | 175 | 122 | 1.43 | 0.36 | 4.08E-05 | 1.94E-04 | 2.40E-05 | 1.35E-04 | 0.83 |
| 152 | hsa-miR-124 | 152 | 86 | 1.77 | 0.57 | 1.20E-05 | 7.51E-05 | 2.42E-05 | 1.35E-04 | 0.86 |
| 153 | hsa-miR-548o | 148 | 67 | 2.20 | 0.79 | 2.69E-06 | 2.22E-05 | 2.44E-05 | 1.35E-04 | 0.86 |
| 154 | hsa-miR-139-3p | 83 | 56 | 1.47 | 0.39 | 2.42E-05 | 1.30E-04 | 2.46E-05 | 1.35E-04 | 0.83 |
| 155 | hsa-miR-513a-3p | 65 | 1 | 64.63 | 4.17 | 6.84E-06 | 4.75E-05 | 2.57E-05 | 1.40E-04 | 0.86 |
| 156 | hsa-miR-92a-1* | 26 | 72 | 0.37 | -1.00 | 1.27E-04 | 4.82E-04 | 2.60E-05 | 1.41E-04 | 0.19 |
| 157 | hsa-miR-553 | 8 | 49 | 0.16 | -1.84 | 1.21E-05 | 7.51E-05 | 2.74E-05 | 1.48E-04 | 0.15 |
| 158 | hsa-miR-1306 | 24 | 91 | 0.27 | -1.32 | 7.20E-05 | 3.10E-04 | 2.80E-05 | 1.50E-04 | 0.18 |
| 159 | hsa-miR-18b* | 94 | 147 | 0.64 | -0.44 | 1.30E-04 | 4.88E-04 | 2.83E-05 | 1.50E-04 | 0.19 |
| 160 | hsa-miR-584 | 81 | 259 | 0.31 | -1.16 | 1.11E-04 | 4.40E-04 | 2.86E-05 | 1.50E-04 | 0.19 |
| 161 | hsa-miR-190 | 5 | 52 | 0.10 | -2.28 | 1.20E-04 | 4.63E-04 | 2.87E-05 | 1.50E-04 | 0.19 |
| 162 | hsa-miR-301a | 492 | 291 | 1.69 | 0.53 | 7.93E-05 | 3.33E-04 | 2.87E-05 | 1.50E-04 | 0.82 |
| 163 | hsa-miR-518a-3p | 86 | 26 | 3.36 | 1.21 | 6.16E-05 | 2.68E-04 | 2.96E-05 | 1.53E-04 | 0.83 |
| 164 | hsa-miR-192 | 5775 | 7787 | 0.74 | -0.30 | 1.57E-04 | 5.57E-04 | 2.96E-05 | 1.53E-04 | 0.19 |
| 165 | hsa-miR-22 | 7787 | 10211 | 0.76 | -0.27 | 6.05E-05 | 2.64E-04 | 3.00E-05 | 1.54E-04 | 0.17 |
| 166 | hsa-miR-9* | 124 | 71 | 1.76 | 0.56 | 3.21E-05 | 1.63E-04 | 3.05E-05 | 1.56E-04 | 0.84 |
| 167 | hsa-miR-517c | 12 | 69 | 0.18 | -1.72 | 1.34E-05 | 8.00E-05 | 3.28E-05 | 1.66E-04 | 0.15 |
| 168 | hsa-miR-302f | 1 | 45 | 0.02 | -3.82 | 1.02E-04 | 4.07E-04 | 3.64E-05 | 1.84E-04 | 0.19 |
| 169 | hsa-miR-769-5p | 14 | 53 | 0.26 | -1.36 | 1.22E-04 | 4.70E-04 | 3.82E-05 | 1.91E-04 | 0.19 |
| 170 | hsa-miR-1226* | 234 | 98 | 2.38 | 0.87 | 4.43E-08 | 1.36E-06 | 3.85E-05 | 1.91E-04 | 0.91 |
| 171 | hsa-miR-181b | 44 | 123 | 0.36 | -1.03 | 1.36E-04 | 5.02E-04 | 3.86E-05 | 1.91E-04 | 0.20 |

FIG. 1 cont.

| | | | | | | | | | |
|---|---|---|---|---|---|---|---|---|---|
| 172 | hsa-miR-505* | 163 | 283 | 0.58 | -0.55 | 7.34E-05 | 3.13E-04 | 3.89E-05 | 1.92E-04 | 0.18 |
| 173 | hsa-miR-548p | 178 | 63 | 2.84 | 1.04 | 8.74E-08 | 2.20E-06 | 3.97E-05 | 1.94E-04 | 0.93 |
| 174 | hsa-miR-509-3-5p | 389 | 155 | 2.50 | 0.92 | 4.69E-07 | 6.11E-06 | 4.04E-05 | 1.97E-04 | 0.91 |
| 175 | hsa-miR-518d-3p | 98 | 49 | 2.01 | 0.70 | 4.03E-05 | 1.93E-04 | 4.10E-05 | 1.99E-04 | 0.83 |
| 176 | hsa-miR-885-3p | 167 | 433 | 0.39 | -0.95 | 3.57E-06 | 2.78E-05 | 4.15E-05 | 1.99E-04 | 0.12 |
| 177 | hsa-miR-346 | 87 | 130 | 0.67 | -0.40 | 1.12E-04 | 4.40E-04 | 4.15E-05 | 1.99E-04 | 0.19 |
| 178 | hsa-miR-519e | 1 | 29 | 0.04 | -3.35 | 2.59E-05 | 1.38E-04 | 4.33E-05 | 2.05E-04 | 0.17 |
| 179 | hsa-miR-455-3p | 178 | 121 | 1.47 | 0.39 | 1.21E-05 | 7.51E-05 | 4.33E-05 | 2.05E-04 | 0.84 |
| 180 | hsa-miR-625 | 87 | 256 | 0.34 | -1.08 | 1.50E-04 | 5.42E-04 | 4.54E-05 | 2.14E-04 | 0.19 |
| 181 | hsa-miR-214 | 414 | 221 | 1.87 | 0.63 | 4.65E-06 | 3.52E-05 | 4.66E-05 | 2.17E-04 | 0.87 |
| 182 | hsa-miR-452* | 721 | 190 | 3.79 | 1.33 | 3.11E-08 | 1.15E-06 | 4.67E-05 | 2.17E-04 | 0.95 |
| 183 | hsa-miR-215 | 408 | 651 | 0.63 | -0.47 | 5.58E-05 | 2.47E-04 | 4.70E-05 | 2.17E-04 | 0.17 |
| 184 | hsa-miR-422a | 133 | 327 | 0.41 | -0.90 | 1.94E-04 | 6.56E-04 | 4.72E-05 | 2.17E-04 | 0.20 |
| 185 | hsa-miR-1283 | 133 | 80 | 1.66 | 0.51 | 4.26E-06 | 3.25E-05 | 5.04E-05 | 2.31E-04 | 0.87 |
| 186 | hsa-miR-525-3p | 96 | 51 | 1.88 | 0.63 | 1.50E-04 | 5.42E-04 | 5.29E-05 | 2.41E-04 | 0.81 |
| 187 | hsa-miR-891a | 124 | 83 | 1.49 | 0.40 | 3.90E-05 | 1.90E-04 | 5.38E-05 | 2.44E-04 | 0.82 |
| 188 | hsa-miR-99a* | 38 | 76 | 0.50 | -0.70 | 3.20E-04 | 1.03E-03 | 5.55E-05 | 2.50E-04 | 0.21 |
| 189 | hsa-miR-20a* | 187 | 111 | 1.68 | 0.52 | 2.99E-06 | 2.37E-05 | 5.78E-05 | 2.59E-04 | 0.88 |
| 190 | hsa-miR-637 | 24 | 74 | 0.33 | -1.11 | 3.44E-04 | 1.10E-03 | 6.44E-05 | 2.87E-04 | 0.21 |
| 191 | hsa-miR-217 | 199 | 106 | 1.88 | 0.63 | 9.69E-08 | 2.22E-06 | 6.86E-05 | 3.04E-04 | 0.93 |
| 192 | hsa-miR-125a-5p | 206 | 418 | 0.49 | -0.71 | 1.74E-04 | 6.02E-04 | 6.99E-05 | 3.09E-04 | 0.19 |
| 193 | hsa-miR-204 | 1 | 26 | 0.04 | -3.26 | 3.62E-04 | 1.14E-03 | 7.18E-05 | 3.14E-04 | 0.23 |
| 194 | hsa-miR-24-1* | 150 | 83 | 1.81 | 0.59 | 1.56E-04 | 5.56E-04 | 7.19E-05 | 3.14E-04 | 0.81 |
| 195 | hsa-miR-31 | 165 | 106 | 1.56 | 0.44 | 4.60E-05 | 2.10E-04 | 7.22E-05 | 3.14E-04 | 0.83 |
| 196 | hsa-let-7g* | 164 | 105 | 1.57 | 0.45 | 1.87E-04 | 6.38E-04 | 7.34E-05 | 3.18E-04 | 0.80 |
| 197 | hsa-miR-1291 | 169 | 86 | 1.97 | 0.68 | 2.73E-06 | 2.23E-05 | 7.63E-05 | 3.28E-04 | 0.88 |
| 198 | hsa-miR-497* | 135 | 76 | 1.79 | 0.58 | 3.32E-04 | 1.07E-03 | 7.83E-05 | 3.35E-04 | 0.79 |
| 199 | hsa-miR-1285 | 246 | 436 | 0.56 | -0.57 | 1.11E-04 | 4.40E-04 | 7.89E-05 | 3.35E-04 | 0.19 |
| 200 | hsa-miR-892a | 18 | 73 | 0.25 | -1.39 | 6.58E-06 | 4.61E-05 | 7.89E-05 | 3.35E-04 | 0.13 |
| 201 | hsa-miR-107 | 2022 | 968 | 2.09 | 0.74 | 8.11E-06 | 5.55E-05 | 8.05E-05 | 3.40E-04 | 0.86 |
| 202 | hsa-miR-99b | 144 | 270 | 0.53 | -0.63 | 8.89E-05 | 3.62E-04 | 8.11E-05 | 3.40E-04 | 0.18 |
| 203 | hsa-miR-23a | 4731 | 8341 | 0.57 | -0.57 | 3.56E-05 | 1.78E-04 | 8.14E-05 | 3.40E-04 | 0.16 |
| 204 | hsa-miR-152 | 240 | 363 | 0.66 | -0.42 | 1.62E-04 | 5.69E-04 | 8.42E-05 | 3.50E-04 | 0.19 |
| 205 | hsa-miR-1284 | 36 | 78 | 0.47 | -0.76 | 2.41E-04 | 8.00E-04 | 8.48E-05 | 3.51E-04 | 0.20 |
| 206 | hsa-miR-127-5p | 169 | 90 | 1.88 | 0.63 | 5.92E-08 | 1.67E-06 | 8.59E-05 | 3.51E-04 | 0.90 |
| 207 | hsa-miR-1290 | 4 | 39 | 0.12 | -2.16 | 4.01E-04 | 1.26E-03 | 8.61E-05 | 3.51E-04 | 0.22 |
| 208 | hsa-miR-32* | 45 | 16 | 2.80 | 1.03 | 9.21E-05 | 3.74E-04 | 8.64E-05 | 3.51E-04 | 0.82 |
| 209 | hsa-miR-933 | 278 | 158 | 1.76 | 0.57 | 2.42E-05 | 1.30E-04 | 8.65E-05 | 3.51E-04 | 0.83 |
| 210 | hsa-miR-604 | 89 | 44 | 2.01 | 0.70 | 5.48E-05 | 2.45E-04 | 8.78E-05 | 3.55E-04 | 0.83 |
| 211 | hsa-miR-519b-5p | 192 | 136 | 1.41 | 0.34 | 4.41E-05 | 2.05E-04 | 9.01E-05 | 3.60E-04 | 0.83 |
| 212 | hsa-miR-520f | 1 | 46 | 0.02 | -3.82 | 4.59E-04 | 1.42E-03 | 9.01E-05 | 3.60E-04 | 0.22 |
| 213 | hsa-let-7d | 4330 | 2703 | 1.60 | 0.47 | 4.55E-05 | 2.10E-04 | 9.49E-05 | 3.78E-04 | 0.83 |
| 214 | hsa-miR-211 | 1 | 38 | 0.03 | -3.64 | 3.62E-05 | 1.79E-04 | 9.79E-05 | 3.88E-04 | 0.18 |
| 215 | hsa-miR-154 | 1 | 48 | 0.02 | -3.88 | 4.99E-06 | 3.73E-05 | 9.84E-05 | 3.88E-04 | 0.15 |

FIG. 1 cont.

| | | | | | | | | | |
|---|---|---|---|---|---|---|---|---|---|
| 216 | hsa-miR-548j | 1 | 47 | 0.02 | -3.85 | 5.29E-04 | 1.59E-03 | 1.01E-04 | 3.95E-04 | 0.23 |
| 217 | hsa-miR-1253 | 96 | 47 | 2.05 | 0.72 | 1.34E-04 | 5.00E-04 | 1.08E-04 | 4.20E-04 | 0.81 |
| 218 | hsa-miR-432 | 1 | 32 | 0.03 | -3.48 | 1.78E-04 | 6.15E-04 | 1.15E-04 | 4.47E-04 | 0.22 |
| 219 | hsa-miR-18b | 553 | 203 | 2.73 | 1.00 | 4.46E-07 | 6.01E-06 | 1.18E-04 | 4.55E-04 | 0.91 |
| 220 | hsa-miR-592 | 78 | 33 | 2.33 | 0.85 | 1.49E-04 | 5.42E-04 | 1.23E-04 | 4.72E-04 | 0.81 |
| 221 | hsa-miR-92a | 17323 | 12067 | 1.44 | 0.36 | 4.16E-05 | 1.97E-04 | 1.25E-04 | 4.79E-04 | 0.83 |
| 222 | hsa-miR-491-3p | 117 | 63 | 1.86 | 0.62 | 1.97E-05 | 1.10E-04 | 1.30E-04 | 4.96E-04 | 0.85 |
| 223 | hsa-miR-942 | 6 | 58 | 0.10 | -2.29 | 4.13E-04 | 1.29E-03 | 1.31E-04 | 5.00E-04 | 0.21 |
| 224 | hsa-miR-1307 | 103 | 157 | 0.66 | -0.42 | 2.44E-04 | 8.04E-04 | 1.44E-04 | 5.46E-04 | 0.21 |
| 225 | hsa-miR-1914 | 28 | 80 | 0.35 | -1.06 | 6.69E-04 | 1.97E-03 | 1.48E-04 | 5.57E-04 | 0.22 |
| 226 | hsa-miR-126 | 3195 | 1402 | 2.28 | 0.82 | 6.16E-04 | 1.83E-03 | 1.52E-04 | 5.69E-04 | 0.78 |
| 227 | hsa-miR-887 | 129 | 99 | 1.30 | 0.26 | 1.36E-04 | 5.02E-04 | 1.54E-04 | 5.75E-04 | 0.80 |
| 228 | hsa-miR-877 | 88 | 159 | 0.55 | -0.59 | 1.59E-03 | 4.04E-03 | 1.67E-04 | 6.21E-04 | 0.24 |
| 229 | hsa-miR-129* | 68 | 107 | 0.64 | -0.45 | 1.25E-04 | 4.75E-04 | 1.77E-04 | 6.57E-04 | 0.20 |
| 230 | hsa-miR-558 | 116 | 35 | 3.29 | 1.19 | 1.63E-04 | 5.73E-04 | 1.88E-04 | 6.94E-04 | 0.81 |
| 231 | hsa-miR-199b-3p | 161 | 85 | 1.89 | 0.64 | 3.68E-04 | 1.16E-03 | 1.91E-04 | 7.01E-04 | 0.79 |
| 232 | hsa-miR-208a | 89 | 55 | 1.61 | 0.47 | 5.38E-04 | 1.61E-03 | 2.11E-04 | 7.68E-04 | 0.78 |
| 233 | hsa-miR-518e* | 219 | 142 | 1.55 | 0.44 | 3.92E-05 | 1.90E-04 | 2.12E-04 | 7.68E-04 | 0.83 |
| 234 | hsa-miR-1279 | 5 | 35 | 0.15 | -1.91 | 8.55E-04 | 2.43E-03 | 2.13E-04 | 7.68E-04 | 0.23 |
| 235 | hsa-miR-450b-3p | 52 | 9 | 5.61 | 1.73 | 1.84E-04 | 6.33E-04 | 2.13E-04 | 7.68E-04 | 0.80 |
| 236 | hsa-miR-186* | 138 | 86 | 1.60 | 0.47 | 1.27E-03 | 3.37E-03 | 2.16E-04 | 7.73E-04 | 0.76 |
| 237 | hsa-miR-194* | 61 | 111 | 0.55 | -0.60 | 1.09E-03 | 2.96E-03 | 2.16E-04 | 7.73E-04 | 0.23 |
| 238 | hsa-miR-139-5p | 201 | 144 | 1.39 | 0.33 | 3.56E-04 | 1.13E-03 | 2.17E-04 | 7.73E-04 | 0.79 |
| 239 | hsa-miR-1206 | 70 | 8 | 9.08 | 2.21 | 8.69E-05 | 3.58E-04 | 2.19E-04 | 7.76E-04 | 0.82 |
| 240 | hsa-miR-503 | 416 | 262 | 1.59 | 0.46 | 9.58E-05 | 3.85E-04 | 2.31E-04 | 8.14E-04 | 0.82 |
| 241 | hsa-miR-545 | 130 | 52 | 2.50 | 0.92 | 1.68E-04 | 5.85E-04 | 2.31E-04 | 8.14E-04 | 0.81 |
| 242 | hsa-miR-1244 | 1 | 20 | 0.05 | -3.01 | 9.49E-05 | 3.83E-04 | 2.32E-04 | 8.14E-04 | 0.20 |
| 243 | hsa-miR-589 | 94 | 163 | 0.58 | -0.55 | 1.87E-04 | 6.38E-04 | 2.45E-04 | 8.56E-04 | 0.20 |
| 244 | hsa-miR-509-5p | 353 | 132 | 2.67 | 0.98 | 2.37E-07 | 4.03E-06 | 2.46E-04 | 8.56E-04 | 0.92 |
| 245 | hsa-miR-522* | 178 | 111 | 1.60 | 0.47 | 2.78E-04 | 9.08E-04 | 2.54E-04 | 8.78E-04 | 0.80 |
| 246 | hsa-miR-185* | 3 | 49 | 0.05 | -2.95 | 1.62E-04 | 5.69E-04 | 2.66E-04 | 9.18E-04 | 0.20 |
| 247 | hsa-miR-126* | 10 | 45 | 0.21 | -1.54 | 1.39E-03 | 3.61E-03 | 2.73E-04 | 9.38E-04 | 0.24 |
| 248 | hsa-miR-512-3p | 35 | 61 | 0.58 | -0.54 | 2.29E-03 | 5.57E-03 | 2.75E-04 | 9.41E-04 | 0.25 |
| 249 | hsa-miR-497 | 205 | 126 | 1.62 | 0.48 | 1.10E-05 | 7.13E-05 | 2.98E-04 | 1.01E-03 | 0.86 |
| 250 | hsa-miR-10b* | 100 | 59 | 1.70 | 0.53 | 1.23E-03 | 3.29E-03 | 2.98E-04 | 1.01E-03 | 0.76 |
| 251 | hsa-miR-32 | 173 | 72 | 2.41 | 0.88 | 6.79E-08 | 1.86E-06 | 3.12E-04 | 1.05E-03 | 0.94 |
| 252 | hsa-miR-548d-5p | 1 | 28 | 0.04 | -3.33 | 1.51E-04 | 5.44E-04 | 3.19E-04 | 1.07E-03 | 0.20 |
| 253 | hsa-miR-30c-1* | 61 | 128 | 0.48 | -0.74 | 7.07E-04 | 2.08E-03 | 3.25E-04 | 1.09E-03 | 0.22 |
| 254 | hsa-miR-1909 | 124 | 173 | 0.72 | -0.33 | 2.01E-04 | 6.78E-04 | 3.34E-04 | 1.11E-03 | 0.20 |
| 255 | hsa-miR-1266 | 138 | 84 | 1.65 | 0.50 | 3.23E-05 | 1.63E-04 | 3.34E-04 | 1.11E-03 | 0.82 |
| 256 | hsa-miR-555 | 49 | 20 | 2.44 | 0.89 | 9.71E-04 | 2.70E-03 | 3.57E-04 | 1.18E-03 | 0.77 |
| 257 | hsa-miR-520c-3p | 1 | 27 | 0.04 | -3.30 | 5.30E-04 | 1.59E-03 | 3.59E-04 | 1.18E-03 | 0.23 |
| 258 | hsa-miR-29a | 790 | 905 | 0.87 | -0.13 | 1.68E-03 | 4.25E-03 | 3.63E-04 | 1.19E-03 | 0.24 |
| 259 | hsa-miR-105 | 52 | 12 | 4.22 | 1.44 | 4.91E-04 | 1.50E-03 | 3.86E-04 | 1.26E-03 | 0.78 |

FIG. 1 cont.

| | | | | | | | | | |
|---|---|---|---|---|---|---|---|---|---|
| 260 | hsa-miR-615-3p | 35 | 67 | 0.53 | -0.64 | 1.75E-03 | 4.40E-03 | 3.96E-04 | 1.29E-03 | 0.25 |
| 261 | hsa-miR-515-3p | 1 | 33 | 0.03 | -3.49 | 1.55E-04 | 5.53E-04 | 3.99E-04 | 1.30E-03 | 0.20 |
| 262 | hsa-miR-541* | 7 | 41 | 0.18 | -1.71 | 5.29E-03 | 1.18E-02 | 4.03E-04 | 1.31E-03 | 0.27 |
| 263 | hsa-miR-30c | 1808 | 2588 | 0.70 | -0.36 | 1.37E-04 | 5.03E-04 | 4.05E-04 | 1.31E-03 | 0.19 |
| 264 | hsa-miR-513c | 10 | 56 | 0.18 | -1.69 | 2.46E-02 | 4.49E-02 | 4.14E-04 | 1.33E-03 | 0.32 |
| 265 | hsa-miR-24-2* | 224 | 132 | 1.70 | 0.53 | 3.21E-04 | 1.03E-03 | 4.29E-04 | 1.37E-03 | 0.79 |
| 266 | hsa-miR-133a | 75 | 31 | 2.41 | 0.88 | 1.08E-03 | 2.96E-03 | 4.35E-04 | 1.39E-03 | 0.77 |
| 267 | hsa-miR-302c* | 32 | 61 | 0.52 | -0.65 | 1.64E-03 | 4.16E-03 | 4.39E-04 | 1.39E-03 | 0.24 |
| 268 | hsa-miR-199a-5p | 357 | 526 | 0.68 | -0.39 | 7.55E-04 | 2.19E-03 | 4.40E-04 | 1.39E-03 | 0.23 |
| 269 | hsa-miR-567 | 86 | 47 | 1.82 | 0.60 | 2.58E-04 | 8.44E-04 | 4.47E-04 | 1.41E-03 | 0.80 |
| 270 | hsa-miR-1305 | 125 | 40 | 3.15 | 1.15 | 1.67E-07 | 3.14E-06 | 4.55E-04 | 1.43E-03 | 0.92 |
| 271 | hsa-miR-141* | 115 | 51 | 2.28 | 0.82 | 2.50E-04 | 8.22E-04 | 4.62E-04 | 1.45E-03 | 0.80 |
| 272 | hsa-miR-455-5p | 26 | 50 | 0.52 | -0.66 | 5.21E-04 | 1.58E-03 | 4.67E-04 | 1.46E-03 | 0.22 |
| 273 | hsa-miR-939 | 56 | 97 | 0.57 | -0.56 | 7.31E-04 | 2.13E-03 | 4.76E-04 | 1.48E-03 | 0.23 |
| 274 | hsa-miR-508-5p | 154 | 94 | 1.64 | 0.49 | 5.54E-06 | 4.02E-05 | 4.78E-04 | 1.48E-03 | 0.87 |
| 275 | hsa-miR-494 | 81 | 179 | 0.45 | -0.79 | 9.84E-04 | 2.71E-03 | 4.86E-04 | 1.49E-03 | 0.23 |
| 276 | hsa-miR-568 | 128 | 79 | 1.61 | 0.48 | 9.53E-04 | 2.66E-03 | 4.86E-04 | 1.49E-03 | 0.77 |
| 277 | hsa-miR-34c-5p | 82 | 53 | 1.53 | 0.42 | 1.27E-03 | 3.37E-03 | 5.05E-04 | 1.55E-03 | 0.76 |
| 278 | hsa-miR-425* | 82 | 142 | 0.57 | -0.56 | 7.56E-04 | 2.19E-03 | 5.22E-04 | 1.59E-03 | 0.23 |
| 279 | hsa-miR-770-5p | 55 | 92 | 0.60 | -0.52 | 7.21E-04 | 2.11E-03 | 5.25E-04 | 1.60E-03 | 0.23 |
| 280 | hsa-miR-302a | 2 | 44 | 0.05 | -2.97 | 1.68E-04 | 5.85E-04 | 5.33E-04 | 1.61E-03 | 0.20 |
| 281 | hsa-let-7b* | 8 | 41 | 0.20 | -1.62 | 1.02E-03 | 2.81E-03 | 5.57E-04 | 1.68E-03 | 0.24 |
| 282 | hsa-miR-515-5p | 228 | 140 | 1.63 | 0.49 | 5.09E-07 | 6.52E-06 | 5.74E-04 | 1.73E-03 | 0.88 |
| 283 | hsa-miR-206 | 3 | 38 | 0.08 | -2.56 | 1.15E-03 | 3.12E-03 | 5.76E-04 | 1.73E-03 | 0.24 |
| 284 | hsa-miR-551b* | 65 | 113 | 0.58 | -0.54 | 1.36E-03 | 3.54E-03 | 5.80E-04 | 1.73E-03 | 0.24 |
| 285 | hsa-miR-18a* | 185 | 322 | 0.57 | -0.56 | 8.63E-04 | 2.43E-03 | 5.84E-04 | 1.73E-03 | 0.23 |
| 286 | hsa-miR-330-3p | 481 | 287 | 1.68 | 0.52 | 1.34E-04 | 5.00E-04 | 5.84E-04 | 1.73E-03 | 0.81 |
| 287 | hsa-miR-184 | 20 | 46 | 0.43 | -0.84 | 8.56E-04 | 2.43E-03 | 6.08E-04 | 1.80E-03 | 0.23 |
| 288 | hsa-miR-15a | 3465 | 5106 | 0.68 | -0.39 | 2.83E-04 | 9.19E-04 | 6.11E-04 | 1.80E-03 | 0.21 |
| 289 | hsa-miR-1912 | 204 | 133 | 1.53 | 0.43 | 1.20E-06 | 1.19E-05 | 6.29E-04 | 1.85E-03 | 0.87 |
| 290 | hsa-miR-135b | 8 | 51 | 0.16 | -1.85 | 6.34E-04 | 1.88E-03 | 6.34E-04 | 1.85E-03 | 0.22 |
| 291 | hsa-miR-519a* | 193 | 116 | 1.66 | 0.50 | 1.59E-03 | 4.04E-03 | 6.35E-04 | 1.85E-03 | 0.76 |
| 292 | hsa-miR-517* | 267 | 159 | 1.67 | 0.51 | 1.20E-04 | 4.63E-04 | 6.58E-04 | 1.91E-03 | 0.81 |
| 293 | hsa-miR-601 | 1 | 33 | 0.03 | -3.49 | 9.73E-04 | 2.70E-03 | 6.62E-04 | 1.91E-03 | 0.24 |
| 294 | hsa-miR-302b | 1 | 32 | 0.03 | -3.46 | 4.58E-05 | 2.10E-04 | 6.64E-04 | 1.91E-03 | 0.18 |
| 295 | hsa-miR-520c-5p | 154 | 86 | 1.79 | 0.58 | 8.88E-05 | 3.62E-04 | 6.71E-04 | 1.92E-03 | 0.82 |
| 296 | hsa-let-7f-2* | 17 | 45 | 0.38 | -0.96 | 2.29E-03 | 5.57E-03 | 6.72E-04 | 1.92E-03 | 0.25 |
| 297 | hsa-miR-660 | 600 | 389 | 1.54 | 0.43 | 5.21E-04 | 1.58E-03 | 6.76E-04 | 1.92E-03 | 0.78 |
| 298 | hsa-miR-644 | 12 | 52 | 0.22 | -1.50 | 8.56E-04 | 2.43E-03 | 6.78E-04 | 1.92E-03 | 0.23 |
| 299 | hsa-miR-769-3p | 8 | 54 | 0.14 | -1.97 | 3.67E-03 | 8.61E-03 | 6.80E-04 | 1.92E-03 | 0.27 |
| 300 | hsa-miR-297 | 75 | 113 | 0.66 | -0.41 | 1.90E-04 | 6.46E-04 | 6.81E-04 | 1.92E-03 | 0.21 |
| 301 | hsa-miR-1249 | 66 | 157 | 0.42 | -0.87 | 2.63E-05 | 1.38E-04 | 6.90E-04 | 1.94E-03 | 0.16 |
| 302 | hsa-miR-149* | 578 | 1482 | 0.39 | -0.94 | 1.20E-04 | 4.63E-04 | 7.08E-04 | 1.99E-03 | 0.19 |

FIG. 1 cont.

| 303 | hsa-miR-1911 | 56 | 95 | 0.59 | -0.53 | 2.04E-03 | 5.07E-03 | 7.16E-04 | 2.00E-03 | 0.25 |
|---|---|---|---|---|---|---|---|---|---|---|
| 304 | hsa-miR-489 | 280 | 169 | 1.66 | 0.51 | 3.12E-03 | 7.46E-03 | 7.58E-04 | 2.11E-03 | 0.74 |
| 305 | hsa-miR-26a-1* | 24 | 48 | 0.49 | -0.71 | 4.06E-03 | 9.45E-03 | 7.65E-04 | 2.13E-03 | 0.27 |
| 306 | hsa-miR-566 | 108 | 67 | 1.60 | 0.47 | 2.33E-04 | 7.74E-04 | 7.75E-04 | 2.15E-03 | 0.80 |
| 307 | hsa-let-7i* | 325 | 201 | 1.62 | 0.48 | 5.40E-04 | 1.61E-03 | 8.09E-04 | 2.24E-03 | 0.78 |
| 308 | hsa-miR-369-3p | 24 | 52 | 0.47 | -0.74 | 1.45E-03 | 3.71E-03 | 8.15E-04 | 2.24E-03 | 0.24 |
| 309 | hsa-miR-518c* | 77 | 108 | 0.71 | -0.34 | 2.17E-04 | 7.26E-04 | 8.22E-04 | 2.25E-03 | 0.20 |
| 310 | hsa-miR-556-3p | 2 | 35 | 0.06 | -2.75 | 4.76E-04 | 1.46E-03 | 8.97E-04 | 2.45E-03 | 0.22 |
| 311 | hsa-miR-377 | 198 | 139 | 1.42 | 0.35 | 6.62E-04 | 1.95E-03 | 9.30E-04 | 2.54E-03 | 0.78 |
| 312 | hsa-miR-148a | 1052 | 815 | 1.29 | 0.26 | 1.59E-03 | 4.04E-03 | 9.90E-04 | 2.69E-03 | 0.76 |
| 313 | hsa-miR-19b-2* | 6 | 32 | 0.19 | -1.68 | 6.18E-03 | 1.36E-02 | 1.14E-03 | 3.09E-03 | 0.28 |
| 314 | hsa-miR-99a | 116 | 219 | 0.53 | -0.63 | 1.32E-03 | 3.45E-03 | 1.14E-03 | 3.09E-03 | 0.24 |
| 315 | hsa-miR-200c | 100 | 151 | 0.66 | -0.42 | 3.03E-03 | 7.26E-03 | 1.26E-03 | 3.38E-03 | 0.26 |
| 316 | hsa-miR-652 | 2115 | 1446 | 1.46 | 0.38 | 1.79E-03 | 4.48E-03 | 1.27E-03 | 3.41E-03 | 0.75 |
| 317 | hsa-miR-423-3p | 1446 | 2253 | 0.64 | -0.44 | 8.29E-04 | 2.38E-03 | 1.35E-03 | 3.62E-03 | 0.23 |
| 318 | hsa-miR-298 | 178 | 93 | 1.91 | 0.65 | 2.93E-05 | 1.53E-04 | 1.38E-03 | 3.67E-03 | 0.82 |
| 319 | hsa-miR-409-3p | 57 | 137 | 0.41 | -0.88 | 1.24E-03 | 3.29E-03 | 1.38E-03 | 3.68E-03 | 0.24 |
| 320 | hsa-miR-19a* | 82 | 39 | 2.12 | 0.75 | 1.28E-03 | 3.37E-03 | 1.40E-03 | 3.71E-03 | 0.76 |
| 321 | hsa-miR-1271 | 309 | 222 | 1.39 | 0.33 | 5.12E-03 | 1.15E-02 | 1.46E-03 | 3.85E-03 | 0.73 |
| 322 | hsa-miR-411 | 79 | 54 | 1.46 | 0.38 | 5.68E-03 | 1.27E-02 | 1.47E-03 | 3.88E-03 | 0.72 |
| 323 | hsa-miR-1303 | 48 | 89 | 0.54 | -0.62 | 1.98E-03 | 4.92E-03 | 1.55E-03 | 4.06E-03 | 0.25 |
| 324 | hsa-miR-526b | 49 | 83 | 0.59 | -0.53 | 6.06E-03 | 1.34E-02 | 1.56E-03 | 4.08E-03 | 0.28 |
| 325 | hsa-miR-548d-3p | 59 | 21 | 2.87 | 1.06 | 4.60E-04 | 1.42E-03 | 1.56E-03 | 4.08E-03 | 0.78 |
| 326 | hsa-miR-518b | 133 | 94 | 1.42 | 0.35 | 1.34E-04 | 5.00E-04 | 1.62E-03 | 4.22E-03 | 0.81 |
| 327 | hsa-miR-765 | 58 | 120 | 0.49 | -0.72 | 6.39E-03 | 1.39E-02 | 1.73E-03 | 4.49E-03 | 0.28 |
| 328 | hsa-miR-128 | 672 | 893 | 0.75 | -0.28 | 1.80E-03 | 4.49E-03 | 1.74E-03 | 4.49E-03 | 0.25 |
| 329 | hsa-miR-509-3p | 1 | 35 | 0.03 | -3.55 | 9.42E-03 | 1.95E-02 | 1.75E-03 | 4.52E-03 | 0.30 |
| 330 | hsa-miR-766 | 401 | 610 | 0.66 | -0.42 | 1.45E-03 | 3.71E-03 | 1.76E-03 | 4.53E-03 | 0.24 |
| 331 | hsa-miR-570 | 106 | 53 | 1.99 | 0.69 | 1.27E-03 | 3.37E-03 | 1.81E-03 | 4.63E-03 | 0.76 |
| 332 | hsa-miR-1278 | 80 | 27 | 2.97 | 1.09 | 8.28E-04 | 2.38E-03 | 1.87E-03 | 4.78E-03 | 0.77 |
| 333 | hsa-miR-29a* | 13 | 37 | 0.34 | -1.07 | 1.35E-02 | 2.68E-02 | 1.88E-03 | 4.78E-03 | 0.30 |
| 334 | hsa-miR-15b* | 75 | 127 | 0.59 | -0.53 | 7.16E-03 | 1.53E-02 | 1.92E-03 | 4.88E-03 | 0.28 |
| 335 | hsa-miR-609 | 1 | 6 | 0.17 | -1.77 | 1.21E-03 | 3.26E-03 | 2.00E-03 | 5.06E-03 | 0.27 |
| 336 | hsa-miR-600 | 95 | 60 | 1.60 | 0.47 | 2.94E-03 | 7.07E-03 | 2.03E-03 | 5.13E-03 | 0.74 |
| 337 | hsa-miR-548i | 7 | 30 | 0.24 | -1.42 | 1.08E-02 | 2.20E-02 | 2.10E-03 | 5.28E-03 | 0.29 |
| 338 | hsa-miR-518d-5p | 197 | 114 | 1.73 | 0.55 | 8.08E-05 | 3.37E-04 | 2.16E-03 | 5.42E-03 | 0.81 |
| 339 | hsa-miR-1202 | 266 | 196 | 1.36 | 0.31 | 1.92E-03 | 4.79E-03 | 2.27E-03 | 5.67E-03 | 0.75 |
| 340 | hsa-miR-378* | 49 | 95 | 0.52 | -0.66 | 4.98E-03 | 1.13E-02 | 2.29E-03 | 5.71E-03 | 0.27 |
| 341 | hsa-miR-627 | 206 | 132 | 1.57 | 0.45 | 2.63E-05 | 1.38E-04 | 2.38E-03 | 5.90E-03 | 0.84 |
| 342 | hsa-miR-151-5p | 7959 | 9959 | 0.80 | -0.22 | 3.34E-03 | 7.94E-03 | 2.38E-03 | 5.90E-03 | 0.26 |
| 343 | hsa-miR-541 | 128 | 79 | 1.62 | 0.48 | 2.11E-03 | 5.20E-03 | 2.40E-03 | 5.93E-03 | 0.75 |
| 344 | hsa-miR-671-3p | 39 | 96 | 0.41 | -0.89 | 4.43E-03 | 1.02E-02 | 2.41E-03 | 5.95E-03 | 0.27 |
| 345 | hsa-miR-612 | 91 | 48 | 1.88 | 0.63 | 4.70E-03 | 1.07E-02 | 2.46E-03 | 6.05E-03 | 0.73 |

FIG. 1 cont.

| 346 | hsa-miR-1181 | 214 | 182 | 1.18 | 0.16 | 1.02E-02 | 2.08E-02 | 2.51E-03 | 6.16E-03 | 0.71 |
|---|---|---|---|---|---|---|---|---|---|---|
| 347 | hsa-miR-155 | 101 | 169 | 0.60 | -0.52 | 9.22E-04 | 2.58E-03 | 2.53E-03 | 6.18E-03 | 0.23 |
| 348 | hsa-miR-502-5p | 28 | 42 | 0.66 | -0.41 | 6.28E-03 | 1.37E-02 | 2.58E-03 | 6.28E-03 | 0.28 |
| 349 | hsa-miR-562 | 48 | 18 | 2.69 | 0.99 | 2.32E-03 | 5.61E-03 | 2.61E-03 | 6.35E-03 | 0.75 |
| 350 | hsa-miR-433 | 106 | 168 | 0.63 | -0.46 | 1.40E-03 | 3.63E-03 | 2.62E-03 | 6.36E-03 | 0.24 |
| 351 | hsa-miR-595 | 127 | 52 | 2.46 | 0.90 | 4.52E-03 | 1.04E-02 | 2.64E-03 | 6.38E-03 | 0.73 |
| 352 | hsa-miR-140-5p | 16 | 44 | 0.36 | -1.03 | 9.31E-03 | 1.93E-02 | 2.74E-03 | 6.60E-03 | 0.29 |
| 353 | hsa-miR-1288 | 125 | 73 | 1.71 | 0.54 | 7.76E-04 | 2.24E-03 | 2.81E-03 | 6.76E-03 | 0.77 |
| 354 | hsa-miR-30a* | 52 | 82 | 0.63 | -0.46 | 4.19E-03 | 9.65E-03 | 2.82E-03 | 6.76E-03 | 0.27 |
| 355 | hsa-miR-1238 | 22 | 58 | 0.37 | -0.98 | 3.68E-03 | 8.61E-03 | 2.85E-03 | 6.81E-03 | 0.26 |
| 356 | hsa-miR-545* | 40 | 1 | 31.77 | 3.46 | 3.48E-04 | 1.11E-03 | 3.14E-03 | 7.47E-03 | 0.79 |
| 357 | hsa-miR-485-3p | 85 | 137 | 0.62 | -0.48 | 9.91E-03 | 2.04E-02 | 3.21E-03 | 7.62E-03 | 0.29 |
| 358 | hsa-let-7a* | 5 | 36 | 0.15 | -1.91 | 2.31E-03 | 5.60E-03 | 3.22E-03 | 7.62E-03 | 0.26 |
| 359 | hsa-miR-421 | 147 | 109 | 1.35 | 0.30 | 2.21E-03 | 5.42E-03 | 3.23E-03 | 7.64E-03 | 0.74 |
| 360 | hsa-miR-122 | 20 | 63 | 0.32 | -1.14 | 4.67E-03 | 1.07E-02 | 3.26E-03 | 7.67E-03 | 0.27 |
| 361 | hsa-miR-874 | 196 | 147 | 1.33 | 0.29 | 1.38E-03 | 3.58E-03 | 3.29E-03 | 7.72E-03 | 0.75 |
| 362 | hsa-miR-30a | 420 | 607 | 0.69 | -0.37 | 1.32E-02 | 2.62E-02 | 3.38E-03 | 7.91E-03 | 0.30 |
| 363 | hsa-miR-133b | 32 | 68 | 0.47 | -0.76 | 1.91E-02 | 3.63E-02 | 3.45E-03 | 8.05E-03 | 0.31 |
| 364 | hsa-miR-1296 | 66 | 37 | 1.79 | 0.58 | 1.43E-03 | 3.68E-03 | 3.66E-03 | 8.51E-03 | 0.76 |
| 365 | hsa-miR-1231 | 112 | 150 | 0.75 | -0.29 | 6.97E-03 | 1.50E-02 | 3.66E-03 | 8.51E-03 | 0.28 |
| 366 | hsa-miR-219-1-3p | 54 | 7 | 7.62 | 2.03 | 9.78E-04 | 2.70E-03 | 3.73E-03 | 8.64E-03 | 0.77 |
| 367 | hsa-miR-1269 | 58 | 80 | 0.73 | -0.32 | 1.74E-02 | 3.34E-02 | 3.80E-03 | 8.78E-03 | 0.31 |
| 368 | hsa-miR-572 | 93 | 71 | 1.32 | 0.27 | 1.18E-02 | 2.38E-02 | 3.81E-03 | 8.78E-03 | 0.70 |
| 369 | hsa-miR-374b | 655 | 357 | 1.83 | 0.61 | 4.19E-03 | 9.65E-03 | 3.93E-03 | 9.03E-03 | 0.73 |
| 370 | hsa-miR-326 | 93 | 83 | 1.12 | 0.11 | 2.57E-02 | 4.66E-02 | 3.95E-03 | 9.05E-03 | 0.68 |
| 371 | hsa-miR-26a-2* | 4 | 26 | 0.17 | -1.77 | 1.07E-02 | 2.19E-02 | 3.96E-03 | 9.05E-03 | 0.30 |
| 372 | hsa-miR-520b | 26 | 43 | 0.61 | -0.50 | 1.15E-02 | 2.32E-02 | 3.97E-03 | 9.05E-03 | 0.29 |
| 373 | hsa-miR-410 | 120 | 98 | 1.23 | 0.21 | 2.57E-02 | 4.66E-02 | 4.00E-03 | 9.10E-03 | 0.68 |
| 374 | hsa-miR-1224-5p | 33 | 52 | 0.63 | -0.46 | 1.37E-02 | 2.71E-02 | 4.19E-03 | 9.48E-03 | 0.30 |
| 375 | hsa-miR-587 | 60 | 123 | 0.49 | -0.71 | 3.73E-03 | 8.71E-03 | 4.19E-03 | 9.48E-03 | 0.26 |
| 376 | hsa-miR-1263 | 100 | 60 | 1.67 | 0.51 | 2.94E-03 | 7.07E-03 | 4.22E-03 | 9.52E-03 | 0.74 |
| 377 | hsa-miR-1293 | 27 | 58 | 0.46 | -0.77 | 1.42E-02 | 2.78E-02 | 4.25E-03 | 9.56E-03 | 0.30 |
| 378 | hsa-miR-802 | 111 | 60 | 1.85 | 0.62 | 1.28E-03 | 3.37E-03 | 4.31E-03 | 9.66E-03 | 0.76 |
| 379 | hsa-miR-576-3p | 13 | 31 | 0.43 | -0.85 | 4.77E-02 | 8.04E-02 | 4.35E-03 | 9.74E-03 | 0.34 |
| 380 | hsa-miR-512-5p | 75 | 35 | 2.14 | 0.76 | 8.59E-04 | 2.43E-03 | 4.37E-03 | 9.74E-03 | 0.77 |
| 381 | hsa-miR-513b | 55 | 29 | 1.91 | 0.64 | 2.24E-03 | 5.47E-03 | 4.39E-03 | 9.77E-03 | 0.75 |
| 382 | hsa-miR-593 | 1 | 24 | 0.04 | -3.16 | 4.76E-04 | 1.46E-03 | 4.46E-03 | 9.89E-03 | 0.23 |
| 383 | hsa-miR-885-5p | 31 | 64 | 0.48 | -0.72 | 1.51E-02 | 2.93E-02 | 4.66E-03 | 1.03E-02 | 0.30 |
| 384 | hsa-miR-485-5p | 45 | 22 | 2.06 | 0.72 | 7.09E-03 | 1.52E-02 | 4.70E-03 | 1.04E-02 | 0.72 |
| 385 | hsa-miR-1228* | 1449 | 2371 | 0.61 | -0.49 | 3.52E-04 | 1.12E-03 | 4.84E-03 | 1.07E-02 | 0.21 |
| 386 | hsa-miR-523* | 179 | 123 | 1.46 | 0.38 | 6.78E-03 | 1.46E-02 | 4.98E-03 | 1.09E-02 | 0.72 |
| 387 | hsa-miR-544 | 56 | 15 | 3.71 | 1.31 | 3.61E-03 | 8.50E-03 | 5.24E-03 | 1.15E-02 | 0.74 |
| 388 | hsa-miR-552 | 28 | 66 | 0.42 | -0.87 | 1.58E-02 | 3.03E-02 | 5.27E-03 | 1.15E-02 | 0.30 |

FIG. 1 cont.

| 389 | hsa-miR-196a* | 184 | 122 | 1.51 | 0.41 | 8.98E-04 | 2.52E-03 | 5.31E-03 | 1.16E-02 | 0.76 |
|---|---|---|---|---|---|---|---|---|---|---|
| 390 | hsa-miR-320d | 769 | 1494 | 0.51 | -0.66 | 3.50E-03 | 8.30E-03 | 5.37E-03 | 1.17E-02 | 0.26 |
| 391 | hsa-miR-185 | 30648 | 34040 | 0.90 | -0.10 | 5.96E-03 | 1.33E-02 | 5.42E-03 | 1.18E-02 | 0.29 |
| 392 | hsa-miR-301b | 190 | 161 | 1.18 | 0.16 | 6.78E-03 | 1.46E-02 | 5.62E-03 | 1.22E-02 | 0.72 |
| 393 | hsa-miR-548b-5p | 6 | 31 | 0.21 | -1.56 | 3.20E-03 | 7.63E-03 | 5.69E-03 | 1.23E-02 | 0.26 |
| 394 | hsa-let-7e* | 20 | 47 | 0.42 | -0.86 | 1.02E-02 | 2.08E-02 | 5.79E-03 | 1.25E-02 | 0.29 |
| 395 | hsa-miR-1299 | 11 | 23 | 0.51 | -0.68 | 4.99E-02 | 8.33E-02 | 5.91E-03 | 1.27E-02 | 0.34 |
| 396 | hsa-miR-504 | 40 | 66 | 0.61 | -0.49 | 2.39E-02 | 4.39E-02 | 5.93E-03 | 1.27E-02 | 0.32 |
| 397 | hsa-miR-602 | 159 | 123 | 1.29 | 0.25 | 1.32E-02 | 2.62E-02 | 5.98E-03 | 1.28E-02 | 0.70 |
| 398 | hsa-miR-325 | 63 | 92 | 0.69 | -0.38 | 6.05E-03 | 1.34E-02 | 6.05E-03 | 1.29E-02 | 0.28 |
| 399 | hsa-miR-200a | 126 | 84 | 1.50 | 0.41 | 2.23E-02 | 4.16E-02 | 6.34E-03 | 1.35E-02 | 0.69 |
| 400 | hsa-miR-100 | 121 | 364 | 0.33 | -1.10 | 7.16E-03 | 1.53E-02 | 6.52E-03 | 1.38E-02 | 0.28 |
| 401 | hsa-miR-202* | 123 | 85 | 1.45 | 0.37 | 1.79E-02 | 3.42E-02 | 6.54E-03 | 1.38E-02 | 0.69 |
| 402 | hsa-miR-296-3p | 78 | 111 | 0.70 | -0.35 | 9.61E-03 | 1.99E-02 | 6.63E-03 | 1.40E-02 | 0.29 |
| 403 | hsa-miR-516b | 50 | 23 | 2.22 | 0.80 | 7.10E-03 | 1.52E-02 | 6.65E-03 | 1.40E-02 | 0.72 |
| 404 | hsa-miR-603 | 197 | 127 | 1.55 | 0.44 | 1.16E-03 | 3.13E-03 | 7.06E-03 | 1.48E-02 | 0.76 |
| 405 | hsa-miR-140-3p | 23520 | 23520 | 1.00 | 0.00 | 3.39E-02 | 5.96E-02 | 7.09E-03 | 1.48E-02 | 0.67 |
| 406 | hsa-miR-521 | 54 | 16 | 3.36 | 1.21 | 3.56E-03 | 8.41E-03 | 7.15E-03 | 1.49E-02 | 0.74 |
| 407 | hsa-miR-195* | 59 | 104 | 0.57 | -0.57 | 1.39E-02 | 2.74E-02 | 7.66E-03 | 1.60E-02 | 0.30 |
| 408 | hsa-miR-125b | 765 | 1232 | 0.62 | -0.48 | 2.07E-02 | 3.90E-02 | 7.69E-03 | 1.60E-02 | 0.31 |
| 409 | hsa-miR-34c-3p | 140 | 63 | 2.21 | 0.79 | 2.11E-03 | 5.20E-03 | 8.08E-03 | 1.68E-02 | 0.75 |
| 410 | hsa-miR-1204 | 9 | 54 | 0.17 | -1.76 | 4.50E-04 | 1.40E-03 | 8.29E-03 | 1.71E-02 | 0.22 |
| 411 | hsa-miR-337-5p | 54 | 31 | 1.73 | 0.55 | 8.21E-03 | 1.73E-02 | 8.50E-03 | 1.75E-02 | 0.72 |
| 412 | hsa-miR-508-3p | 6 | 35 | 0.17 | -1.75 | 2.10E-02 | 3.95E-02 | 8.51E-03 | 1.75E-02 | 0.31 |
| 413 | hsa-miR-105* | 20 | 32 | 0.60 | -0.51 | 2.34E-02 | 4.30E-02 | 8.79E-03 | 1.80E-02 | 0.32 |
| 414 | hsa-miR-1471 | 137 | 106 | 1.29 | 0.26 | 2.76E-02 | 4.96E-02 | 8.80E-03 | 1.80E-02 | 0.68 |
| 415 | hsa-miR-129-5p | 58 | 27 | 2.14 | 0.76 | 4.16E-03 | 9.64E-03 | 8.84E-03 | 1.81E-02 | 0.73 |
| 416 | hsa-miR-1286 | 153 | 131 | 1.17 | 0.16 | 1.25E-02 | 2.51E-02 | 9.10E-03 | 1.86E-02 | 0.70 |
| 417 | hsa-miR-590-5p | 218 | 161 | 1.36 | 0.31 | 9.09E-03 | 1.89E-02 | 9.44E-03 | 1.92E-02 | 0.71 |
| 418 | hsa-miR-101* | 120 | 99 | 1.21 | 0.19 | 1.32E-02 | 2.62E-02 | 1.05E-02 | 2.13E-02 | 0.70 |
| 419 | hsa-miR-624 | 79 | 112 | 0.71 | -0.35 | 8.43E-03 | 1.77E-02 | 1.05E-02 | 2.13E-02 | 0.29 |
| 420 | hsa-miR-574-5p | 1302 | 495 | 2.63 | 0.97 | 1.41E-05 | 8.35E-05 | 1.08E-02 | 2.17E-02 | 0.85 |
| 421 | hsa-miR-150 | 1941 | 1162 | 1.67 | 0.51 | 4.68E-03 | 1.07E-02 | 1.10E-02 | 2.21E-02 | 0.73 |
| 422 | hsa-miR-516a-5p | 236 | 181 | 1.30 | 0.27 | 3.03E-02 | 5.39E-02 | 1.10E-02 | 2.21E-02 | 0.68 |
| 423 | hsa-miR-377* | 1 | 8 | 0.13 | -2.06 | 1.26E-01 | 1.87E-01 | 1.10E-02 | 2.21E-02 | 0.38 |
| 424 | hsa-miR-381 | 116 | 85 | 1.38 | 0.32 | 6.24E-03 | 1.37E-02 | 1.10E-02 | 2.21E-02 | 0.72 |
| 425 | hsa-miR-26b | 596 | 342 | 1.74 | 0.56 | 5.17E-02 | 8.61E-02 | 1.11E-02 | 2.21E-02 | 0.66 |
| 426 | hsa-miR-1254 | 161 | 147 | 1.09 | 0.09 | 3.81E-02 | 6.59E-02 | 1.16E-02 | 2.30E-02 | 0.67 |
| 427 | hsa-miR-196b | 1 | 7 | 0.14 | -1.93 | 5.10E-03 | 1.15E-02 | 1.17E-02 | 2.32E-02 | 0.29 |
| 428 | hsa-miR-495 | 117 | 75 | 1.55 | 0.44 | 9.09E-03 | 1.89E-02 | 1.18E-02 | 2.34E-02 | 0.71 |
| 429 | hsa-miR-219-5p | 53 | 28 | 1.87 | 0.63 | 4.92E-03 | 1.12E-02 | 1.20E-02 | 2.38E-02 | 0.73 |
| 430 | hsa-miR-30d* | 85 | 50 | 1.70 | 0.53 | 1.93E-02 | 3.65E-02 | 1.22E-02 | 2.40E-02 | 0.69 |
| 431 | hsa-miR-125b-1* | 10 | 40 | 0.24 | -1.42 | 3.90E-02 | 6.72E-02 | 1.26E-02 | 2.47E-02 | 0.33 |

FIG. 1 cont.

| 432 | hsa-miR-574-3p | 1954 | 3838 | 0.51 | -0.67 | 2.33E-02 | 4.30E-02 | 1.31E-02 | 2.57E-02 | 0.32 |
|---|---|---|---|---|---|---|---|---|---|---|
| 433 | hsa-miR-522 | 10 | 30 | 0.32 | -1.13 | 2.00E-02 | 3.78E-02 | 1.32E-02 | 2.59E-02 | 0.31 |
| 434 | hsa-miR-876-5p | 44 | 65 | 0.67 | -0.40 | 3.64E-02 | 6.32E-02 | 1.33E-02 | 2.60E-02 | 0.33 |
| 435 | hsa-miR-222* | 85 | 51 | 1.67 | 0.52 | 8.90E-03 | 1.86E-02 | 1.46E-02 | 2.85E-02 | 0.71 |
| 436 | hsa-miR-892b | 40 | 67 | 0.60 | -0.51 | 5.74E-02 | 9.51E-02 | 1.48E-02 | 2.89E-02 | 0.35 |
| 437 | hsa-miR-138-2* | 66 | 30 | 2.25 | 0.81 | 1.54E-02 | 2.97E-02 | 1.58E-02 | 3.06E-02 | 0.70 |
| 438 | hsa-miR-559 | 83 | 50 | 1.67 | 0.51 | 1.50E-02 | 2.91E-02 | 1.66E-02 | 3.22E-02 | 0.70 |
| 439 | hsa-miR-575 | 150 | 121 | 1.24 | 0.21 | 2.76E-02 | 4.96E-02 | 1.71E-02 | 3.31E-02 | 0.68 |
| 440 | hsa-miR-1264 | 38 | 59 | 0.64 | -0.44 | 5.74E-02 | 9.51E-02 | 1.73E-02 | 3.33E-02 | 0.35 |
| 441 | hsa-miR-1243 | 95 | 55 | 1.72 | 0.55 | 6.77E-03 | 1.46E-02 | 1.74E-02 | 3.34E-02 | 0.72 |
| 442 | hsa-miR-335 | 548 | 692 | 0.79 | -0.23 | 3.47E-02 | 6.07E-02 | 1.75E-02 | 3.35E-02 | 0.33 |
| 443 | hsa-miR-300 | 73 | 108 | 0.68 | -0.39 | 6.24E-03 | 1.37E-02 | 1.75E-02 | 3.35E-02 | 0.28 |
| 444 | hsa-miR-203 | 26 | 53 | 0.49 | -0.71 | 2.33E-02 | 4.30E-02 | 1.77E-02 | 3.38E-02 | 0.32 |
| 445 | hsa-miR-198 | 52 | 81 | 0.63 | -0.45 | 2.23E-02 | 4.16E-02 | 1.78E-02 | 3.40E-02 | 0.31 |
| 446 | hsa-miR-1298 | 75 | 50 | 1.52 | 0.42 | 1.42E-02 | 2.78E-02 | 1.82E-02 | 3.45E-02 | 0.70 |
| 447 | hsa-miR-516a-3p | 18 | 38 | 0.49 | -0.72 | 1.21E-01 | 1.81E-01 | 1.86E-02 | 3.53E-02 | 0.37 |
| 448 | hsa-miR-132 | 124 | 192 | 0.65 | -0.44 | 1.12E-03 | 3.05E-03 | 1.92E-02 | 3.63E-02 | 0.24 |
| 449 | hsa-miR-374a* | 65 | 35 | 1.86 | 0.62 | 1.09E-02 | 2.21E-02 | 1.93E-02 | 3.64E-02 | 0.71 |
| 450 | hsa-miR-1322 | 111 | 174 | 0.64 | -0.45 | 6.41E-03 | 1.39E-02 | 2.02E-02 | 3.81E-02 | 0.28 |
| 451 | hsa-miR-30e* | 67 | 111 | 0.61 | -0.50 | 8.78E-02 | 1.38E-01 | 2.03E-02 | 3.82E-02 | 0.36 |
| 452 | hsa-miR-124* | 121 | 100 | 1.21 | 0.19 | 2.45E-02 | 4.48E-02 | 2.04E-02 | 3.82E-02 | 0.68 |
| 453 | hsa-miR-384 | 97 | 81 | 1.20 | 0.18 | 2.76E-02 | 4.96E-02 | 2.04E-02 | 3.82E-02 | 0.68 |
| 454 | hsa-miR-616 | 29 | 56 | 0.52 | -0.66 | 5.99E-02 | 9.90E-02 | 2.04E-02 | 3.82E-02 | 0.35 |
| 455 | hsa-miR-620 | 18 | 34 | 0.52 | -0.65 | 6.70E-02 | 1.09E-01 | 2.07E-02 | 3.86E-02 | 0.35 |
| 456 | hsa-miR-155* | 91 | 49 | 1.86 | 0.62 | 1.93E-02 | 3.65E-02 | 2.08E-02 | 3.87E-02 | 0.69 |
| 457 | hsa-miR-655 | 70 | 44 | 1.61 | 0.48 | 3.17E-02 | 5.58E-02 | 2.11E-02 | 3.92E-02 | 0.67 |
| 458 | hsa-miR-411* | 74 | 48 | 1.53 | 0.43 | 1.74E-02 | 3.34E-02 | 2.16E-02 | 4.00E-02 | 0.69 |
| 459 | hsa-miR-106a* | 169 | 140 | 1.21 | 0.19 | 5.12E-03 | 1.15E-02 | 2.17E-02 | 4.00E-02 | 0.73 |
| 460 | hsa-miR-548a-3p | 114 | 86 | 1.33 | 0.29 | 6.78E-02 | 1.10E-01 | 2.18E-02 | 4.00E-02 | 0.65 |
| 461 | hsa-miR-143 | 248 | 332 | 0.75 | -0.29 | 1.25E-02 | 2.51E-02 | 2.18E-02 | 4.00E-02 | 0.30 |
| 462 | hsa-miR-520d-3p | 1 | 24 | 0.04 | -3.16 | 2.23E-04 | 7.45E-04 | 2.18E-02 | 4.00E-02 | 0.22 |
| 463 | hsa-miR-195 | 809 | 717 | 1.13 | 0.12 | 1.00E-01 | 1.54E-01 | 2.20E-02 | 4.02E-02 | 0.63 |
| 464 | hsa-miR-1282 | 1 | 1 | 1.00 | 0.00 | 7.44E-02 | 1.20E-01 | 2.30E-02 | 4.20E-02 | 0.38 |
| 465 | hsa-miR-624* | 42 | 84 | 0.51 | -0.68 | 4.84E-02 | 8.14E-02 | 2.30E-02 | 4.20E-02 | 0.34 |
| 466 | hsa-miR-148b | 854 | 735 | 1.16 | 0.15 | 9.12E-02 | 1.41E-01 | 2.36E-02 | 4.29E-02 | 0.64 |
| 467 | hsa-miR-448 | 128 | 89 | 1.43 | 0.36 | 2.12E-02 | 3.98E-02 | 2.38E-02 | 4.32E-02 | 0.69 |
| 468 | hsa-miR-331-5p | 51 | 73 | 0.70 | -0.35 | 7.95E-02 | 1.27E-01 | 2.38E-02 | 4.32E-02 | 0.36 |
| 469 | hsa-miR-519b-3p | 43 | 56 | 0.77 | -0.26 | 9.48E-02 | 1.46E-01 | 2.42E-02 | 4.37E-02 | 0.36 |
| 470 | hsa-miR-1292 | 84 | 104 | 0.81 | -0.22 | 6.75E-02 | 1.10E-01 | 2.43E-02 | 4.38E-02 | 0.35 |
| 471 | hsa-miR-146a* | 123 | 81 | 1.52 | 0.42 | 3.16E-02 | 5.58E-02 | 2.43E-02 | 4.38E-02 | 0.67 |
| 472 | hsa-miR-29c* | 1 | 20 | 0.05 | -3.01 | 8.19E-02 | 1.30E-01 | 2.46E-02 | 4.42E-02 | 0.37 |
| 473 | hsa-miR-1234 | 560 | 416 | 1.35 | 0.30 | 2.12E-01 | 2.91E-01 | 2.52E-02 | 4.52E-02 | 0.60 |
| 474 | hsa-miR-1469 | 188 | 239 | 0.79 | -0.24 | 3.98E-02 | 6.83E-02 | 2.58E-02 | 4.62E-02 | 0.33 |

FIG. 1 cont.

| | | | | | | | | | |
|---|---|---|---|---|---|---|---|---|---|
| 475 | hsa-miR-451 | 1407 | 772 | 1.82 | 0.60 | 1.39E-04 | 5.10E-04 | 2.60E-02 | 4.64E-02 | 0.81 |
| 476 | hsa-miR-190b | 1 | 2 | 0.40 | -0.90 | 2.93E-02 | 5.24E-02 | 2.61E-02 | 4.64E-02 | 0.34 |
| 477 | hsa-miR-302e | 21 | 38 | 0.54 | -0.62 | 4.44E-02 | 7.58E-02 | 2.61E-02 | 4.64E-02 | 0.34 |
| 478 | hsa-miR-629* | 100 | 181 | 0.55 | -0.59 | 4.07E-03 | 9.46E-03 | 2.67E-02 | 4.74E-02 | 0.27 |
| 479 | hsa-miR-548l | 1 | 1 | 1.00 | 0.00 | 1.84E-01 | 2.57E-01 | 2.69E-02 | 4.77E-02 | 0.40 |
| 480 | hsa-miR-638 | 354 | 454 | 0.78 | -0.25 | 3.03E-02 | 5.39E-02 | 2.71E-02 | 4.79E-02 | 0.32 |
| 481 | hsa-miR-549 | 87 | 50 | 1.74 | 0.55 | 4.64E-02 | 7.84E-02 | 2.72E-02 | 4.79E-02 | 0.66 |
| 482 | hsa-miR-136* | 92 | 56 | 1.65 | 0.50 | 8.44E-03 | 1.77E-02 | 2.73E-02 | 4.80E-02 | 0.71 |
| 483 | hsa-miR-873 | 82 | 121 | 0.68 | -0.39 | 3.10E-02 | 5.49E-02 | 2.74E-02 | 4.82E-02 | 0.32 |
| 484 | hsa-miR-1294 | 2 | 13 | 0.19 | -1.68 | 1.39E-01 | 2.03E-01 | 1.02E-01 | 1.52E-01 | 0.38 |

FIG. 1 cont.

| Figure 2 | | | | | |
|---|---|---|---|---|---|
| Signature | SEQ ID NOs | miRNA-identifiers | Acc | Spec | Sens |
| SNC-1 | 17, 24, 33 | hsa-miR-20a, hsa-miR-144*, hsa-miR-183 | 96.4% | 92.9% | 99.9% |
| SNC-2 | 1, 12, 21 | hsa-miR-1251, hsa-miR-934, hsa-miR-499-3p | 96.1% | 92.9% | 99.4% |
| SNC-3 | 1, 12 | hsa-miR-1251, hsa-miR-934 | 95.2% | 90.6% | 99.9% |
| SNC-4 | 6, 43, 1 | hsa-miR-640, hsa-miR-34a*, hsa-miR-1251 | 94.8% | 89.7% | 99.9% |
| SNC-5 | 1, 59, 12 | hsa-miR-1251, hsa-miR-658, hsa-miR-934 | 94.6% | 90.6% | 98.7% |
| SNC-6 | 9, 10, 12 | hsa-miR-208b, hsa-miR-145, hsa-miR-934 | 94.4% | 93.4% | 95.4% |
| SNC-7 | 11, 17, 43 | hsa-let-7d*, hsa-miR-20a, hsa-miR-34a* | 94.4% | 93.4% | 95.4% |
| SNC-8 | 8, 10, 12 | hsa-miR-28-3p, hsa-miR-145, hsa-miR-934 | 94.3% | 92.9% | 95.7% |
| SNC-9 | 43, 1, 12 | hsa-miR-34a*, hsa-miR-1251, hsa-miR-934 | 94.3% | 90.6% | 98.0% |
| SNC-10 | 2, 43, 1 | hsa-miR-151-3p, hsa-miR-34a*, hsa-miR-1251 | 94.2% | 93.4% | 95.0% |
| SNC-11 | 79, 1, 12 | hsa-miR-18a, hsa-miR-1251, hsa-miR-934 | 94.0% | 88.0% | 100.0% |
| SNC-12 | 8, 11, 12 | hsa-miR-28-3p, hsa-let-7d*, hsa-miR-934 | 93.7% | 91.3% | 96.1% |
| SNC-13 | 6, 79, 1 | hsa-miR-640, hsa-miR-18a, hsa-miR-1251 | 93.7% | 88.0% | 99.4% |
| SNC-14 | 43, 79, 1 | hsa-miR-34a*, hsa-miR-18a, hsa-miR-1251 | 93.6% | 89.9% | 97.4% |
| SNC-15 | 10, 11, 12 | hsa-miR-145, hsa-let-7d*, hsa-miR-934 | 93.6% | 95.1% | 92.1% |
| SNC-16 | 1, 12, 105 | hsa-miR-1251, hsa-miR-934, hsa-miR-646 | 93.6% | 87.3% | 99.9% |
| SNC-17 | 43, 79, 12 | hsa-miR-34a*, hsa-miR-18a, hsa-miR-934 | 93.5% | 90.3% | 96.7% |
| SNC-18 | 59, 12, 21 | hsa-miR-658, hsa-miR-934, hsa-miR-499-3p | 93.5% | 90.7% | 96.3% |
| SNC-19 | 24, 33, 35 | hsa-miR-144*, hsa-miR-183, hsa-miR-197 | 93.4% | 92.6% | 94.3% |
| SNC-20 | 79, 59, 12 | hsa-miR-18a, hsa-miR-658, hsa-miR-934 | 93.2% | 87.9% | 98.6% |
| SNC-21 | 10, 12, 13 | hsa-miR-145, hsa-miR-934, hsa-miR-17 | 93.2% | 90.7% | 95.7% |
| SNC-22 | 11, 6, 43 | hsa-let-7d*, hsa-miR-640, hsa-miR-34a* | 93.2% | 92.3% | 94.1% |
| SNC-23 | 1, 12, 3 | hsa-miR-1251, hsa-miR-934, hsa-miR-19b | 93.1% | 89.6% | 96.7% |
| SNC-24 | 12, 14, 16 | hsa-miR-934, hsa-miR-596, hsa-miR-664 | 93.1% | 90.1% | 96.1% |
| SNC-25 | 43, 59, 12 | hsa-miR-34a*, hsa-miR-658, hsa-miR-934 | 93.1% | 90.6% | 95.6% |
| SNC-26 | 43, 1, 59 | hsa-miR-34a*, hsa-miR-1251, hsa-miR-658 | 93.0% | 89.4% | 96.6% |
| SNC-27 | 8, 10, 17 | hsa-miR-28-3p, hsa-miR-145, hsa-miR-20a | 93.0% | 89.1% | 96.9% |
| SNC-28 | 16, 17, 24 | hsa-miR-664, hsa-miR-20a, hsa-miR-144* | 92.9% | 86.4% | 99.4% |
| SNC-29 | 6, 2, 1 | hsa-miR-640, hsa-miR-151-3p, hsa-miR-1251 | 92.9% | 89.4% | 96.4% |
| SNC-30 | 12, 21, 69 | hsa-miR-934, hsa-miR-499-3p, hsa-miR-593* | 92.8% | 91.9% | 93.7% |

| SNC-31 | 9, 12, 13 | hsa-miR-208b, hsa-miR-934, hsa-miR-17 | 92.8% | 87.7% | 97.9% |
|---|---|---|---|---|---|
| SNC-32 | 12, 13, 14 | hsa-miR-934, hsa-miR-17, hsa-miR-596 | 92.8% | 91.0% | 94.6% |
| SNC-33 | 15, 17, 24 | hsa-miR-1180, hsa-miR-20a, hsa-miR-144* | 92.8% | 88.0% | 97.6% |
| SNC-34 | 2, 4, 7 | hsa-miR-151-3p, hsa-miR-361-5p, hsa-miR-20b | 92.7% | 89.7% | 95.7% |
| SNC-35 | 14, 15, 17 | hsa-miR-596, hsa-miR-1180, hsa-miR-20a | 92.7% | 89.1% | 96.3% |
| SNC-36 | 2, 1, 12 | hsa-miR-151-3p, hsa-miR-1251, hsa-miR-934 | 92.5% | 88.9% | 96.1% |
| SNC-37 | 79, 12, 3 | hsa-miR-18a, hsa-miR-934, hsa-miR-19b | 92.5% | 88.6% | 96.4% |
| SNC-38 | 59, 12 | hsa-miR-658, hsa-miR-934 | 92.4% | 90.1% | 94.7% |
| SNC-39 | 17, 6, 43 | hsa-miR-20a, hsa-miR-640, hsa-miR-34a* | 92.4% | 89.1% | 95.7% |
| SNC-40 | 12, 13 | hsa-miR-934, hsa-miR-17 | 92.4% | 85.3% | 99.4% |
| SNC-41 | 17, 24 | hsa-miR-20a, hsa-miR-144* | 92.4% | 84.7% | 100.0% |
| SNC-42 | 1, 2, 5 | hsa-miR-1251, hsa-miR-151-3p, hsa-miR-106a | 92.4% | 88.6% | 96.1% |
| SNC-43 | 11, 2 | hsa-let-7d*, hsa-miR-151-3p | 92.3% | 87.7% | 96.9% |
| SNC-44 | 15, 17 | hsa-miR-1180, hsa-miR-20a | 92.1% | 86.6% | 97.7% |
| SNC-45 | 43, 1, 105 | hsa-miR-34a*, hsa-miR-1251, hsa-miR-646 | 92.1% | 88.1% | 96.1% |
| SNC-46 | 43, 12, 105 | hsa-miR-34a*, hsa-miR-934, hsa-miR-646 | 92.1% | 88.4% | 95.7% |
| SNC-47 | 43, 12 | hsa-miR-34a*, hsa-miR-934 | 92.0% | 89.6% | 94.4% |
| SNC-48 | 4, 7, 8 | hsa-miR-361-5p, hsa-miR-20b, hsa-miR-28-3p | 92.0% | 88.9% | 95.1% |
| SNC-49 | 12, 13, 16 | hsa-miR-934, hsa-miR-17, hsa-miR-664 | 92.0% | 84.0% | 100.0% |
| SNC-50 | 13, 15, 17 | hsa-miR-17, hsa-miR-1180, hsa-miR-20a | 92.0% | 85.0% | 99.0% |
| SNC-51 | 10, 12 | hsa-miR-145, hsa-miR-934 | 91.9% | 93.6% | 90.3% |
| SNC-52 | 79, 12, 105 | hsa-miR-18a, hsa-miR-934, hsa-miR-646 | 91.9% | 86.0% | 97.9% |
| SNC-53 | 59, 12, 105 | hsa-miR-658, hsa-miR-934, hsa-miR-646 | 91.9% | 89.6% | 94.1% |
| SNC-54 | 10, 13, 15 | hsa-miR-145, hsa-miR-17, hsa-miR-1180 | 91.9% | 86.0% | 97.7% |
| SNC-55 | 9, 10, 11 | hsa-miR-208b, hsa-miR-145, hsa-let-7d* | 91.8% | 88.1% | 95.4% |
| SNC-56 | 10, 11, 15 | hsa-miR-145, hsa-let-7d*, hsa-miR-1180 | 91.8% | 86.0% | 97.6% |
| SNC-57 | 3, 4, 7 | hsa-miR-19b, hsa-miR-361-5p, hsa-miR-20b | 91.6% | 87.0% | 96.3% |
| SNC-58 | 7, 6, 2 | hsa-miR-20b, hsa-miR-640, hsa-miR-151-3p | 91.6% | 88.9% | 94.3% |
| SNC-59 | 3, 21, 4 | hsa-miR-19b, hsa-miR-499-3p, hsa-miR-361-5p | 91.6% | 88.4% | 94.7% |
| SNC-60 | 12, 3, 21 | hsa-miR-934, hsa-miR-19b, hsa-miR-499-3p | 91.6% | 89.6% | 93.6% |
| SNC-61 | 11, 15, 17 | hsa-let-7d*, hsa-miR-1180, hsa-miR-20a | 91.6% | 88.0% | 95.1% |
| SNC-62 | 4, 7 | hsa-miR-361-5p, hsa-miR-20b | 91.5% | 88.6% | 94.4% |
| SNC-63 | 11, 12 | hsa-let-7d*, hsa-miR-934 | 91.5% | 90.9% | 92.1% |
| SNC-64 | 17, 2, 43 | hsa-miR-20a, hsa-miR-151-3p, hsa-miR-34a* | 91.5% | 89.0% | 94.0% |
| SNC-65 | 17, 24, 26 | hsa-miR-20a, hsa-miR-144*, hsa-miR-564 | 91.5% | 84.1% | 98.9% |
| SNC-66 | 12, 3, 69 | hsa-miR-934, hsa-miR-19b, hsa-miR-593* | 91.5% | 87.7% | 95.3% |
| SNC-67 | 12, 13, 15 | hsa-miR-934, hsa-miR-17, hsa-miR-1180 | 91.4% | 86.9% | 96.0% |
| SNC-68 | 24, 33, 50 | hsa-miR-144*, hsa-miR-183, hsa-miR-720 | 91.3% | 85.1% | 97.4% |
| SNC-69 | 4, 7, 10 | hsa-miR-361-5p, hsa-miR-20b, hsa-miR-145 | 91.3% | 85.7% | 96.9% |
| SNC-70 | 7, 8, 10 | hsa-miR-20b, hsa-miR-28-3p, hsa-miR-145 | 91.3% | 87.3% | 95.3% |
| SNC-71 | 9, 11, 12 | hsa-miR-208b, hsa-let-7d*, hsa-miR-934 | 91.3% | 90.4% | 92.1% |
| SNC-72 | 2, 43, 12 | hsa-miR-151-3p, hsa-miR-34a*, hsa-miR-934 | 91.2% | 90.6% | 91.9% |
| SNC-73 | 17, 6, 2 | hsa-miR-20a, hsa-miR-640, hsa-miR-151-3p | 91.1% | 88.9% | 93.4% |
| SNC-74 | 8, 9, 12 | hsa-miR-28-3p, hsa-miR-208b, hsa-miR-934 | 91.1% | 87.3% | 95.0% |
| SNC-75 | 59, 12, 3 | hsa-miR-658, hsa-miR-934, hsa-miR-19b | 91.1% | 85.9% | 96.4% |
| SNC-76 | 4, 6, 7 | hsa-miR-361-5p, hsa-miR-640, hsa-miR-20b | 91.0% | 86.9% | 95.1% |

FIG. 2 cont.

| | | | | | |
|---|---|---|---|---|---|
| SNC-77 | 11, 2, 43 | hsa-let-7d*, hsa-miR-151-3p, hsa-miR-34a* | 91.0% | 91.0% | 91.0% |
| SNC-78 | 2, 1, 59 | hsa-miR-151-3p, hsa-miR-1251, hsa-miR-658 | 91.0% | 88.1% | 93.9% |
| SNC-79 | 12, 105, 3 | hsa-miR-934, hsa-miR-646, hsa-miR-19b | 90.9% | 87.4% | 94.4% |
| SNC-80 | 33, 50, 53 | hsa-miR-183, hsa-miR-720, hsa-miR-93 | 90.9% | 84.4% | 97.4% |
| SNC-81 | 12, 105, 21 | hsa-miR-934, hsa-miR-646, hsa-miR-499-3p | 90.9% | 89.6% | 92.3% |
| SNC-82 | 43, 1 | hsa-miR-34a*, hsa-miR-1251 | 90.9% | 88.3% | 93.4% |
| SNC-83 | 2, 4, 5 | hsa-miR-151-3p, hsa-miR-361-5p, hsa-miR-106a | 90.9% | 86.0% | 95.7% |
| SNC-84 | 8, 13, 17 | hsa-miR-28-3p, hsa-miR-17, hsa-miR-20a | 90.9% | 82.4% | 99.3% |
| SNC-85 | 79, 12 | hsa-miR-18a, hsa-miR-934 | 90.8% | 84.9% | 96.7% |
| SNC-86 | 11, 17, 6 | hsa-let-7d*, hsa-miR-20a, hsa-miR-640 | 90.8% | 89.6% | 92.0% |
| SNC-87 | 17, 20, 21 | hsa-miR-20a, hsa-miR-183*, hsa-miR-499-3p | 90.8% | 87.4% | 94.1% |
| SNC-88 | 11, 17 | hsa-let-7d*, hsa-miR-20a | 90.7% | 88.3% | 93.1% |
| SNC-89 | 11, 12, 13 | hsa-let-7d*, hsa-miR-934, hsa-miR-17 | 90.7% | 87.7% | 93.7% |
| SNC-90 | 17, 20, 24 | hsa-miR-20a, hsa-miR-183*, hsa-miR-144* | 90.7% | 87.7% | 93.7% |
| SNC-91 | 12, 3 | hsa-miR-934, hsa-miR-19b | 90.6% | 85.7% | 95.6% |
| SNC-92 | 5, 8, 10 | hsa-miR-106a, hsa-miR-28-3p, hsa-miR-145 | 90.6% | 88.1% | 93.1% |
| SNC-93 | 4, 5, 10 | hsa-miR-361-5p, hsa-miR-106a, hsa-miR-145 | 90.6% | 83.7% | 97.4% |
| SNC-94 | 20, 24, 26 | hsa-miR-183*, hsa-miR-144*, hsa-miR-564 | 90.6% | 88.0% | 93.1% |
| SNC-95 | 22, 24, 33 | hsa-miR-1260, hsa-miR-144*, hsa-miR-183 | 90.6% | 83.9% | 97.3% |
| SNC-96 | 69, 39, 5 | hsa-miR-593*, hsa-miR-373, hsa-miR-106a | 90.5% | 84.4% | 96.6% |
| SNC-97 | 10, 12, 14 | hsa-miR-145, hsa-miR-934, hsa-miR-596 | 90.5% | 90.9% | 90.1% |
| SNC-98 | 10, 17, 20 | hsa-miR-145, hsa-miR-20a, hsa-miR-183* | 90.5% | 87.9% | 93.1% |
| SNC-99 | 33, 35, 53 | hsa-miR-183, hsa-miR-197, hsa-miR-93 | 90.4% | 86.9% | 94.0% |
| SNC-100 | 3, 4, 6 | hsa-miR-19b, hsa-miR-361-5p, hsa-miR-640 | 90.4% | 87.7% | 93.0% |
| SNC-101 | 3, 6, 7 | hsa-miR-19b, hsa-miR-640, hsa-miR-20b | 90.4% | 87.4% | 93.3% |
| SNC-102 | 2, 4, 6 | hsa-miR-151-3p, hsa-miR-361-5p, hsa-miR-640 | 90.3% | 86.4% | 94.1% |
| SNC-103 | 5, 24, 13 | hsa-miR-106a, hsa-miR-144*, hsa-miR-17 | 90.3% | 82.1% | 98.4% |
| SNC-104 | 2, 79, 12 | hsa-miR-151-3p, hsa-miR-18a, hsa-miR-934 | 90.3% | 87.0% | 93.6% |
| SNC-105 | 39, 16, 10 | hsa-miR-373, hsa-miR-664, hsa-miR-145 | 90.2% | 84.7% | 95.7% |
| SNC-106 | 10, 17 | hsa-miR-145, hsa-miR-20a | 90.1% | 83.4% | 96.9% |
| SNC-107 | 17, 43 | hsa-miR-20a, hsa-miR-34a* | 90.1% | 87.1% | 93.1% |
| SNC-108 | 3, 4, 5 | hsa-miR-19b, hsa-miR-361-5p, hsa-miR-106a | 90.1% | 84.3% | 96.0% |
| SNC-109 | 7, 9, 10 | hsa-miR-20b, hsa-miR-208b, hsa-miR-145 | 90.1% | 83.9% | 96.4% |
| SNC-110 | 24, 9, 16 | hsa-miR-144*, hsa-miR-208b, hsa-miR-664 | 90.1% | 86.1% | 94.1% |
| SNC-111 | 1, 59, 3 | hsa-miR-1251, hsa-miR-658, hsa-miR-19b | 90.1% | 86.6% | 93.7% |
| SNC-112 | 2, 7, 8 | hsa-miR-151-3p, hsa-miR-20b, hsa-miR-28-3p | 90.1% | 84.9% | 95.3% |
| SNC-113 | 7, 11, 2 | hsa-miR-20b, hsa-let-7d*, hsa-miR-151-3p | 90.1% | 87.0% | 93.1% |
| SNC-114 | 6, 9, 10 | hsa-miR-640, hsa-miR-208b, hsa-miR-145 | 90.1% | 85.1% | 95.0% |
| SNC-115 | 8, 9, 11 | hsa-miR-28-3p, hsa-miR-208b, hsa-let-7d* | 90.1% | 85.1% | 95.0% |
| SNC-116 | 24, 13, 16 | hsa-miR-144*, hsa-miR-17, hsa-miR-664 | 90.1% | 81.0% | 99.1% |
| SNC-117 | 17, 20, 26 | hsa-miR-20a, hsa-miR-183*, hsa-miR-564 | 90.1% | 84.0% | 96.1% |
| SNC-118 | 7, 8 | hsa-miR-20b, hsa-miR-28-3p | 90.0% | 82.7% | 97.3% |
| SNC-119 | 11, 6, 2 | hsa-let-7d*, hsa-miR-640, hsa-miR-151-3p | 90.0% | 87.7% | 92.3% |
| SNC-120 | 17, 2 | hsa-miR-20a, hsa-miR-151-3p | 89.9% | 83.6% | 96.3% |
| SNC-121 | 33, 35, 45 | hsa-miR-183, hsa-miR-197, hsa-miR-1227 | 89.9% | 87.9% | 91.9% |
| SNC-122 | 11, 17, 2 | hsa-let-7d*, hsa-miR-20a, hsa-miR-151-3p | 89.9% | 86.7% | 93.0% |

FIG. 2 cont.

| | | | | | |
|---|---|---|---|---|---|
| SNC-123 | 2, 79, 1 | hsa-miR-151-3p, hsa-miR-18a, hsa-miR-1251 | 89.9% | 89.7% | 90.0% |
| SNC-124 | 2, 3, 6 | hsa-miR-151-3p, hsa-miR-19b, hsa-miR-640 | 89.8% | 87.1% | 92.4% |
| SNC-125 | 17, 43, 79 | hsa-miR-20a, hsa-miR-34a*, hsa-miR-18a | 89.8% | 87.6% | 92.0% |
| SNC-126 | 7, 9, 11 | hsa-miR-20b, hsa-miR-208b, hsa-let-7d* | 89.8% | 83.9% | 95.7% |
| SNC-127 | 7, 8, 13 | hsa-miR-20b, hsa-miR-28-3p, hsa-miR-17 | 89.8% | 82.6% | 97.0% |
| SNC-128 | 7, 10, 13 | hsa-miR-20b, hsa-miR-145, hsa-miR-17 | 89.8% | 84.9% | 94.7% |
| SNC-129 | 6, 2, 43 | hsa-miR-640, hsa-miR-151-3p, hsa-miR-34a* | 89.8% | 88.9% | 90.7% |
| SNC-130 | 21, 69, 4 | hsa-miR-499-3p, hsa-miR-593*, hsa-miR-361-5p | 89.7% | 90.0% | 89.4% |
| SNC-131 | 7, 10 | hsa-miR-20b, hsa-miR-145 | 89.6% | 84.7% | 94.6% |
| SNC-132 | 12, 21 | hsa-miR-934, hsa-miR-499-3p | 89.6% | 90.9% | 88.4% |
| SNC-133 | 5, 7, 10 | hsa-miR-106a, hsa-miR-20b, hsa-miR-145 | 89.6% | 84.9% | 94.4% |
| SNC-134 | 6, 7, 10 | hsa-miR-640, hsa-miR-20b, hsa-miR-145 | 89.6% | 85.6% | 93.7% |
| SNC-135 | 5, 24 | hsa-miR-106a, hsa-miR-144* | 89.6% | 80.4% | 98.7% |
| SNC-136 | 83, 91, 101 | hsa-miR-483-5p, hsa-miR-621, hsa-miR-1908 | 89.5% | 93.3% | 85.7% |
| SNC-137 | 9, 11, 13 | hsa-miR-208b, hsa-let-7d*, hsa-miR-17 | 89.5% | 83.6% | 95.4% |
| SNC-138 | 10, 13, 17 | hsa-miR-145, hsa-miR-17, hsa-miR-20a | 89.5% | 82.3% | 96.7% |
| SNC-139 | 6, 2 | hsa-miR-640, hsa-miR-151-3p | 89.4% | 86.3% | 92.6% |
| SNC-140 | 4, 5, 7 | hsa-miR-361-5p, hsa-miR-106a, hsa-miR-20b | 89.4% | 84.4% | 94.4% |
| SNC-141 | 5, 7, 9 | hsa-miR-106a, hsa-miR-20b, hsa-miR-208b | 89.4% | 81.9% | 97.0% |
| SNC-142 | 24, 13, 9 | hsa-miR-144*, hsa-miR-17, hsa-miR-208b | 89.4% | 81.7% | 97.1% |
| SNC-143 | 14, 16, 17 | hsa-miR-596, hsa-miR-664, hsa-miR-20a | 89.4% | 85.6% | 93.3% |
| SNC-144 | 16, 15, 17 | hsa-miR-664, hsa-miR-1180, hsa-miR-20a | 89.4% | 82.9% | 96.0% |
| SNC-145 | 17, 20, 33 | hsa-miR-20a, hsa-miR-183*, hsa-miR-183 | 89.4% | 85.3% | 93.6% |
| SNC-146 | 39, 30, 10 | hsa-miR-373, hsa-miR-106b, hsa-miR-145 | 89.4% | 87.3% | 91.6% |
| SNC-147 | 9, 11 | hsa-miR-208b, hsa-let-7d* | 89.4% | 83.6% | 95.1% |
| SNC-148 | 7, 17 | hsa-miR-20b, hsa-miR-20a | 89.4% | 81.0% | 97.7% |
| SNC-149 | 6, 2, 79 | hsa-miR-640, hsa-miR-151-3p, hsa-miR-18a | 89.4% | 87.4% | 91.3% |
| SNC-150 | 17, 6 | hsa-miR-20a, hsa-miR-640 | 89.3% | 85.9% | 92.7% |
| SNC-151 | 17, 20 | hsa-miR-20a, hsa-miR-183* | 89.2% | 85.7% | 92.7% |
| SNC-152 | 3, 69 | hsa-miR-19b, hsa-miR-593* | 89.2% | 83.7% | 94.7% |
| SNC-153 | 79, 1, 59 | hsa-miR-18a, hsa-miR-1251, hsa-miR-658 | 89.2% | 87.3% | 91.1% |
| SNC-154 | 13, 14, 15 | hsa-miR-17, hsa-miR-596, hsa-miR-1180 | 89.2% | 83.0% | 95.4% |
| SNC-155 | 13, 16, 17 | hsa-miR-17, hsa-miR-664, hsa-miR-20a | 89.2% | 79.4% | 99.0% |
| SNC-156 | 7, 10, 11 | hsa-miR-20b, hsa-miR-145, hsa-let-7d* | 89.1% | 86.3% | 92.0% |
| SNC-157 | 7, 17, 6 | hsa-miR-20b, hsa-miR-20a, hsa-miR-640 | 89.1% | 83.0% | 95.3% |
| SNC-158 | 91, 101 | hsa-miR-621, hsa-miR-1908 | 89.1% | 91.4% | 86.7% |
| SNC-159 | 24, 13, 182 | hsa-miR-144*, hsa-miR-17, hsa-miR-452* | 89.1% | 78.7% | 99.4% |
| SNC-160 | 6, 8, 10 | hsa-miR-640, hsa-miR-28-3p, hsa-miR-145 | 89.1% | 87.7% | 90.4% |
| SNC-161 | 11, 12, 15 | hsa-let-7d*, hsa-miR-934, hsa-miR-1180 | 89.1% | 89.0% | 89.1% |
| SNC-162 | 11, 13, 17 | hsa-let-7d*, hsa-miR-17, hsa-miR-20a | 89.1% | 84.7% | 93.4% |
| SNC-163 | 17, 22, 33 | hsa-miR-20a, hsa-miR-1260, hsa-miR-183 | 89.1% | 79.0% | 99.1% |
| SNC-164 | 1, 3, 5 | hsa-miR-1251, hsa-miR-19b, hsa-miR-106a | 89.1% | 81.9% | 96.3% |
| SNC-165 | 28, 35, 45 | hsa-miR-607, hsa-miR-197, hsa-miR-1227 | 89.0% | 88.4% | 89.6% |
| SNC-166 | 69, 4, 73 | hsa-miR-593*, hsa-miR-361-5p, hsa-miR-216b | 89.0% | 87.4% | 90.6% |
| SNC-167 | 11, 13, 15 | hsa-let-7d*, hsa-miR-17, hsa-miR-1180 | 89.0% | 85.3% | 92.7% |
| SNC-168 | 11, 16, 17 | hsa-let-7d*, hsa-miR-664, hsa-miR-20a | 89.0% | 83.4% | 94.6% |

FIG. 2 cont.

| | | | | | |
|---|---|---|---|---|---|
| SNC-169 | 15, 17, 20 | hsa-miR-1180, hsa-miR-20a, hsa-miR-183* | 89.0% | 85.9% | 92.1% |
| SNC-170 | 39, 8, 10 | hsa-miR-373, hsa-miR-28-3p, hsa-miR-145 | 89.0% | 87.3% | 90.7% |
| SNC-171 | 39, 5, 24 | hsa-miR-373, hsa-miR-106a, hsa-miR-144* | 89.0% | 81.9% | 96.1% |
| SNC-172 | 2, 5, 6 | hsa-miR-151-3p, hsa-miR-106a, hsa-miR-640 | 88.9% | 87.7% | 90.1% |
| SNC-173 | 87, 91, 101 | hsa-miR-374a, hsa-miR-621, hsa-miR-1908 | 88.9% | 83.9% | 94.0% |
| SNC-174 | 15, 17, 18 | hsa-miR-1180, hsa-miR-20a, hsa-miR-224 | 88.9% | 86.1% | 91.7% |
| SNC-175 | 24, 27, 28 | hsa-miR-144*, hsa-miR-17*, hsa-miR-607 | 88.9% | 80.3% | 97.6% |
| SNC-176 | 24, 26, 33 | hsa-miR-144*, hsa-miR-564, hsa-miR-183 | 88.9% | 89.4% | 88.4% |
| SNC-177 | 2, 43 | hsa-miR-151-3p, hsa-miR-34a* | 88.9% | 89.4% | 88.3% |
| SNC-178 | 33, 35, 50 | hsa-miR-183, hsa-miR-197, hsa-miR-720 | 88.9% | 85.4% | 92.3% |
| SNC-179 | 4, 5, 8 | hsa-miR-361-5p, hsa-miR-106a, hsa-miR-28-3p | 88.9% | 86.4% | 91.3% |
| SNC-180 | 17, 22, 24 | hsa-miR-20a, hsa-miR-1260, hsa-miR-144* | 88.9% | 80.6% | 97.1% |
| SNC-181 | 17, 6, 79 | hsa-miR-20a, hsa-miR-640, hsa-miR-18a | 88.8% | 84.3% | 93.3% |
| SNC-182 | 4, 5, 6 | hsa-miR-361-5p, hsa-miR-106a, hsa-miR-640 | 88.8% | 86.4% | 91.1% |
| SNC-183 | 84, 87, 91 | hsa-miR-130b, hsa-miR-374a, hsa-miR-621 | 88.8% | 82.0% | 95.6% |
| SNC-184 | 16, 17 | hsa-miR-664, hsa-miR-20a | 88.7% | 79.6% | 97.9% |
| SNC-185 | 7, 8, 9 | hsa-miR-20b, hsa-miR-28-3p, hsa-miR-208b | 88.7% | 82.6% | 94.9% |
| SNC-186 | 8, 10, 11 | hsa-miR-28-3p, hsa-miR-145, hsa-let-7d* | 88.7% | 83.6% | 93.9% |
| SNC-187 | 24, 26, 35 | hsa-miR-144*, hsa-miR-564, hsa-miR-197 | 88.7% | 85.0% | 92.4% |
| SNC-188 | 7, 11 | hsa-miR-20b, hsa-let-7d* | 88.6% | 85.4% | 91.9% |
| SNC-189 | 5, 7, 8 | hsa-miR-106a, hsa-miR-20b, hsa-miR-28-3p | 88.6% | 82.4% | 94.9% |
| SNC-190 | 8, 10, 13 | hsa-miR-28-3p, hsa-miR-145, hsa-miR-17 | 88.6% | 85.1% | 92.1% |
| SNC-191 | 7, 11, 17 | hsa-miR-20b, hsa-let-7d*, hsa-miR-20a | 88.6% | 83.6% | 93.7% |
| SNC-192 | 69, 4, 5 | hsa-miR-593*, hsa-miR-361-5p, hsa-miR-106a | 88.6% | 82.7% | 94.6% |
| SNC-193 | 24, 13 | hsa-miR-144*, hsa-miR-17 | 88.6% | 77.9% | 99.3% |
| SNC-194 | 2, 7 | hsa-miR-151-3p, hsa-miR-20b | 88.6% | 81.1% | 96.0% |
| SNC-195 | 16, 22, 24 | hsa-miR-664, hsa-miR-1260, hsa-miR-144* | 88.5% | 80.0% | 97.0% |
| SNC-196 | 26, 33, 35 | hsa-miR-564, hsa-miR-183, hsa-miR-197 | 88.5% | 86.1% | 90.9% |
| SNC-197 | 28, 33, 35 | hsa-miR-607, hsa-miR-183, hsa-miR-197 | 88.5% | 88.6% | 88.4% |
| SNC-198 | 7, 6 | hsa-miR-20b, hsa-miR-640 | 88.4% | 83.7% | 93.1% |
| SNC-199 | 2, 5 | hsa-miR-151-3p, hsa-miR-106a | 88.4% | 82.0% | 94.9% |
| SNC-200 | 2, 5, 8 | hsa-miR-151-3p, hsa-miR-106a, hsa-miR-28-3p | 88.4% | 83.1% | 93.7% |
| SNC-201 | 7, 8, 11 | hsa-miR-20b, hsa-miR-28-3p, hsa-let-7d* | 88.4% | 83.6% | 93.3% |
| SNC-202 | 11, 12, 14 | hsa-let-7d*, hsa-miR-934, hsa-miR-596 | 88.4% | 89.3% | 87.6% |
| SNC-203 | 3, 4, 46 | hsa-miR-19b, hsa-miR-361-5p, hsa-miR-1246 | 88.4% | 81.7% | 95.1% |
| SNC-204 | 17, 2, 79 | hsa-miR-20a, hsa-miR-151-3p, hsa-miR-18a | 88.4% | 80.6% | 96.3% |
| SNC-205 | 12, 14 | hsa-miR-934, hsa-miR-596 | 88.4% | 85.4% | 91.3% |
| SNC-206 | 35, 45 | hsa-miR-197, hsa-miR-1227 | 88.4% | 82.1% | 94.6% |
| SNC-207 | 5, 73, 24 | hsa-miR-106a, hsa-miR-216b, hsa-miR-144* | 88.4% | 83.0% | 93.7% |
| SNC-208 | 2, 3, 5 | hsa-miR-151-3p, hsa-miR-19b, hsa-miR-106a | 88.4% | 80.4% | 96.3% |
| SNC-209 | 12, 15, 16 | hsa-miR-934, hsa-miR-1180, hsa-miR-664 | 88.4% | 82.7% | 94.0% |
| SNC-210 | 4, 8 | hsa-miR-361-5p, hsa-miR-28-3p | 88.3% | 86.6% | 90.0% |
| SNC-211 | 69, 4, 39 | hsa-miR-593*, hsa-miR-361-5p, hsa-miR-373 | 88.3% | 82.6% | 94.0% |
| SNC-212 | 2, 43, 79 | hsa-miR-151-3p, hsa-miR-34a*, hsa-miR-18a | 88.3% | 87.1% | 89.4% |
| SNC-213 | 7, 17, 2 | hsa-miR-20b, hsa-miR-20a, hsa-miR-151-3p | 88.3% | 80.3% | 96.3% |
| SNC-214 | 7, 10, 16 | hsa-miR-20b, hsa-miR-145, hsa-miR-664 | 88.3% | 85.1% | 91.4% |

FIG. 2 cont.

| | | | | | |
|---|---|---|---|---|---|
| SNC-215 | 35, 45, 47 | hsa-miR-197, hsa-miR-1227, hsa-miR-635 | 88.2% | 81.1% | 95.3% |
| SNC-216 | 59, 105, 3 | hsa-miR-658, hsa-miR-646, hsa-miR-19b | 88.2% | 81.9% | 94.6% |
| SNC-217 | 83, 87, 101 | hsa-miR-483-5p, hsa-miR-374a, hsa-miR-1908 | 88.2% | 84.6% | 91.9% |
| SNC-218 | 7, 8, 16 | hsa-miR-20b, hsa-miR-28-3p, hsa-miR-664 | 88.2% | 80.7% | 95.7% |
| SNC-219 | 11, 14, 15 | hsa-let-7d*, hsa-miR-596, hsa-miR-1180 | 88.2% | 83.1% | 93.3% |
| SNC-220 | 10, 13, 20 | hsa-miR-145, hsa-miR-17, hsa-miR-183* | 88.2% | 83.7% | 92.7% |
| SNC-221 | 14, 17, 18 | hsa-miR-596, hsa-miR-20a, hsa-miR-224 | 88.2% | 85.7% | 90.7% |
| SNC-222 | 13, 17, 20 | hsa-miR-17, hsa-miR-20a, hsa-miR-183* | 88.2% | 84.3% | 92.1% |
| SNC-223 | 46, 5, 24 | hsa-miR-1246, hsa-miR-106a, hsa-miR-144* | 88.2% | 79.0% | 97.4% |
| SNC-224 | 24, 35, 38 | hsa-miR-144*, hsa-miR-197, hsa-miR-146a | 88.2% | 88.1% | 88.3% |
| SNC-225 | 3, 69, 46 | hsa-miR-19b, hsa-miR-593*, hsa-miR-1246 | 88.1% | 80.4% | 95.9% |
| SNC-226 | 105, 3, 46 | hsa-miR-646, hsa-miR-19b, hsa-miR-1246 | 88.1% | 80.1% | 96.1% |
| SNC-227 | 21, 4, 39 | hsa-miR-499-3p, hsa-miR-361-5p, hsa-miR-373 | 88.1% | 89.1% | 87.1% |
| SNC-228 | 3, 21, 46 | hsa-miR-19b, hsa-miR-499-3p, hsa-miR-1246 | 88.1% | 80.4% | 95.9% |
| SNC-229 | 24, 28, 33 | hsa-miR-144*, hsa-miR-607, hsa-miR-183 | 88.1% | 89.4% | 86.9% |
| SNC-230 | 3, 4 | hsa-miR-19b, hsa-miR-361-5p | 88.1% | 84.1% | 92.0% |
| SNC-231 | 69, 4 | hsa-miR-593*, hsa-miR-361-5p | 88.1% | 86.6% | 89.6% |
| SNC-232 | 105, 3, 69 | hsa-miR-646, hsa-miR-19b, hsa-miR-593* | 88.1% | 83.7% | 92.4% |
| SNC-233 | 5, 10 | hsa-miR-106a, hsa-miR-145 | 88.0% | 84.0% | 92.0% |
| SNC-234 | 13, 17 | hsa-miR-17, hsa-miR-20a | 88.0% | 77.0% | 99.0% |
| SNC-235 | 24, 33 | hsa-miR-144*, hsa-miR-183 | 88.0% | 88.7% | 87.3% |
| SNC-236 | 35, 45, 50 | hsa-miR-197, hsa-miR-1227, hsa-miR-720 | 88.0% | 87.4% | 88.6% |
| SNC-237 | 105, 21, 4 | hsa-miR-646, hsa-miR-499-3p, hsa-miR-361-5p | 88.0% | 87.7% | 88.3% |
| SNC-238 | 2, 4, 8 | hsa-miR-151-3p, hsa-miR-361-5p, hsa-miR-28-3p | 88.0% | 86.0% | 90.0% |
| SNC-239 | 3, 5, 7 | hsa-miR-19b, hsa-miR-106a, hsa-miR-20b | 88.0% | 80.7% | 95.3% |
| SNC-240 | 84, 91, 101 | hsa-miR-130b, hsa-miR-621, hsa-miR-1908 | 88.0% | 86.6% | 89.4% |
| SNC-241 | 5, 10, 13 | hsa-miR-106a, hsa-miR-145, hsa-miR-17 | 88.0% | 83.7% | 92.3% |
| SNC-242 | 10, 16, 15 | hsa-miR-145, hsa-miR-664, hsa-miR-1180 | 88.0% | 79.7% | 96.3% |
| SNC-243 | 4, 73, 18 | hsa-miR-361-5p, hsa-miR-216b, hsa-miR-224 | 88.0% | 83.9% | 92.1% |
| SNC-244 | 87, 91 | hsa-miR-374a, hsa-miR-621 | 87.9% | 79.7% | 96.1% |
| SNC-245 | 21, 4 | hsa-miR-499-3p, hsa-miR-361-5p | 87.9% | 90.0% | 85.9% |
| SNC-246 | 7, 11, 6 | hsa-miR-20b, hsa-let-7d*, hsa-miR-640 | 87.9% | 85.4% | 90.4% |
| SNC-247 | 5, 18, 24 | hsa-miR-106a, hsa-miR-224, hsa-miR-144* | 87.9% | 78.4% | 97.4% |
| SNC-248 | 14, 17 | hsa-miR-596, hsa-miR-20a | 87.9% | 85.7% | 90.0% |
| SNC-249 | 67, 69, 79 | hsa-miR-144, hsa-miR-593*, hsa-miR-18a | 87.9% | 78.7% | 97.0% |
| SNC-250 | 17, 19, 20 | hsa-miR-20a, hsa-miR-523, hsa-miR-183* | 87.9% | 82.6% | 93.1% |
| SNC-251 | 21, 4, 46 | hsa-miR-499-3p, hsa-miR-361-5p, hsa-miR-1246 | 87.9% | 90.7% | 85.0% |
| SNC-252 | 2, 1 | hsa-miR-151-3p, hsa-miR-1251 | 87.8% | 90.4% | 85.1% |
| SNC-253 | 5, 6, 7 | hsa-miR-106a, hsa-miR-640, hsa-miR-20b | 87.8% | 82.3% | 93.3% |
| SNC-254 | 9, 10, 13 | hsa-miR-208b, hsa-miR-145, hsa-miR-17 | 87.8% | 81.9% | 93.7% |
| SNC-255 | 24, 13, 39 | hsa-miR-144*, hsa-miR-17, hsa-miR-373 | 87.8% | 78.1% | 97.4% |
| SNC-256 | 3, 69, 4 | hsa-miR-19b, hsa-miR-593*, hsa-miR-361-5p | 87.8% | 83.3% | 92.3% |
| SNC-257 | 16, 17, 19 | hsa-miR-664, hsa-miR-20a, hsa-miR-523 | 87.7% | 78.6% | 96.9% |
| SNC-258 | 18, 24, 13 | hsa-miR-224, hsa-miR-144*, hsa-miR-17 | 87.7% | 75.4% | 100.0% |
| SNC-259 | 1, 2, 4 | hsa-miR-1251, hsa-miR-151-3p, hsa-miR-361-5p | 87.7% | 87.3% | 88.1% |
| SNC-260 | 3, 21, 69 | hsa-miR-19b, hsa-miR-499-3p, hsa-miR-593* | 87.7% | 81.0% | 94.4% |

FIG. 2 cont.

| | | | | | |
|---|---|---|---|---|---|
| SNC-261 | 5, 7 | hsa-miR-106a, hsa-miR-20b | 87.6% | 82.6% | 92.7% |
| SNC-262 | 10, 11 | hsa-miR-145, hsa-let-7d* | 87.6% | 86.0% | 89.3% |
| SNC-263 | 6, 43, 79 | hsa-miR-640, hsa-miR-34a*, hsa-miR-18a | 87.6% | 83.9% | 91.4% |
| SNC-264 | 4, 6, 8 | hsa-miR-361-5p, hsa-miR-640, hsa-miR-28-3p | 87.6% | 86.0% | 89.3% |
| SNC-265 | 18, 13, 182 | hsa-miR-224, hsa-miR-17, hsa-miR-452* | 87.6% | 78.6% | 96.7% |
| SNC-266 | 13, 14, 17 | hsa-miR-17, hsa-miR-596, hsa-miR-20a | 87.6% | 82.1% | 93.1% |
| SNC-267 | 20, 33, 35 | hsa-miR-183*, hsa-miR-183, hsa-miR-197 | 87.6% | 88.0% | 87.3% |
| SNC-268 | 69, 39 | hsa-miR-593*, hsa-miR-373 | 87.6% | 79.7% | 95.4% |
| SNC-269 | 11, 6 | hsa-let-7d*, hsa-miR-640 | 87.6% | 87.1% | 88.0% |
| SNC-270 | 69, 46, 5 | hsa-miR-593*, hsa-miR-1246, hsa-miR-106a | 87.6% | 80.3% | 94.9% |
| SNC-271 | 4, 46, 73 | hsa-miR-361-5p, hsa-miR-1246, hsa-miR-216b | 87.6% | 83.6% | 91.6% |
| SNC-272 | 43, 79, 105 | hsa-miR-34a*, hsa-miR-18a, hsa-miR-646 | 87.6% | 85.1% | 90.0% |
| SNC-273 | 80, 87, 91 | hsa-miR-454, hsa-miR-374a, hsa-miR-621 | 87.6% | 79.9% | 95.3% |
| SNC-274 | 5, 10, 11 | hsa-miR-106a, hsa-miR-145, hsa-let-7d* | 87.6% | 87.0% | 88.1% |
| SNC-275 | 4, 39, 5 | hsa-miR-361-5p, hsa-miR-373, hsa-miR-106a | 87.6% | 85.0% | 90.1% |
| SNC-276 | 16, 17, 18 | hsa-miR-664, hsa-miR-20a, hsa-miR-224 | 87.6% | 77.9% | 97.3% |
| SNC-277 | 16, 17, 20 | hsa-miR-664, hsa-miR-20a, hsa-miR-183* | 87.6% | 82.4% | 92.7% |
| SNC-278 | 7, 9 | hsa-miR-20b, hsa-miR-208b | 87.5% | 78.9% | 96.1% |
| SNC-279 | 69, 5, 73 | hsa-miR-593*, hsa-miR-106a, hsa-miR-216b | 87.5% | 84.7% | 90.3% |
| SNC-280 | 3, 5, 6 | hsa-miR-19b, hsa-miR-106a, hsa-miR-640 | 87.5% | 84.9% | 90.1% |
| SNC-281 | 6, 7, 9 | hsa-miR-640, hsa-miR-20b, hsa-miR-208b | 87.5% | 80.9% | 94.1% |
| SNC-282 | 8, 30, 251 | hsa-miR-28-3p, hsa-miR-106b, hsa-miR-32 | 87.5% | 82.0% | 93.0% |
| SNC-283 | 10, 16, 17 | hsa-miR-145, hsa-miR-664, hsa-miR-20a | 87.5% | 81.7% | 93.3% |
| SNC-284 | 16, 17, 22 | hsa-miR-664, hsa-miR-20a, hsa-miR-1260 | 87.5% | 77.0% | 98.0% |
| SNC-285 | 21, 46, 5 | hsa-miR-499-3p, hsa-miR-1246, hsa-miR-106a | 87.5% | 84.7% | 90.3% |
| SNC-286 | 4, 5, 73 | hsa-miR-361-5p, hsa-miR-106a, hsa-miR-216b | 87.4% | 85.4% | 89.4% |
| SNC-287 | 46, 39, 5 | hsa-miR-1246, hsa-miR-373, hsa-miR-106a | 87.4% | 79.9% | 95.0% |
| SNC-288 | 2, 5, 7 | hsa-miR-151-3p, hsa-miR-106a, hsa-miR-20b | 87.4% | 80.7% | 94.0% |
| SNC-289 | 105, 69, 4 | hsa-miR-646, hsa-miR-593*, hsa-miR-361-5p | 87.4% | 87.1% | 87.6% |
| SNC-290 | 79, 105, 3 | hsa-miR-18a, hsa-miR-646, hsa-miR-19b | 87.4% | 81.9% | 92.9% |
| SNC-291 | 1, 3, 4 | hsa-miR-1251, hsa-miR-19b, hsa-miR-361-5p | 87.4% | 82.7% | 92.0% |
| SNC-292 | 10, 13 | hsa-miR-145, hsa-miR-17 | 87.3% | 79.1% | 95.4% |
| SNC-293 | 3, 6 | hsa-miR-19b, hsa-miR-640 | 87.3% | 85.1% | 89.4% |
| SNC-294 | 8, 11, 13 | hsa-miR-28-3p, hsa-let-7d*, hsa-miR-17 | 87.3% | 83.3% | 91.3% |
| SNC-295 | 105, 3 | hsa-miR-646, hsa-miR-19b | 87.2% | 82.3% | 92.1% |
| SNC-296 | 105, 3, 21 | hsa-miR-646, hsa-miR-19b, hsa-miR-499-3p | 87.2% | 81.1% | 93.3% |
| SNC-297 | 15, 17, 19 | hsa-miR-1180, hsa-miR-20a, hsa-miR-523 | 87.2% | 79.6% | 94.9% |
| SNC-298 | 4, 46, 5 | hsa-miR-361-5p, hsa-miR-1246, hsa-miR-106a | 87.2% | 83.1% | 91.3% |
| SNC-299 | 24, 26, 28 | hsa-miR-144*, hsa-miR-564, hsa-miR-607 | 87.2% | 81.6% | 92.9% |
| SNC-300 | 8, 11 | hsa-miR-28-3p, hsa-let-7d* | 87.1% | 84.9% | 89.4% |
| SNC-301 | 12, 105, 69 | hsa-miR-934, hsa-miR-646, hsa-miR-593* | 87.1% | 81.1% | 93.1% |
| SNC-302 | 53, 67, 69 | hsa-miR-93, hsa-miR-144, hsa-miR-593* | 87.1% | 78.4% | 95.9% |
| SNC-303 | 4, 8, 10 | hsa-miR-361-5p, hsa-miR-28-3p, hsa-miR-145 | 87.1% | 83.7% | 90.6% |
| SNC-304 | 10, 11, 13 | hsa-miR-145, hsa-let-7d*, hsa-miR-17 | 87.1% | 86.6% | 87.7% |
| SNC-305 | 12, 14, 15 | hsa-miR-934, hsa-miR-596, hsa-miR-1180 | 87.1% | 85.1% | 89.1% |
| SNC-306 | 5, 8, 9 | hsa-miR-106a, hsa-miR-28-3p, hsa-miR-208b | 87.1% | 82.7% | 91.4% |

FIG. 2 cont.

| | | | | | |
|---|---|---|---|---|---|
| SNC-307 | 17, 18, 20 | hsa-miR-20a, hsa-miR-224, hsa-miR-183* | 87.1% | 83.3% | 90.9% |
| SNC-308 | 6, 43 | hsa-miR-640, hsa-miR-34a* | 87.0% | 86.1% | 87.9% |
| SNC-309 | 69, 4, 46 | hsa-miR-593*, hsa-miR-361-5p, hsa-miR-1246 | 87.0% | 85.4% | 88.6% |
| SNC-310 | 1, 59, 105 | hsa-miR-1251, hsa-miR-658, hsa-miR-646 | 87.0% | 87.1% | 86.9% |
| SNC-311 | 50, 67, 69 | hsa-miR-720, hsa-miR-144, hsa-miR-593* | 87.0% | 88.6% | 85.4% |
| SNC-312 | 22, 24, 26 | hsa-miR-1260, hsa-miR-144*, hsa-miR-564 | 87.0% | 79.1% | 94.9% |
| SNC-313 | 8, 251 | hsa-miR-28-3p, hsa-miR-32 | 86.9% | 80.4% | 93.4% |
| SNC-314 | 17, 18 | hsa-miR-20a, hsa-miR-224 | 86.9% | 75.6% | 98.3% |
| SNC-315 | 73, 24, 13 | hsa-miR-216b, hsa-miR-144*, hsa-miR-17 | 86.9% | 77.0% | 96.9% |
| SNC-316 | 33, 38, 53 | hsa-miR-183, hsa-miR-146a, hsa-miR-93 | 86.9% | 77.7% | 96.1% |
| SNC-317 | 8, 10, 251 | hsa-miR-28-3p, hsa-miR-145, hsa-miR-32 | 86.9% | 79.1% | 94.7% |
| SNC-318 | 4, 39, 18 | hsa-miR-361-5p, hsa-miR-373, hsa-miR-224 | 86.9% | 76.0% | 97.9% |
| SNC-319 | 7, 13 | hsa-miR-20b, hsa-miR-17 | 86.9% | 80.1% | 93.6% |
| SNC-320 | 2, 4 | hsa-miR-151-3p, hsa-miR-361-5p | 86.9% | 85.3% | 88.4% |
| SNC-321 | 6, 7, 8 | hsa-miR-640, hsa-miR-20b, hsa-miR-28-3p | 86.9% | 81.7% | 92.0% |
| SNC-322 | 26, 28, 35 | hsa-miR-564, hsa-miR-607, hsa-miR-197 | 86.9% | 85.1% | 88.6% |
| SNC-323 | 2, 3, 4 | hsa-miR-151-3p, hsa-miR-19b, hsa-miR-361-5p | 86.9% | 82.0% | 91.7% |
| SNC-324 | 1, 4, 5 | hsa-miR-1251, hsa-miR-361-5p, hsa-miR-106a | 86.8% | 80.6% | 93.0% |
| SNC-325 | 73, 18, 13 | hsa-miR-216b, hsa-miR-224, hsa-miR-17 | 86.8% | 79.1% | 94.4% |
| SNC-326 | 7, 13, 16 | hsa-miR-20b, hsa-miR-17, hsa-miR-664 | 86.8% | 77.1% | 96.4% |
| SNC-327 | 13, 182, 39 | hsa-miR-17, hsa-miR-452*, hsa-miR-373 | 86.7% | 78.1% | 95.3% |
| SNC-328 | 4, 46, 18 | hsa-miR-361-5p, hsa-miR-1246, hsa-miR-224 | 86.7% | 80.1% | 93.3% |
| SNC-329 | 12, 105 | hsa-miR-934, hsa-miR-646 | 86.6% | 80.9% | 92.4% |
| SNC-330 | 6, 79 | hsa-miR-640, hsa-miR-18a | 86.6% | 83.6% | 89.7% |
| SNC-331 | 33, 35, 47 | hsa-miR-183, hsa-miR-197, hsa-miR-635 | 86.6% | 86.0% | 87.3% |
| SNC-332 | 33, 38, 50 | hsa-miR-183, hsa-miR-146a, hsa-miR-720 | 86.6% | 79.1% | 94.1% |
| SNC-333 | 8, 10 | hsa-miR-28-3p, hsa-miR-145 | 86.6% | 80.6% | 92.6% |
| SNC-334 | 13, 182 | hsa-miR-17, hsa-miR-452* | 86.6% | 77.7% | 95.4% |
| SNC-335 | 69, 5 | hsa-miR-593*, hsa-miR-106a | 86.6% | 81.6% | 91.6% |
| SNC-336 | 53, 61, 69 | hsa-miR-93, hsa-miR-296-5p, hsa-miR-593* | 86.6% | 79.3% | 93.9% |
| SNC-337 | 5, 7, 11 | hsa-miR-106a, hsa-miR-20b, hsa-let-7d* | 86.6% | 82.3% | 90.9% |
| SNC-338 | 4, 6 | hsa-miR-361-5p, hsa-miR-640 | 86.5% | 82.9% | 90.1% |
| SNC-339 | 9, 10 | hsa-miR-208b, hsa-miR-145 | 86.5% | 83.1% | 89.9% |
| SNC-340 | 12, 15 | hsa-miR-934, hsa-miR-1180 | 86.5% | 83.3% | 89.7% |
| SNC-341 | 24, 26 | hsa-miR-144*, hsa-miR-564 | 86.5% | 80.0% | 93.0% |
| SNC-342 | 61, 69, 79 | hsa-miR-296-5p, hsa-miR-593*, hsa-miR-18a | 86.5% | 78.0% | 95.0% |
| SNC-343 | 10, 13, 16 | hsa-miR-145, hsa-miR-17, hsa-miR-664 | 86.5% | 81.4% | 91.6% |
| SNC-344 | 13, 17, 22 | hsa-miR-17, hsa-miR-20a, hsa-miR-1260 | 86.5% | 77.3% | 95.7% |
| SNC-345 | 22, 24, 38 | hsa-miR-1260, hsa-miR-144*, hsa-miR-146a | 86.5% | 79.3% | 93.7% |
| SNC-346 | 2, 43, 59 | hsa-miR-151-3p, hsa-miR-34a*, hsa-miR-658 | 86.4% | 86.1% | 86.7% |
| SNC-347 | 9, 16, 170 | hsa-miR-208b, hsa-miR-664, hsa-miR-1226* | 86.4% | 80.1% | 92.7% |
| SNC-348 | 8, 16, 17 | hsa-miR-28-3p, hsa-miR-664, hsa-miR-20a | 86.4% | 79.6% | 93.3% |
| SNC-349 | 17, 18, 21 | hsa-miR-20a, hsa-miR-224, hsa-miR-499-3p | 86.4% | 77.4% | 95.4% |
| SNC-350 | 17, 20, 22 | hsa-miR-20a, hsa-miR-183*, hsa-miR-1260 | 86.4% | 82.4% | 90.4% |
| SNC-351 | 20, 24, 28 | hsa-miR-183*, hsa-miR-144*, hsa-miR-607 | 86.4% | 83.9% | 89.0% |
| SNC-352 | 24, 26, 27 | hsa-miR-144*, hsa-miR-564, hsa-miR-17* | 86.4% | 76.1% | 96.7% |

FIG. 2 cont.

| | | | | | |
|---|---|---|---|---|---|
| SNC-353 | 35, 38, 45 | hsa-miR-197, hsa-miR-146a, hsa-miR-1227 | 86.4% | 80.7% | 92.0% |
| SNC-354 | 50, 53, 69 | hsa-miR-720, hsa-miR-93, hsa-miR-593* | 86.4% | 85.7% | 87.0% |
| SNC-355 | 4, 5, 18 | hsa-miR-361-5p, hsa-miR-106a, hsa-miR-224 | 86.4% | 79.3% | 93.4% |
| SNC-356 | 10, 11, 16 | hsa-miR-145, hsa-let-7d*, hsa-miR-664 | 86.4% | 86.0% | 86.7% |
| SNC-357 | 17, 22, 26 | hsa-miR-20a, hsa-miR-1260, hsa-miR-564 | 86.4% | 78.3% | 94.4% |
| SNC-358 | 1, 2, 3 | hsa-miR-1251, hsa-miR-151-3p, hsa-miR-19b | 86.4% | 87.0% | 85.7% |
| SNC-359 | 20, 24, 33 | hsa-miR-183*, hsa-miR-144*, hsa-miR-183 | 86.4% | 84.6% | 88.1% |
| SNC-360 | 20, 26 | hsa-miR-183*, hsa-miR-564 | 86.3% | 80.1% | 92.4% |
| SNC-361 | 2, 79 | hsa-miR-151-3p, hsa-miR-18a | 86.3% | 77.6% | 95.0% |
| SNC-362 | 4, 5 | hsa-miR-361-5p, hsa-miR-106a | 86.3% | 80.1% | 92.4% |
| SNC-363 | 46, 5, 73 | hsa-miR-1246, hsa-miR-106a, hsa-miR-216b | 86.3% | 81.1% | 91.4% |
| SNC-364 | 8, 30, 170 | hsa-miR-28-3p, hsa-miR-106b, hsa-miR-1226* | 86.3% | 76.6% | 96.0% |
| SNC-365 | 13, 14, 16 | hsa-miR-17, hsa-miR-596, hsa-miR-664 | 86.3% | 78.3% | 94.3% |
| SNC-366 | 15, 17, 22 | hsa-miR-1180, hsa-miR-20a, hsa-miR-1260 | 86.3% | 78.6% | 94.0% |
| SNC-367 | 39, 5 | hsa-miR-373, hsa-miR-106a | 86.2% | 81.3% | 91.1% |
| SNC-368 | 13, 182, 9 | hsa-miR-17, hsa-miR-452*, hsa-miR-208b | 86.2% | 77.6% | 94.9% |
| SNC-369 | 7, 11, 13 | hsa-miR-20b, hsa-let-7d*, hsa-miR-17 | 86.2% | 82.4% | 90.0% |
| SNC-370 | 17, 18, 19 | hsa-miR-20a, hsa-miR-224, hsa-miR-523 | 86.2% | 75.0% | 97.4% |
| SNC-371 | 13, 39, 16 | hsa-miR-17, hsa-miR-373, hsa-miR-664 | 86.2% | 76.4% | 96.0% |
| SNC-372 | 23, 24, 26 | hsa-miR-496, hsa-miR-144*, hsa-miR-564 | 86.2% | 79.9% | 92.6% |
| SNC-373 | 11, 13 | hsa-let-7d*, hsa-miR-17 | 86.1% | 84.3% | 88.0% |
| SNC-374 | 10, 251 | hsa-miR-145, hsa-miR-32 | 86.1% | 83.3% | 89.0% |
| SNC-375 | 21, 4, 5 | hsa-miR-499-3p, hsa-miR-361-5p, hsa-miR-106a | 86.1% | 83.7% | 88.6% |
| SNC-376 | 24, 28 | hsa-miR-144*, hsa-miR-607 | 86.1% | 75.6% | 96.6% |
| SNC-377 | 105, 3, 4 | hsa-miR-646, hsa-miR-19b, hsa-miR-361-5p | 86.1% | 83.3% | 88.9% |
| SNC-378 | 5, 6, 9 | hsa-miR-106a, hsa-miR-640, hsa-miR-208b | 86.1% | 82.3% | 89.9% |
| SNC-379 | 67, 69, 71 | hsa-miR-144, hsa-miR-593*, hsa-miR-216a | 86.1% | 75.9% | 96.3% |
| SNC-380 | 24, 9, 39 | hsa-miR-144*, hsa-miR-208b, hsa-miR-373 | 86.1% | 84.4% | 87.7% |
| SNC-381 | 24, 25, 28 | hsa-miR-144*, hsa-miR-613, hsa-miR-607 | 86.1% | 80.9% | 91.3% |
| SNC-382 | 69, 80 | hsa-miR-593*, hsa-miR-454 | 86.0% | 80.0% | 92.0% |
| SNC-383 | 13, 39 | hsa-miR-17, hsa-miR-373 | 86.0% | 76.1% | 95.9% |
| SNC-384 | 3, 5 | hsa-miR-19b, hsa-miR-106a | 86.0% | 78.6% | 93.4% |
| SNC-385 | 21, 69, 39 | hsa-miR-499-3p, hsa-miR-593*, hsa-miR-373 | 86.0% | 82.9% | 89.1% |
| SNC-386 | 13, 16, 15 | hsa-miR-17, hsa-miR-664, hsa-miR-1180 | 86.0% | 78.6% | 93.4% |
| SNC-387 | 79, 1, 3 | hsa-miR-18a, hsa-miR-1251, hsa-miR-19b | 86.0% | 85.4% | 86.6% |
| SNC-388 | 24, 27 | hsa-miR-144*, hsa-miR-17* | 85.9% | 73.0% | 98.9% |
| SNC-389 | 1, 59 | hsa-miR-1251, hsa-miR-658 | 85.9% | 84.1% | 87.7% |
| SNC-390 | 79, 84, 87 | hsa-miR-18a, hsa-miR-130b, hsa-miR-374a | 85.9% | 77.3% | 94.6% |
| SNC-391 | 13, 9, 8 | hsa-miR-17, hsa-miR-208b, hsa-miR-28-3p | 85.9% | 81.4% | 90.4% |
| SNC-392 | 4, 73 | hsa-miR-361-5p, hsa-miR-216b | 85.9% | 84.9% | 86.9% |
| SNC-393 | 1, 105, 3 | hsa-miR-1251, hsa-miR-646, hsa-miR-19b | 85.9% | 83.3% | 88.4% |
| SNC-394 | 5, 6, 8 | hsa-miR-106a, hsa-miR-640, hsa-miR-28-3p | 85.9% | 82.9% | 88.9% |
| SNC-395 | 5, 8, 11 | hsa-miR-106a, hsa-miR-28-3p, hsa-let-7d* | 85.9% | 82.3% | 89.4% |
| SNC-396 | 20, 21, 24 | hsa-miR-183*, hsa-miR-499-3p, hsa-miR-144* | 85.9% | 81.4% | 90.3% |
| SNC-397 | 5, 73, 18 | hsa-miR-106a, hsa-miR-216b, hsa-miR-224 | 85.9% | 82.3% | 89.4% |
| SNC-398 | 67, 69 | hsa-miR-144, hsa-miR-593* | 85.8% | 78.0% | 93.6% |

FIG. 2 cont.

| SNC-399 | 5, 73 | hsa-miR-106a, hsa-miR-216b | 85.8% | 82.7% | 88.9% |
|---|---|---|---|---|---|
| SNC-400 | 67, 69, 80 | hsa-miR-144, hsa-miR-593*, hsa-miR-454 | 85.8% | 76.9% | 94.7% |
| SNC-401 | 30, 10, 251 | hsa-miR-106b, hsa-miR-145, hsa-miR-32 | 85.8% | 80.4% | 91.1% |
| SNC-402 | 69, 79 | hsa-miR-593*, hsa-miR-18a | 85.7% | 74.0% | 97.4% |
| SNC-403 | 14, 16 | hsa-miR-596, hsa-miR-664 | 85.7% | 79.0% | 92.4% |
| SNC-404 | 33, 35 | hsa-miR-183, hsa-miR-197 | 85.7% | 87.0% | 84.4% |
| SNC-405 | 39, 5, 73 | hsa-miR-373, hsa-miR-106a, hsa-miR-216b | 85.7% | 81.7% | 89.7% |
| SNC-406 | 69, 79, 80 | hsa-miR-593*, hsa-miR-18a, hsa-miR-454 | 85.7% | 76.3% | 95.1% |
| SNC-407 | 20, 24, 35 | hsa-miR-183*, hsa-miR-144*, hsa-miR-197 | 85.7% | 82.6% | 88.9% |
| SNC-408 | 45, 47, 50 | hsa-miR-1227, hsa-miR-635, hsa-miR-720 | 85.6% | 86.7% | 84.6% |
| SNC-409 | 24, 28, 35 | hsa-miR-144*, hsa-miR-607, hsa-miR-197 | 85.6% | 82.3% | 89.0% |
| SNC-410 | 5, 6 | hsa-miR-106a, hsa-miR-640 | 85.6% | 83.4% | 87.7% |
| SNC-411 | 1, 4 | hsa-miR-1251, hsa-miR-361-5p | 85.6% | 80.6% | 90.6% |
| SNC-412 | 35, 47, 50 | hsa-miR-197, hsa-miR-635, hsa-miR-720 | 85.6% | 89.0% | 82.1% |
| SNC-413 | 10, 11, 14 | hsa-miR-145, hsa-let-7d*, hsa-miR-596 | 85.6% | 85.1% | 86.0% |
| SNC-414 | 22, 33, 35 | hsa-miR-1260, hsa-miR-183, hsa-miR-197 | 85.6% | 81.4% | 89.7% |
| SNC-415 | 59, 105 | hsa-miR-658, hsa-miR-646 | 85.5% | 79.3% | 91.7% |
| SNC-416 | 11, 14 | hsa-let-7d*, hsa-miR-596 | 85.5% | 87.6% | 83.4% |
| SNC-417 | 28, 35 | hsa-miR-607, hsa-miR-197 | 85.5% | 86.4% | 84.6% |
| SNC-418 | 73, 18, 24 | hsa-miR-216b, hsa-miR-224, hsa-miR-144* | 85.5% | 80.3% | 90.7% |
| SNC-419 | 22, 26, 33 | hsa-miR-1260, hsa-miR-564, hsa-miR-183 | 85.5% | 77.3% | 93.7% |
| SNC-420 | 24, 35 | hsa-miR-144*, hsa-miR-197 | 85.4% | 79.9% | 91.0% |
| SNC-421 | 28, 35, 38 | hsa-miR-607, hsa-miR-197, hsa-miR-146a | 85.4% | 83.0% | 87.9% |
| SNC-422 | 43, 79, 59 | hsa-miR-34a*, hsa-miR-18a, hsa-miR-658 | 85.4% | 82.3% | 88.6% |
| SNC-423 | 5, 7, 13 | hsa-miR-106a, hsa-miR-20b, hsa-miR-17 | 85.4% | 77.1% | 93.7% |
| SNC-424 | 11, 13, 14 | hsa-let-7d*, hsa-miR-17, hsa-miR-596 | 85.4% | 82.6% | 88.3% |
| SNC-425 | 18, 13, 9 | hsa-miR-224, hsa-miR-17, hsa-miR-208b | 85.4% | 76.3% | 94.6% |
| SNC-426 | 43, 79 | hsa-miR-34a*, hsa-miR-18a | 85.4% | 84.0% | 86.7% |
| SNC-427 | 11, 16 | hsa-let-7d*, hsa-miR-664 | 85.4% | 83.1% | 87.6% |
| SNC-428 | 13, 15 | hsa-miR-17, hsa-miR-1180 | 85.4% | 77.4% | 93.3% |
| SNC-429 | 9, 8, 170 | hsa-miR-208b, hsa-miR-28-3p, hsa-miR-1226* | 85.4% | 78.9% | 91.9% |
| SNC-430 | 69, 71, 79 | hsa-miR-593*, hsa-miR-216a, hsa-miR-18a | 85.4% | 72.6% | 98.1% |
| SNC-431 | 24, 182, 16 | hsa-miR-144*, hsa-miR-452*, hsa-miR-664 | 85.4% | 78.7% | 92.0% |
| SNC-432 | 8, 9, 10 | hsa-miR-28-3p, hsa-miR-208b, hsa-miR-145 | 85.4% | 83.3% | 87.4% |
| SNC-433 | 17, 19, 21 | hsa-miR-20a, hsa-miR-523, hsa-miR-499-3p | 85.4% | 83.4% | 87.3% |
| SNC-434 | 16, 170 | hsa-miR-664, hsa-miR-1226* | 85.3% | 78.6% | 92.0% |
| SNC-435 | 79, 1, 105 | hsa-miR-18a, hsa-miR-1251, hsa-miR-646 | 85.3% | 84.7% | 85.9% |
| SNC-436 | 18, 24, 182 | hsa-miR-224, hsa-miR-144*, hsa-miR-452* | 85.3% | 78.0% | 92.6% |
| SNC-437 | 22, 35, 38 | hsa-miR-1260, hsa-miR-197, hsa-miR-146a | 85.3% | 77.7% | 92.9% |
| SNC-438 | 33, 35, 38 | hsa-miR-183, hsa-miR-197, hsa-miR-146a | 85.2% | 86.0% | 84.4% |
| SNC-439 | 11, 13, 16 | hsa-let-7d*, hsa-miR-17, hsa-miR-664 | 85.2% | 82.6% | 87.9% |
| SNC-440 | 11, 16, 15 | hsa-let-7d*, hsa-miR-664, hsa-miR-1180 | 85.2% | 79.3% | 91.1% |
| SNC-441 | 9, 12 | hsa-miR-208b, hsa-miR-934 | 85.1% | 81.7% | 88.6% |
| SNC-442 | 22, 24 | hsa-miR-1260, hsa-miR-144* | 85.1% | 72.0% | 98.3% |
| SNC-443 | 3, 46 | hsa-miR-19b, hsa-miR-1246 | 85.1% | 78.4% | 91.9% |
| SNC-444 | 13, 182, 8 | hsa-miR-17, hsa-miR-452*, hsa-miR-28-3p | 85.1% | 74.1% | 96.1% |

FIG. 2 cont.

| | | | | | |
|---|---|---|---|---|---|
| SNC-445 | 83, 87, 91 | hsa-miR-483-5p, hsa-miR-374a, hsa-miR-621 | 85.1% | 80.1% | 90.1% |
| SNC-446 | 8, 170 | hsa-miR-28-3p, hsa-miR-1226* | 85.1% | 75.0% | 95.1% |
| SNC-447 | 11, 15 | hsa-let-7d*, hsa-miR-1180 | 85.1% | 80.9% | 89.3% |
| SNC-448 | 4, 39, 73 | hsa-miR-361-5p, hsa-miR-373, hsa-miR-216b | 85.1% | 81.3% | 88.9% |
| SNC-449 | 16, 30, 170 | hsa-miR-664, hsa-miR-106b, hsa-miR-1226* | 85.1% | 75.9% | 94.3% |
| SNC-450 | 79, 80, 87 | hsa-miR-18a, hsa-miR-454, hsa-miR-374a | 85.1% | 75.0% | 95.1% |
| SNC-451 | 10, 13, 14 | hsa-miR-145, hsa-miR-17, hsa-miR-596 | 85.1% | 79.9% | 90.3% |
| SNC-452 | 43, 59 | hsa-miR-34a*, hsa-miR-658 | 85.0% | 84.3% | 85.7% |
| SNC-453 | 1, 105 | hsa-miR-1251, hsa-miR-646 | 85.0% | 87.9% | 82.1% |
| SNC-454 | 6, 8 | hsa-miR-640, hsa-miR-28-3p | 85.0% | 81.0% | 89.0% |
| SNC-455 | 24, 38, 50 | hsa-miR-144*, hsa-miR-146a, hsa-miR-720 | 85.0% | 83.7% | 86.3% |
| SNC-456 | 38, 53, 67 | hsa-miR-146a, hsa-miR-93, hsa-miR-144 | 85.0% | 77.3% | 92.7% |
| SNC-457 | 13, 15, 20 | hsa-miR-17, hsa-miR-1180, hsa-miR-183* | 85.0% | 82.6% | 87.4% |
| SNC-458 | 24, 33, 38 | hsa-miR-144*, hsa-miR-183, hsa-miR-146a | 85.0% | 86.0% | 84.0% |
| SNC-459 | 33, 50 | hsa-miR-183, hsa-miR-720 | 84.9% | 77.0% | 92.9% |
| SNC-460 | 79, 59, 105 | hsa-miR-18a, hsa-miR-658, hsa-miR-646 | 84.9% | 77.3% | 92.6% |
| SNC-461 | 14, 15, 16 | hsa-miR-596, hsa-miR-1180, hsa-miR-664 | 84.9% | 78.3% | 91.6% |
| SNC-462 | 5, 73, 13 | hsa-miR-106a, hsa-miR-216b, hsa-miR-17 | 84.9% | 81.3% | 88.6% |
| SNC-463 | 13, 20 | hsa-miR-17, hsa-miR-183* | 84.9% | 79.4% | 90.3% |
| SNC-464 | 16, 8, 170 | hsa-miR-664, hsa-miR-28-3p, hsa-miR-1226* | 84.9% | 79.3% | 90.4% |
| SNC-465 | 19, 20, 21 | hsa-miR-523, hsa-miR-183*, hsa-miR-499-3p | 84.9% | 85.3% | 84.4% |
| SNC-466 | 46, 18, 24 | hsa-miR-1246, hsa-miR-224, hsa-miR-144* | 84.9% | 76.4% | 93.3% |
| SNC-467 | 22, 24, 35 | hsa-miR-1260, hsa-miR-144*, hsa-miR-197 | 84.8% | 78.9% | 90.7% |
| SNC-468 | 59, 3, 21 | hsa-miR-658, hsa-miR-19b, hsa-miR-499-3p | 84.8% | 77.3% | 92.3% |
| SNC-469 | 21, 69, 5 | hsa-miR-499-3p, hsa-miR-593*, hsa-miR-106a | 84.8% | 80.4% | 89.1% |
| SNC-470 | 8, 13 | hsa-miR-28-3p, hsa-miR-17 | 84.7% | 74.9% | 94.6% |
| SNC-471 | 18, 13 | hsa-miR-224, hsa-miR-17 | 84.7% | 76.1% | 93.3% |
| SNC-472 | 24, 182, 9 | hsa-miR-144*, hsa-miR-452*, hsa-miR-208b | 84.7% | 80.0% | 89.4% |
| SNC-473 | 8, 10, 16 | hsa-miR-28-3p, hsa-miR-145, hsa-miR-664 | 84.7% | 80.0% | 89.4% |
| SNC-474 | 15, 20, 24 | hsa-miR-1180, hsa-miR-183*, hsa-miR-144* | 84.7% | 81.7% | 87.7% |
| SNC-475 | 5, 8 | hsa-miR-106a, hsa-miR-28-3p | 84.6% | 79.9% | 89.4% |
| SNC-476 | 61, 67, 69 | hsa-miR-296-5p, hsa-miR-144, hsa-miR-593* | 84.6% | 75.9% | 93.4% |
| SNC-477 | 23, 24, 27 | hsa-miR-496, hsa-miR-144*, hsa-miR-17* | 84.6% | 75.0% | 94.3% |
| SNC-478 | 53, 69 | hsa-miR-93, hsa-miR-593* | 84.6% | 74.0% | 95.1% |
| SNC-479 | 38, 47, 53 | hsa-miR-146a, hsa-miR-635, hsa-miR-93 | 84.6% | 76.7% | 92.4% |
| SNC-480 | 5, 18, 13 | hsa-miR-106a, hsa-miR-224, hsa-miR-17 | 84.6% | 78.4% | 90.7% |
| SNC-481 | 8, 30, 10 | hsa-miR-28-3p, hsa-miR-106b, hsa-miR-145 | 84.6% | 79.1% | 90.0% |
| SNC-482 | 13, 9, 39 | hsa-miR-17, hsa-miR-208b, hsa-miR-373 | 84.6% | 76.9% | 92.3% |
| SNC-483 | 24, 25, 26 | hsa-miR-144*, hsa-miR-613, hsa-miR-564 | 84.6% | 77.4% | 91.7% |
| SNC-484 | 18, 24 | hsa-miR-224, hsa-miR-144* | 84.5% | 72.1% | 96.9% |
| SNC-485 | 79, 1 | hsa-miR-18a, hsa-miR-1251 | 84.5% | 81.9% | 87.1% |
| SNC-486 | 5, 8, 13 | hsa-miR-106a, hsa-miR-28-3p, hsa-miR-17 | 84.5% | 77.1% | 91.9% |
| SNC-487 | 73, 13, 182 | hsa-miR-216b, hsa-miR-17, hsa-miR-452* | 84.5% | 76.4% | 92.6% |
| SNC-488 | 26, 35, 38 | hsa-miR-564, hsa-miR-197, hsa-miR-146a | 84.5% | 81.1% | 87.9% |
| SNC-489 | 6, 9 | hsa-miR-640, hsa-miR-208b | 84.4% | 80.9% | 88.0% |
| SNC-490 | 87, 101 | hsa-miR-374a, hsa-miR-1908 | 84.4% | 73.1% | 95.7% |

FIG. 2 cont.

| | | | | | |
|---|---|---|---|---|---|
| SNC-491 | 17, 19 | hsa-miR-20a, hsa-miR-523 | 84.4% | 74.6% | 94.3% |
| SNC-492 | 69, 71, 80 | hsa-miR-593*, hsa-miR-216a, hsa-miR-454 | 84.4% | 76.4% | 92.4% |
| SNC-493 | 35, 38, 50 | hsa-miR-197, hsa-miR-146a, hsa-miR-720 | 84.4% | 84.3% | 84.4% |
| SNC-494 | 50, 53, 61 | hsa-miR-720, hsa-miR-93, hsa-miR-296-5p | 84.4% | 82.6% | 86.1% |
| SNC-495 | 39, 16, 8 | hsa-miR-373, hsa-miR-664, hsa-miR-28-3p | 84.4% | 78.7% | 90.0% |
| SNC-496 | 38, 50, 53 | hsa-miR-146a, hsa-miR-720, hsa-miR-93 | 84.3% | 85.3% | 83.3% |
| SNC-497 | 16, 10, 251 | hsa-miR-664, hsa-miR-145, hsa-miR-32 | 84.3% | 79.7% | 88.9% |
| SNC-498 | 8, 11, 16 | hsa-miR-28-3p, hsa-let-7d*, hsa-miR-664 | 84.3% | 81.3% | 87.3% |
| SNC-499 | 16, 18, 20 | hsa-miR-664, hsa-miR-224, hsa-miR-183* | 84.3% | 80.6% | 88.0% |
| SNC-500 | 20, 26, 28 | hsa-miR-183*, hsa-miR-564, hsa-miR-607 | 84.3% | 81.3% | 87.3% |
| SNC-501 | 17, 22 | hsa-miR-20a, hsa-miR-1260 | 84.2% | 74.1% | 94.3% |
| SNC-502 | 46, 5 | hsa-miR-1246, hsa-miR-106a | 84.2% | 78.1% | 90.3% |
| SNC-503 | 45, 50, 53 | hsa-miR-1227, hsa-miR-720, hsa-miR-93 | 84.2% | 82.6% | 85.9% |
| SNC-504 | 69, 46, 73 | hsa-miR-593*, hsa-miR-1246, hsa-miR-216b | 84.2% | 81.3% | 87.1% |
| SNC-505 | 18, 24, 9 | hsa-miR-224, hsa-miR-144*, hsa-miR-208b | 84.2% | 77.9% | 90.6% |
| SNC-506 | 18, 20, 21 | hsa-miR-224, hsa-miR-183*, hsa-miR-499-3p | 84.2% | 79.9% | 88.6% |
| SNC-507 | 13, 9, 16 | hsa-miR-17, hsa-miR-208b, hsa-miR-664 | 84.1% | 76.4% | 91.9% |
| SNC-508 | 24, 182 | hsa-miR-144*, hsa-miR-452* | 84.1% | 76.4% | 91.7% |
| SNC-509 | 21, 69 | hsa-miR-499-3p, hsa-miR-593* | 84.1% | 80.6% | 87.6% |
| SNC-510 | 1, 105, 21 | hsa-miR-1251, hsa-miR-646, hsa-miR-499-3p | 84.1% | 84.3% | 83.9% |
| SNC-511 | 35, 38, 61 | hsa-miR-197, hsa-miR-146a, hsa-miR-296-5p | 84.1% | 78.6% | 89.6% |
| SNC-512 | 6, 8, 9 | hsa-miR-640, hsa-miR-28-3p, hsa-miR-208b | 84.1% | 80.6% | 87.6% |
| SNC-513 | 16, 8, 251 | hsa-miR-664, hsa-miR-28-3p, hsa-miR-32 | 84.1% | 76.6% | 91.6% |
| SNC-514 | 13, 20, 22 | hsa-miR-17, hsa-miR-183*, hsa-miR-1260 | 84.1% | 79.0% | 89.1% |
| SNC-515 | 16, 30, 10 | hsa-miR-664, hsa-miR-106b, hsa-miR-145 | 84.1% | 79.9% | 88.3% |
| SNC-516 | 16, 20, 24 | hsa-miR-664, hsa-miR-183*, hsa-miR-144* | 84.1% | 81.1% | 87.0% |
| SNC-517 | 105, 69 | hsa-miR-646, hsa-miR-593* | 84.0% | 76.4% | 91.6% |
| SNC-518 | 47, 50, 60 | hsa-miR-635, hsa-miR-720, hsa-miR-200a* | 84.0% | 84.4% | 83.6% |
| SNC-519 | 105, 21, 69 | hsa-miR-646, hsa-miR-499-3p, hsa-miR-593* | 84.0% | 78.3% | 89.7% |
| SNC-520 | 39, 5, 18 | hsa-miR-373, hsa-miR-106a, hsa-miR-224 | 84.0% | 78.0% | 90.0% |
| SNC-521 | 9, 39, 16 | hsa-miR-208b, hsa-miR-373, hsa-miR-664 | 84.0% | 79.9% | 88.1% |
| SNC-522 | 38, 47, 50 | hsa-miR-146a, hsa-miR-635, hsa-miR-720 | 83.9% | 87.7% | 80.1% |
| SNC-523 | 14, 16, 18 | hsa-miR-596, hsa-miR-664, hsa-miR-224 | 83.9% | 76.3% | 91.6% |
| SNC-524 | 21, 22, 24 | hsa-miR-499-3p, hsa-miR-1260, hsa-miR-144* | 83.9% | 73.1% | 94.7% |
| SNC-525 | 24, 38 | hsa-miR-144*, hsa-miR-146a | 83.8% | 78.9% | 88.7% |
| SNC-526 | 35, 38, 53 | hsa-miR-197, hsa-miR-146a, hsa-miR-93 | 83.8% | 79.6% | 88.0% |
| SNC-527 | 35, 38 | hsa-miR-197, hsa-miR-146a | 83.7% | 82.1% | 85.3% |
| SNC-528 | 69, 46, 39 | hsa-miR-593*, hsa-miR-1246, hsa-miR-373 | 83.7% | 74.7% | 92.7% |
| SNC-529 | 73, 24, 182 | hsa-miR-216b, hsa-miR-144*, hsa-miR-452* | 83.7% | 77.6% | 89.9% |
| SNC-530 | 9, 39, 8 | hsa-miR-208b, hsa-miR-373, hsa-miR-28-3p | 83.7% | 77.4% | 90.0% |
| SNC-531 | 38, 50, 67 | hsa-miR-146a, hsa-miR-720, hsa-miR-144 | 83.6% | 83.7% | 83.6% |
| SNC-532 | 47, 53, 57 | hsa-miR-635, hsa-miR-93, hsa-miR-1225-5p | 83.6% | 77.1% | 90.1% |
| SNC-533 | 13, 182, 16 | hsa-miR-17, hsa-miR-452*, hsa-miR-664 | 83.6% | 71.9% | 95.4% |
| SNC-534 | 79, 83, 87 | hsa-miR-18a, hsa-miR-483-5p, hsa-miR-374a | 83.6% | 77.6% | 89.7% |
| SNC-535 | 35, 50, 61 | hsa-miR-197, hsa-miR-720, hsa-miR-296-5p | 83.6% | 88.1% | 79.0% |
| SNC-536 | 53, 69, 71 | hsa-miR-93, hsa-miR-593*, hsa-miR-216a | 83.6% | 71.3% | 95.9% |

FIG. 2 cont.

| | | | | | |
|---|---|---|---|---|---|
| SNC-537 | 18, 182, 9 | hsa-miR-224, hsa-miR-452*, hsa-miR-208b | 83.6% | 79.3% | 87.9% |
| SNC-538 | 39, 18, 24 | hsa-miR-373, hsa-miR-224, hsa-miR-144* | 83.6% | 76.6% | 90.6% |
| SNC-539 | 38, 50, 61 | hsa-miR-146a, hsa-miR-720, hsa-miR-296-5p | 83.5% | 77.0% | 90.0% |
| SNC-540 | 105, 69, 46 | hsa-miR-646, hsa-miR-593*, hsa-miR-1246 | 83.5% | 74.1% | 92.9% |
| SNC-541 | 18, 19, 20 | hsa-miR-224, hsa-miR-523, hsa-miR-183* | 83.5% | 81.0% | 86.0% |
| SNC-542 | 24, 25, 27 | hsa-miR-144*, hsa-miR-613, hsa-miR-17* | 83.5% | 74.7% | 92.3% |
| SNC-543 | 26, 35 | hsa-miR-564, hsa-miR-197 | 83.4% | 83.6% | 83.3% |
| SNC-544 | 50, 53, 67 | hsa-miR-720, hsa-miR-93, hsa-miR-144 | 83.4% | 84.0% | 82.9% |
| SNC-545 | 19, 21, 23 | hsa-miR-523, hsa-miR-499-3p, hsa-miR-496 | 83.4% | 81.9% | 85.0% |
| SNC-546 | 3, 21 | hsa-miR-19b, hsa-miR-499-3p | 83.4% | 77.0% | 89.7% |
| SNC-547 | 35, 53, 61 | hsa-miR-197, hsa-miR-93, hsa-miR-296-5p | 83.4% | 83.0% | 83.7% |
| SNC-548 | 50, 61, 67 | hsa-miR-720, hsa-miR-296-5p, hsa-miR-144 | 83.4% | 83.7% | 83.0% |
| SNC-549 | 69, 80, 83 | hsa-miR-593*, hsa-miR-454, hsa-miR-483-5p | 83.4% | 75.3% | 91.4% |
| SNC-550 | 20, 21, 22 | hsa-miR-183*, hsa-miR-499-3p, hsa-miR-1260 | 83.4% | 75.9% | 90.9% |
| SNC-551 | 13, 9 | hsa-miR-17, hsa-miR-208b | 83.3% | 72.4% | 94.1% |
| SNC-552 | 4, 39 | hsa-miR-361-5p, hsa-miR-373 | 83.3% | 74.9% | 91.7% |
| SNC-553 | 50, 61, 69 | hsa-miR-720, hsa-miR-296-5p, hsa-miR-593* | 83.3% | 80.3% | 86.3% |
| SNC-554 | 1, 3, 21 | hsa-miR-1251, hsa-miR-19b, hsa-miR-499-3p | 83.3% | 80.9% | 85.7% |
| SNC-555 | 46, 5, 18 | hsa-miR-1246, hsa-miR-106a, hsa-miR-224 | 83.3% | 76.6% | 90.0% |
| SNC-556 | 26, 28, 33 | hsa-miR-564, hsa-miR-607, hsa-miR-183 | 83.3% | 83.1% | 83.4% |
| SNC-557 | 16, 19, 20 | hsa-miR-664, hsa-miR-523, hsa-miR-183* | 83.2% | 81.1% | 85.3% |
| SNC-558 | 22, 24, 28 | hsa-miR-1260, hsa-miR-144*, hsa-miR-607 | 83.2% | 75.3% | 91.1% |
| SNC-559 | 5, 18 | hsa-miR-106a, hsa-miR-224 | 83.1% | 78.1% | 88.0% |
| SNC-560 | 21, 24 | hsa-miR-499-3p, hsa-miR-144* | 83.1% | 71.4% | 94.7% |
| SNC-561 | 10, 16, 20 | hsa-miR-145, hsa-miR-664, hsa-miR-183* | 83.1% | 79.4% | 86.7% |
| SNC-562 | 13, 14 | hsa-miR-17, hsa-miR-596 | 83.0% | 77.1% | 88.9% |
| SNC-563 | 1, 3 | hsa-miR-1251, hsa-miR-19b | 83.0% | 84.1% | 81.9% |
| SNC-564 | 73, 13 | hsa-miR-216b, hsa-miR-17 | 83.0% | 76.0% | 90.0% |
| SNC-565 | 24, 35, 50 | hsa-miR-144*, hsa-miR-197, hsa-miR-720 | 83.0% | 81.1% | 84.9% |
| SNC-566 | 15, 22, 24 | hsa-miR-1180, hsa-miR-1260, hsa-miR-144* | 83.0% | 74.1% | 91.9% |
| SNC-567 | 47, 50 | hsa-miR-635, hsa-miR-720 | 82.9% | 85.4% | 80.4% |
| SNC-568 | 45, 47, 53 | hsa-miR-1227, hsa-miR-635, hsa-miR-93 | 82.9% | 76.3% | 89.6% |
| SNC-569 | 8, 13, 16 | hsa-miR-28-3p, hsa-miR-17, hsa-miR-664 | 82.9% | 73.3% | 92.6% |
| SNC-570 | 19, 20, 23 | hsa-miR-523, hsa-miR-183*, hsa-miR-496 | 82.9% | 83.9% | 82.0% |
| SNC-571 | 20, 22, 24 | hsa-miR-183*, hsa-miR-1260, hsa-miR-144* | 82.9% | 78.0% | 87.9% |
| SNC-572 | 20, 24 | hsa-miR-183*, hsa-miR-144* | 82.9% | 78.6% | 87.1% |
| SNC-573 | 35, 50 | hsa-miR-197, hsa-miR-720 | 82.9% | 87.1% | 78.6% |
| SNC-574 | 21, 69, 46 | hsa-miR-499-3p, hsa-miR-593*, hsa-miR-1246 | 82.9% | 78.1% | 87.6% |
| SNC-575 | 50, 53, 57 | hsa-miR-720, hsa-miR-93, hsa-miR-1225-5p | 82.9% | 81.6% | 84.1% |
| SNC-576 | 4, 46 | hsa-miR-361-5p, hsa-miR-1246 | 82.8% | 78.4% | 87.1% |
| SNC-577 | 47, 50, 57 | hsa-miR-635, hsa-miR-720, hsa-miR-1225-5p | 82.8% | 83.7% | 81.9% |
| SNC-578 | 20, 23, 24 | hsa-miR-183*, hsa-miR-496, hsa-miR-144* | 82.8% | 77.3% | 88.3% |
| SNC-579 | 23, 24 | hsa-miR-496, hsa-miR-144* | 82.7% | 75.0% | 90.4% |
| SNC-580 | 69, 79, 83 | hsa-miR-593*, hsa-miR-18a, hsa-miR-483-5p | 82.7% | 72.3% | 93.1% |
| SNC-581 | 20, 22, 26 | hsa-miR-183*, hsa-miR-1260, hsa-miR-564 | 82.7% | 76.0% | 89.4% |
| SNC-582 | 69, 46 | hsa-miR-593*, hsa-miR-1246 | 82.6% | 76.7% | 88.6% |

FIG. 2 cont.

| SNC-583 | 20, 21 | hsa-miR-183*, hsa-miR-499-3p | 82.6% | 76.9% | 88.4% |
|---|---|---|---|---|---|
| SNC-584 | 182, 9, 8 | hsa-miR-452*, hsa-miR-208b, hsa-miR-28-3p | 82.6% | 79.6% | 85.7% |
| SNC-585 | 2, 3 | hsa-miR-151-3p, hsa-miR-19b | 82.6% | 81.4% | 83.7% |
| SNC-586 | 35, 38, 47 | hsa-miR-197, hsa-miR-146a, hsa-miR-635 | 82.6% | 77.7% | 87.4% |
| SNC-587 | 9, 30, 170 | hsa-miR-208b, hsa-miR-106b, hsa-miR-1226* | 82.6% | 76.0% | 89.1% |
| SNC-588 | 35, 53 | hsa-miR-197, hsa-miR-93 | 82.5% | 83.0% | 82.0% |
| SNC-589 | 39, 73, 24 | hsa-miR-373, hsa-miR-216b, hsa-miR-144* | 82.5% | 80.9% | 84.1% |
| SNC-590 | 13, 16, 20 | hsa-miR-17, hsa-miR-664, hsa-miR-183* | 82.5% | 79.6% | 85.4% |
| SNC-591 | 46, 4, 39 | hsa-miR-1246, hsa-miR-361-5p, hsa-miR-373 | 82.5% | 78.6% | 86.4% |
| SNC-592 | 69, 71 | hsa-miR-593*, hsa-miR-216a | 82.4% | 71.0% | 93.9% |
| SNC-593 | 79, 105 | hsa-miR-18a, hsa-miR-646 | 82.4% | 70.7% | 94.1% |
| SNC-594 | 10, 16 | hsa-miR-145, hsa-miR-664 | 82.4% | 78.7% | 86.1% |
| SNC-595 | 22, 33 | hsa-miR-1260, hsa-miR-183 | 82.4% | 74.9% | 90.0% |
| SNC-596 | 67, 79, 80 | hsa-miR-144, hsa-miR-18a, hsa-miR-454 | 82.4% | 69.1% | 95.7% |
| SNC-597 | 19, 20, 22 | hsa-miR-523, hsa-miR-183*, hsa-miR-1260 | 82.4% | 78.6% | 86.3% |
| SNC-598 | 53, 67, 71 | hsa-miR-93, hsa-miR-144, hsa-miR-216a | 82.4% | 70.0% | 94.7% |
| SNC-599 | 47, 53, 60 | hsa-miR-635, hsa-miR-93, hsa-miR-200a* | 82.3% | 73.3% | 91.3% |
| SNC-600 | 18, 19, 21 | hsa-miR-224, hsa-miR-523, hsa-miR-499-3p | 82.3% | 79.0% | 85.6% |
| SNC-601 | 46, 73, 18 | hsa-miR-1246, hsa-miR-216b, hsa-miR-224 | 82.2% | 79.6% | 84.9% |
| SNC-602 | 80, 84, 91 | hsa-miR-454, hsa-miR-130b, hsa-miR-621 | 82.2% | 69.6% | 94.9% |
| SNC-603 | 21, 23, 24 | hsa-miR-499-3p, hsa-miR-496, hsa-miR-144* | 82.2% | 72.6% | 91.9% |
| SNC-604 | 38, 53, 61 | hsa-miR-146a, hsa-miR-93, hsa-miR-296-5p | 82.1% | 73.6% | 90.7% |
| SNC-605 | 20, 22, 35 | hsa-miR-183*, hsa-miR-1260, hsa-miR-197 | 82.1% | 76.3% | 88.0% |
| SNC-606 | 30, 251 | hsa-miR-106b, hsa-miR-32 | 82.1% | 71.3% | 92.9% |
| SNC-607 | 13, 16 | hsa-miR-17, hsa-miR-664 | 82.1% | 73.7% | 90.4% |
| SNC-608 | 38, 45, 50 | hsa-miR-146a, hsa-miR-1227, hsa-miR-720 | 82.1% | 80.7% | 83.4% |
| SNC-609 | 53, 61, 67 | hsa-miR-93, hsa-miR-296-5p, hsa-miR-144 | 82.1% | 77.7% | 86.4% |
| SNC-610 | 26, 28, 38 | hsa-miR-564, hsa-miR-607, hsa-miR-146a | 82.1% | 78.0% | 86.1% |
| SNC-611 | 9, 8 | hsa-miR-208b, hsa-miR-28-3p | 82.0% | 79.4% | 84.6% |
| SNC-612 | 73, 24 | hsa-miR-216b, hsa-miR-144* | 81.9% | 75.9% | 88.0% |
| SNC-613 | 15, 16, 19 | hsa-miR-1180, hsa-miR-664, hsa-miR-523 | 81.9% | 71.7% | 92.1% |
| SNC-614 | 47, 50, 53 | hsa-miR-635, hsa-miR-720, hsa-miR-93 | 81.9% | 82.3% | 81.4% |
| SNC-615 | 20, 21, 23 | hsa-miR-183*, hsa-miR-499-3p, hsa-miR-496 | 81.9% | 76.4% | 87.3% |
| SNC-616 | 50, 57 | hsa-miR-720, hsa-miR-1225-5p | 81.8% | 81.7% | 81.9% |
| SNC-617 | 26, 27 | hsa-miR-564, hsa-miR-17* | 81.8% | 71.0% | 92.6% |
| SNC-618 | 2, 79, 59 | hsa-miR-151-3p, hsa-miR-18a, hsa-miR-658 | 81.8% | 77.7% | 85.9% |
| SNC-619 | 30, 10 | hsa-miR-106b, hsa-miR-145 | 81.7% | 77.6% | 85.9% |
| SNC-620 | 22, 23, 24 | hsa-miR-1260, hsa-miR-496, hsa-miR-144* | 81.7% | 70.9% | 92.6% |
| SNC-621 | 38, 45, 53 | hsa-miR-146a, hsa-miR-1227, hsa-miR-93 | 81.6% | 74.6% | 88.7% |
| SNC-622 | 19, 21 | hsa-miR-523, hsa-miR-499-3p | 81.6% | 81.9% | 81.3% |
| SNC-623 | 38, 53 | hsa-miR-146a, hsa-miR-93 | 81.6% | 71.4% | 91.7% |
| SNC-624 | 38, 50 | hsa-miR-146a, hsa-miR-720 | 81.5% | 81.7% | 81.3% |
| SNC-625 | 45, 50 | hsa-miR-1227, hsa-miR-720 | 81.5% | 82.1% | 80.9% |
| SNC-626 | 46, 73, 24 | hsa-miR-1246, hsa-miR-216b, hsa-miR-144* | 81.5% | 77.1% | 85.9% |
| SNC-627 | 24, 182, 39 | hsa-miR-144*, hsa-miR-452*, hsa-miR-373 | 81.5% | 78.1% | 84.9% |
| SNC-628 | 83, 84, 101 | hsa-miR-483-5p, hsa-miR-130b, hsa-miR-1908 | 81.5% | 84.6% | 78.4% |

FIG. 2 cont.

| | | | | | |
|---|---|---|---|---|---|
| SNC-629 | 14, 15, 18 | hsa-miR-596, hsa-miR-1180, hsa-miR-224 | 81.5% | 77.4% | 85.6% |
| SNC-630 | 9, 16, 30 | hsa-miR-208b, hsa-miR-664, hsa-miR-106b | 81.5% | 76.6% | 86.4% |
| SNC-631 | 26, 33 | hsa-miR-564, hsa-miR-183 | 81.4% | 78.9% | 84.0% |
| SNC-632 | 35, 50, 53 | hsa-miR-197, hsa-miR-720, hsa-miR-93 | 81.4% | 85.1% | 77.7% |
| SNC-633 | 182, 9, 16 | hsa-miR-452*, hsa-miR-208b, hsa-miR-664 | 81.4% | 77.7% | 85.1% |
| SNC-634 | 39, 8, 30 | hsa-miR-373, hsa-miR-28-3p, hsa-miR-106b | 81.4% | 77.9% | 85.0% |
| SNC-635 | 22, 33, 38 | hsa-miR-1260, hsa-miR-183, hsa-miR-146a | 81.4% | 75.4% | 87.4% |
| SNC-636 | 105, 21 | hsa-miR-646, hsa-miR-499-3p | 81.4% | 71.0% | 91.7% |
| SNC-637 | 24, 9 | hsa-miR-144*, hsa-miR-208b | 81.4% | 79.1% | 83.6% |
| SNC-638 | 19, 20 | hsa-miR-523, hsa-miR-183* | 81.4% | 80.7% | 82.0% |
| SNC-639 | 16, 30, 251 | hsa-miR-664, hsa-miR-106b, hsa-miR-32 | 81.4% | 74.3% | 88.4% |
| SNC-640 | 9, 30 | hsa-miR-208b, hsa-miR-106b | 81.2% | 79.7% | 82.7% |
| SNC-641 | 59, 105, 21 | hsa-miR-658, hsa-miR-646, hsa-miR-499-3p | 81.2% | 74.3% | 88.1% |
| SNC-642 | 79, 80, 84 | hsa-miR-18a, hsa-miR-454, hsa-miR-130b | 81.2% | 70.0% | 92.4% |
| SNC-643 | 18, 20, 22 | hsa-miR-224, hsa-miR-183*, hsa-miR-1260 | 81.1% | 77.7% | 84.6% |
| SNC-644 | 47, 53 | hsa-miR-635, hsa-miR-93 | 81.1% | 73.6% | 88.6% |
| SNC-645 | 61, 69 | hsa-miR-296-5p, hsa-miR-593* | 81.1% | 73.9% | 88.3% |
| SNC-646 | 79, 59 | hsa-miR-18a, hsa-miR-658 | 81.1% | 76.1% | 86.0% |
| SNC-647 | 20, 22 | hsa-miR-183*, hsa-miR-1260 | 81.0% | 75.9% | 86.1% |
| SNC-648 | 50, 53 | hsa-miR-720, hsa-miR-93 | 80.9% | 81.7% | 80.0% |
| SNC-649 | 30, 170 | hsa-miR-106b, hsa-miR-1226* | 80.9% | 68.1% | 93.6% |
| SNC-650 | 59, 3 | hsa-miR-658, hsa-miR-19b | 80.9% | 74.7% | 87.0% |
| SNC-651 | 24, 25 | hsa-miR-144*, hsa-miR-613 | 80.8% | 72.3% | 89.3% |
| SNC-652 | 33, 45, 47 | hsa-miR-183, hsa-miR-1227, hsa-miR-635 | 80.7% | 78.4% | 83.0% |
| SNC-653 | 45, 50, 57 | hsa-miR-1227, hsa-miR-720, hsa-miR-1225-5p | 80.7% | 81.6% | 79.9% |
| SNC-654 | 20, 22, 28 | hsa-miR-183*, hsa-miR-1260, hsa-miR-607 | 80.7% | 79.9% | 81.6% |
| SNC-655 | 50, 61 | hsa-miR-720, hsa-miR-296-5p | 80.6% | 78.7% | 82.6% |
| SNC-656 | 39, 16, 30 | hsa-miR-373, hsa-miR-664, hsa-miR-106b | 80.6% | 71.1% | 90.1% |
| SNC-657 | 67, 79 | hsa-miR-144, hsa-miR-18a | 80.6% | 68.0% | 93.1% |
| SNC-658 | 73, 18, 182 | hsa-miR-216b, hsa-miR-224, hsa-miR-452* | 80.5% | 70.6% | 90.4% |
| SNC-659 | 16, 18, 19 | hsa-miR-664, hsa-miR-224, hsa-miR-523 | 80.4% | 71.4% | 89.4% |
| SNC-660 | 47, 57 | hsa-miR-635, hsa-miR-1225-5p | 80.4% | 76.4% | 84.3% |
| SNC-661 | 16, 20 | hsa-miR-664, hsa-miR-183* | 80.4% | 81.4% | 79.3% |
| SNC-662 | 50, 53, 60 | hsa-miR-720, hsa-miR-93, hsa-miR-200a* | 80.4% | 80.9% | 79.9% |
| SNC-663 | 50, 57, 61 | hsa-miR-720, hsa-miR-1225-5p, hsa-miR-296-5p | 80.4% | 77.1% | 83.6% |
| SNC-664 | 182, 39, 8 | hsa-miR-452*, hsa-miR-373, hsa-miR-28-3p | 80.4% | 74.6% | 86.1% |
| SNC-665 | 182, 9 | hsa-miR-452*, hsa-miR-208b | 80.3% | 78.1% | 82.4% |
| SNC-666 | 21, 24, 25 | hsa-miR-499-3p, hsa-miR-144*, hsa-miR-613 | 80.2% | 72.6% | 87.9% |
| SNC-667 | 22, 24, 25 | hsa-miR-1260, hsa-miR-144*, hsa-miR-613 | 80.2% | 73.1% | 87.3% |
| SNC-668 | 20, 22, 33 | hsa-miR-183*, hsa-miR-1260, hsa-miR-183 | 80.2% | 74.3% | 86.1% |
| SNC-669 | 50, 57, 60 | hsa-miR-720, hsa-miR-1225-5p, hsa-miR-200a* | 80.1% | 80.6% | 79.7% |
| SNC-670 | 53, 61, 71 | hsa-miR-93, hsa-miR-296-5p, hsa-miR-216a | 80.1% | 76.3% | 84.0% |
| SNC-671 | 71, 79, 80 | hsa-miR-216a, hsa-miR-18a, hsa-miR-454 | 80.1% | 65.4% | 94.9% |
| SNC-672 | 84, 87, 101 | hsa-miR-130b, hsa-miR-374a, hsa-miR-1908 | 80.0% | 73.6% | 86.4% |
| SNC-673 | 182, 9, 39 | hsa-miR-452*, hsa-miR-208b, hsa-miR-373 | 79.9% | 77.1% | 82.7% |
| SNC-674 | 53, 57, 61 | hsa-miR-93, hsa-miR-1225-5p, hsa-miR-296-5p | 79.9% | 72.3% | 87.4% |

FIG. 2 cont.

| | | | | | |
|---|---|---|---|---|---|
| SNC-675 | 53, 61, 65 | hsa-miR-93, hsa-miR-296-5p, hsa-miR-328 | 79.9% | 76.3% | 83.4% |
| SNC-676 | 18, 182 | hsa-miR-224, hsa-miR-452* | 79.8% | 66.4% | 93.1% |
| SNC-677 | 14, 15 | hsa-miR-596, hsa-miR-1180 | 79.8% | 78.7% | 80.9% |
| SNC-678 | 61, 67, 79 | hsa-miR-296-5p, hsa-miR-144, hsa-miR-18a | 79.8% | 72.0% | 87.6% |
| SNC-679 | 182, 9, 30 | hsa-miR-452*, hsa-miR-208b, hsa-miR-106b | 79.8% | 74.1% | 85.4% |
| SNC-680 | 35, 47 | hsa-miR-197, hsa-miR-635 | 79.7% | 76.4% | 83.0% |
| SNC-681 | 61, 71, 79 | hsa-miR-296-5p, hsa-miR-216a, hsa-miR-18a | 79.7% | 71.4% | 88.0% |
| SNC-682 | 23, 24, 25 | hsa-miR-496, hsa-miR-144*, hsa-miR-613 | 79.7% | 71.4% | 88.0% |
| SNC-683 | 16, 18 | hsa-miR-664, hsa-miR-224 | 79.6% | 71.3% | 88.0% |
| SNC-684 | 18, 20 | hsa-miR-224, hsa-miR-183* | 79.6% | 80.9% | 78.4% |
| SNC-685 | 39, 16 | hsa-miR-373, hsa-miR-664 | 79.6% | 69.0% | 90.3% |
| SNC-686 | 9, 39, 30 | hsa-miR-208b, hsa-miR-373, hsa-miR-106b | 79.6% | 75.6% | 83.7% |
| SNC-687 | 79, 84 | hsa-miR-18a, hsa-miR-130b | 79.6% | 67.0% | 92.1% |
| SNC-688 | 15, 18 | hsa-miR-1180, hsa-miR-224 | 79.6% | 74.1% | 85.0% |
| SNC-689 | 61, 69, 71 | hsa-miR-296-5p, hsa-miR-593*, hsa-miR-216a | 79.6% | 67.4% | 91.7% |
| SNC-690 | 16, 20, 22 | hsa-miR-664, hsa-miR-183*, hsa-miR-1260 | 79.6% | 74.6% | 84.6% |
| SNC-691 | 26, 27, 28 | hsa-miR-564, hsa-miR-17*, hsa-miR-607 | 79.6% | 76.3% | 82.9% |
| SNC-692 | 57, 65 | hsa-miR-1225-5p, hsa-miR-328 | 79.5% | 85.7% | 73.3% |
| SNC-693 | 67, 71, 79 | hsa-miR-144, hsa-miR-216a, hsa-miR-18a | 79.5% | 65.4% | 93.6% |
| SNC-694 | 13, 16, 22 | hsa-miR-17, hsa-miR-664, hsa-miR-1260 | 79.5% | 68.3% | 90.7% |
| SNC-695 | 20, 22, 23 | hsa-miR-183*, hsa-miR-1260, hsa-miR-496 | 79.5% | 76.1% | 82.9% |
| SNC-696 | 28, 38, 45 | hsa-miR-607, hsa-miR-146a, hsa-miR-1227 | 79.4% | 82.1% | 76.7% |
| SNC-697 | 71, 79 | hsa-miR-216a, hsa-miR-18a | 79.3% | 63.4% | 95.1% |
| SNC-698 | 20, 23 | hsa-miR-183*, hsa-miR-496 | 79.3% | 80.4% | 78.1% |
| SNC-699 | 50, 67 | hsa-miR-720, hsa-miR-144 | 79.2% | 80.6% | 77.9% |
| SNC-700 | 33, 45 | hsa-miR-183, hsa-miR-1227 | 79.2% | 79.7% | 78.7% |
| SNC-701 | 182, 39, 16 | hsa-miR-452*, hsa-miR-373, hsa-miR-664 | 79.2% | 69.9% | 88.6% |
| SNC-702 | 39, 8 | hsa-miR-373, hsa-miR-28-3p | 79.1% | 77.3% | 81.0% |
| SNC-703 | 53, 67 | hsa-miR-93, hsa-miR-144 | 79.1% | 67.9% | 90.3% |
| SNC-704 | 15, 16, 18 | hsa-miR-1180, hsa-miR-664, hsa-miR-224 | 79.1% | 73.9% | 84.3% |
| SNC-705 | 9, 16 | hsa-miR-208b, hsa-miR-664 | 79.0% | 78.0% | 80.0% |
| SNC-706 | 53, 57, 65 | hsa-miR-93, hsa-miR-1225-5p, hsa-miR-328 | 78.9% | 80.9% | 77.0% |
| SNC-707 | 53, 61 | hsa-miR-93, hsa-miR-296-5p | 78.9% | 75.1% | 82.6% |
| SNC-708 | 15, 18, 19 | hsa-miR-1180, hsa-miR-224, hsa-miR-523 | 78.9% | 71.6% | 86.1% |
| SNC-709 | 105, 21, 46 | hsa-miR-646, hsa-miR-499-3p, hsa-miR-1246 | 78.7% | 69.4% | 88.0% |
| SNC-710 | 9, 16, 8 | hsa-miR-208b, hsa-miR-664, hsa-miR-28-3p | 78.7% | 77.6% | 79.9% |
| SNC-711 | 45, 53, 57 | hsa-miR-1227, hsa-miR-93, hsa-miR-1225-5p | 78.6% | 78.6% | 78.6% |
| SNC-712 | 50, 60, 61 | hsa-miR-720, hsa-miR-200a*, hsa-miR-296-5p | 78.5% | 76.7% | 80.3% |
| SNC-713 | 80, 83, 87 | hsa-miR-454, hsa-miR-483-5p, hsa-miR-374a | 78.5% | 69.4% | 87.6% |
| SNC-714 | 16, 15, 20 | hsa-miR-664, hsa-miR-1180, hsa-miR-183* | 78.4% | 75.3% | 81.6% |
| SNC-715 | 84, 91 | hsa-miR-130b, hsa-miR-621 | 78.4% | 69.7% | 87.0% |
| SNC-716 | 28, 33, 45 | hsa-miR-607, hsa-miR-183, hsa-miR-1227 | 78.4% | 81.7% | 75.0% |
| SNC-717 | 182, 16, 30 | hsa-miR-452*, hsa-miR-664, hsa-miR-106b | 78.4% | 64.7% | 92.0% |
| SNC-718 | 53, 60, 61 | hsa-miR-93, hsa-miR-200a*, hsa-miR-296-5p | 78.3% | 76.0% | 80.6% |
| SNC-719 | 33, 38, 47 | hsa-miR-183, hsa-miR-146a, hsa-miR-635 | 78.2% | 74.1% | 82.3% |
| SNC-720 | 79, 80 | hsa-miR-18a, hsa-miR-454 | 78.1% | 66.3% | 90.0% |

FIG. 2 cont.

| | | | | | |
|---|---|---|---|---|---|
| SNC-721 | 45, 47, 57 | hsa-miR-1227, hsa-miR-635, hsa-miR-1225-5p | 78.1% | 79.6% | 76.6% |
| SNC-722 | 27, 28 | hsa-miR-17*, hsa-miR-607 | 78.0% | 79.4% | 76.6% |
| SNC-723 | 28, 38 | hsa-miR-607, hsa-miR-146a | 78.0% | 75.0% | 81.0% |
| SNC-724 | 28, 33, 38 | hsa-miR-607, hsa-miR-183, hsa-miR-146a | 78.0% | 76.7% | 79.3% |
| SNC-725 | 80, 83, 91 | hsa-miR-454, hsa-miR-483-5p, hsa-miR-621 | 77.9% | 69.7% | 86.1% |
| SNC-726 | 16, 19 | hsa-miR-664, hsa-miR-523 | 77.9% | 70.9% | 84.9% |
| SNC-727 | 26, 28 | hsa-miR-564, hsa-miR-607 | 77.8% | 77.4% | 78.1% |
| SNC-728 | 19, 21, 22 | hsa-miR-523, hsa-miR-499-3p, hsa-miR-1260 | 77.8% | 75.7% | 79.9% |
| SNC-729 | 39, 30 | hsa-miR-373, hsa-miR-106b | 77.6% | 67.4% | 87.9% |
| SNC-730 | 73, 18 | hsa-miR-216b, hsa-miR-224 | 77.6% | 77.7% | 77.6% |
| SNC-731 | 19, 22, 23 | hsa-miR-523, hsa-miR-1260, hsa-miR-496 | 77.6% | 71.3% | 84.0% |
| SNC-732 | 53, 57, 60 | hsa-miR-93, hsa-miR-1225-5p, hsa-miR-200a* | 77.6% | 73.7% | 81.4% |
| SNC-733 | 45, 53 | hsa-miR-1227, hsa-miR-93 | 77.5% | 72.7% | 82.3% |
| SNC-734 | 71, 79, 84 | hsa-miR-216a, hsa-miR-18a, hsa-miR-130b | 77.4% | 65.4% | 89.4% |
| SNC-735 | 22, 28, 33 | hsa-miR-1260, hsa-miR-607, hsa-miR-183 | 77.4% | 75.6% | 79.3% |
| SNC-736 | 38, 47 | hsa-miR-146a, hsa-miR-635 | 77.4% | 68.4% | 86.3% |
| SNC-737 | 69, 71, 83 | hsa-miR-593*, hsa-miR-216a, hsa-miR-483-5p | 77.4% | 65.9% | 88.9% |
| SNC-738 | 26, 33, 38 | hsa-miR-564, hsa-miR-183, hsa-miR-146a | 77.4% | 74.1% | 80.6% |
| SNC-739 | 33, 38, 45 | hsa-miR-183, hsa-miR-146a, hsa-miR-1227 | 77.3% | 77.6% | 77.0% |
| SNC-740 | 16, 22 | hsa-miR-664, hsa-miR-1260 | 77.2% | 69.3% | 85.1% |
| SNC-741 | 20, 33 | hsa-miR-183*, hsa-miR-183 | 77.2% | 71.3% | 83.1% |
| SNC-742 | 15, 20 | hsa-miR-1180, hsa-miR-183* | 77.1% | 72.4% | 81.9% |
| SNC-743 | 47, 57, 60 | hsa-miR-635, hsa-miR-1225-5p, hsa-miR-200a* | 77.1% | 74.3% | 80.0% |
| SNC-744 | 9, 39 | hsa-miR-208b, hsa-miR-373 | 77.1% | 73.4% | 80.7% |
| SNC-745 | 25, 26, 28 | hsa-miR-613, hsa-miR-564, hsa-miR-607 | 77.1% | 73.6% | 80.6% |
| SNC-746 | 16, 8 | hsa-miR-664, hsa-miR-28-3p | 77.0% | 68.7% | 85.3% |
| SNC-747 | 16, 15 | hsa-miR-664, hsa-miR-1180 | 77.0% | 70.9% | 83.1% |
| SNC-748 | 21, 46, 39 | hsa-miR-499-3p, hsa-miR-1246, hsa-miR-373 | 77.0% | 75.1% | 78.9% |
| SNC-749 | 18, 19, 22 | hsa-miR-224, hsa-miR-523, hsa-miR-1260 | 77.0% | 67.4% | 86.6% |
| SNC-750 | 182, 39 | hsa-miR-452*, hsa-miR-373 | 76.9% | 72.9% | 81.0% |
| SNC-751 | 21, 46 | hsa-miR-499-3p, hsa-miR-1246 | 76.9% | 69.6% | 84.3% |
| SNC-752 | 23, 26, 27 | hsa-miR-496, hsa-miR-564, hsa-miR-17* | 76.9% | 68.9% | 85.0% |
| SNC-753 | 25, 26, 27 | hsa-miR-613, hsa-miR-564, hsa-miR-17* | 76.9% | 70.9% | 83.0% |
| SNC-754 | 18, 19 | hsa-miR-224, hsa-miR-523 | 76.9% | 69.3% | 84.4% |
| SNC-755 | 46, 18 | hsa-miR-1246, hsa-miR-224 | 76.8% | 70.6% | 83.0% |
| SNC-756 | 50, 60 | hsa-miR-720, hsa-miR-200a* | 76.7% | 77.7% | 75.7% |
| SNC-757 | 53, 57 | hsa-miR-93, hsa-miR-1225-5p | 76.7% | 71.0% | 82.4% |
| SNC-758 | 38, 45 | hsa-miR-146a, hsa-miR-1227 | 76.7% | 75.0% | 78.4% |
| SNC-759 | 21, 23, 25 | hsa-miR-499-3p, hsa-miR-496, hsa-miR-613 | 76.7% | 69.3% | 84.1% |
| SNC-760 | 23, 25, 26 | hsa-miR-496, hsa-miR-613, hsa-miR-564 | 76.7% | 70.3% | 83.1% |
| SNC-761 | 182, 8, 30 | hsa-miR-452*, hsa-miR-28-3p, hsa-miR-106b | 76.6% | 66.1% | 87.1% |
| SNC-762 | 22, 35 | hsa-miR-1260, hsa-miR-197 | 76.5% | 75.3% | 77.7% |
| SNC-763 | 60, 65 | hsa-miR-200a*, hsa-miR-328 | 76.4% | 82.3% | 70.6% |
| SNC-764 | 83, 87 | hsa-miR-483-5p, hsa-miR-374a | 76.4% | 71.7% | 81.1% |
| SNC-765 | 182, 16 | hsa-miR-452*, hsa-miR-664 | 76.4% | 65.7% | 87.1% |
| SNC-766 | 53, 60, 65 | hsa-miR-93, hsa-miR-200a*, hsa-miR-328 | 76.4% | 77.9% | 75.0% |

FIG. 2 cont.

| | | | | | |
|---|---|---|---|---|---|
| SNC-767 | 15, 20, 22 | hsa-miR-1180, hsa-miR-183*, hsa-miR-1260 | 76.4% | 73.0% | 79.9% |
| SNC-768 | 84, 101 | hsa-miR-130b, hsa-miR-1908 | 76.4% | 73.1% | 79.6% |
| SNC-769 | 182, 8 | hsa-miR-452*, hsa-miR-28-3p | 76.4% | 69.4% | 83.3% |
| SNC-770 | 38, 45, 47 | hsa-miR-146a, hsa-miR-1227, hsa-miR-635 | 76.4% | 72.0% | 80.7% |
| SNC-771 | 182, 16, 8 | hsa-miR-452*, hsa-miR-664, hsa-miR-28-3p | 76.4% | 70.7% | 82.0% |
| SNC-772 | 22, 26 | hsa-miR-1260, hsa-miR-564 | 76.3% | 65.4% | 87.1% |
| SNC-773 | 61, 66 | hsa-miR-296-5p, hsa-miR-556-5p | 76.2% | 66.7% | 85.7% |
| SNC-774 | 16, 15, 22 | hsa-miR-664, hsa-miR-1180, hsa-miR-1260 | 76.1% | 67.3% | 85.0% |
| SNC-775 | 57, 65, 66 | hsa-miR-1225-5p, hsa-miR-328, hsa-miR-556-5p | 76.1% | 78.4% | 73.7% |
| SNC-776 | 46, 73 | hsa-miR-1246, hsa-miR-216b | 76.0% | 71.6% | 80.4% |
| SNC-777 | 65, 66 | hsa-miR-328, hsa-miR-556-5p | 76.0% | 78.9% | 73.1% |
| SNC-778 | 60, 65, 66 | hsa-miR-200a*, hsa-miR-328, hsa-miR-556-5p | 76.0% | 77.3% | 74.7% |
| SNC-779 | 28, 33 | hsa-miR-607, hsa-miR-183 | 75.9% | 77.9% | 74.0% |
| SNC-780 | 16, 8, 30 | hsa-miR-664, hsa-miR-28-3p, hsa-miR-106b | 75.9% | 66.3% | 85.6% |
| SNC-781 | 39, 73 | hsa-miR-373, hsa-miR-216b | 75.9% | 72.4% | 79.3% |
| SNC-782 | 23, 26 | hsa-miR-496, hsa-miR-564 | 75.8% | 68.1% | 83.4% |
| SNC-783 | 79, 80, 83 | hsa-miR-18a, hsa-miR-454, hsa-miR-483-5p | 75.8% | 64.1% | 87.4% |
| SNC-784 | 83, 84, 91 | hsa-miR-483-5p, hsa-miR-130b, hsa-miR-621 | 75.7% | 70.0% | 81.4% |
| SNC-785 | 22, 26, 28 | hsa-miR-1260, hsa-miR-564, hsa-miR-607 | 75.7% | 72.7% | 78.7% |
| SNC-786 | 46, 39 | hsa-miR-1246, hsa-miR-373 | 75.6% | 70.4% | 80.9% |
| SNC-787 | 57, 60, 65 | hsa-miR-1225-5p, hsa-miR-200a*, hsa-miR-328 | 75.6% | 78.7% | 72.4% |
| SNC-788 | 16, 30 | hsa-miR-664, hsa-miR-106b | 75.5% | 64.6% | 86.4% |
| SNC-789 | 45, 47 | hsa-miR-1227, hsa-miR-635 | 75.5% | 73.0% | 78.0% |
| SNC-790 | 19, 22 | hsa-miR-523, hsa-miR-1260 | 75.4% | 66.0% | 84.9% |
| SNC-791 | 39, 73, 18 | hsa-miR-373, hsa-miR-216b, hsa-miR-224 | 75.3% | 72.3% | 78.3% |
| SNC-792 | 21, 22, 23 | hsa-miR-499-3p, hsa-miR-1260, hsa-miR-496 | 75.3% | 66.4% | 84.1% |
| SNC-793 | 25, 26 | hsa-miR-613, hsa-miR-564 | 75.2% | 71.4% | 79.0% |
| SNC-794 | 57, 60, 66 | hsa-miR-1225-5p, hsa-miR-200a*, hsa-miR-556-5p | 75.1% | 70.6% | 79.7% |
| SNC-795 | 15, 22 | hsa-miR-1180, hsa-miR-1260 | 75.1% | 71.1% | 79.0% |
| SNC-796 | 80, 87 | hsa-miR-454, hsa-miR-374a | 75.0% | 58.7% | 91.3% |

FIG. 2 cont.

| Figure 5b | | | |
|---|---|---|---|
| Signature | #miRNA | Accuracy | miRNAs |
| SNC-lin1 | 3 | 97.8% | hsa-miR-423-5p, hsa-miR-197, hsa-miR-1247 |
| SNC-lin2 | 4 | 97.5% | hsa-miR-423-5p, hsa-miR-197, hsa-miR-1247, hsa-miR-1294 |
| SNC-lin3 | 5 | 97.5% | hsa-miR-423-5p, hsa-miR-609, hsa-miR-197, hsa-miR-1247, hsa-miR-1294 |
| SNC-lin4 | 7 | 97.3% | hsa-miR-1282, hsa-miR-423-5p, hsa-miR-934, hsa-miR-640, hsa-miR-34a*, hsa-miR-197, hsa-miR-214* |
| SNC-lin5 | 8 | 97.1% | hsa-miR-1282, hsa-miR-574-3p, hsa-miR-423-5p, hsa-miR-609, hsa-miR-197, hsa-miR-1247, hsa-miR-1294, hsa-miR-214*, |
| SNC-lin6 | 9 | 97.0% | hsa-miR-1282, hsa-miR-574-3p, hsa-miR-423-5p, hsa-let-7d*, hsa-miR-934, hsa-miR-609, hsa-miR-34a*, hsa-miR-197 |
| SNC-lin7 | 10 | 97.2% | hsa-miR-485-5p, hsa-miR-1282, hsa-miR-423-5p, hsa-miR-604, hsa-miR-934, hsa-miR-640, hsa-miR-34a*, hsa-miR-1324, hsa-miR-197 |
| SNC-rbf1 | 2 | 97.5% | hsa-miR-197, hsa-miR-1247 |
| SNC-rbf2 | 5 | 98.6% | hsa-miR-1282, hsa-miR-423-5p, hsa-miR-34a*, hsa-miR-520d-3p, hsa-miR-197 |
| SNC-rbf3 | 6 | 98.2% | hsa-miR-1282, hsa-miR-423-5p, hsa-miR-609, hsa-miR-197, hsa-miR-1247, hsa-miR-214* |
| SNC-rbf4 | 7 | 98.1% | hsa-miR-1282, hsa-miR-574-3p, hsa-miR-423-5p, hsa-miR-609, hsa-miR-197, hsa-miR-1247, hsa-miR-214* |
| SNC-rbf5 | 8 | 98.0% | hsa-miR-1282, hsa-miR-423-5p, hsa-miR-604, hsa-miR-934, hsa-miR-640, hsa-miR-34a*, hsa-miR-197, hsa-miR-214*, |
| SNC-rbf6 | 9 | 98.0% | hsa-miR-485-5p, hsa-miR-1282, hsa-miR-423-5p, hsa-miR-604, hsa-miR-934, hsa-miR-640, hsa-miR-34a*, hsa-miR-197 |
| SNC-rbf7 | 10 | 97.9% | hsa-miR-1282, hsa-miR-574-3p, hsa-miR-423-5p, hsa-let-7d*, hsa-miR-609, hsa-miR-34a*, hsa-miR-197, hsa-miR-1247, hsa-miR-1294 |

| Figure 6 | | | | | | | | | |
|---|---|---|---|---|---|---|---|---|---|
| SEQ ID NO | GeneName | median g1 | median g2 | qmedian | ttest rawp | ttest adjp | AUC | limma rawp | limma adjp |
| 35 | hsa-miR-197 | 601 | 2236 | 0.27 | 4.13E-18 | 1.75E-15 | 0.96 | 4.06E-17 | 1.15E-14 |
| 121 | hsa-miR-423-5p | 2711 | 10945 | 0.25 | 3.66E-18 | 1.75E-15 | 0.96 | 6.82E-17 | 1.45E-14 |
| 11 | hsa-let-7d* | 72 | 325 | 0.22 | 1.34E-15 | 3.78E-13 | 0.95 | 1.68E-17 | 7.14E-15 |
| 50 | hsa-miR-720 | 3983 | 13344 | 0.30 | 8.84E-15 | 1.87E-12 | 0.92 | 5.06E-12 | 3.45E-10 |
| 43 | hsa-miR-34a* | 91 | 19 | 4.87 | 2.13E-14 | 3.61E-12 | 0.04 | 2.79E-21 | 2.37E-18 |
| 12 | hsa-miR-934 | 77 | 22 | 3.50 | 8.22E-14 | 1.16E-11 | 0.07 | 1.57E-15 | 2.22E-13 |
| 111 | hsa-miR-1324 | 117 | 41 | 2.82 | 1.15E-12 | 1.39E-10 | 0.06 | 1.24E-14 | 1.50E-12 |
| 4 | hsa-miR-361-5p | 378 | 1255 | 0.30 | 1.66E-12 | 1.56E-10 | 0.90 | 2.17E-11 | 9.70E-10 |
| 251 | hsa-miR-32 | 136 | 57 | 2.40 | 1.52E-12 | 1.56E-10 | 0.10 | 9.40E-12 | 5.31E-10 |
| 55 | hsa-miR-483-3p | 29 | 87 | 0.34 | 2.12E-12 | 1.80E-10 | 0.89 | 1.41E-11 | 7.04E-10 |
| 6 | hsa-miR-640 | 93 | 30 | 3.12 | 3.17E-12 | 2.45E-10 | 0.09 | 5.24E-13 | 5.55E-11 |
| 342 | hsa-miR-151-5p | 4860 | 11250 | 0.43 | 5.05E-12 | 3.57E-10 | 0.87 | 4.26E-09 | 7.19E-08 |
| 1 | hsa-miR-1251 | 122 | 35 | 3.49 | 1.47E-11 | 9.58E-10 | 0.05 | 2.22E-16 | 3.76E-14 |
| 98 | hsa-miR-891b | 89 | 29 | 3.10 | 2.24E-11 | 1.35E-09 | 0.11 | 5.29E-12 | 3.45E-10 |
| 44 | hsa-miR-214* | 60 | 26 | 2.32 | 3.23E-11 | 1.82E-09 | 0.10 | 5.22E-12 | 3.45E-10 |
| 136 | hsa-miR-33b | 149 | 58 | 2.56 | 3.77E-11 | 1.88E-09 | 0.12 | 7.00E-11 | 2.05E-09 |
| 485 | hsa-miR-744 | 558 | 1483 | 0.38 | 3.70E-11 | 1.88E-09 | 0.89 | 3.23E-11 | 1.25E-09 |
| 94 | hsa-miR-219-2-3p | 17 | 50 | 0.34 | 6.21E-11 | 2.92E-09 | 0.87 | 4.09E-10 | 9.47E-09 |
| 179 | hsa-miR-455-3p | 165 | 81 | 2.03 | 1.09E-10 | 4.85E-09 | 0.10 | 2.45E-10 | 6.10E-09 |

| 390 | hsa-miR-320d | 693 | 1678 | 0.41 | 1.71E-10 | 7.25E-09 | 0.86 | 2.30E-09 | 4.15E-08 |
|---|---|---|---|---|---|---|---|---|---|
| 101 | hsa-miR-1908 | 860 | 3008 | 0.29 | 2.15E-10 | 8.66E-09 | 0.89 | 3.10E-11 | 1.25E-09 |
| 203 | hsa-miR-23a | 4172 | 9611 | 0.43 | 2.49E-10 | 9.59E-09 | 0.85 | 9.83E-09 | 1.39E-07 |
| 3 | hsa-miR-19b | 10494 | 28576 | 0.37 | 3.16E-10 | 1.16E-08 | 0.85 | 6.20E-09 | 9.56E-08 |
| 69 | hsa-miR-593* | 276 | 109 | 2.54 | 3.28E-10 | 1.16E-08 | 0.10 | 1.41E-10 | 3.87E-09 |
| 2 | hsa-miR-151-3p | 562 | 1526 | 0.37 | 3.66E-10 | 1.24E-08 | 0.86 | 4.71E-11 | 1.60E-09 |
| 26 | hsa-miR-564 | 158 | 59 | 2.67 | 4.14E-10 | 1.31E-08 | 0.14 | 1.06E-08 | 1.48E-07 |
| 76 | hsa-miR-153 | 110 | 38 | 2.85 | 4.47E-10 | 1.31E-08 | 0.13 | 8.76E-11 | 2.48E-09 |
| 105 | hsa-miR-646 | 231 | 87 | 2.65 | 4.20E-10 | 1.31E-08 | 0.14 | 1.01E-09 | 2.19E-08 |
| 118 | hsa-miR-629 | 88 | 255 | 0.35 | 4.44E-10 | 1.31E-08 | 0.85 | 2.81E-09 | 4.97E-08 |
| 290 | hsa-miR-135b | 15 | 40 | 0.39 | 5.39E-10 | 1.52E-08 | 0.86 | 4.63E-09 | 7.41E-08 |
| 170 | hsa-miR-1226* | 177 | 67 | 2.63 | 7.62E-10 | 2.08E-08 | 0.12 | 2.18E-10 | 5.61E-09 |
| 112 | hsa-miR-193a-5p | 69 | 152 | 0.45 | 9.29E-10 | 2.46E-08 | 0.87 | 1.25E-09 | 2.64E-08 |
| 10 | hsa-miR-145 | 146 | 400 | 0.36 | 1.02E-09 | 2.62E-08 | 0.87 | 6.27E-11 | 1.96E-09 |
| 52 | hsa-miR-23b | 3248 | 7343 | 0.44 | 1.19E-09 | 2.98E-08 | 0.85 | 1.23E-08 | 1.63E-07 |
| 241 | hsa-miR-545 | 115 | 39 | 2.97 | 1.96E-09 | 4.76E-08 | 0.11 | 1.86E-11 | 8.78E-10 |
| 143 | hsa-miR-1207-5p | 400 | 1431 | 0.28 | 2.29E-09 | 5.25E-08 | 0.86 | 6.47E-11 | 1.96E-09 |
| 182 | hsa-miR-452* | 322 | 142 | 2.27 | 2.27E-09 | 5.25E-08 | 0.12 | 4.57E-11 | 1.60E-09 |
| 34 | hsa-miR-650 | 124 | 53 | 2.33 | 3.13E-09 | 6.99E-08 | 0.12 | 4.13E-10 | 9.47E-09 |
| 73 | hsa-miR-216b | 127 | 47 | 2.72 | 3.25E-09 | 7.07E-08 | 0.12 | 7.84E-12 | 4.75E-10 |
| 124 | hsa-miR-431 | 160 | 71 | 2.27 | 3.60E-09 | 7.62E-08 | 0.15 | 2.62E-07 | 2.29E-06 |
| 22 | hsa-miR-1260 | 2513 | 6101 | 0.41 | 3.78E-09 | 7.82E-08 | 0.83 | 1.15E-07 | 1.16E-06 |
| 142 | hsa-miR-188-3p | 134 | 73 | 1.85 | 3.97E-09 | 8.01E-08 | 0.15 | 2.68E-08 | 3.07E-07 |
| 47 | hsa-miR-635 | 98 | 54 | 1.81 | 4.24E-09 | 8.36E-08 | 0.14 | 2.06E-09 | 3.89E-08 |
| 56 | hsa-miR-125a-3p | 28 | 74 | 0.38 | 4.59E-09 | 8.66E-08 | 0.89 | 1.03E-11 | 5.44E-10 |
| 187 | hsa-miR-891a | 116 | 56 | 2.07 | 4.50E-09 | 8.66E-08 | 0.14 | 5.67E-08 | 6.01E-07 |
| 62 | hsa-miR-654-5p | 173 | 80 | 2.18 | 5.17E-09 | 9.54E-08 | 0.10 | 5.02E-11 | 1.64E-09 |
| 140 | hsa-miR-135a* | 20 | 47 | 0.43 | 5.88E-09 | 1.04E-07 | 0.85 | 9.84E-10 | 2.19E-08 |
| 200 | hsa-miR-892a | 22 | 51 | 0.43 | 5.86E-09 | 1.04E-07 | 0.90 | 5.03E-12 | 3.45E-10 |
| 9 | hsa-miR-208b | 61 | 28 | 2.20 | 6.50E-09 | 1.13E-07 | 0.16 | 2.42E-08 | 2.81E-07 |
| 173 | hsa-miR-548p | 110 | 48 | 2.27 | 8.39E-09 | 1.42E-07 | 0.15 | 3.03E-09 | 5.24E-08 |
| 317 | hsa-miR-423-3p | 991 | 2402 | 0.41 | 8.75E-09 | 1.46E-07 | 0.84 | 3.52E-08 | 3.79E-07 |
| 31 | hsa-miR-26b* | 22 | 54 | 0.41 | 1.07E-08 | 1.75E-07 | 0.84 | 3.53E-08 | 3.79E-07 |
| 132 | hsa-miR-31* | 168 | 58 | 2.89 | 1.09E-08 | 1.75E-07 | 0.10 | 2.51E-11 | 1.07E-09 |
| 385 | hsa-miR-1228* | 1071 | 2663 | 0.40 | 1.20E-08 | 1.89E-07 | 0.84 | 2.25E-09 | 4.14E-08 |
| 253 | hsa-miR-30c-1* | 43 | 88 | 0.49 | 1.40E-08 | 2.16E-07 | 0.83 | 3.41E-07 | 2.78E-06 |
| 102 | hsa-miR-554 | 90 | 40 | 2.24 | 1.75E-08 | 2.66E-07 | 0.17 | 8.38E-08 | 8.66E-07 |
| 15 | hsa-miR-1180 | 66 | 135 | 0.49 | 1.86E-08 | 2.76E-07 | 0.80 | 2.63E-06 | 1.61E-05 |
| 191 | hsa-miR-217 | 146 | 74 | 1.96 | 2.14E-08 | 3.13E-07 | 0.16 | 3.32E-07 | 2.73E-06 |
| 154 | hsa-miR-139-3p | 72 | 41 | 1.73 | 2.25E-08 | 3.23E-07 | 0.15 | 6.12E-09 | 9.56E-08 |
| 107 | hsa-miR-1272 | 137 | 57 | 2.39 | 2.32E-08 | 3.28E-07 | 0.13 | 2.90E-10 | 7.02E-09 |
| 29 | hsa-miR-1208 | 86 | 40 | 2.18 | 2.41E-08 | 3.35E-07 | 0.14 | 1.80E-09 | 3.47E-08 |
| 85 | hsa-miR-143* | 110 | 57 | 1.93 | 2.46E-08 | 3.36E-07 | 0.12 | 4.48E-09 | 7.31E-08 |
| 19 | hsa-miR-523 | 81 | 34 | 2.38 | 2.97E-08 | 3.96E-07 | 0.17 | 6.36E-08 | 6.65E-07 |
| 302 | hsa-miR-149* | 542 | 1413 | 0.38 | 2.99E-08 | 3.96E-07 | 0.83 | 2.01E-08 | 2.47E-07 |
| 270 | hsa-miR-1305 | 78 | 33 | 2.38 | 3.35E-08 | 4.37E-07 | 0.17 | 8.97E-08 | 9.17E-07 |

FIG. 6 cont.

| | | | | | | | | |
|---|---|---|---|---|---|---|---|---|
| 14 | hsa-miR-596 | 65 | 34 | 1.92 | 3.54E-08 | 4.55E-07 | 0.15 | 9.56E-09 | 1.37E-07 |
| 87 | hsa-miR-374a | 273 | 104 | 2.62 | 4.85E-08 | 6.14E-07 | 0.16 | 1.25E-08 | 1.63E-07 |
| 282 | hsa-miR-515-5p | 157 | 94 | 1.66 | 5.34E-08 | 6.66E-07 | 0.13 | 2.59E-06 | 1.61E-05 |
| 432 | hsa-miR-574-3p | 1642 | 3915 | 0.42 | 5.49E-08 | 6.75E-07 | 0.88 | 1.50E-12 | 1.41E-10 |
| 46 | hsa-miR-1246 | 19 | 50 | 0.37 | 8.11E-08 | 9.60E-07 | 0.83 | 2.13E-08 | 2.58E-07 |
| 75 | hsa-miR-1274a | 142 | 280 | 0.51 | 8.02E-08 | 9.60E-07 | 0.81 | 1.30E-07 | 1.26E-06 |
| 176 | hsa-miR-885-3p | 194 | 447 | 0.43 | 8.15E-08 | 9.60E-07 | 0.83 | 6.98E-09 | 1.06E-07 |
| 319 | hsa-miR-409-3p | 38 | 92 | 0.41 | 9.05E-08 | 1.05E-06 | 0.84 | 1.67E-08 | 2.08E-07 |
| 66 | hsa-miR-556-5p | 120 | 49 | 2.43 | 9.95E-08 | 1.14E-06 | 0.16 | 5.80E-07 | 4.43E-06 |
| 109 | hsa-miR-33a | 101 | 54 | 1.88 | 1.04E-07 | 1.17E-06 | 0.18 | 5.55E-06 | 3.08E-05 |
| 486 | hsa-miR-93* | 908 | 1796 | 0.51 | 1.06E-07 | 1.18E-06 | 0.83 | 1.31E-07 | 1.26E-06 |
| 16 | hsa-miR-664 | 275 | 799 | 0.34 | 1.15E-07 | 1.26E-06 | 0.81 | 1.31E-07 | 1.26E-06 |
| 63 | hsa-miR-135a | 14 | 35 | 0.40 | 1.23E-07 | 1.33E-06 | 0.84 | 7.66E-09 | 1.14E-07 |
| 41 | hsa-miR-1247 | 58 | 29 | 2.03 | 1.33E-07 | 1.42E-06 | 0.16 | 1.74E-07 | 1.62E-06 |
| 59 | hsa-miR-658 | 45 | 105 | 0.43 | 1.33E-07 | 1.42E-06 | 0.84 | 1.41E-09 | 2.91E-08 |
| 210 | hsa-miR-604 | 81 | 36 | 2.26 | 1.36E-07 | 1.42E-06 | 0.14 | 4.24E-11 | 1.56E-09 |
| 487 | hsa-miR-484 | 7267 | 14077 | 0.52 | 1.47E-07 | 1.52E-06 | 0.78 | 3.93E-06 | 2.32E-05 |
| 70 | hsa-miR-132* | 14 | 39 | 0.35 | 1.61E-07 | 1.65E-06 | 0.86 | 1.77E-10 | 4.69E-09 |
| 128 | hsa-miR-1289 | 90 | 43 | 2.12 | 1.71E-07 | 1.73E-06 | 0.16 | 1.97E-07 | 1.78E-06 |
| 148 | hsa-miR-425 | 13775 | 27351 | 0.50 | 1.75E-07 | 1.75E-06 | 0.80 | 9.07E-06 | 4.72E-05 |
| 28 | hsa-miR-607 | 80 | 39 | 2.07 | 1.95E-07 | 1.86E-06 | 0.15 | 1.76E-09 | 3.46E-08 |
| 91 | hsa-miR-621 | 313 | 154 | 2.04 | 1.90E-07 | 1.86E-06 | 0.14 | 4.32E-09 | 7.19E-08 |
| 391 | hsa-miR-185 | 24880 | 46146 | 0.54 | 1.95E-07 | 1.86E-06 | 0.77 | 4.78E-05 | 1.95E-04 |
| 392 | hsa-miR-301b | 183 | 103 | 1.78 | 1.93E-07 | 1.86E-06 | 0.15 | 2.23E-08 | 2.65E-07 |
| 244 | hsa-miR-509-5p | 219 | 94 | 2.33 | 2.17E-07 | 2.04E-06 | 0.15 | 1.17E-07 | 1.16E-06 |
| 78 | hsa-miR-653 | 37 | 69 | 0.53 | 2.42E-07 | 2.26E-06 | 0.79 | 3.01E-06 | 1.82E-05 |
| 20 | hsa-miR-183* | 98 | 185 | 0.53 | 2.50E-07 | 2.30E-06 | 0.82 | 5.89E-07 | 4.46E-06 |
| 141 | hsa-miR-539 | 18 | 39 | 0.46 | 2.70E-07 | 2.46E-06 | 0.84 | 2.25E-08 | 2.65E-07 |
| 174 | hsa-miR-509-3-5p | 227 | 108 | 2.10 | 2.77E-07 | 2.50E-06 | 0.20 | 4.04E-06 | 2.35E-05 |
| 306 | hsa-miR-566 | 90 | 49 | 1.83 | 2.84E-07 | 2.54E-06 | 0.17 | 8.69E-09 | 1.27E-07 |
| 103 | hsa-miR-1301 | 210 | 113 | 1.86 | 2.99E-07 | 2.64E-06 | 0.14 | 1.27E-08 | 1.63E-07 |
| 265 | hsa-miR-24-2* | 151 | 84 | 1.79 | 3.07E-07 | 2.68E-06 | 0.15 | 1.45E-09 | 2.92E-08 |
| 37 | hsa-miR-548m | 19 | 47 | 0.40 | 3.17E-07 | 2.74E-06 | 0.81 | 2.69E-07 | 2.33E-06 |
| 134 | hsa-miR-633 | 65 | 29 | 2.22 | 3.42E-07 | 2.90E-06 | 0.19 | 5.75E-07 | 4.43E-06 |
| 139 | hsa-miR-767-5p | 164 | 79 | 2.07 | 3.39E-07 | 2.90E-06 | 0.16 | 1.10E-08 | 1.50E-07 |
| 147 | hsa-miR-186 | 42 | 88 | 0.48 | 3.58E-07 | 3.01E-06 | 0.79 | 1.22E-06 | 8.27E-06 |
| 196 | hsa-let-7g* | 125 | 75 | 1.67 | 3.98E-07 | 3.31E-06 | 0.18 | 5.59E-07 | 4.35E-06 |
| 488 | hsa-miR-1281 | 77 | 138 | 0.56 | 4.21E-07 | 3.46E-06 | 0.79 | 1.27E-05 | 6.29E-05 |
| 81 | hsa-miR-188-5p | 106 | 65 | 1.62 | 4.36E-07 | 3.55E-06 | 0.17 | 8.10E-07 | 5.87E-06 |
| 249 | hsa-miR-497 | 174 | 83 | 2.11 | 4.65E-07 | 3.76E-06 | 0.18 | 6.38E-07 | 4.75E-06 |
| 57 | hsa-miR-1225-5p | 65 | 129 | 0.50 | 5.88E-07 | 4.70E-06 | 0.79 | 1.78E-06 | 1.15E-05 |
| 289 | hsa-miR-1912 | 157 | 91 | 1.72 | 7.08E-07 | 5.61E-06 | 0.17 | 3.53E-07 | 2.85E-06 |
| 65 | hsa-miR-328 | 59 | 152 | 0.39 | 8.44E-07 | 6.62E-06 | 0.80 | 1.51E-07 | 1.44E-06 |
| 51 | hsa-miR-490-3p | 83 | 41 | 2.02 | 9.68E-07 | 7.48E-06 | 0.18 | 9.52E-07 | 6.78E-06 |
| 389 | hsa-miR-196a* | 137 | 74 | 1.84 | 9.71E-07 | 7.48E-06 | 0.21 | 6.75E-06 | 3.58E-05 |
| 224 | hsa-miR-1307 | 76 | 113 | 0.67 | 9.85E-07 | 7.52E-06 | 0.76 | 4.14E-05 | 1.74E-04 |

FIG. 6 cont.

| | | | | | | | | | |
|---|---|---|---|---|---|---|---|---|---|
| 49 | hsa-miR-28-5p | 366 | 713 | 0.51 | 1.06E-06 | 7.99E-06 | 0.82 | 2.99E-07 | 2.55E-06 |
| 93 | hsa-miR-492 | 77 | 40 | 1.92 | 1.06E-06 | 7.99E-06 | 0.20 | 6.73E-06 | 3.58E-05 |
| 198 | hsa-miR-497* | 109 | 56 | 1.97 | 1.12E-06 | 8.33E-06 | 0.16 | 3.45E-08 | 3.79E-07 |
| 8 | hsa-miR-28-3p | 181 | 302 | 0.60 | 1.20E-06 | 8.81E-06 | 0.78 | 1.04E-05 | 5.32E-05 |
| 489 | hsa-miR-551b | 84 | 43 | 1.95 | 1.21E-06 | 8.81E-06 | 0.23 | 1.43E-05 | 6.95E-05 |
| 21 | hsa-miR-499-3p | 83 | 40 | 2.07 | 1.22E-06 | 8.82E-06 | 0.19 | 1.13E-06 | 7.76E-06 |
| 92 | hsa-miR-182 | 4486 | 9199 | 0.49 | 1.35E-06 | 9.60E-06 | 0.79 | 1.12E-06 | 7.76E-06 |
| 110 | hsa-miR-221* | 98 | 49 | 2.01 | 1.34E-06 | 9.60E-06 | 0.18 | 1.15E-08 | 1.55E-07 |
| 96 | hsa-miR-597 | 67 | 26 | 2.55 | 1.40E-06 | 9.91E-06 | 0.18 | 3.03E-08 | 3.43E-07 |
| 268 | hsa-miR-199a-5p | 228 | 482 | 0.47 | 1.55E-06 | 1.09E-05 | 0.79 | 2.48E-06 | 1.57E-05 |
| 239 | hsa-miR-1206 | 53 | 21 | 2.59 | 1.64E-06 | 1.14E-05 | 0.20 | 1.70E-07 | 1.60E-06 |
| 33 | hsa-miR-183 | 365 | 1012 | 0.36 | 1.78E-06 | 1.23E-05 | 0.80 | 2.02E-07 | 1.81E-06 |
| 114 | hsa-miR-193b* | 33 | 85 | 0.38 | 1.88E-06 | 1.27E-05 | 0.79 | 1.27E-06 | 8.44E-06 |
| 330 | hsa-miR-766 | 360 | 644 | 0.56 | 1.87E-06 | 1.27E-05 | 0.77 | 2.07E-05 | 9.57E-05 |
| 303 | hsa-miR-1911 | 32 | 59 | 0.54 | 1.91E-06 | 1.29E-05 | 0.79 | 1.10E-05 | 5.57E-05 |
| 199 | hsa-miR-1285 | 257 | 397 | 0.65 | 1.95E-06 | 1.30E-05 | 0.81 | 2.13E-05 | 9.83E-05 |
| 286 | hsa-miR-330-3p | 351 | 251 | 1.40 | 2.15E-06 | 1.41E-05 | 0.21 | 6.62E-05 | 2.60E-04 |
| 490 | hsa-miR-24 | 1896 | 3349 | 0.57 | 2.13E-06 | 1.41E-05 | 0.78 | 4.69E-06 | 2.67E-05 |
| 95 | hsa-miR-1261 | 17 | 39 | 0.44 | 2.20E-06 | 1.44E-05 | 0.80 | 2.59E-07 | 2.29E-06 |
| 491 | hsa-miR-532-3p | 3227 | 5266 | 0.61 | 2.23E-06 | 1.44E-05 | 0.77 | 1.58E-05 | 7.52E-05 |
| 492 | hsa-miR-320a | 13641 | 24789 | 0.55 | 2.26E-06 | 1.45E-05 | 0.78 | 6.76E-06 | 3.58E-05 |
| 493 | hsa-let-7b | 750 | 2226 | 0.34 | 2.31E-06 | 1.47E-05 | 0.76 | 1.42E-05 | 6.91E-05 |
| 39 | hsa-miR-373 | 20 | 38 | 0.52 | 2.34E-06 | 1.48E-05 | 0.80 | 1.14E-06 | 7.76E-06 |
| 164 | hsa-miR-192 | 5577 | 11085 | 0.50 | 2.44E-06 | 1.53E-05 | 0.78 | 6.05E-06 | 3.31E-05 |
| 42 | hsa-miR-505 | 33 | 59 | 0.55 | 2.50E-06 | 1.56E-05 | 0.77 | 3.85E-05 | 1.65E-04 |
| 17 | hsa-miR-20a | 3397 | 1482 | 2.29 | 2.56E-06 | 1.58E-05 | 0.20 | 7.73E-07 | 5.65E-06 |
| 230 | hsa-miR-558 | 84 | 31 | 2.70 | 2.59E-06 | 1.59E-05 | 0.19 | 3.01E-07 | 2.55E-06 |
| 32 | hsa-miR-450b-5p | 56 | 29 | 1.90 | 2.83E-06 | 1.73E-05 | 0.19 | 1.04E-06 | 7.32E-06 |
| 255 | hsa-miR-1266 | 105 | 56 | 1.87 | 2.99E-06 | 1.80E-05 | 0.20 | 5.40E-07 | 4.25E-06 |
| 494 | hsa-miR-1274b | 616 | 1186 | 0.52 | 3.00E-06 | 1.80E-05 | 0.77 | 1.53E-05 | 7.33E-05 |
| 177 | hsa-miR-346 | 61 | 83 | 0.74 | 3.37E-06 | 2.01E-05 | 0.76 | 1.71E-04 | 5.92E-04 |
| 280 | hsa-miR-302a | 16 | 35 | 0.46 | 3.55E-06 | 2.11E-05 | 0.82 | 1.44E-08 | 1.82E-07 |
| 207 | hsa-miR-1290 | 15 | 35 | 0.43 | 3.68E-06 | 2.17E-05 | 0.81 | 1.92E-07 | 1.75E-06 |
| 495 | hsa-miR-320b | 2344 | 4431 | 0.53 | 3.82E-06 | 2.23E-05 | 0.79 | 4.93E-06 | 2.79E-05 |
| 64 | hsa-miR-488 | 18 | 40 | 0.46 | 4.20E-06 | 2.44E-05 | 0.80 | 4.00E-06 | 2.34E-05 |
| 229 | hsa-miR-129* | 44 | 70 | 0.63 | 4.41E-06 | 2.54E-05 | 0.77 | 1.97E-05 | 9.20E-05 |
| 304 | hsa-miR-489 | 191 | 109 | 1.75 | 4.55E-06 | 2.61E-05 | 0.22 | 5.72E-06 | 3.15E-05 |
| 384 | hsa-miR-485-5p | 47 | 25 | 1.85 | 4.74E-06 | 2.70E-05 | 0.22 | 6.54E-06 | 3.53E-05 |
| 325 | hsa-miR-548d-3p | 48 | 22 | 2.13 | 4.78E-06 | 2.70E-05 | 0.20 | 1.98E-06 | 1.27E-05 |
| 68 | hsa-miR-367* | 48 | 25 | 1.93 | 4.93E-06 | 2.76E-05 | 0.21 | 7.22E-06 | 3.80E-05 |
| 214 | hsa-miR-211 | 13 | 33 | 0.41 | 4.95E-06 | 2.76E-05 | 0.81 | 5.41E-07 | 4.25E-06 |
| 197 | hsa-miR-1291 | 110 | 58 | 1.92 | 5.29E-06 | 2.93E-05 | 0.23 | 4.22E-05 | 1.77E-04 |
| 180 | hsa-miR-625 | 68 | 191 | 0.36 | 5.33E-06 | 2.94E-05 | 0.78 | 2.49E-06 | 1.57E-05 |
| 166 | hsa-miR-9* | 89 | 46 | 1.92 | 6.50E-06 | 3.55E-05 | 0.21 | 8.16E-06 | 4.27E-05 |
| 195 | hsa-miR-31 | 128 | 77 | 1.67 | 7.45E-06 | 4.02E-05 | 0.19 | 3.22E-06 | 1.94E-05 |
| 343 | hsa-miR-541 | 94 | 54 | 1.73 | 7.49E-06 | 4.02E-05 | 0.21 | 1.23E-06 | 8.27E-06 |

FIG. 6 cont.

| 496 | hsa-miR-210 | 685 | 1591 | 0.43 | 7.46E-06 | 4.02E-05 | 0.77 | 3.56E-06 | 2.12E-05 |
| --- | --- | --- | --- | --- | --- | --- | --- | --- | --- |
| 468 | hsa-miR-331-5p | 29 | 52 | 0.56 | 8.24E-06 | 4.39E-05 | 0.76 | 3.75E-05 | 1.61E-04 |
| 361 | hsa-miR-874 | 159 | 103 | 1.55 | 8.35E-06 | 4.43E-05 | 0.22 | 3.47E-05 | 1.50E-04 |
| 274 | hsa-miR-508-5p | 105 | 64 | 1.64 | 8.53E-06 | 4.49E-05 | 0.21 | 4.08E-06 | 2.35E-05 |
| 295 | hsa-miR-520c-5p | 137 | 56 | 2.44 | 8.72E-06 | 4.56E-05 | 0.20 | 3.04E-07 | 2.55E-06 |
| 181 | hsa-miR-214 | 281 | 171 | 1.64 | 8.89E-06 | 4.62E-05 | 0.21 | 2.96E-04 | 9.60E-04 |
| 133 | hsa-miR-92b | 260 | 548 | 0.47 | 9.34E-06 | 4.83E-05 | 0.77 | 2.84E-05 | 1.27E-04 |
| 54 | hsa-miR-218-1* | 72 | 41 | 1.77 | 1.01E-05 | 5.17E-05 | 0.19 | 4.53E-07 | 3.63E-06 |
| 497 | hsa-miR-15b | 15,571 | 24841 | 0.63 | 1.09E-05 | 5.55E-05 | 0.72 | 3.54E-04 | 1.10E-03 |
| 163 | hsa-miR-518a-3p | 57 | 28 | 2.01 | 1.12E-05 | 5.69E-05 | 0.21 | 5.04E-06 | 2.83E-05 |
| 113 | hsa-miR-1226 | 55 | 107 | 0.52 | 1.18E-05 | 5.90E-05 | 0.79 | 1.15E-05 | 5.76E-05 |
| 126 | hsa-miR-92b* | 127 | 258 | 0.49 | 1.17E-05 | 5.90E-05 | 0.78 | 1.82E-07 | 1.68E-06 |
| 245 | hsa-miR-522* | 148 | 72 | 2.06 | 1.27E-05 | 6.35E-05 | 0.20 | 3.31E-07 | 2.73E-06 |
| 137 | hsa-miR-330-5p | 28 | 58 | 0.49 | 1.31E-05 | 6.48E-05 | 0.79 | 3.91E-06 | 2.32E-05 |
| 212 | hsa-miR-520f | 16 | 36 | 0.45 | 1.31E-05 | 6.48E-05 | 0.78 | 1.33E-06 | 8.73E-06 |
| 328 | hsa-miR-128 | 585 | 1100 | 0.53 | 1.33E-05 | 6.53E-05 | 0.78 | 2.62E-06 | 1.61E-05 |
| 161 | hsa-miR-190 | 18 | 39 | 0.45 | 1.37E-05 | 6.68E-05 | 0.78 | 4.53E-06 | 2.59E-05 |
| 189 | hsa-miR-20a* | 141 | 80 | 1.77 | 1.41E-05 | 6.84E-05 | 0.20 | 5.03E-05 | 2.04E-04 |
| 217 | hsa-miR-1253 | 75 | 36 | 2.05 | 1.43E-05 | 6.90E-05 | 0.21 | 1.34E-05 | 6.58E-05 |
| 104 | hsa-miR-96 | 162 | 67 | 2.42 | 1.75E-05 | 8.37E-05 | 0.19 | 3.50E-08 | 3.79E-07 |
| 100 | hsa-miR-1275 | 56 | 123 | 0.45 | 1.83E-05 | 8.72E-05 | 0.79 | 1.27E-06 | 8.44E-06 |
| 40 | hsa-miR-340 | 171 | 284 | 0.60 | 1.84E-05 | 8.73E-05 | 0.75 | 4.13E-05 | 1.74E-04 |
| 120 | hsa-miR-380* | 78 | 38 | 2.08 | 1.96E-05 | 9.24E-05 | 0.21 | 2.50E-06 | 1.57E-05 |
| 165 | hsa-miR-22 | 7954 | 14467 | 0.55 | 1.99E-05 | 9.34E-05 | 0.75 | 1.63E-04 | 5.70E-04 |
| 77 | hsa-miR-342-5p | 126 | 174 | 0.72 | 2.04E-05 | 9.50E-05 | 0.76 | 8.36E-05 | 3.19E-04 |
| 370 | hsa-miR-326 | 85 | 55 | 1.55 | 2.10E-05 | 9.72E-05 | 0.23 | 2.32E-05 | 1.06E-04 |
| 190 | hsa-miR-637 | 25 | 51 | 0.49 | 2.32E-05 | 1.07E-04 | 0.77 | 2.89E-05 | 1.29E-04 |
| 345 | hsa-miR-612 | 76 | 37 | 2.06 | 2.32E-05 | 1.07E-04 | 0.21 | 8.35E-07 | 6.00E-06 |
| 86 | hsa-miR-1321 | 25 | 47 | 0.53 | 2.46E-05 | 1.12E-04 | 0.76 | 3.20E-05 | 1.41E-04 |
| 74 | hsa-miR-194 | 6649 | 12646 | 0.53 | 2.51E-05 | 1.13E-04 | 0.75 | 8.68E-05 | 3.29E-04 |
| 151 | hsa-miR-631 | 133 | 85 | 1.56 | 2.50E-05 | 1.13E-04 | 0.18 | 7.17E-07 | 5.28E-06 |
| 408 | hsa-miR-125b | 436 | 1060 | 0.41 | 2.53E-05 | 1.13E-04 | 0.77 | 1.11E-05 | 5.61E-05 |
| 127 | hsa-miR-490-5p | 122 | 73 | 1.69 | 2.56E-05 | 1.14E-04 | 0.20 | 2.59E-06 | 1.61E-05 |
| 82 | hsa-miR-1270 | 30 | 73 | 0.40 | 2.58E-05 | 1.14E-04 | 0.79 | 6.26E-06 | 3.40E-05 |
| 437 | hsa-miR-138-2* | 59 | 29 | 2.03 | 2.69E-05 | 1.19E-04 | 0.22 | 5.56E-06 | 3.08E-05 |
| 227 | hsa-miR-887 | 102 | 68 | 1.50 | 2.77E-05 | 1.22E-04 | 0.24 | 3.68E-04 | 1.14E-03 |
| 498 | hsa-miR-191 | 11336 | 18887 | 0.60 | 2.84E-05 | 1.24E-04 | 0.74 | 1.29E-04 | 4.66E-04 |
| 307 | hsa-let-7i* | 249 | 138 | 1.81 | 2.93E-05 | 1.28E-04 | 0.22 | 2.57E-05 | 1.16E-04 |
| 259 | hsa-miR-105 | 39 | 23 | 1.68 | 3.05E-05 | 1.32E-04 | 0.24 | 6.32E-05 | 2.52E-04 |
| 371 | hsa-miR-26a-2* | 15 | 29 | 0.52 | 3.27E-05 | 1.41E-04 | 0.78 | 1.01E-06 | 7.12E-06 |
| 80 | hsa-miR-454 | 121 | 77 | 1.58 | 3.57E-05 | 1.53E-04 | 0.24 | 1.49E-05 | 7.20E-05 |
| 271 | hsa-miR-141* | 77 | 43 | 1.79 | 3.61E-05 | 1.54E-04 | 0.20 | 6.06E-07 | 4.55E-06 |
| 499 | hsa-miR-320c | 646 | 1097 | 0.59 | 3.81E-05 | 1.61E-04 | 0.75 | 6.42E-05 | 2.53E-04 |
| 429 | hsa-miR-219-5p | 53 | 29 | 1.80 | 3.97E-05 | 1.67E-04 | 0.23 | 1.83E-05 | 8.61E-05 |
| 48 | hsa-miR-487b | 52 | 32 | 1.61 | 4.37E-05 | 1.84E-04 | 0.23 | 2.51E-05 | 1.14E-04 |
| 138 | hsa-miR-202 | 28 | 48 | 0.58 | 4.71E-05 | 1.97E-04 | 0.73 | 1.65E-04 | 5.75E-04 |

FIG. 6 cont.

| | | | | | | | | | |
|---|---|---|---|---|---|---|---|---|---|
| 175 | hsa-miR-518d-3p | 61 | 38 | 1.61 | 4.84E-05 | 2.01E-04 | 0.25 | 3.23E-05 | 1.42E-04 |
| 341 | hsa-miR-627 | 144 | 86 | 1.67 | 4.99E-05 | 2.07E-04 | 0.22 | 1.59E-06 | 1.04E-05 |
| 406 | hsa-miR-521 | 50 | 24 | 2.05 | 5.15E-05 | 2.12E-04 | 0.23 | 1.71E-05 | 8.10E-05 |
| 84 | hsa-miR-130b | 1433 | 2477 | 0.58 | 5.37E-05 | 2.20E-04 | 0.74 | 4.34E-05 | 1.81E-04 |
| 153 | hsa-miR-548o | 96 | 50 | 1.93 | 5.42E-05 | 2.21E-04 | 0.24 | 1.03E-04 | 3.82E-04 |
| 500 | hsa-miR-888* | 39 | 26 | 1.52 | 5.56E-05 | 2.26E-04 | 0.26 | 1.55E-04 | 5.45E-04 |
| 215 | hsa-miR-154 | 15 | 40 | 0.38 | 7.79E-05 | 3.15E-04 | 0.76 | 2.26E-05 | 1.04E-04 |
| 24 | hsa-miR-144* | 646 | 383 | 1.68 | 7.95E-05 | 3.19E-04 | 0.24 | 8.01E-05 | 3.12E-04 |
| 206 | hsa-miR-127-5p | 130 | 68 | 1.91 | 8.41E-05 | 3.36E-04 | 0.25 | 8.58E-04 | 2.39E-03 |
| 169 | hsa-miR-769-5p | 28 | 40 | 0.71 | 8.54E-05 | 3.39E-04 | 0.71 | 1.00E-03 | 2.76E-03 |
| 267 | hsa-miR-302c* | 31 | 46 | 0.69 | 8.56E-05 | 3.39E-04 | 0.74 | 8.12E-05 | 3.15E-04 |
| 7 | hsa-miR-20b | 3360 | 1546 | 2.17 | 8.94E-05 | 3.51E-04 | 0.26 | 8.26E-05 | 3.17E-04 |
| 235 | hsa-miR-450b-3p | 37 | 23 | 1.62 | 8.93E-05 | 3.51E-04 | 0.25 | 1.74E-04 | 6.00E-04 |
| 234 | hsa-miR-1279 | 17 | 31 | 0.53 | 9.21E-05 | 3.60E-04 | 0.78 | 1.04E-05 | 5.33E-05 |
| 228 | hsa-miR-877 | 60 | 104 | 0.58 | 9.35E-05 | 3.64E-04 | 0.75 | 1.17E-04 | 4.32E-04 |
| 337 | hsa-miR-548i | 21 | 29 | 0.73 | 9.63E-05 | 3.73E-04 | 0.76 | 9.72E-06 | 5.03E-05 |
| 309 | hsa-miR-518c* | 52 | 74 | 0.70 | 9.68E-05 | 3.73E-04 | 0.76 | 2.69E-04 | 8.81E-04 |
| 36 | hsa-miR-628-3p | 187 | 301 | 0.62 | 9.92E-05 | 3.81E-04 | 0.75 | 1.20E-04 | 4.39E-04 |
| 501 | hsa-miR-16 | 16443 | 26888 | 0.61 | 1.13E-04 | 4.30E-04 | 0.70 | 5.61E-04 | 1.64E-03 |
| 502 | hsa-miR-588 | 117 | 66 | 1.78 | 1.15E-04 | 4.37E-04 | 0.23 | 5.29E-05 | 2.13E-04 |
| 18 | hsa-miR-224 | 49 | 62 | 0.79 | 1.26E-04 | 4.78E-04 | 0.70 | 5.80E-04 | 1.68E-03 |
| 209 | hsa-miR-933 | 203 | 108 | 1.89 | 1.35E-04 | 5.10E-04 | 0.24 | 1.21E-04 | 4.41E-04 |
| 185 | hsa-miR-1283 | 91 | 56 | 1.61 | 1.40E-04 | 5.25E-04 | 0.24 | 2.94E-05 | 1.31E-04 |
| 318 | hsa-miR-298 | 116 | 61 | 1.91 | 1.40E-04 | 5.25E-04 | 0.26 | 1.04E-03 | 2.83E-03 |
| 201 | hsa-miR-107 | 1380 | 943 | 1.46 | 1.42E-04 | 5.28E-04 | 0.26 | 2.33E-04 | 7.76E-04 |
| 131 | hsa-miR-606 | 67 | 43 | 1.56 | 1.43E-04 | 5.28E-04 | 0.27 | 6.19E-05 | 2.48E-04 |
| 503 | hsa-miR-331-3p | 683 | 1417 | 0.48 | 1.46E-04 | 5.37E-04 | 0.72 | 3.83E-04 | 1.18E-03 |
| 362 | hsa-miR-30a | 296 | 574 | 0.52 | 1.46E-04 | 5.38E-04 | 0.74 | 1.19E-05 | 5.92E-05 |
| 504 | hsa-miR-616* | 53 | 34 | 1.57 | 1.48E-04 | 5.42E-04 | 0.27 | 1.54E-04 | 5.45E-04 |
| 108 | hsa-miR-199b-5p | 25 | 40 | 0.63 | 1.51E-04 | 5.49E-04 | 0.75 | 3.30E-04 | 1.04E-03 |
| 331 | hsa-miR-570 | 80 | 42 | 1.92 | 1.51E-04 | 5.49E-04 | 0.24 | 8.68E-05 | 3.29E-04 |
| 505 | hsa-miR-378 | 260 | 428 | 0.61 | 1.54E-04 | 5.55E-04 | 0.73 | 1.21E-04 | 4.41E-04 |
| 149 | hsa-miR-491-5p | 87 | 150 | 0.58 | 1.55E-04 | 5.56E-04 | 0.77 | 6.36E-05 | 2.52E-04 |
| 38 | hsa-miR-146a | 199 | 335 | 0.59 | 1.64E-04 | 5.84E-04 | 0.74 | 3.40E-05 | 1.48E-04 |
| 351 | hsa-miR-595 | 87 | 39 | 2.21 | 1.64E-04 | 5.84E-04 | 0.29 | 4.77E-04 | 1.42E-03 |
| 263 | hsa-miR-30e | 1833 | 3523 | 0.52 | 1.72E-04 | 6.09E-04 | 0.72 | 2.69E-04 | 8.81E-04 |
| 506 | hsa-miR-26a | 6938 | 11752 | 0.59 | 1.72E-04 | 6.09E-04 | 0.72 | 4.78E-04 | 1.42E-03 |
| 157 | hsa-miR-553 | 23 | 37 | 0.62 | 1.77E-04 | 6.23E-04 | 0.74 | 8.17E-05 | 3.15E-04 |
| 160 | hsa-miR-584 | 96 | 224 | 0.43 | 1.83E-04 | 6.42E-04 | 0.72 | 2.09E-04 | 7.08E-04 |
| 145 | hsa-miR-20b* | 69 | 43 | 1.59 | 1.87E-04 | 6.53E-04 | 0.25 | 4.51E-04 | 1.37E-03 |
| 507 | hsa-miR-9 | 18 | 29 | 0.62 | 1.89E-04 | 6.55E-04 | 0.74 | 5.63E-04 | 1.64E-03 |
| 25 | hsa-miR-613 | 19 | 42 | 0.46 | 1.92E-04 | 6.66E-04 | 0.72 | 7.13E-04 | 2.00E-03 |
| 508 | hsa-miR-502-3p | 564 | 1074 | 0.53 | 1.93E-04 | 6.66E-04 | 0.75 | 3.39E-05 | 1.48E-04 |
| 130 | hsa-miR-125b-2* | 40 | 66 | 0.60 | 1.97E-04 | 6.73E-04 | 0.71 | 6.14E-04 | 1.76E-03 |
| 509 | hsa-miR-223 | 1758 | 4094 | 0.43 | 1.97E-04 | 6.73E-04 | 0.72 | 2.45E-04 | 8.12E-04 |
| 510 | hsa-miR-25 | 6501 | 10926 | 0.60 | 2.01E-04 | 6.81E-04 | 0.72 | 5.93E-04 | 1.72E-03 |

FIG. 6 cont.

| | | | | | | | | | |
|---|---|---|---|---|---|---|---|---|---|
| 511 | hsa-miR-1184 | 189 | 127 | 1.48 | 2.00E-04 | 6.81E-04 | 0.26 | 1.52E-04 | 5.39E-04 |
| 247 | hsa-miR-126* | 21 | 34 | 0.62 | 2.07E-04 | 7.01E-04 | 0.76 | 9.08E-05 | 3.41E-04 |
| 332 | hsa-miR-1278 | 59 | 27 | 2.17 | 2.22E-04 | 7.44E-04 | 0.25 | 1.90E-05 | 8.90E-05 |
| 375 | hsa-miR-587 | 43 | 79 | 0.55 | 2.22E-04 | 7.44E-04 | 0.73 | 4.41E-04 | 1.35E-03 |
| 115 | hsa-miR-632 | 32 | 52 | 0.61 | 2.28E-04 | 7.62E-04 | 0.73 | 5.11E-04 | 1.51E-03 |
| 416 | hsa-miR-1286 | 127 | 89 | 1.42 | 2.37E-04 | 7.88E-04 | 0.26 | 3.44E-03 | 7.91E-03 |
| 427 | hsa-miR-196b | 13 | 21 | 0.61 | 2.39E-04 | 7.93E-04 | 0.77 | 1.69E-04 | 5.87E-04 |
| 512 | hsa-miR-7-1* | 287 | 464 | 0.62 | 2.55E-04 | 8.40E-04 | 0.72 | 6.01E-04 | 1.73E-03 |
| 338 | hsa-miR-518d-5p | 144 | 81 | 1.77 | 2.57E-04 | 8.45E-04 | 0.25 | 2.24E-04 | 7.50E-04 |
| 262 | hsa-miR-541* | 18 | 34 | 0.54 | 2.59E-04 | 8.48E-04 | 0.74 | 8.83E-05 | 3.33E-04 |
| 513 | hsa-miR-641 | 68 | 42 | 1.63 | 2.60E-04 | 8.49E-04 | 0.25 | 3.99E-05 | 1.70E-04 |
| 394 | hsa-let-7e* | 23 | 36 | 0.63 | 2.68E-04 | 8.71E-04 | 0.73 | 1.48E-04 | 5.28E-04 |
| 155 | hsa-miR-513a-3p | 34 | 18 | 1.90 | 2.70E-04 | 8.73E-04 | 0.28 | 2.30E-04 | 7.68E-04 |
| 88 | hsa-miR-571 | 44 | 29 | 1.51 | 2.81E-04 | 9.07E-04 | 0.27 | 1.31E-04 | 4.72E-04 |
| 439 | hsa-miR-575 | 123 | 82 | 1.49 | 2.87E-04 | 9.22E-04 | 0.25 | 1.88E-04 | 6.44E-04 |
| 45 | hsa-miR-1227 | 65 | 102 | 0.63 | 2.90E-04 | 9.29E-04 | 0.75 | 3.11E-04 | 9.99E-04 |
| 106 | hsa-miR-376b | 61 | 34 | 1.80 | 2.97E-04 | 9.46E-04 | 0.27 | 3.90E-04 | 1.20E-03 |
| 167 | hsa-miR-517c | 29 | 47 | 0.61 | 3.08E-04 | 9.77E-04 | 0.72 | 3.18E-04 | 1.01E-03 |
| 61 | hsa-miR-296-5p | 260 | 458 | 0.57 | 3.15E-04 | 9.95E-04 | 0.72 | 5.64E-04 | 1.64E-03 |
| 393 | hsa-miR-548b-5p | 17 | 30 | 0.56 | 3.18E-04 | 1.00E-03 | 0.76 | 1.37E-05 | 6.72E-05 |
| 452 | hsa-miR-124* | 97 | 66 | 1.46 | 3.25E-04 | 1.02E-03 | 0.26 | 6.22E-04 | 1.78E-03 |
| 514 | hsa-miR-324-3p | 697 | 1067 | 0.65 | 3.39E-04 | 1.06E-03 | 0.72 | 3.70E-04 | 1.15E-03 |
| 323 | hsa-miR-1303 | 34 | 58 | 0.59 | 3.62E-04 | 1.13E-03 | 0.76 | 1.12E-04 | 4.15E-04 |
| 237 | hsa-miR-194* | 44 | 73 | 0.61 | 3.68E-04 | 1.14E-03 | 0.71 | 1.27E-03 | 3.34E-03 |
| 168 | hsa-miR-302f | 18 | 36 | 0.51 | 3.70E-04 | 1.14E-03 | 0.74 | 4.74E-05 | 1.94E-04 |
| 23 | hsa-miR-496 | 65 | 36 | 1.81 | 3.72E-04 | 1.15E-03 | 0.26 | 1.43E-04 | 5.14E-04 |
| 284 | hsa-miR-551b* | 39 | 77 | 0.50 | 3.74E-04 | 1.15E-03 | 0.79 | 4.48E-05 | 1.85E-04 |
| 414 | hsa-miR-1471 | 122 | 66 | 1.85 | 4.05E-04 | 1.24E-03 | 0.25 | 6.89E-04 | 1.93E-03 |
| 515 | hsa-miR-339-5p | 520 | 849 | 0.61 | 4.14E-04 | 1.26E-03 | 0.71 | 4.54E-04 | 1.37E-03 |
| 288 | hsa-miR-15a | 4128 | 6493 | 0.64 | 4.52E-04 | 1.38E-03 | 0.71 | 7.89E-04 | 2.20E-03 |
| 194 | hsa-miR-24-1* | 87 | 56 | 1.54 | 4.73E-04 | 1.43E-03 | 0.27 | 3.12E-04 | 9.99E-04 |
| 443 | hsa-miR-300 | 49 | 66 | 0.74 | 4.75E-04 | 1.43E-03 | 0.70 | 2.12E-03 | 5.23E-03 |
| 205 | hsa-miR-1284 | 32 | 53 | 0.59 | 4.83E-04 | 1.45E-03 | 0.73 | 2.93E-04 | 9.53E-04 |
| 305 | hsa-miR-26a-1* | 24 | 39 | 0.61 | 4.92E-04 | 1.47E-03 | 0.72 | 4.44E-04 | 1.35E-03 |
| 242 | hsa-miR-1244 | 14 | 26 | 0.53 | 4.95E-04 | 1.48E-03 | 0.73 | 5.48E-04 | 1.61E-03 |
| 516 | hsa-let-7c | 382 | 914 | 0.42 | 5.11E-04 | 1.52E-03 | 0.70 | 6.40E-04 | 1.82E-03 |
| 71 | hsa-miR-216a | 137 | 75 | 1.83 | 5.30E-04 | 1.56E-03 | 0.26 | 3.17E-04 | 1.01E-03 |
| 116 | hsa-miR-96* | 124 | 72 | 1.72 | 5.27E-04 | 1.56E-03 | 0.26 | 4.62E-03 | 1.03E-02 |
| 183 | hsa-miR-215 | 370 | 654 | 0.57 | 5.31E-04 | 1.56E-03 | 0.73 | 5.12E-05 | 2.07E-04 |
| 409 | hsa-miR-34c-3p | 86 | 51 | 1.68 | 5.60E-04 | 1.64E-03 | 0.28 | 3.35E-04 | 1.05E-03 |
| 193 | hsa-miR-204 | 15 | 26 | 0.56 | 5.64E-04 | 1.65E-03 | 0.73 | 4.50E-05 | 1.85E-04 |
| 336 | hsa-miR-600 | 69 | 40 | 1.70 | 5.76E-04 | 1.68E-03 | 0.29 | 1.05E-03 | 2.88E-03 |
| 412 | hsa-miR-508-3p | 16 | 31 | 0.51 | 5.79E-04 | 1.68E-03 | 0.74 | 9.28E-05 | 3.47E-04 |
| 122 | hsa-miR-1267 | 41 | 59 | 0.70 | 6.09E-04 | 1.76E-03 | 0.71 | 1.19E-03 | 3.21E-03 |
| 477 | hsa-miR-302e | 22 | 35 | 0.62 | 6.27E-04 | 1.81E-03 | 0.73 | 2.10E-04 | 7.09E-04 |
| 459 | hsa-miR-106a* | 135 | 99 | 1.36 | 6.41E-04 | 1.84E-03 | 0.29 | 1.60E-03 | 4.11E-03 |

FIG. 6 cont.

| | | | | | | | | |
|---|---|---|---|---|---|---|---|---|
| 231 | hsa-miR-199b-3p | 105 | 53 | 1.99 | 6.55E-04 | 1.88E-03 | 0.27 | 4.49E-05 | 1.85E-04 |
| 129 | hsa-miR-137 | 68 | 41 | 1.66 | 7.03E-04 | 2.01E-03 | 0.30 | 2.42E-03 | 5.87E-03 |
| 404 | hsa-miR-603 | 127 | 79 | 1.62 | 7.39E-04 | 2.10E-03 | 0.30 | 2.08E-03 | 5.15E-03 |
| 150 | hsa-miR-1233 | 77 | 49 | 1.58 | 7.49E-04 | 2.13E-03 | 0.26 | 6.28E-04 | 1.79E-03 |
| 152 | hsa-miR-124 | 91 | 62 | 1.47 | 7.60E-04 | 2.15E-03 | 0.28 | 2.04E-03 | 5.08E-03 |
| 333 | hsa-miR-29a* | 20 | 33 | 0.60 | 7.66E-04 | 2.15E-03 | 0.71 | 4.62E-04 | 1.39E-03 |
| 517 | hsa-miR-146b-3p | 71 | 44 | 1.63 | 7.65E-04 | 2.15E-03 | 0.29 | 1.46E-03 | 3.78E-03 |
| 123 | hsa-miR-1268 | 330 | 443 | 0.74 | 7.79E-04 | 2.17E-03 | 0.67 | 1.45E-03 | 3.78E-03 |
| 192 | hsa-miR-125a-5p | 192 | 358 | 0.54 | 7.76E-04 | 2.17E-03 | 0.72 | 1.46E-04 | 5.22E-04 |
| 339 | hsa-miR-1202 | 237 | 150 | 1.59 | 7.81E-04 | 2.17E-03 | 0.23 | 4.61E-03 | 1.03E-02 |
| 518 | hsa-miR-187* | 130 | 189 | 0.69 | 7.86E-04 | 2.18E-03 | 0.68 | 3.92E-03 | 8.94E-03 |
| 313 | hsa-miR-19b-2* | 20 | 30 | 0.65 | 8.47E-04 | 2.34E-03 | 0.73 | 4.68E-04 | 1.40E-03 |
| 519 | hsa-miR-30d | 5482 | 9305 | 0.59 | 8.64E-04 | 2.38E-03 | 0.70 | 1.32E-03 | 3.46E-03 |
| 520 | hsa-miR-663 | 292 | 428 | 0.68 | 9.22E-04 | 2.53E-03 | 0.73 | 7.57E-05 | 2.96E-04 |
| 521 | hsa-miR-628-5p | 90 | 52 | 1.72 | 9.29E-04 | 2.54E-03 | 0.27 | 2.46E-03 | 5.91E-03 |
| 399 | hsa-miR-200a | 95 | 53 | 1.79 | 9.71E-04 | 2.65E-03 | 0.27 | 6.57E-04 | 1.85E-03 |
| 299 | hsa-miR-769-3p | 22 | 41 | 0.54 | 1.06E-03 | 2.89E-03 | 0.71 | 8.71E-04 | 2.41E-03 |
| 442 | hsa-miR-335 | 400 | 690 | 0.58 | 1.08E-03 | 2.93E-03 | 0.71 | 2.23E-04 | 7.50E-04 |
| 522 | hsa-miR-1207-3p | 42 | 29 | 1.49 | 1.12E-03 | 3.04E-03 | 0.30 | 1.21E-03 | 3.23E-03 |
| 523 | hsa-miR-591 | 52 | 30 | 1.74 | 1.15E-03 | 3.09E-03 | 0.27 | 3.00E-04 | 9.67E-04 |
| 218 | hsa-miR-432 | 17 | 31 | 0.53 | 1.16E-03 | 3.11E-03 | 0.71 | 1.74E-03 | 4.43E-03 |
| 156 | hsa-miR-92a-1* | 26 | 48 | 0.54 | 1.22E-03 | 3.27E-03 | 0.72 | 1.17E-03 | 3.17E-03 |
| 252 | hsa-miR-548d-5p | 18 | 29 | 0.64 | 1.23E-03 | 3.27E-03 | 0.72 | 1.65E-03 | 4.21E-03 |
| 524 | hsa-miR-302d | 15 | 25 | 0.60 | 1.25E-03 | 3.32E-03 | 0.72 | 2.46E-04 | 8.12E-04 |
| 99 | hsa-miR-1825 | 45 | 69 | 0.65 | 1.27E-03 | 3.38E-03 | 0.69 | 2.43E-03 | 5.87E-03 |
| 356 | hsa-miR-545* | 32 | 20 | 1.63 | 1.31E-03 | 3.46E-03 | 0.27 | 6.49E-04 | 1.84E-03 |
| 216 | hsa-miR-548j | 18 | 37 | 0.48 | 1.35E-03 | 3.54E-03 | 0.73 | 1.75E-04 | 6.00E-04 |
| 461 | hsa-miR-143 | 207 | 290 | 0.71 | 1.39E-03 | 3.65E-03 | 0.73 | 1.08E-03 | 2.94E-03 |
| 525 | hsa-miR-33b* | 142 | 97 | 1.47 | 1.42E-03 | 3.72E-03 | 0.30 | 7.35E-03 | 1.56E-02 |
| 380 | hsa-miR-512-5p | 49 | 32 | 1.53 | 1.43E-03 | 3.72E-03 | 0.27 | 3.33E-04 | 1.05E-03 |
| 294 | hsa-miR-302b | 19 | 30 | 0.62 | 1.45E-03 | 3.78E-03 | 0.73 | 4.45E-04 | 1.35E-03 |
| 117 | hsa-miR-25* | 58 | 98 | 0.60 | 1.48E-03 | 3.83E-03 | 0.72 | 6.55E-04 | 1.85E-03 |
| 526 | hsa-miR-1225-3p | 149 | 115 | 1.29 | 1.48E-03 | 3.83E-03 | 0.31 | 2.62E-03 | 6.22E-03 |
| 256 | hsa-miR-555 | 37 | 26 | 1.41 | 1.53E-03 | 3.93E-03 | 0.31 | 2.64E-03 | 6.22E-03 |
| 285 | hsa-miR-18a* | 167 | 282 | 0.59 | 1.53E-03 | 3.93E-03 | 0.69 | 2.83E-03 | 6.59E-03 |
| 308 | hsa-miR-369-3p | 27 | 40 | 0.68 | 1.54E-03 | 3.93E-03 | 0.71 | 2.64E-03 | 6.22E-03 |
| 204 | hsa-miR-152 | 238 | 322 | 0.74 | 1.56E-03 | 3.97E-03 | 0.70 | 4.74E-03 | 1.05E-02 |
| 381 | hsa-miR-513b | 41 | 29 | 1.44 | 1.56E-03 | 3.97E-03 | 0.29 | 2.67E-03 | 6.27E-03 |
| 527 | hsa-miR-576-5p | 17 | 24 | 0.72 | 1.56E-03 | 3.97E-03 | 0.71 | 2.92E-04 | 9.52E-04 |
| 376 | hsa-miR-1263 | 62 | 42 | 1.46 | 1.60E-03 | 4.04E-03 | 0.30 | 2.62E-03 | 6.22E-03 |
| 528 | hsa-miR-337-3p | 23 | 40 | 0.59 | 1.60E-03 | 4.04E-03 | 0.70 | 2.81E-03 | 6.58E-03 |
| 222 | hsa-miR-491-3p | 81 | 48 | 1.70 | 1.66E-03 | 4.18E-03 | 0.30 | 4.07E-03 | 9.22E-03 |
| 158 | hsa-miR-1306 | 36 | 59 | 0.61 | 1.69E-03 | 4.24E-03 | 0.68 | 2.40E-03 | 5.87E-03 |
| 236 | hsa-miR-186* | 97 | 62 | 1.56 | 1.73E-03 | 4.32E-03 | 0.28 | 3.49E-04 | 1.09E-03 |
| 232 | hsa-miR-208a | 60 | 41 | 1.48 | 1.89E-03 | 4.71E-03 | 0.30 | 1.27E-03 | 3.34E-03 |
| 260 | hsa-miR-615-3p | 33 | 50 | 0.65 | 1.92E-03 | 4.77E-03 | 0.71 | 1.81E-03 | 4.56E-03 |

FIG. 6 cont.

| 291 | hsa-miR-519a* | 153 | 75 | 2.05 | 1.97E-03 | 4.88E-03 | 0.28 | 2.17E-03 | 5.32E-03 |
| --- | --- | --- | --- | --- | --- | --- | --- | --- | --- |
| 346 | hsa-miR-1181 | 173 | 131 | 1.31 | 2.00E-03 | 4.95E-03 | 0.30 | 3.64E-03 | 8.34E-03 |
| 184 | hsa-miR-422a | 143 | 261 | 0.55 | 2.05E-03 | 5.06E-03 | 0.72 | 1.99E-04 | 6.78E-04 |
| 529 | hsa-miR-1183 | 93 | 68 | 1.36 | 2.09E-03 | 5.13E-03 | 0.31 | 2.16E-03 | 5.31E-03 |
| 90 | hsa-miR-92a-2* | 22 | 41 | 0.53 | 2.20E-03 | 5.39E-03 | 0.69 | 3.44E-03 | 7.91E-03 |
| 269 | hsa-miR-567 | 48 | 34 | 1.41 | 2.23E-03 | 5.45E-03 | 0.31 | 1.36E-03 | 3.55E-03 |
| 435 | hsa-miR-222* | 61 | 40 | 1.52 | 2.28E-03 | 5.55E-03 | 0.30 | 1.00E-03 | 2.76E-03 |
| 186 | hsa-miR-525-3p | 59 | 39 | 1.51 | 2.29E-03 | 5.57E-03 | 0.29 | 1.03E-03 | 2.83E-03 |
| 159 | hsa-miR-18b* | 74 | 96 | 0.77 | 2.43E-03 | 5.88E-03 | 0.69 | 8.83E-03 | 1.83E-02 |
| 530 | hsa-miR-507 | 25 | 40 | 0.63 | 2.47E-03 | 5.96E-03 | 0.69 | 5.46E-04 | 1.61E-03 |
| 83 | hsa-miR-483-5p | 169 | 271 | 0.62 | 2.74E-03 | 6.58E-03 | 0.66 | 2.43E-03 | 5.87E-03 |
| 531 | hsa-miR-760 | 44 | 28 | 1.53 | 2.74E-03 | 6.58E-03 | 0.32 | 5.43E-03 | 1.19E-02 |
| 458 | hsa-miR-411* | 50 | 36 | 1.38 | 2.77E-03 | 6.64E-03 | 0.30 | 1.24E-03 | 3.30E-03 |
| 296 | hsa-let-7f-2* | 23 | 37 | 0.63 | 2.89E-03 | 6.89E-03 | 0.69 | 3.33E-03 | 7.72E-03 |
| 532 | hsa-miR-1280 | 3209 | 5589 | 0.57 | 2.89E-03 | 6.89E-03 | 0.66 | 9.19E-03 | 1.89E-02 |
| 378 | hsa-miR-802 | 68 | 42 | 1.62 | 3.09E-03 | 7.35E-03 | 0.30 | 3.40E-03 | 7.85E-03 |
| 273 | hsa-miR-939 | 47 | 66 | 0.71 | 3.18E-03 | 7.54E-03 | 0.68 | 1.83E-03 | 4.60E-03 |
| 424 | hsa-miR-381 | 91 | 59 | 1.54 | 3.26E-03 | 7.70E-03 | 0.29 | 3.94E-03 | 8.96E-03 |
| 310 | hsa-miR-556-3p | 19 | 32 | 0.58 | 3.32E-03 | 7.81E-03 | 0.70 | 2.54E-03 | 6.11E-03 |
| 211 | hsa-miR-519b-5p | 126 | 90 | 1.41 | 3.41E-03 | 7.97E-03 | 0.30 | 8.45E-03 | 1.77E-02 |
| 359 | hsa-miR-421 | 86 | 69 | 1.25 | 3.41E-03 | 7.97E-03 | 0.32 | 4.71E-03 | 1.05E-02 |
| 533 | hsa-miR-342-3p | 3107 | 4954 | 0.63 | 3.41E-03 | 7.97E-03 | 0.68 | 6.67E-03 | 1.44E-02 |
| 534 | hsa-miR-519d | 58 | 33 | 1.76 | 3.44E-03 | 8.01E-03 | 0.28 | 1.91E-03 | 4.79E-03 |
| 480 | hsa-miR-638 | 295 | 473 | 0.62 | 3.53E-03 | 8.20E-03 | 0.67 | 1.78E-03 | 4.51E-03 |
| 275 | hsa-miR-494 | 69 | 125 | 0.55 | 3.58E-03 | 8.28E-03 | 0.71 | 1.92E-03 | 4.81E-03 |
| 535 | hsa-miR-611 | 103 | 61 | 1.70 | 3.58E-03 | 8.28E-03 | 0.27 | 1.07E-02 | 2.18E-02 |
| 536 | hsa-miR-647 | 68 | 46 | 1.46 | 3.77E-03 | 8.68E-03 | 0.30 | 1.08E-03 | 2.94E-03 |
| 537 | hsa-miR-142-5p | 678 | 1431 | 0.47 | 3.97E-03 | 9.13E-03 | 0.70 | 1.20E-03 | 3.23E-03 |
| 538 | hsa-miR-409-5p | 79 | 55 | 1.44 | 4.00E-03 | 9.17E-03 | 0.30 | 1.56E-03 | 4.04E-03 |
| 539 | hsa-miR-532-5p | 203 | 275 | 0.74 | 4.09E-03 | 9.34E-03 | 0.68 | 7.07E-03 | 1.51E-02 |
| 444 | hsa-miR-203 | 25 | 40 | 0.62 | 4.16E-03 | 9.48E-03 | 0.69 | 1.57E-03 | 4.05E-03 |
| 540 | hsa-miR-19a | 2690 | 4351 | 0.62 | 4.29E-03 | 9.75E-03 | 0.68 | 2.90E-03 | 6.74E-03 |
| 220 | hsa-miR-592 | 49 | 32 | 1.52 | 4.35E-03 | 9.86E-03 | 0.30 | 1.63E-03 | 4.17E-03 |
| 541 | hsa-miR-30b | 7814 | 13065 | 0.60 | 4.38E-03 | 9.91E-03 | 0.66 | 7.10E-03 | 1.51E-02 |
| 542 | hsa-miR-138-1* | 95 | 72 | 1.31 | 4.42E-03 | 9.97E-03 | 0.32 | 1.91E-02 | 3.58E-02 |
| 379 | hsa-miR-576-3p | 19 | 30 | 0.63 | 4.57E-03 | 1.03E-02 | 0.69 | 1.27E-03 | 3.34E-03 |
| 383 | hsa-miR-885-5p | 26 | 49 | 0.53 | 4.92E-03 | 1.10E-02 | 0.70 | 1.26E-03 | 3.34E-03 |
| 543 | hsa-miR-1255a | 48 | 34 | 1.43 | 5.02E-03 | 1.12E-02 | 0.35 | 1.91E-02 | 3.58E-02 |
| 178 | hsa-miR-519e | 19 | 28 | 0.67 | 5.07E-03 | 1.13E-02 | 0.68 | 8.14E-03 | 1.71E-02 |
| 278 | hsa-miR-425* | 77 | 98 | 0.79 | 5.07E-03 | 1.13E-02 | 0.67 | 9.50E-03 | 1.95E-02 |
| 544 | hsa-miR-16-1* | 77 | 54 | 1.44 | 5.07E-03 | 1.13E-02 | 0.30 | 4.48E-03 | 1.01E-02 |
| 364 | hsa-miR-1296 | 45 | 32 | 1.41 | 5.15E-03 | 1.14E-02 | 0.32 | 2.75E-03 | 6.45E-03 |
| 60 | hsa-miR-200a* | 63 | 41 | 1.54 | 5.18E-03 | 1.14E-02 | 0.31 | 5.16E-03 | 1.14E-02 |
| 545 | hsa-miR-518a-5p | 169 | 125 | 1.35 | 5.30E-03 | 1.17E-02 | 0.32 | 1.14E-02 | 2.31E-02 |
| 546 | hsa-miR-1258 | 15 | 24 | 0.63 | 5.54E-03 | 1.22E-02 | 0.70 | 2.64E-03 | 6.22E-03 |
| 411 | hsa-miR-337-5p | 43 | 30 | 1.46 | 5.64E-03 | 1.24E-02 | 0.33 | 1.30E-02 | 2.58E-02 |

FIG. 6 cont.

| 547 | hsa-let-7i | 585 | 1184 | 0.49 | 5.77E-03 | 1.26E-02 | 0.66 | 8.18E-03 | 1.72E-02 |
| 481 | hsa-miR-549* | 57 | 40 | 1.43 | 6.12E-03 | 1.33E-02 | 0.33 | 4.90E-03 | 1.08E-02 |
| 365 | hsa-miR-1231 | 86 | 102 | 0.84 | 6.16E-03 | 1.34E-02 | 0.64 | 1.61E-02 | 3.09E-02 |
| 283 | hsa-miR-206 | 19 | 31 | 0.59 | 6.20E-03 | 1.34E-02 | 0.69 | 6.27E-03 | 1.36E-02 |
| 548 | hsa-miR-1 | 25 | 39 | 0.64 | 6.30E-03 | 1.36E-02 | 0.68 | 2.05E-03 | 5.10E-03 |
| 403 | hsa-miR-516b | 37 | 27 | 1.37 | 6.36E-03 | 1.37E-02 | 0.34 | 8.83E-03 | 1.83E-02 |
| 549 | hsa-miR-605 | 27 | 40 | 0.68 | 6.51E-03 | 1.40E-02 | 0.68 | 2.63E-03 | 6.22E-03 |
| 550 | hsa-miR-130b* | 18 | 26 | 0.68 | 6.74E-03 | 1.45E-02 | 0.67 | 4.89E-03 | 1.08E-02 |
| 257 | hsa-miR-520c-3p | 18 | 29 | 0.62 | 7.02E-03 | 1.50E-02 | 0.69 | 2.42E-03 | 5.87E-03 |
| 448 | hsa-miR-132 | 103 | 138 | 0.74 | 7.03E-03 | 1.50E-02 | 0.65 | 2.26E-02 | 4.16E-02 |
| 551 | hsa-miR-493* | 35 | 41 | 0.85 | 7.02E-03 | 1.50E-02 | 0.64 | 1.26E-02 | 2.53E-02 |
| 354 | hsa-miR-30a* | 40 | 52 | 0.77 | 7.47E-03 | 1.59E-02 | 0.65 | 1.30E-02 | 2.58E-02 |
| 292 | hsa-miR-517* | 160 | 118 | 1.36 | 7.57E-03 | 1.60E-02 | 0.31 | 7.80E-03 | 1.64E-02 |
| 552 | hsa-miR-1256 | 61 | 40 | 1.51 | 7.62E-03 | 1.61E-02 | 0.33 | 2.10E-03 | 5.19E-03 |
| 454 | hsa-miR-616 | 28 | 40 | 0.69 | 7.73E-03 | 1.63E-02 | 0.68 | 6.67E-03 | 1.44E-02 |
| 348 | hsa-miR-502-5p | 26 | 36 | 0.73 | 7.80E-03 | 1.64E-02 | 0.67 | 4.35E-03 | 9.82E-03 |
| 553 | hsa-miR-1200 | 78 | 59 | 1.32 | 7.81E-03 | 1.64E-02 | 0.32 | 4.16E-03 | 9.40E-03 |
| 311 | hsa-miR-377 | 123 | 91 | 1.36 | 7.91E-03 | 1.66E-02 | 0.33 | 1.31E-02 | 2.60E-02 |
| 272 | hsa-miR-455-5p | 30 | 40 | 0.75 | 8.26E-03 | 1.73E-02 | 0.68 | 8.64E-03 | 1.80E-02 |
| 397 | hsa-miR-602 | 111 | 83 | 1.34 | 8.34E-03 | 1.74E-02 | 0.31 | 5.48E-03 | 1.19E-02 |
| 300 | hsa-miR-297 | 52 | 76 | 0.68 | 8.36E-03 | 1.74E-02 | 0.70 | 5.39E-03 | 1.18E-02 |
| 554 | hsa-miR-129-3p | 87 | 63 | 1.39 | 8.39E-03 | 1.74E-02 | 0.33 | 1.24E-02 | 2.49E-02 |
| 555 | hsa-miR-424* | 127 | 182 | 0.70 | 8.41E-03 | 1.74E-02 | 0.67 | 1.14E-02 | 2.31E-02 |
| 144 | hsa-miR-181d | 30 | 52 | 0.58 | 8.52E-03 | 1.76E-02 | 0.67 | 6.50E-03 | 1.41E-02 |
| 556 | hsa-miR-1915 | 524 | 905 | 0.58 | 8.56E-03 | 1.76E-02 | 0.66 | 1.27E-03 | 3.34E-03 |
| 417 | hsa-miR-590-5p | 174 | 106 | 1.64 | 8.63E-03 | 1.77E-02 | 0.29 | 2.55E-03 | 6.11E-03 |
| 162 | hsa-miR-301a | 297 | 190 | 1.56 | 8.72E-03 | 1.79E-02 | 0.32 | 3.67E-03 | 8.39E-03 |
| 557 | hsa-miR-623 | 55 | 40 | 1.38 | 9.02E-03 | 1.84E-02 | 0.33 | 4.61E-03 | 1.03E-02 |
| 347 | hsa-miR-155 | 89 | 119 | 0.75 | 9.14E-03 | 1.86E-02 | 0.67 | 1.21E-02 | 2.44E-02 |
| 469 | hsa-miR-519b-3p | 33 | 37 | 0.90 | 9.14E-03 | 1.86E-02 | 0.64 | 6.93E-03 | 1.48E-02 |
| 326 | hsa-miR-518b | 92 | 68 | 1.36 | 9.60E-03 | 1.95E-02 | 0.31 | 1.07E-02 | 2.18E-02 |
| 558 | hsa-let-7f | 441 | 811 | 0.54 | 9.62E-03 | 1.95E-02 | 0.64 | 1.40E-02 | 2.75E-02 |
| 261 | hsa-miR-515-3p | 19 | 31 | 0.62 | 9.85E-03 | 1.99E-02 | 0.68 | 7.48E-03 | 1.58E-02 |
| 478 | hsa-miR-629* | 84 | 132 | 0.64 | 9.87E-03 | 1.99E-02 | 0.67 | 1.36E-02 | 2.69E-02 |
| 451 | hsa-miR-30e* | 44 | 78 | 0.56 | 1.01E-02 | 2.02E-02 | 0.69 | 1.81E-03 | 4.56E-03 |
| 72 | hsa-miR-936 | 70 | 103 | 0.68 | 1.07E-02 | 2.15E-02 | 0.68 | 6.22E-03 | 1.35E-02 |
| 135 | hsa-miR-941 | 100 | 128 | 0.78 | 1.11E-02 | 2.21E-02 | 0.70 | 1.69E-02 | 3.22E-02 |
| 559 | hsa-miR-580 | 43 | 60 | 0.72 | 1.14E-02 | 2.28E-02 | 0.65 | 1.76E-02 | 3.33E-02 |
| 560 | hsa-miR-130a | 1193 | 2083 | 0.57 | 1.15E-02 | 2.29E-02 | 0.67 | 6.75E-03 | 1.45E-02 |
| 561 | hsa-miR-1203 | 199 | 157 | 1.26 | 1.16E-02 | 2.30E-02 | 0.34 | 2.55E-02 | 4.63E-02 |
| 562 | hsa-miR-1295 | 105 | 70 | 1.51 | 1.16E-02 | 2.30E-02 | 0.30 | 1.91E-02 | 3.58E-02 |
| 301 | hsa-miR-1249 | 77 | 97 | 0.79 | 1.16E-02 | 2.30E-02 | 0.61 | 3.16E-02 | 5.59E-02 |
| 563 | hsa-miR-1273 | 100 | 67 | 1.51 | 1.20E-02 | 2.37E-02 | 0.33 | 2.22E-02 | 4.09E-02 |
| 264 | hsa-miR-513c | 24 | 42 | 0.56 | 1.24E-02 | 2.44E-02 | 0.65 | 7.10E-03 | 1.51E-02 |
| 564 | hsa-miR-922 | 144 | 95 | 1.51 | 1.27E-02 | 2.50E-02 | 0.33 | 1.55E-02 | 3.01E-02 |
| 388 | hsa-miR-552 | 31 | 46 | 0.68 | 1.33E-02 | 2.60E-02 | 0.68 | 8.60E-03 | 1.80E-02 |

FIG. 6 cont.

| | | | | | | | | | |
|---|---|---|---|---|---|---|---|---|---|
| 473 | hsa-miR-1234 | 478 | 334 | 1.43 | 1.33E-02 | 2.61E-02 | 0.35 | 3.41E-02 | 5.96E-02 |
| 89 | hsa-miR-1538 | 78 | 102 | 0.76 | 1.34E-02 | 2.62E-02 | 0.63 | 3.72E-02 | 6.46E-02 |
| 5 | hsa-miR-106a | 6819 | 4383 | 1.56 | 1.36E-02 | 2.65E-02 | 0.33 | 1.07E-02 | 2.18E-02 |
| 316 | hsa-miR-652 | 1093 | 1711 | 0.64 | 1.37E-02 | 2.65E-02 | 0.65 | 1.77E-02 | 3.34E-02 |
| 238 | hsa-miR-139-5p | 127 | 100 | 1.26 | 1.38E-02 | 2.66E-02 | 0.34 | 8.99E-03 | 1.85E-02 |
| 565 | hsa-miR-181a | 480 | 893 | 0.54 | 1.38E-02 | 2.66E-02 | 0.67 | 5.27E-03 | 1.16E-02 |
| 363 | hsa-miR-133b | 28 | 44 | 0.64 | 1.40E-02 | 2.70E-02 | 0.67 | 1.02E-02 | 2.08E-02 |
| 373 | hsa-miR-410 | 70 | 61 | 1.15 | 1.42E-02 | 2.73E-02 | 0.35 | 1.56E-02 | 3.01E-02 |
| 276 | hsa-miR-568 | 66 | 53 | 1.25 | 1.43E-02 | 2.74E-02 | 0.35 | 2.21E-02 | 4.09E-02 |
| 314 | hsa-miR-99a | 110 | 161 | 0.68 | 1.49E-02 | 2.85E-02 | 0.65 | 1.31E-02 | 2.61E-02 |
| 566 | hsa-miR-223* | 37 | 26 | 1.41 | 1.49E-02 | 2.85E-02 | 0.34 | 1.44E-02 | 2.82E-02 |
| 567 | hsa-miR-582-3p | 69 | 89 | 0.77 | 1.53E-02 | 2.92E-02 | 0.66 | 1.80E-02 | 3.39E-02 |
| 219 | hsa-miR-18b | 194 | 152 | 1.28 | 1.56E-02 | 2.97E-02 | 0.36 | 2.60E-02 | 4.70E-02 |
| 568 | hsa-miR-520d-5p | 52 | 64 | 0.82 | 1.63E-02 | 3.10E-02 | 0.64 | 4.07E-02 | 6.89E-02 |
| 329 | hsa-miR-509-3p | 18 | 30 | 0.60 | 1.64E-02 | 3.10E-02 | 0.66 | 2.32E-02 | 4.26E-02 |
| 386 | hsa-miR-523* | 130 | 87 | 1.48 | 1.64E-02 | 3.10E-02 | 0.33 | 1.56E-02 | 3.01E-02 |
| 223 | hsa-miR-942 | 24 | 41 | 0.58 | 1.70E-02 | 3.20E-02 | 0.68 | 8.67E-03 | 1.80E-02 |
| 258 | hsa-miR-29a | 691 | 1006 | 0.69 | 1.75E-02 | 3.29E-02 | 0.64 | 1.37E-02 | 2.69E-02 |
| 569 | hsa-miR-598 | 55 | 39 | 1.41 | 1.77E-02 | 3.32E-02 | 0.35 | 1.97E-02 | 3.66E-02 |
| 570 | hsa-miR-193a-3p | 125 | 95 | 1.31 | 1.77E-02 | 3.32E-02 | 0.33 | 4.83E-02 | 8.00E-02 |
| 571 | hsa-miR-511 | 33 | 43 | 0.77 | 1.82E-02 | 3.40E-02 | 0.65 | 2.62E-02 | 4.73E-02 |
| 572 | hsa-miR-1911* | 89 | 62 | 1.44 | 1.84E-02 | 3.42E-02 | 0.33 | 1.64E-02 | 3.14E-02 |
| 573 | hsa-miR-21* | 89 | 69 | 1.30 | 1.84E-02 | 3.43E-02 | 0.34 | 3.34E-02 | 5.86E-02 |
| 387 | hsa-miR-544 | 35 | 23 | 1.55 | 1.91E-02 | 3.55E-02 | 0.34 | 1.84E-02 | 3.45E-02 |
| 250 | hsa-miR-10b* | 53 | 41 | 1.30 | 1.94E-02 | 3.59E-02 | 0.35 | 1.27E-02 | 2.54E-02 |
| 574 | hsa-miR-675 | 140 | 183 | 0.77 | 2.02E-02 | 3.72E-02 | 0.63 | 1.43E-02 | 2.80E-02 |
| 575 | hsa-miR-524-5p | 56 | 45 | 1.26 | 2.02E-02 | 3.73E-02 | 0.35 | 2.98E-02 | 5.31E-02 |
| 422 | hsa-miR-516a-5p | 187 | 132 | 1.41 | 2.09E-02 | 3.85E-02 | 0.32 | 3.21E-02 | 5.68E-02 |
| 576 | hsa-miR-182* | 46 | 35 | 1.32 | 2.20E-02 | 4.05E-02 | 0.34 | 1.51E-02 | 2.93E-02 |
| 577 | hsa-miR-486-3p | 278 | 369 | 0.75 | 2.22E-02 | 4.07E-02 | 0.64 | 3.82E-02 | 6.58E-02 |
| 171 | hsa-miR-181b | 52 | 85 | 0.61 | 2.29E-02 | 4.18E-02 | 0.65 | 2.49E-02 | 4.56E-02 |
| 578 | hsa-miR-367 | 81 | 64 | 1.26 | 2.29E-02 | 4.18E-02 | 0.35 | 2.66E-02 | 4.78E-02 |
| 579 | hsa-miR-944 | 29 | 41 | 0.71 | 2.30E-02 | 4.19E-02 | 0.67 | 4.06E-02 | 6.88E-02 |
| 248 | hsa-miR-512-3p | 42 | 45 | 0.93 | 2.32E-02 | 4.22E-02 | 0.59 | 5.58E-02 | 9.08E-02 |
| 350 | hsa-miR-433 | 93 | 115 | 0.81 | 2.33E-02 | 4.22E-02 | 0.63 | 4.22E-02 | 7.12E-02 |
| 580 | hsa-miR-561 | 43 | 31 | 1.41 | 2.34E-02 | 4.23E-02 | 0.35 | 1.18E-02 | 2.38E-02 |
| 581 | hsa-miR-486-5p | 36611 | 47370 | 0.77 | 2.37E-02 | 4.27E-02 | 0.62 | 7.15E-02 | 1.11E-01 |
| 582 | hsa-miR-15a* | 109 | 77 | 1.41 | 2.39E-02 | 4.31E-02 | 0.33 | 3.28E-02 | 5.78E-02 |
| 583 | hsa-miR-506 | 42 | 53 | 0.79 | 2.40E-02 | 4.31E-02 | 0.63 | 3.59E-02 | 6.25E-02 |
| 146 | hsa-miR-181a-2* | 103 | 117 | 0.88 | 2.48E-02 | 4.44E-02 | 0.64 | 2.51E-02 | 4.58E-02 |
| 584 | hsa-miR-122* | 58 | 80 | 0.73 | 2.48E-02 | 4.44E-02 | 0.64 | 2.57E-02 | 4.65E-02 |
| 368 | hsa-miR-572 | 62 | 41 | 1.53 | 2.55E-02 | 4.56E-02 | 0.35 | 1.40E-02 | 2.75E-02 |
| 405 | hsa-miR-140-3p | 20097 | 28711 | 0.70 | 2.63E-02 | 4.68E-02 | 0.63 | 3.96E-02 | 6.79E-02 |
| 456 | hsa-miR-155* | 53 | 41 | 1.28 | 2.64E-02 | 4.68E-02 | 0.35 | 1.76E-02 | 3.33E-02 |
| 585 | hsa-miR-199a-3p | 108 | 84 | 1.29 | 2.63E-02 | 4.68E-02 | 0.34 | 1.66E-02 | 3.18E-02 |
| 367 | hsa-miR-1269 | 42 | 54 | 0.77 | 2.65E-02 | 4.70E-02 | 0.64 | 2.92E-02 | 5.22E-02 |

FIG. 6 cont.

| 586 | hsa-miR-100* | 69 | 52 | 1.32 | 2.68E-02 | 4.73E-02 | 0.34 | 3.62E-02 | 6.29E-02 |
| --- | --- | --- | --- | --- | --- | --- | --- | --- | --- |
| 587 | hsa-miR-1537 | 36 | 26 | 1.38 | 2.75E-02 | 4.84E-02 | 0.36 | 2.66E-02 | 4.78E-02 |
| 588 | hsa-miR-889 | 36 | 50 | 0.72 | 2.77E-02 | 4.88E-02 | 0.64 | 4.90E-02 | 8.06E-02 |
| 466 | hsa-miR-148b | 541 | 761 | 0.71 | 2.83E-02 | 4.97E-02 | 0.64 | 1.44E-02 | 2.82E-02 |
| 172 | hsa-miR-505* | 184 | 247 | 0.74 | 2.84E-02 | 4.98E-02 | 0.67 | 1.49E-02 | 2.90E-02 |
| 357 | hsa-miR-485-3p | 61 | 91 | 0.67 | 2.85E-02 | 4.98E-02 | 0.65 | 2.10E-02 | 3.91E-02 |
| 366 | hsa-miR-219-1-3p | 28 | 19 | 1.48 | 2.88E-02 | 5.03E-02 | 0.35 | 2.53E-02 | 4.60E-02 |
| 463 | hsa-miR-195 | 592 | 726 | 0.82 | 2.89E-02 | 5.03E-02 | 0.64 | 5.21E-02 | 8.52E-02 |
| 462 | hsa-miR-520d-3p | 17 | 26 | 0.64 | 2.94E-02 | 5.11E-02 | 0.67 | 4.90E-02 | 8.06E-02 |
| 243 | hsa-miR-589 | 77 | 117 | 0.66 | 3.06E-02 | 5.29E-02 | 0.70 | 2.14E-02 | 3.97E-02 |
| 254 | hsa-miR-1909 | 111 | 121 | 0.92 | 3.07E-02 | 5.29E-02 | 0.61 | 4.90E-02 | 8.06E-02 |
| 79 | hsa-miR-18a | 1143 | 834 | 1.37 | 3.31E-02 | 5.69E-02 | 0.34 | 4.63E-02 | 7.70E-02 |
| 277 | hsa-miR-34c-5p | 51 | 40 | 1.27 | 3.46E-02 | 5.93E-02 | 0.37 | 3.37E-02 | 5.90E-02 |
| 349 | hsa-miR-562 | 34 | 25 | 1.33 | 3.48E-02 | 5.95E-02 | 0.37 | 3.79E-02 | 6.55E-02 |
| 369 | hsa-miR-374b | 560 | 301 | 1.86 | 3.74E-02 | 6.38E-02 | 0.36 | 1.75E-02 | 3.32E-02 |
| 402 | hsa-miR-296-3p | 57 | 75 | 0.76 | 3.90E-02 | 6.62E-02 | 0.60 | 7.73E-02 | 1.18E-01 |
| 396 | hsa-miR-504 | 36 | 46 | 0.79 | 4.00E-02 | 6.78E-02 | 0.61 | 4.56E-02 | 7.59E-02 |
| 233 | hsa-miR-518e* | 141 | 98 | 1.44 | 4.03E-02 | 6.81E-02 | 0.34 | 4.28E-02 | 7.18E-02 |
| 467 | hsa-miR-448 | 89 | 66 | 1.36 | 4.15E-02 | 7.01E-02 | 0.35 | 4.28E-02 | 7.18E-02 |
| 324 | hsa-miR-526b | 44 | 57 | 0.77 | 4.49E-02 | 7.54E-02 | 0.64 | 3.84E-02 | 6.60E-02 |
| 208 | hsa-miR-32* | 28 | 24 | 1.13 | 4.53E-02 | 7.58E-02 | 0.40 | 6.84E-02 | 1.07E-01 |
| 460 | hsa-miR-548a-3p | 73 | 56 | 1.28 | 4.78E-02 | 7.98E-02 | 0.39 | 3.77E-02 | 6.52E-02 |
| 246 | hsa-miR-185* | 27 | 35 | 0.77 | 4.81E-02 | 8.02E-02 | 0.62 | 4.16E-02 | 7.03E-02 |
| 221 | hsa-miR-92a | 11492 | 16684 | 0.69 | 4.92E-02 | 8.17E-02 | 0.60 | 6.92E-02 | 1.08E-01 |
| 372 | hsa-miR-520b | 26 | 35 | 0.74 | 5.05E-02 | 8.35E-02 | 0.64 | 3.57E-02 | 6.23E-02 |
| 327 | hsa-miR-765 | 46 | 78 | 0.59 | 5.15E-02 | 8.50E-02 | 0.64 | 2.27E-02 | 4.18E-02 |
| 447 | hsa-miR-516a-3p | 23 | 36 | 0.64 | 5.19E-02 | 8.55E-02 | 0.63 | 4.31E-02 | 7.22E-02 |
| 471 | hsa-miR-146a* | 76 | 55 | 1.37 | 5.28E-02 | 8.68E-02 | 0.38 | 7.67E-02 | 1.18E-01 |
| 119 | hsa-miR-382 | 25 | 48 | 0.51 | 5.48E-02 | 8.90E-02 | 0.63 | 9.84E-02 | 1.45E-01 |
| 418 | hsa-miR-101* | 75 | 62 | 1.22 | 5.69E-02 | 9.20E-02 | 0.36 | 6.83E-02 | 1.07E-01 |
| 401 | hsa-miR-202* | 66 | 60 | 1.10 | 5.71E-02 | 9.20E-02 | 0.40 | 7.00E-02 | 1.09E-01 |
| 398 | hsa-miR-325 | 54 | 68 | 0.79 | 6.02E-02 | 9.63E-02 | 0.63 | 6.49E-02 | 1.03E-01 |
| 433 | hsa-miR-522 | 21 | 25 | 0.82 | 6.18E-02 | 9.82E-02 | 0.62 | 5.12E-02 | 8.37E-02 |
| 475 | hsa-miR-451 | 1201 | 933 | 1.29 | 6.18E-02 | 9.82E-02 | 0.37 | 6.47E-02 | 1.03E-01 |
| 344 | hsa-miR-671-3p | 40 | 61 | 0.65 | 6.45E-02 | 1.02E-01 | 0.64 | 5.77E-02 | 9.37E-02 |
| 374 | hsa-miR-1224-5p | 34 | 41 | 0.83 | 6.59E-02 | 1.04E-01 | 0.59 | 6.44E-02 | 1.03E-01 |
| 395 | hsa-miR-1299 | 37 | 26 | 1.44 | 6.61E-02 | 1.04E-01 | 0.41 | 9.12E-02 | 1.36E-01 |
| 428 | hsa-miR-495 | 71 | 56 | 1.29 | 6.62E-02 | 1.04E-01 | 0.38 | 7.54E-02 | 1.16E-01 |
| 266 | hsa-miR-133a | 46 | 30 | 1.55 | 6.78E-02 | 1.06E-01 | 0.39 | 6.79E-02 | 1.07E-01 |
| 287 | hsa-miR-184 | 31 | 36 | 0.86 | 7.45E-02 | 1.15E-01 | 0.60 | 6.75E-02 | 1.07E-01 |
| 353 | hsa-miR-1288 | 65 | 50 | 1.31 | 7.45E-02 | 1.15E-01 | 0.37 | 4.73E-02 | 7.85E-02 |
| 322 | hsa-miR-411 | 52 | 44 | 1.19 | 7.94E-02 | 1.21E-01 | 0.39 | 5.82E-02 | 9.43E-02 |
| 434 | hsa-miR-876-5p | 37 | 41 | 0.90 | 8.17E-02 | 1.24E-01 | 0.61 | 8.04E-02 | 1.23E-01 |
| 465 | hsa-miR-624* | 34 | 54 | 0.62 | 8.33E-02 | 1.26E-01 | 0.64 | 5.95E-02 | 9.61E-02 |
| 358 | hsa-let-7a* | 22 | 31 | 0.71 | 8.50E-02 | 1.29E-01 | 0.62 | 1.10E-01 | 1.59E-01 |
| 360 | hsa-miR-122 | 30 | 46 | 0.66 | 9.19E-02 | 1.38E-01 | 0.61 | 6.31E-02 | 1.02E-01 |

FIG. 6 cont.

| | | | | | | | | | |
|---|---|---|---|---|---|---|---|---|---|
| 431 | hsa-miR-125b-1* | 21 | 34 | 0.62 | 9.36E-02 | 1.40E-01 | 0.61 | 6.44E-02 | 1.03E-01 |
| 125 | hsa-miR-103 | 8148 | 5487 | 1.49 | 9.51E-02 | 1.42E-01 | 0.39 | 1.11E-01 | 1.60E-01 |
| 297 | hsa-miR-660 | 479 | 351 | 1.36 | 9.78E-02 | 1.45E-01 | 0.38 | 9.18E-02 | 1.37E-01 |
| 449 | hsa-miR-374a* | 37 | 31 | 1.18 | 9.91E-02 | 1.47E-01 | 0.40 | 9.88E-02 | 1.45E-01 |
| 482 | hsa-miR-136* | 56 | 41 | 1.38 | 1.01E-01 | 1.50E-01 | 0.38 | 9.63E-02 | 1.43E-01 |
| 312 | hsa-miR-148a | 992 | 826 | 1.20 | 1.08E-01 | 1.59E-01 | 0.40 | 1.21E-01 | 1.74E-01 |
| 474 | hsa-miR-1469 | 155 | 196 | 0.79 | 1.13E-01 | 1.64E-01 | 0.61 | 7.08E-02 | 1.10E-01 |
| 423 | hsa-miR-377* | 14 | 19 | 0.77 | 1.19E-01 | 1.72E-01 | 0.59 | 5.82E-02 | 9.43E-02 |
| 440 | hsa-miR-1264 | 34 | 43 | 0.78 | 1.20E-01 | 1.72E-01 | 0.63 | 6.47E-02 | 1.03E-01 |
| 400 | hsa-miR-100 | 133 | 241 | 0.55 | 1.23E-01 | 1.76E-01 | 0.59 | 7.85E-02 | 1.20E-01 |
| 281 | hsa-let-7b* | 27 | 32 | 0.85 | 1.25E-01 | 1.78E-01 | 0.60 | 1.48E-01 | 2.06E-01 |
| 352 | hsa-miR-140-5p | 31 | 34 | 0.93 | 1.37E-01 | 1.92E-01 | 0.59 | 1.53E-01 | 2.12E-01 |
| 293 | hsa-miR-601 | 21 | 28 | 0.73 | 1.43E-01 | 2.01E-01 | 0.61 | 1.26E-01 | 1.80E-01 |
| 413 | hsa-miR-105* | 24 | 29 | 0.84 | 1.43E-01 | 2.01E-01 | 0.59 | 8.88E-02 | 1.33E-01 |
| 420 | hsa-miR-574-5p | 718 | 477 | 1.51 | 1.48E-01 | 2.07E-01 | 0.37 | 1.39E-01 | 1.96E-01 |
| 298 | hsa-miR-644 | 34 | 40 | 0.86 | 1.49E-01 | 2.08E-01 | 0.60 | 1.56E-01 | 2.15E-01 |
| 410 | hsa-miR-1204 | 30 | 35 | 0.87 | 1.55E-01 | 2.15E-01 | 0.59 | 1.80E-01 | 2.44E-01 |
| 436 | hsa-miR-892b | 36 | 50 | 0.72 | 1.56E-01 | 2.15E-01 | 0.60 | 1.14E-01 | 1.64E-01 |
| 455 | hsa-miR-620 | 25 | 29 | 0.86 | 1.56E-01 | 2.16E-01 | 0.59 | 1.29E-01 | 1.84E-01 |
| 202 | hsa-miR-99b | 175 | 211 | 0.83 | 1.58E-01 | 2.18E-01 | 0.62 | 1.44E-01 | 2.02E-01 |
| 382 | hsa-miR-593 | 20 | 26 | 0.76 | 1.64E-01 | 2.26E-01 | 0.59 | 1.98E-01 | 2.65E-01 |
| 340 | hsa-miR-378* | 53 | 63 | 0.85 | 1.70E-01 | 2.32E-01 | 0.59 | 1.46E-01 | 2.04E-01 |
| 441 | hsa-miR-1243 | 57 | 39 | 1.48 | 1.86E-01 | 2.51E-01 | 0.40 | 1.92E-01 | 2.59E-01 |
| 213 | hsa-let-7d | 2148 | 2764 | 0.78 | 1.87E-01 | 2.53E-01 | 0.58 | 1.74E-01 | 2.38E-01 |
| 479 | hsa-miR-548l | 15 | 18 | 0.82 | 1.92E-01 | 2.58E-01 | 0.60 | 2.26E-01 | 2.98E-01 |
| 419 | hsa-miR-624 | 54 | 72 | 0.74 | 1.94E-01 | 2.60E-01 | 0.60 | 1.73E-01 | 2.37E-01 |
| 470 | hsa-miR-1292 | 61 | 68 | 0.90 | 1.97E-01 | 2.63E-01 | 0.58 | 2.14E-01 | 2.84E-01 |
| 188 | hsa-miR-99a* | 44 | 54 | 0.81 | 2.00E-01 | 2.67E-01 | 0.57 | 2.45E-01 | 3.20E-01 |
| 472 | hsa-miR-29c* | 19 | 25 | 0.76 | 2.11E-01 | 2.82E-01 | 0.58 | 1.50E-01 | 2.07E-01 |
| 446 | hsa-miR-1298 | 43 | 38 | 1.11 | 2.16E-01 | 2.87E-01 | 0.43 | 2.05E-01 | 2.74E-01 |
| 279 | hsa-miR-770-5p | 60 | 63 | 0.96 | 2.20E-01 | 2.91E-01 | 0.58 | 2.60E-01 | 3.36E-01 |
| 13 | hsa-miR-17 | 6278 | 5211 | 1.20 | 2.25E-01 | 2.96E-01 | 0.41 | 2.46E-01 | 3.22E-01 |
| 321 | hsa-miR-1271 | 171 | 172 | 1.00 | 2.31E-01 | 3.02E-01 | 0.52 | 3.37E-01 | 4.21E-01 |
| 377 | hsa-miR-1293 | 31 | 40 | 0.77 | 2.31E-01 | 3.02E-01 | 0.59 | 2.58E-01 | 3.35E-01 |
| 450 | hsa-miR-1322 | 100 | 118 | 0.85 | 2.42E-01 | 3.14E-01 | 0.59 | 2.55E-01 | 3.31E-01 |
| 425 | hsa-miR-26b | 341 | 277 | 1.23 | 2.86E-01 | 3.66E-01 | 0.42 | 2.60E-01 | 3.36E-01 |
| 315 | hsa-miR-200c | 94 | 103 | 0.91 | 3.09E-01 | 3.90E-01 | 0.57 | 3.33E-01 | 4.18E-01 |
| 53 | hsa-miR-93 | 4033 | 3036 | 1.33 | 3.11E-01 | 3.92E-01 | 0.42 | 3.41E-01 | 4.25E-01 |
| 67 | hsa-miR-144 | 2310 | 1810 | 1.28 | 3.13E-01 | 3.93E-01 | 0.42 | 3.29E-01 | 4.15E-01 |
| 438 | hsa-miR-559 | 48 | 38 | 1.26 | 3.25E-01 | 4.06E-01 | 0.43 | 3.28E-01 | 4.13E-01 |
| 453 | hsa-miR-384 | 64 | 55 | 1.17 | 3.31E-01 | 4.12E-01 | 0.42 | 3.86E-01 | 4.73E-01 |
| 30 | hsa-miR-106b | 10828 | 14005 | 0.77 | 3.32E-01 | 4.13E-01 | 0.55 | 3.55E-01 | 4.40E-01 |
| 240 | hsa-miR-503 | 242 | 225 | 1.08 | 3.46E-01 | 4.28E-01 | 0.40 | 4.07E-01 | 4.94E-01 |
| 426 | hsa-miR-1254 | 122 | 102 | 1.19 | 3.49E-01 | 4.31E-01 | 0.40 | 4.50E-01 | 5.33E-01 |
| 335 | hsa-miR-609 | 17 | 21 | 0.82 | 3.55E-01 | 4.37E-01 | 0.58 | 3.68E-01 | 4.53E-01 |
| 334 | hsa-miR-15b* | 75 | 87 | 0.86 | 3.72E-01 | 4.58E-01 | 0.58 | 3.02E-01 | 3.84E-01 |

FIG. 6 cont.

| | | | | | | | | |
|---|---|---|---|---|---|---|---|---|
| 464 | hsa-miR-1282 | 14 | 16 | 0.83 | 3.85E-01 | 4.69E-01 | 0.58 | 4.01E-01 | 4.88E-01 |
| 484 | hsa-miR-1294 | 22 | 21 | 1.07 | 3.87E-01 | 4.70E-01 | 0.47 | 4.22E-01 | 5.07E-01 |
| 355 | hsa-miR-1238 | 35 | 41 | 0.86 | 3.95E-01 | 4.77E-01 | 0.55 | 4.41E-01 | 5.25E-01 |
| 320 | hsa-miR-19a* | 41 | 34 | 1.22 | 4.16E-01 | 4.95E-01 | 0.46 | 4.85E-01 | 5.67E-01 |
| 476 | hsa-miR-190b | 18 | 18 | 0.95 | 4.27E-01 | 5.05E-01 | 0.56 | 4.16E-01 | 5.03E-01 |
| 415 | hsa-miR-129-5p | 32 | 28 | 1.12 | 4.55E-01 | 5.33E-01 | 0.44 | 5.06E-01 | 5.86E-01 |
| 445 | hsa-miR-198 | 52 | 54 | 0.96 | 4.97E-01 | 5.75E-01 | 0.53 | 5.27E-01 | 6.06E-01 |
| 430 | hsa-miR-30d* | 51 | 39 | 1.32 | 5.25E-01 | 6.02E-01 | 0.45 | 5.56E-01 | 6.33E-01 |
| 483 | hsa-miR-873 | 75 | 84 | 0.89 | 5.28E-01 | 6.04E-01 | 0.51 | 5.56E-01 | 6.33E-01 |
| 225 | hsa-miR-1914 | 57 | 52 | 1.09 | 5.87E-01 | 6.61E-01 | 0.47 | 6.06E-01 | 6.77E-01 |
| 97 | hsa-miR-551a | 64 | 65 | 0.98 | 6.19E-01 | 6.88E-01 | 0.49 | 6.93E-01 | 7.54E-01 |
| 457 | hsa-miR-655 | 32 | 37 | 0.86 | 6.38E-01 | 7.05E-01 | 0.53 | 6.67E-01 | 7.29E-01 |
| 226 | hsa-miR-126 | 1882 | 1454 | 1.29 | 7.31E-01 | 7.82E-01 | 0.46 | 7.37E-01 | 7.89E-01 |
| 421 | hsa-miR-150 | 1318 | 1675 | 0.79 | 7.46E-01 | 7.93E-01 | 0.51 | 7.42E-01 | 7.91E-01 |
| 58 | hsa-miR-101 | 583 | 568 | 1.03 | 8.04E-01 | 8.41E-01 | 0.48 | 8.05E-01 | 8.40E-01 |
| 27 | hsa-miR-17* | 564 | 584 | 0.97 | 8.58E-01 | 8.87E-01 | 0.50 | 8.66E-01 | 8.92E-01 |
| 407 | hsa-miR-195* | 72 | 69 | 1.04 | 8.70E-01 | 8.97E-01 | 0.47 | 8.77E-01 | 9.02E-01 |

FIG. 6 cont.

| Figure 7 | | | | | | |
|---|---|---|---|---|---|---|
| Signature | SEQ ID-NO | miRNA | Accuracy | Specificity | Sensitivity | Bal. Acc. |
| SNC-797 | 35, 11 | hsa-miR-197, hsa-let-7d* | 89.8% | 86.1% | 98.8% | 92.4% |
| SNC-798 | 35, 4 | hsa-miR-197, hsa-miR-361-5p | 86.3% | 81.2% | 98.4% | 89.8% |
| SNC-799 | 35, 12 | hsa-miR-197, hsa-miR-934 | 91.4% | 88.2% | 98.9% | 93.6% |
| SNC-800 | 35, 1 | hsa-miR-197, hsa-miR-1251 | 93.9% | 91.4% | 99.8% | 95.6% |
| SNC-801 | 35, 6 | hsa-miR-197, hsa-miR-640 | 87.0% | 82.3% | 98.2% | 90.2% |
| SNC-802 | 35, 43 | hsa-miR-197, hsa-miR-34a* | 93.6% | 92.3% | 96.8% | 94.5% |
| SNC-803 | 35, 50 | hsa-miR-197, hsa-miR-720 | 90.3% | 86.2% | 100.0% | 93.1% |
| SNC-804 | 35, 121 | hsa-miR-197, hsa-miR-423-5p | 85.4% | 79.5% | 99.1% | 89.3% |
| SNC-805 | 35, 111 | hsa-miR-197, hsa-miR-1324 | 93.6% | 90.9% | 100.0% | 95.5% |
| SNC-806 | 35, 390 | hsa-miR-197, hsa-miR-320d | 84.8% | 79.8% | 96.6% | 88.2% |
| SNC-807 | 35, 342 | hsa-miR-197, hsa-miR-151-5p | 87.0% | 82.3% | 97.9% | 90.1% |
| SNC-808 | 35, 485 | hsa-miR-197, hsa-miR-744 | 87.2% | 81.8% | 99.8% | 90.8% |
| SNC-809 | 35, 136 | hsa-miR-197, hsa-miR-33b | 85.7% | 81.3% | 96.1% | 88.7% |
| SNC-810 | 35, 179 | hsa-miR-197, hsa-miR-455-3p | 90.7% | 88.3% | 96.4% | 92.3% |
| SNC-811 | 35, 251 | hsa-miR-197, hsa-miR-32 | 86.9% | 82.3% | 97.5% | 89.9% |
| SNC-812 | 35, 44 | hsa-miR-197, hsa-miR-214* | 91.1% | 88.4% | 97.3% | 92.9% |
| SNC-813 | 35, 55 | hsa-miR-197, hsa-miR-483-3p | 90.2% | 86.3% | 99.5% | 92.9% |
| SNC-814 | 35, 98 | hsa-miR-197, hsa-miR-891b | 88.5% | 83.6% | 100.0% | 91.8% |
| SNC-815 | 35, 94 | hsa-miR-197, hsa-miR-219-2-3p | 93.5% | 91.7% | 97.9% | 94.8% |
| SNC-816 | 11, 4 | hsa-let-7d*, hsa-miR-361-5p | 74.6% | 73.2% | 78.0% | 75.6% |
| SNC-817 | 11, 12 | hsa-let-7d*, hsa-miR-934 | 83.0% | 79.8% | 90.5% | 85.2% |

| | | | | | | |
|---|---|---|---|---|---|---|
| SNC-818 | 11, 1 | hsa-let-7d*, hsa-miR-1251 | 84.0% | 79.4% | 94.8% | 87.1% |
| SNC-819 | 11, 6 | hsa-let-7d*, hsa-miR-640 | 81.1% | 80.6% | 82.1% | 81.4% |
| SNC-820 | 11, 43 | hsa-let-7d*, hsa-miR-34a* | 89.6% | 87.7% | 94.1% | 90.9% |
| SNC-821 | 11, 50 | hsa-let-7d*, hsa-miR-720 | 83.1% | 76.7% | 98.2% | 87.5% |
| SNC-822 | 11, 121 | hsa-let-7d*, hsa-miR-423-5p | 89.9% | 86.2% | 98.8% | 92.5% |
| SNC-823 | 11, 111 | hsa-let-7d*, hsa-miR-1324 | 86.3% | 83.9% | 91.8% | 87.9% |
| SNC-824 | 11, 390 | hsa-let-7d*, hsa-miR-320d | 80.4% | 73.6% | 96.6% | 85.1% |
| SNC-825 | 11, 342 | hsa-let-7d*, hsa-miR-151-5p | 79.9% | 73.0% | 96.3% | 84.6% |
| SNC-826 | 11, 485 | hsa-let-7d*, hsa-miR-744 | 84.8% | 79.4% | 97.5% | 88.4% |
| SNC-827 | 11, 136 | hsa-let-7d*, hsa-miR-33b | 74.5% | 68.9% | 87.5% | 78.2% |
| SNC-828 | 11, 179 | hsa-let-7d*, hsa-miR-455-3p | 79.6% | 72.5% | 96.3% | 84.4% |
| SNC-829 | 11, 251 | hsa-let-7d*, hsa-miR-32 | 84.7% | 80.1% | 95.5% | 87.8% |
| SNC-830 | 11, 44 | hsa-let-7d*, hsa-miR-214* | 88.8% | 84.0% | 100.0% | 92.0% |
| SNC-831 | 11, 55 | hsa-let-7d*, hsa-miR-483-3p | 82.3% | 79.6% | 88.6% | 84.1% |
| SNC-832 | 11, 98 | hsa-let-7d*, hsa-miR-891b | 78.0% | 74.2% | 87.0% | 80.6% |
| SNC-833 | 11, 94 | hsa-let-7d*, hsa-miR-219-2-3p | 88.4% | 85.0% | 96.4% | 90.7% |
| SNC-834 | 4, 12 | hsa-miR-361-5p, hsa-miR-934 | 76.9% | 74.7% | 82.1% | 78.4% |
| SNC-835 | 4, 1 | hsa-miR-361-5p, hsa-miR-1251 | 80.6% | 76.4% | 90.5% | 83.4% |
| SNC-836 | 4, 6 | hsa-miR-361-5p, hsa-miR-640 | 75.3% | 73.6% | 79.3% | 76.5% |
| SNC-837 | 4, 43 | hsa-miR-361-5p, hsa-miR-34a* | 90.5% | 89.2% | 93.4% | 91.3% |
| SNC-838 | 4, 50 | hsa-miR-361-5p, hsa-miR-720 | 76.9% | 70.9% | 90.9% | 80.9% |
| SNC-839 | 4, 121 | hsa-miR-361-5p, hsa-miR-423-5p | 80.8% | 73.2% | 98.8% | 86.0% |
| SNC-840 | 4, 111 | hsa-miR-361-5p, hsa-miR-1324 | 74.5% | 69.4% | 86.6% | 78.0% |
| SNC-841 | 4, 390 | hsa-miR-361-5p, hsa-miR-320d | 72.4% | 66.1% | 87.1% | 76.6% |
| SNC-842 | 4, 342 | hsa-miR-361-5p, hsa-miR-151-5p | 68.9% | 61.4% | 86.6% | 74.0% |
| SNC-843 | 4, 485 | hsa-miR-361-5p, hsa-miR-744 | 66.5% | 55.0% | 93.8% | 74.4% |
| SNC-844 | 4, 136 | hsa-miR-361-5p, hsa-miR-33b | 69.2% | 59.2% | 92.9% | 76.0% |
| SNC-845 | 4, 179 | hsa-miR-361-5p, hsa-miR-455-3p | 76.4% | 67.9% | 96.4% | 82.2% |
| SNC-846 | 4, 251 | hsa-miR-361-5p, hsa-miR-32 | 81.1% | 74.5% | 96.6% | 85.5% |
| SNC-847 | 4, 44 | hsa-miR-361-5p, hsa-miR-214* | 80.2% | 74.7% | 93.0% | 83.9% |
| SNC-848 | 4, 55 | hsa-miR-361-5p, hsa-miR-483-3p | 80.2% | 76.1% | 89.6% | 82.9% |
| SNC-849 | 4, 98 | hsa-miR-361-5p, hsa-miR-891b | 63.2% | 54.2% | 84.5% | 69.4% |
| SNC-850 | 4, 94 | hsa-miR-361-5p, hsa-miR-219-2-3p | 84.9% | 81.6% | 92.9% | 87.2% |
| SNC-851 | 12, 1 | hsa-miR-934, hsa-miR-1251 | 88.4% | 84.7% | 97.0% | 90.8% |
| SNC-852 | 12, 6 | hsa-miR-934, hsa-miR-640 | 82.8% | 77.9% | 94.5% | 86.2% |
| SNC-853 | 12, 43 | hsa-miR-934, hsa-miR-34a* | 87.9% | 85.9% | 92.5% | 89.2% |
| SNC-854 | 12, 50 | hsa-miR-934, hsa-miR-720 | 82.9% | 78.3% | 93.9% | 86.1% |
| SNC-855 | 12, 121 | hsa-miR-934, hsa-miR-423-5p | 80.2% | 73.4% | 96.1% | 84.7% |
| SNC-856 | 12, 111 | hsa-miR-934, hsa-miR-1324 | 83.2% | 77.0% | 97.9% | 87.4% |
| SNC-857 | 12, 390 | hsa-miR-934, hsa-miR-320d | 80.5% | 78.2% | 86.1% | 82.1% |
| SNC-858 | 12, 342 | hsa-miR-934, hsa-miR-151-5p | 78.3% | 71.5% | 94.3% | 82.9% |
| SNC-859 | 12, 485 | hsa-miR-934, hsa-miR-744 | 78.9% | 72.0% | 95.4% | 83.7% |
| SNC-860 | 12, 136 | hsa-miR-934, hsa-miR-33b | 78.9% | 72.3% | 94.5% | 83.4% |
| SNC-861 | 12, 179 | hsa-miR-934, hsa-miR-455-3p | 87.6% | 83.8% | 96.4% | 90.1% |
| SNC-862 | 12, 251 | hsa-miR-934, hsa-miR-32 | 82.0% | 74.6% | 99.3% | 87.0% |
| SNC-863 | 12, 44 | hsa-miR-934, hsa-miR-214* | 84.9% | 78.6% | 99.8% | 89.2% |

FIG. 7 cont.

| SNC-864 | 12, 55 | hsa-miR-934, hsa-miR-483-3p | 83.0% | 77.9% | 95.0% | 86.4% |
|---|---|---|---|---|---|---|
| SNC-865 | 12, 98 | hsa-miR-934, hsa-miR-891b | 79.6% | 75.0% | 90.4% | 82.7% |
| SNC-866 | 12, 94 | hsa-miR-934, hsa-miR-219-2-3p | 80.3% | 76.0% | 90.4% | 83.2% |
| SNC-867 | 1, 6 | hsa-miR-1251, hsa-miR-640 | 85.3% | 82.9% | 90.9% | 86.9% |
| SNC-868 | 1, 43 | hsa-miR-1251, hsa-miR-34a* | 89.0% | 86.1% | 95.7% | 90.9% |
| SNC-869 | 1, 50 | hsa-miR-1251, hsa-miR-720 | 90.6% | 86.7% | 99.8% | 93.2% |
| SNC-870 | 1, 121 | hsa-miR-1251, hsa-miR-423-5p | 93.0% | 91.1% | 97.3% | 94.2% |
| SNC-871 | 1, 111 | hsa-miR-1251, hsa-miR-1324 | 91.8% | 89.6% | 96.8% | 93.2% |
| SNC-872 | 1, 390 | hsa-miR-1251, hsa-miR-320d | 81.2% | 75.2% | 95.4% | 85.3% |
| SNC-873 | 1, 342 | hsa-miR-1251, hsa-miR-151-5p | 77.8% | 68.6% | 99.5% | 84.1% |
| SNC-874 | 1, 485 | hsa-miR-1251, hsa-miR-744 | 86.5% | 82.4% | 96.1% | 89.2% |
| SNC-875 | 1, 136 | hsa-miR-1251, hsa-miR-33b | 87.5% | 84.2% | 95.4% | 89.8% |
| SNC-876 | 1, 179 | hsa-miR-1251, hsa-miR-455-3p | 79.4% | 75.4% | 88.8% | 82.1% |
| SNC-877 | 1, 251 | hsa-miR-1251, hsa-miR-32 | 86.1% | 81.7% | 96.4% | 89.1% |
| SNC-878 | 1, 44 | hsa-miR-1251, hsa-miR-214* | 88.3% | 83.9% | 98.8% | 91.3% |
| SNC-879 | 1, 55 | hsa-miR-1251, hsa-miR-483-3p | 79.2% | 72.5% | 95.0% | 83.8% |
| SNC-880 | 1, 98 | hsa-miR-1251, hsa-miR-891b | 88.2% | 85.7% | 94.3% | 90.0% |
| SNC-881 | 1, 94 | hsa-miR-1251, hsa-miR-219-2-3p | 88.7% | 84.7% | 98.2% | 91.5% |
| SNC-882 | 6, 43 | hsa-miR-640, hsa-miR-34a* | 78.5% | 76.8% | 82.3% | 79.6% |
| SNC-883 | 6, 50 | hsa-miR-640, hsa-miR-720 | 82.4% | 79.5% | 89.3% | 84.4% |
| SNC-884 | 6, 121 | hsa-miR-640, hsa-miR-423-5p | 83.5% | 80.8% | 89.8% | 85.3% |
| SNC-885 | 6, 111 | hsa-miR-640, hsa-miR-1324 | 81.3% | 81.5% | 80.9% | 81.2% |
| SNC-886 | 6, 390 | hsa-miR-640, hsa-miR-320d | 77.9% | 71.1% | 93.8% | 82.4% |
| SNC-887 | 6, 342 | hsa-miR-640, hsa-miR-151-5p | 86.0% | 82.0% | 95.4% | 88.7% |
| SNC-888 | 6, 485 | hsa-miR-640, hsa-miR-744 | 83.7% | 78.9% | 94.8% | 86.9% |
| SNC-889 | 6, 136 | hsa-miR-640, hsa-miR-33b | 78.8% | 74.1% | 89.8% | 82.0% |
| SNC-890 | 6, 179 | hsa-miR-640, hsa-miR-455-3p | 77.0% | 73.2% | 86.1% | 79.6% |
| SNC-891 | 6, 251 | hsa-miR-640, hsa-miR-32 | 84.1% | 80.4% | 92.9% | 86.6% |
| SNC-892 | 6, 44 | hsa-miR-640, hsa-miR-214* | 82.7% | 80.5% | 87.9% | 84.2% |
| SNC-893 | 6, 55 | hsa-miR-640, hsa-miR-483-3p | 78.3% | 73.9% | 88.6% | 81.3% |
| SNC-894 | 6, 98 | hsa-miR-640, hsa-miR-891b | 79.0% | 75.8% | 86.6% | 81.2% |
| SNC-895 | 6, 94 | hsa-miR-640, hsa-miR-219-2-3p | 81.1% | 76.0% | 93.0% | 84.5% |
| SNC-896 | 43, 50 | hsa-miR-34a*, hsa-miR-720 | 83.0% | 79.1% | 92.3% | 85.7% |
| SNC-897 | 43, 121 | hsa-miR-34a*, hsa-miR-423-5p | 91.2% | 89.5% | 95.2% | 92.4% |
| SNC-898 | 43, 111 | hsa-miR-34a*, hsa-miR-1324 | 83.5% | 79.8% | 92.1% | 86.0% |
| SNC-899 | 43, 390 | hsa-miR-34a*, hsa-miR-320d | 79.3% | 74.0% | 91.6% | 82.8% |
| SNC-900 | 43, 342 | hsa-miR-34a*, hsa-miR-151-5p | 85.5% | 80.8% | 96.4% | 88.6% |
| SNC-901 | 43, 485 | hsa-miR-34a*, hsa-miR-744 | 83.6% | 79.2% | 93.9% | 86.6% |
| SNC-902 | 43, 136 | hsa-miR-34a*, hsa-miR-33b | 87.8% | 83.6% | 97.5% | 90.6% |
| SNC-903 | 43, 179 | hsa-miR-34a*, hsa-miR-455-3p | 78.6% | 74.9% | 87.3% | 81.1% |
| SNC-904 | 43, 251 | hsa-miR-34a*, hsa-miR-32 | 90.6% | 88.3% | 96.3% | 92.3% |
| SNC-905 | 43, 44 | hsa-miR-34a*, hsa-miR-214* | 79.7% | 74.4% | 92.1% | 83.3% |
| SNC-906 | 43, 55 | hsa-miR-34a*, hsa-miR-483-3p | 89.4% | 87.7% | 93.2% | 90.5% |
| SNC-907 | 43, 98 | hsa-miR-34a*, hsa-miR-891b | 76.4% | 70.2% | 91.1% | 80.6% |
| SNC-908 | 43, 94 | hsa-miR-34a*, hsa-miR-219-2-3p | 81.3% | 77.1% | 91.3% | 84.2% |
| SNC-909 | 50, 121 | hsa-miR-720, hsa-miR-423-5p | 83.3% | 78.0% | 95.9% | 86.9% |

FIG. 7 cont.

| | | | | | | |
|---|---|---|---|---|---|---|
| SNC-910 | 50, 111 | hsa-miR-720, hsa-miR-1324 | 78.1% | 73.3% | 89.3% | 81.3% |
| SNC-911 | 50, 390 | hsa-miR-720, hsa-miR-320d | 76.4% | 66.6% | 99.6% | 83.1% |
| SNC-912 | 50, 342 | hsa-miR-720, hsa-miR-151-5p | 80.3% | 71.9% | 100.0% | 85.9% |
| SNC-913 | 50, 485 | hsa-miR-720, hsa-miR-744 | 76.4% | 67.1% | 98.2% | 82.7% |
| SNC-914 | 50, 136 | hsa-miR-720, hsa-miR-33b | 74.1% | 66.3% | 92.7% | 79.5% |
| SNC-915 | 50, 179 | hsa-miR-720, hsa-miR-455-3p | 77.2% | 70.5% | 93.0% | 81.8% |
| SNC-916 | 50, 251 | hsa-miR-720, hsa-miR-32 | 85.6% | 79.5% | 100.0% | 89.7% |
| SNC-917 | 50, 44 | hsa-miR-720, hsa-miR-214* | 83.5% | 76.4% | 100.0% | 88.2% |
| SNC-918 | 50, 55 | hsa-miR-720, hsa-miR-483-3p | 81.9% | 75.7% | 96.4% | 86.1% |
| SNC-919 | 50, 98 | hsa-miR-720, hsa-miR-891b | 74.3% | 67.7% | 90.0% | 78.8% |
| SNC-920 | 50, 94 | hsa-miR-720, hsa-miR-219-2-3p | 89.0% | 89.2% | 88.4% | 88.8% |
| SNC-921 | 121, 111 | hsa-miR-423-5p, hsa-miR-1324 | 83.0% | 80.0% | 90.0% | 85.0% |
| SNC-922 | 121, 390 | hsa-miR-423-5p, hsa-miR-320d | 69.6% | 60.3% | 91.4% | 75.9% |
| SNC-923 | 121, 342 | hsa-miR-423-5p, hsa-miR-151-5p | 71.6% | 63.3% | 91.1% | 77.2% |
| SNC-924 | 121, 485 | hsa-miR-423-5p, hsa-miR-744 | 70.6% | 63.8% | 86.6% | 75.2% |
| SNC-925 | 121, 136 | hsa-miR-423-5p, hsa-miR-33b | 71.0% | 62.3% | 91.3% | 76.8% |
| SNC-926 | 121, 179 | hsa-miR-423-5p, hsa-miR-455-3p | 80.6% | 75.8% | 92.0% | 83.9% |
| SNC-927 | 121, 251 | hsa-miR-423-5p, hsa-miR-32 | 88.2% | 85.5% | 94.6% | 90.1% |
| SNC-928 | 121, 44 | hsa-miR-423-5p, hsa-miR-214* | 84.9% | 81.2% | 93.8% | 87.5% |
| SNC-929 | 121, 55 | hsa-miR-423-5p, hsa-miR-483-3p | 89.9% | 85.8% | 99.8% | 92.8% |
| SNC-930 | 121, 98 | hsa-miR-423-5p, hsa-miR-891b | 86.1% | 83.2% | 93.0% | 88.1% |
| SNC-931 | 121, 94 | hsa-miR-423-5p, hsa-miR-219-2-3p | 85.2% | 83.2% | 90.0% | 86.6% |
| SNC-932 | 111, 390 | hsa-miR-1324, hsa-miR-320d | 82.5% | 77.2% | 95.0% | 86.1% |
| SNC-933 | 111, 342 | hsa-miR-1324, hsa-miR-151-5p | 73.9% | 66.4% | 91.6% | 79.0% |
| SNC-934 | 111, 485 | hsa-miR-1324, hsa-miR-744 | 73.9% | 65.8% | 93.0% | 79.4% |
| SNC-935 | 111, 136 | hsa-miR-1324, hsa-miR-33b | 82.0% | 78.9% | 89.3% | 84.1% |
| SNC-936 | 111, 179 | hsa-miR-1324, hsa-miR-455-3p | 80.1% | 73.7% | 95.2% | 84.4% |
| SNC-937 | 111, 251 | hsa-miR-1324, hsa-miR-32 | 84.3% | 82.2% | 89.3% | 85.7% |
| SNC-938 | 111, 44 | hsa-miR-1324, hsa-miR-214* | 84.5% | 82.2% | 90.0% | 86.1% |
| SNC-939 | 111, 55 | hsa-miR-1324, hsa-miR-483-3p | 83.1% | 79.4% | 92.0% | 85.7% |
| SNC-940 | 111, 98 | hsa-miR-1324, hsa-miR-891b | 72.8% | 65.3% | 90.5% | 77.9% |
| SNC-941 | 111, 94 | hsa-miR-1324, hsa-miR-219-2-3p | 82.1% | 78.6% | 90.4% | 84.5% |
| SNC-942 | 390, 342 | hsa-miR-320d, hsa-miR-151-5p | 65.4% | 58.0% | 82.9% | 70.4% |
| SNC-943 | 390, 485 | hsa-miR-320d, hsa-miR-744 | 70.1% | 58.9% | 96.4% | 77.7% |
| SNC-944 | 390, 136 | hsa-miR-320d, hsa-miR-33b | 65.8% | 56.4% | 87.9% | 72.1% |
| SNC-945 | 390, 179 | hsa-miR-320d, hsa-miR-455-3p | 57.4% | 42.0% | 93.6% | 67.8% |
| SNC-946 | 390, 251 | hsa-miR-320d, hsa-miR-32 | 79.4% | 72.7% | 95.4% | 84.0% |
| SNC-947 | 390, 44 | hsa-miR-320d, hsa-miR-214* | 77.1% | 68.9% | 96.6% | 82.7% |
| SNC-948 | 390, 55 | hsa-miR-320d, hsa-miR-483-3p | 74.9% | 66.7% | 94.5% | 80.6% |
| SNC-949 | 390, 98 | hsa-miR-320d, hsa-miR-891b | 79.8% | 73.3% | 95.0% | 84.2% |
| SNC-950 | 390, 94 | hsa-miR-320d, hsa-miR-219-2-3p | 77.4% | 72.4% | 89.3% | 80.9% |
| SNC-951 | 342, 485 | hsa-miR-151-5p, hsa-miR-744 | 73.8% | 62.7% | 100.0% | 81.3% |
| SNC-952 | 342, 136 | hsa-miR-151-5p, hsa-miR-33b | 71.4% | 60.7% | 96.6% | 78.6% |
| SNC-953 | 342, 179 | hsa-miR-151-5p, hsa-miR-455-3p | 70.6% | 60.9% | 93.4% | 77.2% |
| SNC-954 | 342, 251 | hsa-miR-151-5p, hsa-miR-32 | 81.9% | 75.8% | 96.3% | 86.0% |
| SNC-955 | 342, 44 | hsa-miR-151-5p, hsa-miR-214* | 80.6% | 73.6% | 97.0% | 85.3% |

FIG. 7 cont.

| | | | | | | |
|---|---|---|---|---|---|---|
| SNC-956 | 342, 55 | hsa-miR-151-5p, hsa-miR-483-3p | 85.1% | 78.8% | 100.0% | 89.4% |
| SNC-957 | 342, 98 | hsa-miR-151-5p, hsa-miR-891b | 70.3% | 61.2% | 91.6% | 76.4% |
| SNC-958 | 342, 94 | hsa-miR-151-5p, hsa-miR-219-2-3p | 80.7% | 76.0% | 92.0% | 84.0% |
| SNC-959 | 485, 136 | hsa-miR-744, hsa-miR-33b | 71.0% | 61.5% | 93.2% | 77.4% |
| SNC-960 | 485, 179 | hsa-miR-744, hsa-miR-455-3p | 74.4% | 66.1% | 94.1% | 80.1% |
| SNC-961 | 485, 251 | hsa-miR-744, hsa-miR-32 | 82.8% | 78.2% | 93.6% | 85.9% |
| SNC-962 | 485, 44 | hsa-miR-744, hsa-miR-214* | 78.1% | 70.1% | 97.0% | 83.5% |
| SNC-963 | 485, 55 | hsa-miR-744, hsa-miR-483-3p | 81.6% | 75.1% | 97.0% | 86.0% |
| SNC-964 | 485, 98 | hsa-miR-744, hsa-miR-891b | 71.4% | 63.9% | 89.1% | 76.5% |
| SNC-965 | 485, 94 | hsa-miR-744, hsa-miR-219-2-3p | 76.9% | 71.5% | 89.6% | 80.6% |
| SNC-966 | 136, 179 | hsa-miR-33b, hsa-miR-455-3p | 81.2% | 75.8% | 94.1% | 84.9% |
| SNC-967 | 136, 251 | hsa-miR-33b, hsa-miR-32 | 85.8% | 81.1% | 96.8% | 89.0% |
| SNC-968 | 136, 44 | hsa-miR-33b, hsa-miR-214* | 81.6% | 75.5% | 96.1% | 85.8% |
| SNC-969 | 136, 55 | hsa-miR-33b, hsa-miR-483-3p | 83.6% | 78.6% | 95.4% | 87.0% |
| SNC-970 | 136, 98 | hsa-miR-33b, hsa-miR-891b | 79.5% | 74.8% | 90.7% | 82.7% |
| SNC-971 | 136, 94 | hsa-miR-33b, hsa-miR-219-2-3p | 82.8% | 75.8% | 99.5% | 87.6% |
| SNC-972 | 179, 251 | hsa-miR-455-3p, hsa-miR-32 | 84.8% | 81.3% | 93.2% | 87.3% |
| SNC-973 | 179, 44 | hsa-miR-455-3p, hsa-miR-214* | 81.9% | 78.9% | 88.9% | 83.9% |
| SNC-974 | 179, 55 | hsa-miR-455-3p, hsa-miR-483-3p | 78.0% | 72.2% | 91.6% | 81.9% |
| SNC-975 | 179, 98 | hsa-miR-455-3p, hsa-miR-891b | 81.6% | 77.2% | 92.0% | 84.6% |
| SNC-976 | 179, 94 | hsa-miR-455-3p, hsa-miR-219-2-3p | 75.2% | 68.8% | 90.4% | 79.6% |
| SNC-977 | 251, 44 | hsa-miR-32, hsa-miR-214* | 86.1% | 80.7% | 98.8% | 89.7% |
| SNC-978 | 251, 55 | hsa-miR-32, hsa-miR-483-3p | 83.7% | 77.0% | 99.3% | 88.2% |
| SNC-979 | 251, 98 | hsa-miR-32, hsa-miR-891b | 75.4% | 67.5% | 94.1% | 80.8% |
| SNC-980 | 251, 94 | hsa-miR-32, hsa-miR-219-2-3p | 84.9% | 79.6% | 97.5% | 88.6% |
| SNC-981 | 44, 55 | hsa-miR-214*, hsa-miR-483-3p | 75.3% | 67.6% | 93.6% | 80.6% |
| SNC-982 | 44, 98 | hsa-miR-214*, hsa-miR-891b | 78.2% | 72.0% | 92.7% | 82.4% |
| SNC-983 | 44, 94 | hsa-miR-214*, hsa-miR-219-2-3p | 82.6% | 77.7% | 94.3% | 86.0% |
| SNC-984 | 55, 98 | hsa-miR-483-3p, hsa-miR-891b | 76.9% | 69.2% | 94.8% | 82.0% |
| SNC-985 | 55, 94 | hsa-miR-483-3p, hsa-miR-219-2-3p | 81.6% | 74.8% | 97.7% | 86.2% |
| SNC-986 | 98, 94 | hsa-miR-891b, hsa-miR-219-2-3p | 75.6% | 69.7% | 89.5% | 79.6% |
| SNC-987 | 35, 11, 4 | hsa-miR-197, hsa-let-7d*, hsa-miR-361-5p | 90.5% | 87.3% | 98.0% | 92.7% |
| SNC-988 | 35, 4, 12 | hsa-miR-197, hsa-let-7d*, hsa-miR-934 | 93.4% | 93.4% | 93.4% | 93.4% |
| SNC-989 | 35, 12, 1 | hsa-miR-197, hsa-let-7d*, hsa-miR-1251 | 94.5% | 92.3% | 99.8% | 96.0% |
| SNC-990 | 35, 1, 6 | hsa-miR-197, hsa-let-7d*, hsa-miR-640 | 90.4% | 89.2% | 93.2% | 91.2% |
| SNC-991 | 35, 6, 43 | hsa-miR-197, hsa-let-7d*, hsa-miR-34a* | 95.9% | 94.6% | 98.8% | 96.7% |
| SNC-992 | 35, 43, 50 | hsa-miR-197, hsa-let-7d*, hsa-miR-720 | 91.4% | 88.0% | 99.5% | 93.7% |
| SNC-993 | 35, 50, 121 | hsa-miR-197, hsa-let-7d*, hsa-miR-423-5p | 89.9% | 88.8% | 92.7% | 90.7% |
| SNC-994 | 35, 121, 111 | hsa-miR-197, hsa-let-7d*, hsa-miR-1324 | 93.2% | 91.7% | 97.0% | 94.3% |
| SNC-995 | 35, 111, | hsa-miR-197, hsa-miR-361-5p, hsa-miR-934 | 91.1% | 91.1% | 91.1% | 91.1% |
| SNC-996 | 35, 4, 1 | hsa-miR-197, hsa-miR-361-5p, hsa-miR-1251 | 92.9% | 90.8% | 98.0% | 94.4% |
| SNC-997 | 35, 4, 6 | hsa-miR-197, hsa-miR-361-5p, hsa-miR-640 | 86.0% | 85.8% | 86.6% | 86.2% |
| SNC-998 | 35, 4, 43 | hsa-miR-197, hsa-miR-361-5p, hsa-miR-34a* | 94.5% | 93.5% | 96.8% | 95.1% |
| SNC-999 | 35, 4, 50 | hsa-miR-197, hsa-miR-361-5p, hsa-miR-720 | 87.3% | 83.3% | 96.8% | 90.0% |
| SNC-1000 | 35, 4, 121 | hsa-miR-197, hsa-miR-361-5p, hsa-miR-423-5p | 86.3% | 81.6% | 97.5% | 89.5% |
| SNC-1001 | 35, 4, 111 | hsa-miR-197, hsa-miR-361-5p, hsa-miR-1324 | 92.2% | 90.5% | 96.3% | 93.4% |

FIG. 7 cont.

| | | | | | | |
|---|---|---|---|---|---|---|
| SNC-1002 | 35, 12, 1 | hsa-miR-197, hsa-miR-934, hsa-miR-1251 | 97.7% | 96.7% | 100.0% | 98.3% |
| SNC-1003 | 35, 12, 6 | hsa-miR-197, hsa-miR-934, hsa-miR-640 | 89.6% | 86.9% | 95.9% | 91.4% |
| SNC-1004 | 35, 12, 43 | hsa-miR-197, hsa-miR-934, hsa-miR-34a* | 94.4% | 93.5% | 96.6% | 95.0% |
| SNC-1005 | 35, 12, 50 | hsa-miR-197, hsa-miR-934, hsa-miR-720 | 89.7% | 86.5% | 97.3% | 91.9% |
| SNC-1006 | 35, 12, 121 | hsa-miR-197, hsa-miR-934, hsa-miR-423-5p | 89.8% | 87.5% | 95.2% | 91.3% |
| SNC-1007 | 35, 12, 111 | hsa-miR-197, hsa-miR-934, hsa-miR-1324 | 92.4% | 89.7% | 98.9% | 94.3% |
| SNC-1008 | 35, 1, 6 | hsa-miR-197, hsa-miR-1251, hsa-miR-640 | 92.7% | 92.6% | 92.9% | 92.7% |
| SNC-1009 | 35, 1, 43 | hsa-miR-197, hsa-miR-1251, hsa-miR-34a* | 94.4% | 93.1% | 97.3% | 95.2% |
| SNC-1010 | 35, 1, 50 | hsa-miR-197, hsa-miR-1251, hsa-miR-720 | 93.5% | 91.3% | 98.6% | 94.9% |
| SNC-1011 | 35, 1, 121 | hsa-miR-197, hsa-miR-1251, hsa-miR-423-5p | 93.4% | 91.8% | 97.1% | 94.5% |
| SNC-1012 | 35, 1, 111 | hsa-miR-197, hsa-miR-1251, hsa-miR-1324 | 97.3% | 96.7% | 98.8% | 97.7% |
| SNC-1013 | 35, 6, 43 | hsa-miR-197, hsa-miR-640, hsa-miR-34a* | 94.5% | 92.9% | 98.4% | 95.6% |
| SNC-1014 | 35, 6, 50 | hsa-miR-197, hsa-miR-640, hsa-miR-720 | 87.8% | 85.1% | 94.3% | 89.7% |
| SNC-1015 | 35, 6, 121 | hsa-miR-197, hsa-miR-640, hsa-miR-423-5p | 86.9% | 84.5% | 92.5% | 88.5% |
| SNC-1016 | 35, 6, 111 | hsa-miR-197, hsa-miR-640, hsa-miR-1324 | 93.4% | 92.3% | 96.1% | 94.2% |
| SNC-1017 | 35, 43, 50 | hsa-miR-197, hsa-miR-34a*, hsa-miR-720 | 93.4% | 92.0% | 96.4% | 94.2% |
| SNC-1018 | 35, 43, 121 | hsa-miR-197, hsa-miR-34a*, hsa-miR-423-5p | 95.6% | 94.2% | 99.1% | 96.6% |
| SNC-1019 | 35, 43, 111 | hsa-miR-197, hsa-miR-34a*, hsa-miR-1324 | 92.7% | 91.6% | 95.4% | 93.5% |
| SNC-1020 | 35, 50, 121 | hsa-miR-197, hsa-miR-720, hsa-miR-423-5p | 90.0% | 86.7% | 97.9% | 92.3% |
| SNC-1021 | 35, 50, 111 | hsa-miR-197, hsa-miR-720, hsa-miR-1324 | 94.0% | 91.7% | 99.5% | 95.6% |
| SNC-1022 | 35, 121, 111 | hsa-miR-197, hsa-miR-423-5p, hsa-miR-1324 | 92.6% | 89.7% | 99.5% | 94.6% |
| SNC-1023 | 11, 4, 12 | hsa-let-7d*, hsa-miR-361-5p, hsa-miR-934 | 84.4% | 85.3% | 82.1% | 83.7% |
| SNC-1024 | 11, 4, 1 | hsa-let-7d*, hsa-miR-361-5p, hsa-miR-1251 | 86.9% | 83.9% | 94.1% | 89.0% |
| SNC-1025 | 11, 4, 6 | hsa-let-7d*, hsa-miR-361-5p, hsa-miR-640 | 83.8% | 82.4% | 87.0% | 84.7% |
| SNC-1026 | 11, 4, 43 | hsa-let-7d*, hsa-miR-361-5p, hsa-miR-34a* | 93.2% | 92.6% | 94.8% | 93.7% |
| SNC-1027 | 11, 4, 50 | hsa-let-7d*, hsa-miR-361-5p, hsa-miR-720 | 86.0% | 82.8% | 93.6% | 88.2% |
| SNC-1028 | 11, 4, 121 | hsa-let-7d*, hsa-miR-361-5p, hsa-miR-423-5p | 91.3% | 89.1% | 96.4% | 92.8% |
| SNC-1029 | 11, 4, 111 | hsa-let-7d*, hsa-miR-361-5p, hsa-miR-1324 | 86.1% | 86.5% | 85.0% | 85.8% |
| SNC-1030 | 11, 4, | hsa-let-7d*, hsa-miR-934, hsa-miR-1251 | 90.1% | 89.2% | 92.3% | 90.7% |
| SNC-1031 | 11, 4, | hsa-let-7d*, hsa-miR-934, hsa-miR-640 | 89.0% | 87.1% | 93.6% | 90.3% |
| SNC-1032 | 11, 4, | hsa-let-7d*, hsa-miR-934, hsa-miR-34a* | 93.9% | 93.0% | 96.3% | 94.6% |
| SNC-1033 | 11, 12, 50 | hsa-let-7d*, hsa-miR-934, hsa-miR-720 | 87.3% | 83.9% | 95.4% | 89.6% |
| SNC-1034 | 11, 12, 121 | hsa-let-7d*, hsa-miR-934, hsa-miR-423-5p | 90.3% | 89.7% | 91.8% | 90.7% |
| SNC-1035 | 11, 12, 111 | hsa-let-7d*, hsa-miR-934, hsa-miR-1324 | 87.3% | 85.5% | 91.6% | 88.6% |
| SNC-1036 | 11, 1, 6 | hsa-let-7d*, hsa-miR-1251, hsa-miR-640 | 89.3% | 88.1% | 92.1% | 90.1% |
| SNC-1037 | 11, 1, 43 | hsa-let-7d*, hsa-miR-1251, hsa-miR-34a* | 91.8% | 90.1% | 95.9% | 93.0% |
| SNC-1038 | 11, 1, 50 | hsa-let-7d*, hsa-miR-1251, hsa-miR-720 | 94.5% | 92.2% | 99.8% | 96.0% |
| SNC-1039 | 11, 1, 121 | hsa-let-7d*, hsa-miR-1251, hsa-miR-423-5p | 94.0% | 92.7% | 97.3% | 95.0% |
| SNC-1040 | 11, 1, 111 | hsa-let-7d*, hsa-miR-1251, hsa-miR-1324 | 94.4% | 94.1% | 95.0% | 94.5% |
| SNC-1041 | 11, 6, 43 | hsa-let-7d*, hsa-miR-640, hsa-miR-34a* | 92.3% | 94.9% | 86.3% | 90.6% |
| SNC-1042 | 11, 6, 50 | hsa-let-7d*, hsa-miR-640, hsa-miR-720 | 84.2% | 81.0% | 91.8% | 86.4% |
| SNC-1043 | 11, 6, 121 | hsa-let-7d*, hsa-miR-640, hsa-miR-423-5p | 91.8% | 90.8% | 94.1% | 92.5% |
| SNC-1044 | 11, 6, 111 | hsa-let-7d*, hsa-miR-640, hsa-miR-1324 | 91.2% | 91.7% | 90.0% | 90.8% |
| SNC-1045 | 11, 43, 50 | hsa-let-7d*, hsa-miR-34a*, hsa-miR-720 | 92.3% | 91.3% | 94.8% | 93.1% |
| SNC-1046 | 11, 43, 121 | hsa-let-7d*, hsa-miR-34a*, hsa-miR-423-5p | 96.2% | 95.7% | 97.3% | 96.5% |
| SNC-1047 | 11, 43, 111 | hsa-let-7d*, hsa-miR-34a*, hsa-miR-1324 | 92.4% | 93.8% | 89.3% | 91.5% |

FIG. 7 cont.

| | | | | | | |
|---|---|---|---|---|---|---|
| SNC-1048 | 11, 50, 121 | hsa-let-7d*, hsa-miR-720, hsa-miR-423-5p | 91.1% | 88.3% | 97.7% | 93.0% |
| SNC-1049 | 11, 50, 111 | hsa-let-7d*, hsa-miR-720, hsa-miR-1324 | 92.0% | 90.8% | 94.8% | 92.8% |
| SNC-1050 | 11, 121, 111 | hsa-let-7d*, hsa-miR-423-5p, hsa-miR-1324 | 90.7% | 89.8% | 93.0% | 91.4% |
| SNC-1051 | 4, 12, 1 | hsa-miR-361-5p, hsa-miR-934, hsa-miR-1251 | 90.9% | 87.7% | 98.6% | 93.1% |
| SNC-1052 | 4, 12, 6 | hsa-miR-361-5p, hsa-miR-934, hsa-miR-640 | 86.1% | 85.1% | 88.6% | 86.8% |
| SNC-1053 | 4, 12, 43 | hsa-miR-361-5p, hsa-miR-934, hsa-miR-34a* | 92.1% | 90.8% | 95.2% | 93.0% |
| SNC-1054 | 4, 12, 50 | hsa-miR-361-5p, hsa-miR-934, hsa-miR-720 | 81.4% | 80.8% | 83.0% | 81.9% |
| SNC-1055 | 4, 12, 121 | hsa-miR-361-5p, hsa-miR-934, hsa-miR-423-5p | 81.4% | 83.6% | 76.4% | 80.0% |
| SNC-1056 | 4, 12, 111 | hsa-miR-361-5p, hsa-miR-934, hsa-miR-1324 | 80.5% | 79.5% | 82.7% | 81.3% |
| SNC-1057 | 4, 1, 6 | hsa-miR-361-5p, hsa-miR-1251, hsa-miR-640 | 87.7% | 86.7% | 89.8% | 88.3% |
| SNC-1058 | 4, 1, 43 | hsa-miR-361-5p, hsa-miR-1251, hsa-miR-34a* | 93.3% | 92.2% | 95.9% | 94.0% |
| SNC-1059 | 4, 1, 50 | hsa-miR-361-5p, hsa-miR-1251, hsa-miR-720 | 90.1% | 87.6% | 95.9% | 91.7% |
| SNC-1060 | 4, 1, 121 | hsa-miR-361-5p, hsa-miR-1251, hsa-miR-423-5p | 92.6% | 89.9% | 98.9% | 94.4% |
| SNC-1061 | 4, 1, 111 | hsa-miR-361-5p, hsa-miR-1251, hsa-miR-1324 | 91.0% | 89.5% | 94.3% | 91.9% |
| SNC-1062 | 4, 6, 43 | hsa-miR-361-5p, hsa-miR-640, hsa-miR-34a* | 92.0% | 90.6% | 95.4% | 93.0% |
| SNC-1063 | 4, 6, 50 | hsa-miR-361-5p, hsa-miR-640, hsa-miR-720 | 83.7% | 83.9% | 83.4% | 83.6% |
| SNC-1064 | 4, 6, 121 | hsa-miR-361-5p, hsa-miR-640, hsa-miR-423-5p | 87.5% | 85.6% | 92.0% | 88.8% |
| SNC-1065 | 4, 6, 111 | hsa-miR-361-5p, hsa-miR-640, hsa-miR-1324 | 86.0% | 87.0% | 83.6% | 85.3% |
| SNC-1066 | 4, 43, 50 | hsa-miR-361-5p, hsa-miR-34a*, hsa-miR-720 | 91.0% | 89.6% | 94.3% | 92.0% |
| SNC-1067 | 4, 43, 121 | hsa-miR-361-5p, hsa-miR-34a*, hsa-miR-423-5p | 92.0% | 90.3% | 95.9% | 93.1% |
| SNC-1068 | 4, 43, 111 | hsa-miR-361-5p, hsa-miR-34a*, hsa-miR-1324 | 92.2% | 90.6% | 96.1% | 93.3% |
| SNC-1069 | 4, 50, 121 | hsa-miR-361-5p, hsa-miR-720, hsa-miR-423-5p | 85.1% | 79.5% | 98.2% | 88.8% |
| SNC-1070 | 4, 50, 111 | hsa-miR-361-5p, hsa-miR-720, hsa-miR-1324 | 85.4% | 83.0% | 91.1% | 87.0% |
| SNC-1071 | 4, 121, 111 | hsa-miR-361-5p, hsa-miR-423-5p, hsa-miR-1324 | 83.9% | 81.3% | 90.0% | 85.6% |
| SNC-1072 | 12, 1, 6 | hsa-miR-934, hsa-miR-1251, hsa-miR-640 | 86.6% | 86.0% | 88.0% | 87.0% |
| SNC-1073 | 12, 1, 43 | hsa-miR-934, hsa-miR-1251, hsa-miR-34a* | 89.4% | 87.0% | 95.0% | 91.0% |
| SNC-1074 | 12, 1, 50 | hsa-miR-934, hsa-miR-1251, hsa-miR-720 | 90.7% | 89.1% | 94.5% | 91.8% |
| SNC-1075 | 12, 1, 121 | hsa-miR-934, hsa-miR-1251, hsa-miR-423-5p | 96.3% | 95.2% | 99.1% | 97.1% |
| SNC-1076 | 12, 1, 111 | hsa-miR-934, hsa-miR-1251, hsa-miR-1324 | 91.7% | 92.3% | 90.4% | 91.3% |
| SNC-1077 | 12, 6, 43 | hsa-miR-934, hsa-miR-640, hsa-miR-34a* | 86.5% | 85.5% | 88.9% | 87.2% |
| SNC-1078 | 12, 6, 50 | hsa-miR-934, hsa-miR-640, hsa-miR-720 | 91.8% | 88.7% | 99.1% | 93.9% |
| SNC-1079 | 12, 6, 121 | hsa-miR-934, hsa-miR-640, hsa-miR-423-5p | 84.7% | 82.9% | 89.1% | 86.0% |
| SNC-1080 | 12, 6, 111 | hsa-miR-934, hsa-miR-640, hsa-miR-1324 | 84.8% | 83.9% | 87.0% | 85.4% |
| SNC-1081 | 12, 43, 50 | hsa-miR-934, hsa-miR-34a*, hsa-miR-720 | 89.1% | 87.8% | 92.3% | 90.1% |
| SNC-1082 | 12, 43, 121 | hsa-miR-934, hsa-miR-34a*, hsa-miR-423-5p | 93.8% | 91.1% | 100.0% | 95.6% |
| SNC-1083 | 12, 43, 111 | hsa-miR-934, hsa-miR-34a*, hsa-miR-1324 | 88.2% | 86.7% | 91.8% | 89.2% |
| SNC-1084 | 12, 50, 121 | hsa-miR-934, hsa-miR-720, hsa-miR-423-5p | 86.1% | 83.8% | 91.6% | 87.7% |
| SNC-1085 | 12, 50, 111 | hsa-miR-934, hsa-miR-720, hsa-miR-1324 | 86.9% | 84.2% | 93.4% | 88.8% |
| SNC-1086 | 12, 121, 111 | hsa-miR-934, hsa-miR-423-5p, hsa-miR-1324 | 84.6% | 85.1% | 83.6% | 84.3% |
| SNC-1087 | 1, 6, 43 | hsa-miR-1251, hsa-miR-640, hsa-miR-34a* | 89.4% | 88.6% | 91.4% | 90.0% |
| SNC-1088 | 1, 6, 50 | hsa-miR-1251, hsa-miR-640, hsa-miR-720 | 89.8% | 89.0% | 91.8% | 90.4% |
| SNC-1089 | 1, 6, 121 | hsa-miR-1251, hsa-miR-640, hsa-miR-423-5p | 95.7% | 93.9% | 100.0% | 96.9% |
| SNC-1090 | 1, 6, 111 | hsa-miR-1251, hsa-miR-640, hsa-miR-1324 | 94.6% | 93.9% | 96.1% | 95.0% |
| SNC-1091 | 1, 43, 50 | hsa-miR-1251, hsa-miR-34a*, hsa-miR-720 | 93.2% | 91.7% | 97.0% | 94.3% |
| SNC-1092 | 1, 43, 121 | hsa-miR-1251, hsa-miR-34a*, hsa-miR-423-5p | 96.9% | 95.6% | 100.0% | 97.8% |
| SNC-1093 | 1, 43, 111 | hsa-miR-1251, hsa-miR-34a*, hsa-miR-1324 | 93.0% | 91.8% | 95.7% | 93.8% |

FIG. 7 cont.

| | | | | | | |
|---|---|---|---|---|---|---|
| SNC-1094 | 1, 50, 121 | hsa-miR-1251, hsa-miR-720, hsa-miR-423-5p | 92.4% | 91.0% | 95.9% | 93.4% |
| SNC-1095 | 1, 50, 111 | hsa-miR-1251, hsa-miR-720, hsa-miR-1324 | 91.8% | 92.1% | 90.9% | 91.5% |
| SNC-1096 | 1, 121, 111 | hsa-miR-1251, hsa-miR-423-5p, hsa-miR-1324 | 94.3% | 93.9% | 95.2% | 94.6% |
| SNC-1097 | 6, 43, 50 | hsa-miR-640, hsa-miR-34a*, hsa-miR-720 | 92.0% | 90.7% | 95.0% | 92.8% |
| SNC-1098 | 6, 43, 121 | hsa-miR-640, hsa-miR-34a*, hsa-miR-423-5p | 93.0% | 91.9% | 95.5% | 93.7% |
| SNC-1099 | 6, 43, 111 | hsa-miR-640, hsa-miR-34a*, hsa-miR-1324 | 87.2% | 89.7% | 81.3% | 85.5% |
| SNC-1100 | 6, 50, 121 | hsa-miR-640, hsa-miR-720, hsa-miR-423-5p | 91.4% | 88.7% | 97.7% | 93.2% |
| SNC-1101 | 6, 50, 111 | hsa-miR-640, hsa-miR-720, hsa-miR-1324 | 84.9% | 86.3% | 81.8% | 84.0% |
| SNC-1102 | 6, 121, 111 | hsa-miR-640, hsa-miR-423-5p, hsa-miR-1324 | 88.6% | 87.5% | 91.3% | 89.4% |
| SNC-1103 | 43, 50, 121 | hsa-miR-34a*, hsa-miR-720, hsa-miR-423-5p | 92.6% | 90.2% | 98.0% | 94.1% |
| SNC-1104 | 43, 50, 111 | hsa-miR-34a*, hsa-miR-720, hsa-miR-1324 | 86.7% | 84.8% | 91.3% | 88.0% |
| SNC-1105 | 43, 121, 111 | hsa-miR-34a*, hsa-miR-423-5p, hsa-miR-1324 | 92.6% | 91.2% | 95.7% | 93.5% |
| SNC-1106 | 50, 121, 111 | hsa-miR-720, hsa-miR-423-5p, hsa-miR-1324 | 88.9% | 86.9% | 93.8% | 90.3% |
| SNC-1107 | 200, 11, 43 | hsa-miR-892a, hsa-let-7d*, hsa-miR-34a* | 94.9% | 93.9% | 97.3% | 95.6% |
| SNC-1108 | 200, 11, 43, 6 | hsa-miR-892a, hsa-let-7d*, hsa-miR-640, hsa-miR-34a* | 94.1% | 93.9% | 94.5% | 94.2% |
| SNC-1109 | 200, 11, 43, 432, 6 | hsa-miR-892a, hsa-let-7d*, hsa-miR-574-3p, hsa-miR-640, hsa-miR-34a* | 94.8% | 94.2% | 96.4% | 95.3% |
| SNC-1110 | 200, 1, 432, 6, 11, 43 | hsa-miR-892a, hsa-miR-1251, hsa-let-7d*, hsa-miR-574-3p, hsa-miR-640, hsa-miR-34a* | 93.6% | 94.9% | 90.5% | 92.7% |
| SNC-1111 | 200, 1, 432, 6, 11, 43, 44 | hsa-miR-892a, hsa-miR-1251, hsa-let-7d*, hsa-miR-574-3p, hsa-miR-640, hsa-miR-34a*, hsa-miR-214* | 94.7% | 95.2% | 93.8% | 94.5% |
| SNC-1112 | 200, 1, 432, 6, 251, 11, 43, 44 | hsa-miR-892a, hsa-miR-1251, hsa-let-7d*, hsa-miR-574-3p, hsa-miR-640, hsa-miR-34a*, hsa-miR-32, hsa-miR-214* | 94.6% | 94.9% | 93.9% | 94.4% |
| SNC-1113 | 200, 1, 432, 6, 121, 251, 11, 43, 44 | hsa-miR-892a, hsa-miR-1251, hsa-let-7d*, hsa-miR-574-3p, hsa-miR-640, hsa-miR-423-5p, hsa-miR-34a*, hsa-miR-32, hsa-miR-214* | 95.9% | 96.4% | 94.6% | 95.5% |
| SNC-1114 | 200, 1, 432, 107, 6, 121, 251, 11, 43, 44 | hsa-miR-892a, hsa-miR-1251, hsa-let-7d*, hsa-miR-574-3p, hsa-miR-1272, hsa-miR-640, hsa-miR-423-5p, hsa-miR-34a*, hsa-miR-32, hsa-miR-214* | 95.2% | 95.1% | 95.5% | 95.3% |
| SNC-1115 | 200, 1, 432, 107, 6, 121, 12, 251, 11, 43, 44 | hsa-miR-892a, hsa-miR-1251, hsa-let-7d*, hsa-miR-574-3p, hsa-miR-1272, hsa-miR-640, hsa-miR-423-5p, hsa-miR-34a*, hsa-miR-934, hsa-miR-32, hsa-miR-214* | 95.6% | 95.3% | 96.4% | 95.9% |
| SNC-1116 | 200, 1, 432, 107, 6, 121, 12, 251, 76, 11, 43, 44 | hsa-miR-892a, hsa-miR-1251, hsa-let-7d*, hsa-miR-574-3p, hsa-miR-1272, hsa-miR-640, hsa-miR-423-5p, hsa-miR-34a*, hsa-miR-934, hsa-miR-32, hsa-miR-153, hsa-miR-214* | 95.7% | 94.9% | 97.5% | 96.2% |
| SNC-1117 | 200, 1, h432, 107, 6, 121, 12, 136, 251, 76, 11, 43, 44 | hsa-miR-892a, hsa-miR-1251, hsa-let-7d*, hsa-miR-574-3p, hsa-miR-1272, hsa-miR-640, hsa-miR-423-5p, hsa-miR-34a*, hsa-miR-934, hsa-miR-33b, hsa-miR-32, hsa-miR-153, hsa-miR-214* | 95.5% | 94.9% | 97.0% | 95.9% |
| SNC-1118 | 200, 1, 432, 107, 6, 121, 12, 136, 251, 179, 76, 11, 43, 44 | hsa-miR-892a, hsa-miR-1251, hsa-let-7d*, hsa-miR-574-3p, hsa-miR-1272, hsa-miR-640, hsa-miR-423-5p, hsa-miR-34a*, hsa-miR-934, hsa-miR-33b, hsa-miR-32, hsa-miR-455-3p, hsa-miR-153, hsa-miR-214* | 95.5% | 94.4% | 98.0% | 96.2% |
| SNC-1119 | 200, 1, 432, 107, 6, 121, 12, 136, 251, 179, 76, 11, 43, 44, 132 | hsa-miR-31*, hsa-miR-892a, hsa-miR-1251, hsa-let-7d*, hsa-miR-574-3p, hsa-miR-1272, hsa-miR-640, hsa-miR-423-5p, hsa-miR-34a*, hsa-miR-934, hsa-miR-33b, hsa-miR-32, hsa-miR-455-3p, hsa-miR-153, hsa-miR-214* | 96.2% | 95.5% | 97.9% | 96.7% |
| SNC-1120 | 200, 1, 432, 35, 107, 6, 121, 12, 136, 251, 179, 76, 11, 43, 44, 132 | hsa-miR-31*, hsa-miR-892a, hsa-miR-1251, hsa-let-7d*, hsa-miR-574-3p, hsa-miR-197, hsa-miR-1272, hsa-miR-640, hsa-miR-423-5p, hsa-miR-34a*, hsa-miR-934, hsa-miR-33b, hsa-miR-32, hsa-miR-455-3p, hsa-miR-153, hsa-miR-214* | 97.9% | 97.5% | 98.9% | 98.2% |

FIG. 7 cont.

| ID | Numbers | miRNAs | % | % | % | % |
|---|---|---|---|---|---|---|
| SNC-1121 | 200, 1, 432, 62, 35, 107, 6, 121, 12, 136, 251, 179, 76, 11, 43, 44, 132 | hsa-miR-31*, hsa-miR-892a, hsa-miR-1251, hsa-let-7d*, hsa-miR-574-3p, hsa-miR-654-5p, hsa-miR-197, hsa-miR-1272, hsa-miR-640, hsa-miR-423-5p, hsa-miR-34a*, hsa-miR-934, hsa-miR-33b, hsa-miR-32, hsa-miR-455-3p, hsa-miR-153, hsa-miR-214* | 97.7% | 97.0% | 99.3% | 98.2% |
| SNC-1122 | 200, 1, 432, 62, 35, 107, 6, 121, 12, 136, 251, 55, 179, 76, 11, 43, 44, 132 | hsa-miR-31*, hsa-miR-892a, hsa-miR-1251, hsa-let-7d*, hsa-miR-574-3p, hsa-miR-654-5p, hsa-miR-197, hsa-miR-1272, hsa-miR-640, hsa-miR-423-5p, hsa-miR-34a*, hsa-miR-934, hsa-miR-33b, hsa-miR-32, hsa-miR-483-3p, hsa-miR-455-3p, hsa-miR-153, hsa-miR-214* | 97.7% | 96.7% | 100.0% | 98.4% |
| SNC-1123 | 200, 1, 432, 62, 35, 107, 6, 121, 2, 12, 136, 251, 55, 179, 7611, 43, 44, 132 | hsa-miR-31*, hsa-miR-892a, hsa-miR-1251, hsa-let-7d*, hsa-miR-574-3p, hsa-miR-654-5p, hsa-miR-197, hsa-miR-1272, hsa-miR-640, hsa-miR-423-5p, hsa-miR-151-3p, hsa-miR-34a*, hsa-miR-934, hsa-miR-33b, hsa-miR-32, hsa-miR-483-3p, hsa-miR-455-3p, hsa-miR-153, hsa-miR-214* | 98.0% | 97.4% | 99.5% | 98.4% |
| SNC-1124 | 200, 1, 432, 62, 35, 4, 107, 6, 121, 2, 12, 136, 251, 55, 179, 76, 11, 43, 44, 132 | hsa-miR-31*, hsa-miR-892a, hsa-miR-1251, hsa-let-7d*, hsa-miR-574-3p, hsa-miR-654-5p, hsa-miR-197, hsa-miR-361-5p, hsa-miR-1272, hsa-miR-640, hsa-miR-423-5p, hsa-miR-151-3p, hsa-miR-34a*, hsa-miR-934, hsa-miR-33b, hsa-miR-32, hsa-miR-483-3p, hsa-miR-455-3p, hsa-miR-153, hsa-miR-214* | 98.1% | 97.5% | 99.5% | 98.5% |
| SNC-1125 | 200, 1, 432, 62, 210, 35, 4, 107, 6, 121, 2, 12, 136, 251, 55, 179, 76, 11, 43, 44, 132 | hsa-miR-31*, hsa-miR-892a, hsa-miR-1251, hsa-let-7d*, hsa-miR-574-3p, hsa-miR-654-5p, hsa-miR-604, hsa-miR-197, hsa-miR-361-5p, hsa-miR-1272, hsa-miR-640, hsa-miR-423-5p, hsa-miR-151-3p, hsa-miR-34a*, hsa-miR-934, hsa-miR-33b, hsa-miR-32, hsa-miR-483-3p, hsa-miR-455-3p, hsa-miR-153, hsa-miR-214* | 98.9% | 98.4% | 100.0% | 99.2% |
| SNC-1126 | 200, 1, 432, 62, 210, 35, 4, 107, 6, 121, 2, 12, 136, 251, 182, 55, 179, 76, 11, 43, 44, 132 | hsa-miR-31*, hsa-miR-892a, hsa-miR-1251, hsa-let-7d*, hsa-miR-574-3p, hsa-miR-654-5p, hsa-miR-604, hsa-miR-197, hsa-miR-361-5p, hsa-miR-1272, hsa-miR-640, hsa-miR-423-5p, hsa-miR-151-3p, hsa-miR-34a*, hsa-miR-934, hsa-miR-33b, hsa-miR-32, hsa-miR-452*, hsa-miR-483-3p, hsa-miR-455-3p, hsa-miR-153, hsa-miR-214* | 98.8% | 98.3% | 100.0% | 99.1% |
| SNC-1127 | 200, 1, 432, 62, 210, 35, 73, 4, 107, 6, 121, 2, 12, 136, 251, 182, 55, 179, 76, 11, 43, 44, 132 | hsa-miR-31*, hsa-miR-892a, hsa-miR-1251, hsa-let-7d*, hsa-miR-574-3p, hsa-miR-654-5p, hsa-miR-604, hsa-miR-197, hsa-miR-216b, hsa-miR-361-5p, hsa-miR-1272, hsa-miR-640, hsa-miR-423-5p, hsa-miR-151-3p, hsa-miR-34a*, hsa-miR-934, hsa-miR-33b, hsa-miR-32, hsa-miR-452*, hsa-miR-483-3p, hsa-miR-455-3p, hsa-miR-153, hsa-miR-214* | 98.8% | 98.3% | 100.0% | 99.2% |
| SNC-1128 | 200, 1, 432, 62, 210, 35, 73, 4, 107, 6, 121, 2, 12, 136, 251, 55, 179, 76, 11, 43, 44, 132, 182, 69 | hsa-miR-31*, hsa-miR-892a, hsa-miR-1251, hsa-let-7d*, hsa-miR-574-3p, hsa-miR-654-5p, hsa-miR-604, hsa-miR-197, hsa-miR-216b, hsa-miR-361-5p, hsa-miR-1272, hsa-miR-640, hsa-miR-423-5p, hsa-miR-593*, hsa-miR-151-3p, hsa-miR-34a*, hsa-miR-934, hsa-miR-33b, hsa-miR-32, hsa-miR-452*, hsa-miR-483-3p, hsa-miR-455-3p, hsa-miR-153, hsa-miR-214* | 98.4% | 97.7% | 100.0% | 98.8% |
| SNC-1129 | 200, 1, 432, 62, 210, 35, 73, 4, 107, 6, 121, 2, 12, 136, 251, 55, 179, 76, 11, 43, 44, 132, 56, 182, 69 | hsa-miR-31*, hsa-miR-892a, hsa-miR-1251, hsa-let-7d*, hsa-miR-574-3p, hsa-miR-654-5p, hsa-miR-604, hsa-miR-197, hsa-miR-216b, hsa-miR-361-5p, hsa-miR-1272, hsa-miR-640, hsa-miR-423-5p, hsa-miR-593*, hsa-miR-151-3p, hsa-miR-34a*, hsa-miR-934, hsa-miR-33b, hsa-miR-32, hsa-miR-452*, hsa-miR-483-3p, hsa-miR-455-3p, hsa-miR-153, hsa-miR-214*, hsa-miR-125a-3p | 97.7% | 97.2% | 98.8% | 98.0% |

FIG. 7 cont.

| | | | | | | |
|---|---|---|---|---|---|---|
| SNC-1130 | 200, 1, 432, 62, 210, 35, 73, 4, 107, 6, 121, 69, 2, 12, 136, 251, 182, 485, 55, 179, 76, 11, 43, 44, 132, 56 | hsa-miR-31*, hsa-miR-892a, hsa-miR-1251, hsa-let-7d*, hsa-miR-574-3p, hsa-miR-654-5p, hsa-miR-604, hsa-miR-197, hsa-miR-216b, hsa-miR-361-5p, hsa-miR-1272, hsa-miR-640, hsa-miR-423-5p, hsa-miR-593*, hsa-miR-151-3p, hsa-miR-34a*, hsa-miR-934, hsa-miR-33b, hsa-miR-32, hsa-miR-452*, hsa-miR-744, hsa-miR-483-3p, hsa-miR-455-3p, hsa-miR-153, hsa-miR-214*, hsa-miR-125a-3p | 99.8% | 99.7% | 100.0% | 99.8% |
| SNC-1131 | hsa-miR-31*, 200, 1, hsa-let-7d*, 111, 432, 62, 210, 35, 73, 4, 107, 6, 121, 69, 2, 12, 136, 251, 182, 485, 55, 179, 76, 11, 43, 44, 132, 56 | hsa-miR-31*, hsa-miR-892a, hsa-miR-1251, hsa-let-7d*, hsa-miR-1324, hsa-miR-574-3p, hsa-miR-654-5p, hsa-miR-604, hsa-miR-197, hsa-miR-216b, hsa-miR-361-5p, hsa-miR-1272, hsa-miR-640, hsa-miR-423-5p, hsa-miR-593*, hsa-miR-151-3p, hsa-miR-34a*, hsa-miR-934, hsa-miR-33b, hsa-miR-32, hsa-miR-452*, hsa-miR-744, hsa-miR-483-3p, hsa-miR-455-3p, hsa-miR-153, hsa-miR-214*, hsa-miR-125a-3p | 99.4% | 99.2% | 100.0% | 99.6% |
| SNC-1132 | 200, 1, 111, 432, 62, 210, 35, 73, 4, 107, 6, 121, 69, 2, 50, 12, 136, 251, 182, 485, 55, 179, 76, 11, 43, 44, 132, 56 | hsa-miR-31*, hsa-miR-892a, hsa-miR-1251, hsa-let-7d*, hsa-miR-1324, hsa-miR-574-3p, hsa-miR-654-5p, hsa-miR-604, hsa-miR-197, hsa-miR-216b, hsa-miR-361-5p, hsa-miR-1272, hsa-miR-640, hsa-miR-423-5p, hsa-miR-593*, hsa-miR-151-3p, hsa-miR-34a*, hsa-miR-720, hsa-miR-934, hsa-miR-33b, hsa-miR-32, hsa-miR-452*, hsa-miR-744, hsa-miR-483-3p, hsa-miR-455-3p, hsa-miR-153, hsa-miR-214*, hsa-miR-125a-3p | 99.1% | 98.8% | 100.0% | 99.4% |
| SNC-1133 | 200, 1, 111, 432, 98, 62, 210, 35, 73, 4, 107, 6, 121, 69, 2, 50, 12, 136, 251, 182, 485, 55, 179, 76, 11, 43, 44, 132, 56 | hsa-miR-31*, hsa-miR-892a, hsa-miR-1251, hsa-let-7d*, hsa-miR-1324, hsa-miR-574-3p, hsa-miR-891b, hsa-miR-654-5p, hsa-miR-604, hsa-miR-197, hsa-miR-216b, hsa-miR-361-5p, hsa-miR-1272, hsa-miR-640, hsa-miR-423-5p, hsa-miR-593*, hsa-miR-151-3p, hsa-miR-34a*, hsa-miR-720, hsa-miR-934, hsa-miR-33b, hsa-miR-32, hsa-miR-452*, hsa-miR-744, hsa-miR-483-3p, hsa-miR-455-3p, hsa-miR-153, hsa-miR-214*, hsa-miR-125a-3p | 98.4% | 97.7% | 100.0% | 98.9% |
| SNC-1134 | 200, 1, 111, 432, 241, 98, 62, 210, 35, 73, 4, 107, 6, 121, 69, 2, 50, 12, 136, 251, 182, 485, 55, 179, 76, 11, 43, 44, 132, 56 | hsa-miR-31*, hsa-miR-892a, hsa-miR-1251, hsa-let-7d*, hsa-miR-1324, hsa-miR-574-3p, hsa-miR-545, hsa-miR-891b, hsa-miR-654-5p, hsa-miR-604, hsa-miR-197, hsa-miR-216b, hsa-miR-361-5p, hsa-miR-1272, hsa-miR-640, hsa-miR-423-5p, hsa-miR-593*, hsa-miR-151-3p, hsa-miR-34a*, hsa-miR-720, hsa-miR-934, hsa-miR-33b, hsa-miR-32, hsa-miR-452*, hsa-miR-744, hsa-miR-483-3p, hsa-miR-455-3p, hsa-miR-153, hsa-miR-214*, hsa-miR-125a-3p | 98.8% | 98.3% | 100.0% | 99.1% |

FIG. 7 cont.

a) Upregulated miRNAs hsa-miR-197, hsa-miR-423-5p, hsa-let-7d*, hsa-miR-720, hsa-miR-361-5p, hsa-miR-483-3p, hsa-miR-151-5p, hsa-miR-744, hsa-miR-219-2-3p, hsa-miR-320d, hsa-miR-1908, hsa-miR-23a, hsa-miR-19b, hsa-miR-151-3p, hsa-miR-629, hsa-miR-135b, hsa-miR-193a-5p, hsa-miR-145, hsa-miR-23b, hsa-miR-1207-5p, hsa-miR-1260, hsa-miR-125a-3p, hsa-miR-135a*, hsa-miR-892a, hsa-miR-423-3p, hsa-miR-26b*, hsa-miR-1228*, hsa-miR-30c-1*, hsa-miR-1180, hsa-miR-149*, hsa-miR-574-3p, hsa-miR-1246, hsa-miR-1274a, hsa-miR-885-3p, hsa-miR-409-3p, hsa-miR-93*, hsa-miR-664, hsa-miR-135a, hsa-miR-658, hsa-miR-484, hsa-miR-132*, hsa-miR-425, hsa-miR-185, hsa-miR-653, hsa-miR-183*, hsa-miR-539, hsa-miR-548m, hsa-miR-186, hsa-miR-1281, hsa-miR-1225-5p, hsa-miR-328, hsa-miR-1307, hsa-miR-28-5p, hsa-miR-28-3p, hsa-miR-182, hsa-miR-199a-5p, hsa-miR-183, hsa-miR-193b*, hsa-miR-766, hsa-miR-1911, hsa-miR-1285, hsa-miR-24, hsa-miR-1261, hsa-miR-532-3p, hsa-miR-320a, hsa-let-7b, hsa-miR-373, hsa-miR-192, hsa-miR-505, hsa-miR-1274b, hsa-miR-346, hsa-miR-302a, hsa-miR-1290, hsa-miR-320b, hsa-miR-488, hsa-miR-129*, hsa-miR-211, hsa-miR-625, hsa-miR-210, hsa-miR-331-5p, hsa-miR-92b, hsa-miR-15b, hsa-miR-1226, hsa-miR-92b*, hsa-miR-330-5p, hsa-miR-520f, hsa-miR-128, hsa-miR-190, hsa-miR-1275, hsa-miR-340, hsa-miR-22, hsa-miR-342-5p, hsa-miR-637, hsa-miR-1321, hsa-miR-194, hsa-miR-125b, hsa-miR-1270, hsa-miR-191, hsa-miR-26a-2*, hsa-miR-320c, hsa-miR-202, hsa-miR-130b, hsa-miR-154, hsa-miR-769-5p, hsa-miR-302c*, hsa-miR-1279, hsa-miR-877, hsa-miR-548i, hsa-miR-518c*, hsa-miR-628-3p, hsa-miR-16, hsa-miR-224, hsa-miR-331-3p, hsa-miR-30a, hsa-miR-199b-5p, hsa-miR-378, hsa-miR-491-5p, hsa-miR-146a, hsa-miR-30c, hsa-miR-26a, hsa-miR-553, hsa-miR-584, hsa-miR-9, hsa-miR-613, hsa-miR-502-3p, hsa-miR-125b-2*, hsa-miR-223, hsa-miR-25, hsa-miR-126*, hsa-miR-587, hsa-miR-632, hsa-miR-196b, hsa-miR-7-1*, hsa-miR-541*, hsa-let-7e*, hsa-miR-1227, hsa-miR-517c, hsa-miR-296-5p, hsa-miR-548b-5p, hsa-miR-324-3p, hsa-miR-1303, hsa-miR-194*, hsa-miR-302f, hsa-miR-551b*, hsa-miR-339-5p, hsa-miR-15a, hsa-miR-300, hsa-miR-1284, hsa-miR-26a-1*, hsa-miR-1244, hsa-let-7c, hsa-miR-215, hsa-miR-204, hsa-miR-508-3p, hsa-miR-1267, hsa-miR-302e, hsa-miR-29a*, hsa-miR-1268, hsa-miR-125a-5p, hsa-miR-187*, hsa-miR-19b-2*, hsa-miR-30d, hsa-miR-663, hsa-miR-769-3p, hsa-miR-335, hsa-miR-432, hsa-miR-92a-1*, hsa-miR-548d-5p, hsa-miR-302d, hsa-miR-1825, hsa-miR-548j, hsa-miR-143, hsa-miR-302b, hsa-miR-25*, hsa-miR-18a*, hsa-miR-369-3p, hsa-miR-152, hsa-miR-576-5p, hsa-miR-337-3p, hsa-miR-1306, hsa-miR-615-3p, hsa-miR-422a, hsa-miR-92a-2*, hsa-miR-18b*, hsa-miR-507, hsa-miR-483-5p, hsa-let-7f-2*, hsa-miR-1280, hsa-miR-939, hsa-miR-556-3p, hsa-miR-342-3p, hsa-miR-638, hsa-miR-494, hsa-miR-142-5p, hsa-miR-532-5p, hsa-miR-203, hsa-miR-19a, hsa-miR-30b, hsa-miR-576-3p, hsa-miR-885-5p, hsa-miR-519e, hsa-miR-425*, hsa-miR-1258, hsa-let-7i, hsa-miR-1231, hsa-miR-206, hsa-miR-1, hsa-miR-605, hsa-miR-130b*, hsa-miR-520c-3p, hsa-miR-132, hsa-miR-493*, hsa-miR-30a*, hsa-miR-616, hsa-miR-502-5p, hsa-miR-455-5p, hsa-miR-297, hsa-miR-424*, hsa-miR-181d, hsa-miR-1915, hsa-miR-155, hsa-miR-519b-3p, hsa-let-7f, hsa-miR-515-3p, hsa-miR-629*, hsa-miR-30e*, hsa-miR-936, hsa-miR-941, hsa-miR-580, hsa-miR-130a, hsa-miR-1249, hsa-miR-513c, hsa-miR-552, hsa-miR-1538, hsa-miR-181a, hsa-miR-133b, hsa-miR-99a, hsa-miR-582-3p, hsa-miR-520d-5p, hsa-miR-509-3p, hsa-miR-942, hsa-miR-29a, hsa-miR-511, hsa-miR-675, hsa-miR-486-3p, hsa-miR-181b, hsa-miR-944, hsa-miR-512-3p, hsa-miR-433, hsa-miR-486-5p, hsa-miR-506, hsa-miR-181a-2*, hsa-miR-122*, hsa-miR-1269, hsa-miR-889, hsa-miR-505*, hsa-miR-485-3p, hsa-miR-520d-3p, hsa-miR-589, hsa-miR-1909, hsa-miR-296-3p, hsa-miR-504, hsa-miR-526b, hsa-miR-185*, hsa-miR-520b, hsa-miR-765, hsa-miR-516a-3p, hsa-miR-382, hsa-miR-325, hsa-miR-522, hsa-miR-671-3p, hsa-miR-1224-5p, hsa-miR-184, hsa-miR-876-5p, hsa-miR-624*, hsa-let-7a*, hsa-miR-122, hsa-miR-125b-1*, hsa-miR-1469, hsa-miR-377*, hsa-miR-1264, hsa-miR-100, hsa-let-7b*, hsa-miR-140-5p, hsa-miR-601, hsa-miR-105*, hsa-miR-644, hsa-miR-1204, hsa-miR-892b, hsa-miR-620, hsa-miR-99b, hsa-miR-593, hsa-miR-378*, hsa-miR-624, hsa-miR-1292, hsa-miR-99a*, hsa-miR-29c*, hsa-miR-770-5p, hsa-miR-1293, hsa-miR-1322, hsa-miR-200c, hsa-miR-609, hsa-miR-15b*, hsa-miR-1238, hsa-miR-190b, hsa-miR-198, hsa-miR-873, hsa-miR-551a

FIG. 8a b) Strong upregulated miRNAs (FC > 1.5)

hsa-miR-197, hsa-miR-423-5p, hsa-let-7d*, hsa-miR-720, hsa-miR-361-5p, hsa-miR-151-5p, hsa-miR-744, hsa-miR-320d, hsa-miR-1908, hsa-miR-23a, hsa-miR-19b, hsa-miR-151-3p, hsa-miR-629, hsa-miR-193a-5p, hsa-miR-145, hsa-miR-23b, hsa-miR-1207-5p, hsa-miR-1260, hsa-miR-423-3p, hsa-miR-1228*, hsa-miR-1180, hsa-miR-149*, hsa-miR-574-3p, hsa-miR-1274a, hsa-miR-885-3p, hsa-miR-93*, hsa-miR-664, hsa-miR-484, hsa-miR-425, hsa-miR-185, hsa-miR-183*, hsa-miR-1281, hsa-miR-1225-5p, hsa-miR-328, hsa-miR-28-5p, hsa-miR-28-3p, hsa-miR-182, hsa-miR-199a-5p, hsa-miR-183, hsa-miR-766, hsa-miR-1285, hsa-miR-24, hsa-miR-532-3p, hsa-miR-320a, hsa-let-7b, hsa-miR-192, hsa-miR-1274b, hsa-miR-320b, hsa-miR-625, hsa-miR-210, hsa-miR-92b, hsa-miR-15b, hsa-miR-1226, hsa-miR-92b*, hsa-miR-128, hsa-miR-1275, hsa-miR-340, hsa-miR-22, hsa-miR-194, hsa-miR-125b, hsa-miR-191, hsa-miR-320c, hsa-miR-130b, hsa-miR-877, hsa-miR-628-3p, hsa-miR-16, hsa-miR-331-3p, hsa-miR-30a, hsa-miR-378, hsa-miR-491-5p, hsa-miR-146a, hsa-miR-30c, hsa-miR-26a, hsa-miR-584, hsa-miR-502-3p, hsa-miR-223, hsa-miR-25, hsa-miR-7-1*, hsa-miR-1227, hsa-miR-296-5p, hsa-miR-324-3p, hsa-miR-339-5p, hsa-miR-15a, hsa-let-7c, hsa-miR-215, hsa-miR-125a-5p, hsa-miR-30d, hsa-miR-335, hsa-miR-25*, hsa-miR-18a*, hsa-miR-422a, hsa-miR-483-5p, hsa-miR-1280, hsa-miR-342-3p, hsa-miR-638, hsa-miR-494, hsa-miR-142-5p, hsa-miR-19a, hsa-miR-30b, hsa-let-7i, hsa-miR-1915, hsa-let-7f, hsa-miR-629*, hsa-miR-130a, hsa-miR-181a, hsa-miR-181b, hsa-miR-589, hsa-miR-100

FIG. 8b c) Very strong downregulated miRNAs (FC >2)

hsa-miR-197, hsa-miR-423-5p, hsa-let-7d*, hsa-miR-720, hsa-miR-361-5p, hsa-miR-151-5p, hsa-miR-744, hsa-miR-320d, hsa-miR-1908, hsa-miR-23a, hsa-miR-19b, hsa-miR-151-3p, hsa-miR-629, hsa-miR-193a-5p, hsa-miR-145, hsa-miR-23b, hsa-miR-1207-5p, hsa-miR-1260, hsa-miR-423-3p, hsa-miR-1228*, hsa-miR-1180, hsa-miR-149*, hsa-miR-574-3p, hsa-miR-885-3p, hsa-miR-664, hsa-miR-328, hsa-miR-182, hsa-miR-199a-5p, hsa-miR-183, hsa-let-7b, hsa-miR-625, hsa-miR-210, hsa-miR-92b, hsa-miR-92b*, hsa-miR-1275, hsa-miR-125b, hsa-miR-331-3p, hsa-miR-584, hsa-miR-223, hsa-let-7c, hsa-miR-142-5p, hsa-let-7i

FIG. 8c a) Downregulated miRNAs hsa-miR-34a*, hsa-miR-934, hsa-miR-1324, hsa-miR-32, hsa-miR-640, hsa-miR-1251, hsa-miR-891b, hsa-miR-214*, hsa-miR-33b, hsa-miR-455-3p, hsa-miR-593*, hsa-miR-564, hsa-miR-153, hsa-miR-646, hsa-miR-1226*, hsa-miR-545, hsa-miR-452*, hsa-miR-650, hsa-miR-216b, hsa-miR-431, hsa-miR-188-3p, hsa-miR-635, hsa-miR-891a, hsa-miR-654-5p, hsa-miR-208b, hsa-miR-548p, hsa-miR-31*, hsa-miR-554, hsa-miR-217, hsa-miR-139-3p, hsa-miR-1272, hsa-miR-1208, hsa-miR-143*, hsa-miR-523, hsa-miR-1305, hsa-miR-596, hsa-miR-374a, hsa-miR-515-5p, hsa-miR-556-5p, hsa-miR-33a, hsa-miR-1247, hsa-miR-604, hsa-miR-1289, hsa-miR-607, hsa-miR-621, hsa-miR-301b, hsa-miR-509-5p, hsa-miR-509-3-5p, hsa-miR-566, hsa-miR-1301, hsa-miR-24-2*, hsa-miR-633, hsa-miR-767-5p, hsa-let-7g*, hsa-miR-188-5p, hsa-miR-497, hsa-miR-1912, hsa-miR-490-3p, hsa-miR-196a*, hsa-miR-492, hsa-miR-497*, hsa-miR-551b, hsa-miR-499-3p, hsa-miR-221*, hsa-miR-597, hsa-miR-1206, hsa-miR-330-3p, hsa-miR-20a, hsa-miR-558, hsa-miR-450b-5p, hsa-miR-1266, hsa-miR-489, hsa-miR-485-5p, hsa-miR-548d-3p, hsa-miR-367*, hsa-miR-1291, hsa-miR-9*, hsa-miR-31, hsa-miR-541, hsa-miR-874, hsa-miR-508-5p, hsa-miR-520c-5p, hsa-miR-214, hsa-miR-218-1*, hsa-miR-518a-3p, hsa-miR-522*, hsa-miR-20a*, hsa-miR-1253, hsa-miR-96, hsa-miR-380*, hsa-miR-326, hsa-miR-612, hsa-miR-631, hsa-miR-490-5p, hsa-miR-138-2*, hsa-miR-887, hsa-let-7i*, hsa-miR-105, hsa-miR-454, hsa-miR-141*, hsa-miR-219-5p, hsa-miR-487b, hsa-miR-518d-3p, hsa-miR-627, hsa-miR-521, hsa-miR-548o, hsa-miR-888*, hsa-miR-144*, hsa-miR-127-5p, hsa-miR-20b, hsa-miR-450b-3p, hsa-miR-588, hsa-miR-933, hsa-miR-1283, hsa-miR-298, hsa-miR-107, hsa-miR-606, hsa-miR-616*, hsa-miR-570, hsa-miR-595, hsa-miR-20b*, hsa-miR-1184, hsa-miR-1278, hsa-

FIG. 9a miR-1286, hsa-miR-518d-5p, hsa-miR-641, hsa-miR-513a-3p, hsa-miR-571, hsa-miR-575, hsa-miR-376b, hsa-miR-124*, hsa-miR-496, hsa-miR-1471, hsa-miR-24-1*, hsa-miR-216a, hsa-miR-96*, hsa-miR-34c-3p, hsa-miR-600, hsa-miR-106a*, hsa-miR-199b-3p, hsa-miR-137, hsa-miR-603, hsa-miR-1233, hsa-miR-124, hsa-miR-146b-3p, hsa-miR-1202, hsa-miR-628-5p, hsa-miR-200a, hsa-miR-1207-3p, hsa-miR-591, hsa-miR-545*, hsa-miR-33b*, hsa-miR-512-5p, hsa-miR-1225-3p, hsa-miR-555, hsa-miR-513b, hsa-miR-1263, hsa-miR-491-3p, hsa-miR-186*, hsa-miR-208a, hsa-miR-519a*, hsa-miR-1181, hsa-miR-1183, hsa-miR-567, hsa-miR-222*, hsa-miR-525-3p, hsa-miR-760, hsa-miR-411*, hsa-miR-802, hsa-miR-381, hsa-miR-519b-5p, hsa-miR-421, hsa-miR-519d, hsa-miR-611, hsa-miR-647, hsa-miR-409-5p, hsa-miR-592, hsa-miR-138-1*, hsa-miR-1255a, hsa-miR-16-1*, hsa-miR-1296, hsa-miR-200a*, hsa-miR-518a-5p, hsa-miR-337-5p, hsa-miR-549, hsa-miR-516b, hsa-miR-517*, hsa-miR-1256, hsa-miR-1200, hsa-miR-377, hsa-miR-602, hsa-miR-129-3p, hsa-miR-590-5p, hsa-miR-301a, hsa-miR-623, hsa-miR-518b, hsa-miR-1203, hsa-miR-1295, hsa-miR-1273, hsa-miR-922, hsa-miR-1234, hsa-miR-106a, hsa-miR-139-5p, hsa-miR-410, hsa-miR-568, hsa-miR-223*, hsa-miR-18b, hsa-miR-523*, hsa-miR-598, hsa-miR-193a-3p, hsa-miR-1911*, hsa-miR-21*, hsa-miR-544, hsa-miR-10b*, hsa-miR-524-5p, hsa-miR-516a-5p, hsa-miR-182*, hsa-miR-367, hsa-miR-561, hsa-miR-15a*, hsa-miR-572, hsa-miR-155*, hsa-miR-199a-3p, hsa-miR-100*, hsa-miR-1537, hsa-miR-219-1-3p, hsa-miR-18a, hsa-miR-34c-5p, hsa-miR-562, hsa-miR-374b, hsa-miR-518e*, hsa-miR-448, hsa-miR-32*, hsa-miR-548a-3p, hsa-miR-146a*, hsa-miR-101*, hsa-miR-202*, hsa-miR-451, hsa-miR-495, hsa-miR-133a, hsa-miR-1288, hsa-miR-411, hsa-miR-103, hsa-miR-660, hsa-miR-374a*, hsa-miR-136*, hsa-miR-148a, hsa-miR-574-5p, hsa-miR-1243, hsa-miR-1298, hsa-miR-17, hsa-miR-26b, hsa-miR-93, hsa-miR-144, hsa-miR-559, hsa-miR-384, hsa-miR-503, hsa-miR-1254, hsa-miR-19a*, hsa-miR-129-5p, hsa-miR-30d*, hsa-miR-126, hsa-miR-101

FIG. 9a cont.

b) Strong downregulated miRNAs (FC > 1.5)
hsa-miR-34a*, hsa-miR-934, hsa-miR-1324, hsa-miR-32, hsa-miR-640, hsa-miR-1251, hsa-miR-891b, hsa-miR-33b, hsa-miR-455-3p, hsa-miR-593*, hsa-miR-564, hsa-miR-153, hsa-miR-646, hsa-miR-1226*, hsa-miR-545, hsa-miR-452*, hsa-miR-650, hsa-miR-216b, hsa-miR-431, hsa-miR-188-3p, hsa-miR-635, hsa-miR-891a, hsa-miR-654-5p, hsa-miR-31*, hsa-miR-217, hsa-miR-1272, hsa-miR-143*, hsa-miR-374a, hsa-miR-515-5p, hsa-miR-33a, hsa-miR-621, hsa-miR-301b, hsa-miR-509-5p, hsa-miR-509-3-5p, hsa-miR-1301, hsa-miR-24-2*, hsa-miR-767-5p, hsa-let-7g*, hsa-miR-188-5p, hsa-miR-497, hsa-miR-1912, hsa-miR-196a*, hsa-miR-497*, hsa-miR-597, hsa-miR-1206, hsa-miR-20a, hsa-miR-558, hsa-miR-1266, hsa-miR-489, hsa-miR-1291, hsa-miR-31, hsa-miR-541, hsa-miR-874, hsa-miR-508-5p, hsa-miR-520c-5p, hsa-miR-214, hsa-miR-522*, hsa-miR-20a*, hsa-miR-96, hsa-miR-326, hsa-miR-631, hsa-miR-490-5p, hsa-miR-887, hsa-let-7i*, hsa-miR-454, hsa-miR-627, hsa-miR-144*, hsa-miR-127-5p, hsa-miR-20b, hsa-miR-588, hsa-miR-933, hsa-miR-1283, hsa-miR-298, hsa-miR-518d-5p, hsa-miR-1471, hsa-miR-24-1*, hsa-miR-216a, hsa-miR-96*, hsa-miR-34c-3p, hsa-miR-199b-3p, hsa-miR-603, hsa-miR-1202, hsa-miR-628-5p, hsa-miR-200a, hsa-miR-186*, hsa-miR-519a*, hsa-miR-381, hsa-miR-611, hsa-miR-590-5p, hsa-miR-301a, hsa-miR-1295, hsa-miR-1273, hsa-miR-922, hsa-miR-106a, hsa-miR-374b, hsa-miR-574-5p

FIG. 9b c) Very strong downregulated miRNAs (FC >2)
hsa-miR-32, hsa-miR-33b, hsa-miR-455-3p, hsa-miR-593*, hsa-miR-564, hsa-miR-646, hsa-miR-1226*, hsa-miR-452*, hsa-miR-650, hsa-miR-431, hsa-miR-891a, hsa-miR-654-5p, hsa-miR-31*, hsa-miR-1272, hsa-miR-374a, hsa-miR-621, hsa-miR-509-5p, hsa-miR-509-3-5p, hsa-miR-767-5p, hsa-miR-497, hsa-miR-20a, hsa-miR-520c-5p, hsa-miR-522*, hsa-miR-96, hsa-miR-20b, hsa-miR-519a*

FIG. 9c

COMPLEX SETS OF MIRNAS AS NON-INVASIVE BIOMARKERS FOR COLON CANCER

CROSS-REFERENCE TO RELATED APPLICATIONS

This is a divisional application of U.S. Ser. No. 14/239,264 filed Feb. 18, 2014, now U.S. Pat. No. 9,249,469 issued Feb. 2, 2016, which claims priority to PCT/EP2012/065278 filed Aug. 3, 2012, which claims the priority to EP Application EP11178155.5 filed Aug. 19, 2011, the entire disclosures of which are expressly incorporated herein by reference.

SEQUENCE LISTING

The instant application contains a Sequence Listing which has been submitted via EFS-web and is hereby incorporated by reference in its entirety. The ASCII copy, created on Jul. 17, 2012, is namedFP-008_PCTColonCancer_SeqListing_ST25.txt, and is 87 kb bytes in size.

TECHNICAL FIELD OF THE INVENTION

The present invention relates to a method for diagnosing and/or prognosing of colon cancer based on the determination of expression profiles of sets of miRNAs representative for colon cancer compared to a reference. Furthermore, the present invention relates to sets of polynucleotides and/or primer pairs for detecting sets of miRNAs for diagnosing and/or prognosing of colon cancer in a biological sample from a subject. Further, the present invention relates to means for diagnosing and/or prognosing of colon cancer comprising said sets of primer pairs and/or polynucleotides. In addition, the present invention relates to a kit for diagnosing and/or prognosing of colon cancer comprising means for determining expression profiles of sets of miRNAs representative for colon cancer and at least one reference. Further, the present invention relates to use of polynucleotides and/or primer pairs for diagnosing and/or prognosing of colon cancer in a biological sample of a subject.

BACKGROUND OF THE INVENTION

Today, biomarkers play a key role in early diagnosis, risk stratification, and therapeutic management of various diseases. While progress in biomarker research has accelerated over the last 5 years, the clinical translation of disease biomarkers as endpoints in disease management and as the foundation for diagnostic products still poses a challenge.

MicroRNAs (miRNAs) are a new class of biomarkers. They represent a group of small noncoding RNAs that regulate gene expression at the posttranslational level by degrading or blocking translation of messenger RNA (mRNA) targets. MiRNAs are important players when it comes to regulate cellular functions and in several diseases, including cancer.

So far, miRNAs have been extensively studied in tissue material. It has been found that miRNAs are expressed in a highly tissue-specific manner. Disease-specific expression of miRNAs have been reported in many human cancers employing primarily tissue material as the miRNA source. In this context miRNAs expression profiles were found to be useful in identifying the tissue of origin for cancers of unknown primary origin.

Since recently it is known that miRNAs are not only present in tissues but also in other body fluid samples, including human blood. Nevertheless, the mechanism why miRNAs are found in body fluids, especially in blood, or their function in these body fluids is not understood yet.

Various miRNA biomarkers found in tissue material have been proposed to be correlated with certain diseases, e.g. cancer. However, there is still a need for novel miRNAs as biomarkers for the detection and/or prediction of these and other types of diseases. Especially desirable are non-invasive biomarkers, that allow for quick, easy and cost-effective diagnosis/prognosis which cause only minimal stress for the patient eliminating the need for surgical intervention Particularly, the potential role of miRNAs as non-invasive biomarkers for the diagnosis and/or prognosis of colon cancer has not been systematically evaluated yet. In addition, many of the miRNA biomarkers presently available for diagnosing and/or prognosing of diseases have shortcomings such as reduced sensitivity, not sufficient specificity or do not allow timely diagnosis or represent invasive biomarkers. Accordingly, there is still a need for novel and efficient miRNAs or sets of miRNAs as markers, effective methods and kits for the non-invasive diagnosis and/or prognosis of diseases such as colon cancer.

The inventors of the present invention assessed for the first time the expression of miRNAs on a whole-genome level in subjects with colon cancer as non-invasive biomarkers from body fluids, preferably in blood. They surprisingly found that miRNAs are significantly dysregulated in blood of colon cancer subjects in comparison to healthy controls and thus, miRNAs are appropriated non-invasive biomarkers for diagnosing and/or prognosing of colon cancer. This finding is surprising, since there is nearly no overlap of the miRNA biomarkers found in blood and the miRNA biomarkers found in tissue material representing the origin of the disease. The inventors of the present invention surprisingly found miRNA biomarkers in body fluids, especially in blood, that have not been found to be correlated to colon cancer when tissues material was used for this kind of analysis. Therefore, the inventors of the invention identified for the first time miRNAs as non-invasive surrogate biomarkers for diagnosis and/or prognosis of colon cancer. The inventors of the present invention identified single miRNAs which predict colon cancer with high specificity, sensitivity and accuracy. The inventors of the present invention also pursued a multiple biomarker strategy, thus implementing sets of miRNA biomarkers for diagnosing and/or prognosing of colon cancer leading to added specificity, sensitivity, accuracy and predictive power, thereby circumventing the limitations of single biomarker. In detail, by using a machine learning algorithms, they identified unique sets of miRNAs (miRNA signatures) that allow for non-invasive diagnosis of colon cancer with even higher power, indicating that sets of miRNAs (miRNA signatures) derived from a body fluid sample, such as blood from a subject (e.g. human) can be used as novel non-invasive biomarkers.

SUMMARY OF THE INVENTION

In a first aspect, the invention provides a method for diagnosing and/or prognosing of colon cancer comprising the steps of:
(i) determining an expression profile of a set comprising at least two miRNAs representative for colon cancer in a body fluid sample from a subject, and (ii) comparing said expression profile to a reference, wherein the comparison of said expression profile to said reference allows for the diagnosis and/or prognosis of colon cancer, In a second aspect, the invention provides a set comprising polynucleotides for detecting a set comprising at least two miRNAs for diagnosing and/or prognosing of colon cancer in a body fluid sample from a subject.

In a third aspect, the invention provides a use of a set of polynucleotides according to the second aspect of the invention for diagnosing and/or prognosing colon cancer in a subject In a fourth aspect, the invention provides a set of primer pairs for determining the expression level of a set of miRNAs in a body fluid sample of a subject suffering or suspected of suffering from colon cancer.

In a fifth aspect, the invention provides a use of set of primer pairs according to the fourth aspect of the invention for diagnosing and/or prognosing colon cancer in a subject In a sixth aspect, the invention provides means for diagnosing and/or prognosing of colon cancer in a body fluid sample of a subject comprising:
(i) a set of at least two polynucleotides according to the second aspect of the invention or
(ii) a set of primer pairs according the fourth aspect of the invention.

In a seventh aspect, the invention provides a kit for diagnosing and/or prognosing of colon cancer comprising
(i) means for determining an expression profile of a set comprising at least two miRNAs representative for colon cancer in a body fluid sample from a subject, and
(ii) at least one reference.

In an eighth aspect, the invention provides a set of miRNAs in a body fluid sample isolated from a subject for diagnosing and/or prognosing of colon cancer.

In a ninth aspect, the invention provides a use of a set of miRNAs according to the eighth aspect of the invention for diagnosing and/or prognosing of colon cancer in a subject, This summary of the invention does not necessarily describe all features of the invention.

BRIEF DESCRIPTION OF THE DRAWINGS

FIG. 1: MiRNAs for diagnosis or prognosis of colon cancer. Experimental data obtained for analysis of miRNAs according to SEQ ID NO: 1 to 484. Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with colon cancer, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.

FIG. 2: Sets of miRNAs (miRNA-signatures SNC-1 to SNC-796) that allow for effective diagnosis and/or prognosis of colon cancer when differentiating colon cancer and healthy controls. Experimental details: SEQ ID NO: sequence identification number, miRNA: identifier of the miRNA according to miRBase, Acc=accuracy, Spec=specificity, Sens=sensitivity.

FIG. 5a-5b: Further sets of miRNAs (miRNA-signatures SNC-lin1 to SNC-lin7 and SNC-rbf1 to SNC-rbf7) that allow for effective diagnosis and/or prognosis of colon cancer when differentiating colon cancer and healthy controls//5a: Graphical representation of Accuracy, Balanced Accuracy, Sensitivity and Specificity in relation to the number of miRNA-biomarkers within the sets of miRNAs (miRNA-signatures)//5b: Experimental details: miRNA-signatures (SNC-lin1 to SNC-lin7 and SNC-rbf1 to SNC-rbf7), # of miRNA contained in the miRNA-Signature; miRNA: identifier of the miRNA according to miRBase, Accuracy FIG. 6: MiRNAs for diagnosis or prognosis of colon cancer. Experimental data obtained for analysis of miRNAs according to SEQ ID NO: 1 to 588. Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with colon cancer, qmedian: ratio of median g1/median g2, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.

FIG. 7: Further sets of miRNAs (miRNA-signatures SNC-797 to SNC-1134) that allow for effective diagnosis and/or prognosis of colon cancer when differentiating colon cancer and healthy controls. With of Signature NO SNC-797 to SNC-1134; SEQ ID NO: sequence identification number; miRNAs contained in the respective miRNA-Signature with miRNA identifier according to miRBase; Accuracy, Specificity, Sensitivity and Balanced Accuracy (Bal. Acc.) in Percent.

FIG. 8a-8c: miRNAs that are up-regulated in colon cancer compared to healthy controls that allow for effective diagnosis and/or prognosis of colon cancer. With a) miRNAs that are up-regulated in colon cancer, b) miRNAs that are strong up-regulated in colon cancer (Fold Change>1.5) and c) miRNAs that are very strong up-regulated in colon cancer (Fold Change>2.0) compared to healthy controls that allow for effective diagnosis and/or prognosis of colon cancer.

FIG. 9a-9c: miRNAs that are down-regulated in colon cancer compared to healthy controls that allow for effective diagnosis and/or prognosis of colon cancer. With a) miRNAs that are down-regulated in colon cancer, b) miRNAs that are strong down-regulated in colon cancer (Fold Change>1.5) and c) miRNAs that are very strong down-regulated in colon cancer (Fold Change>2.0) compared to healthy controls that allow for effective diagnosis and/or prognosis of colon cancer.

DETAILED DESCRIPTION OF THE INVENTION

Figure 3:
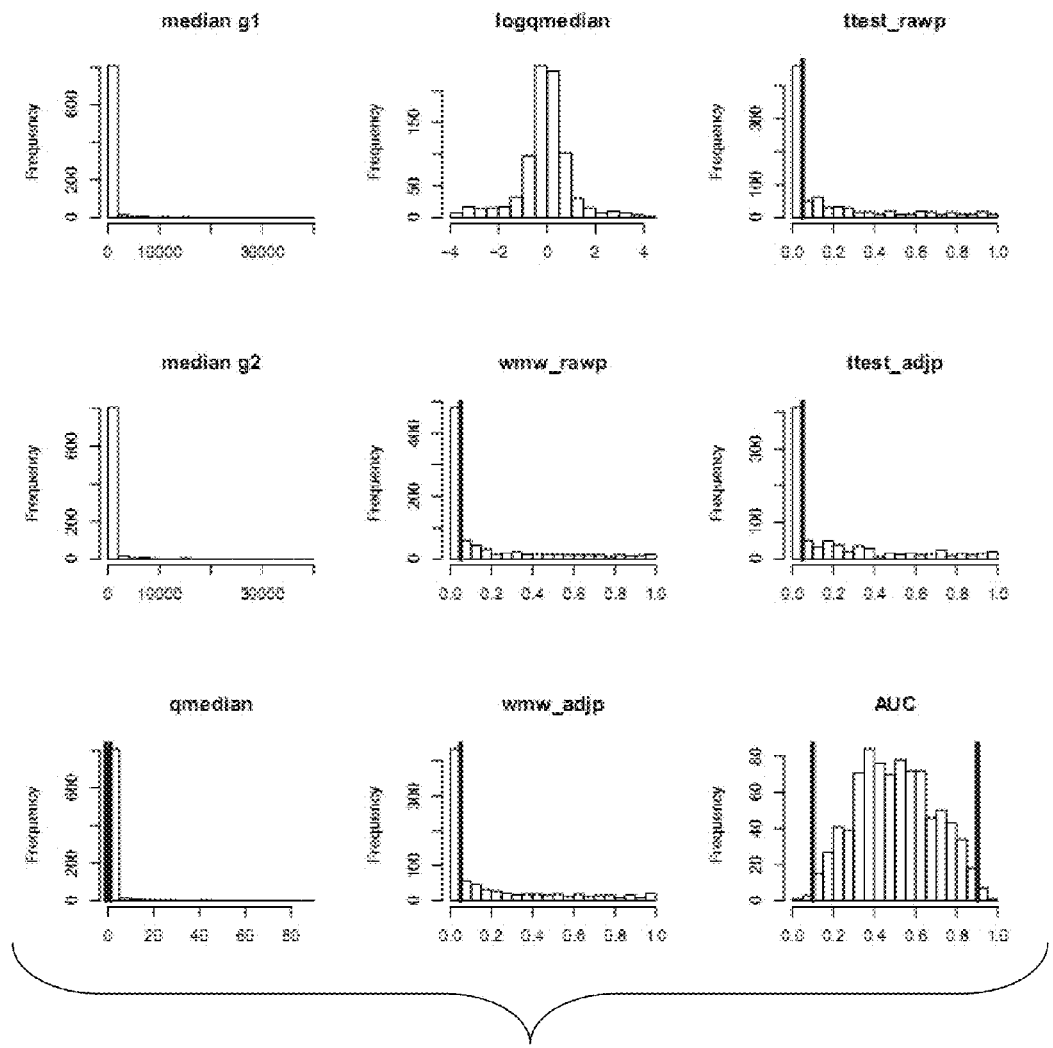
FIG. 3: Graphical representation of the experimental data on miRNAs for diagnosis or prognosis of colon cancer. The histograms show the distribution curve obtained when 862 miRNAs biomarkers were analyzed on microarrays. The thick lines separate the high informative miRNA biomarkers for diagnosis or prognosis of colon cancer in comparison to healthy controls from the non-informative ones. Experimental details: median g1: median intensity obtained from microarray analysis for healthy controls, median g2: median intensity obtained from microarray analysis for individuals with colon cancer, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.
Figure 4:
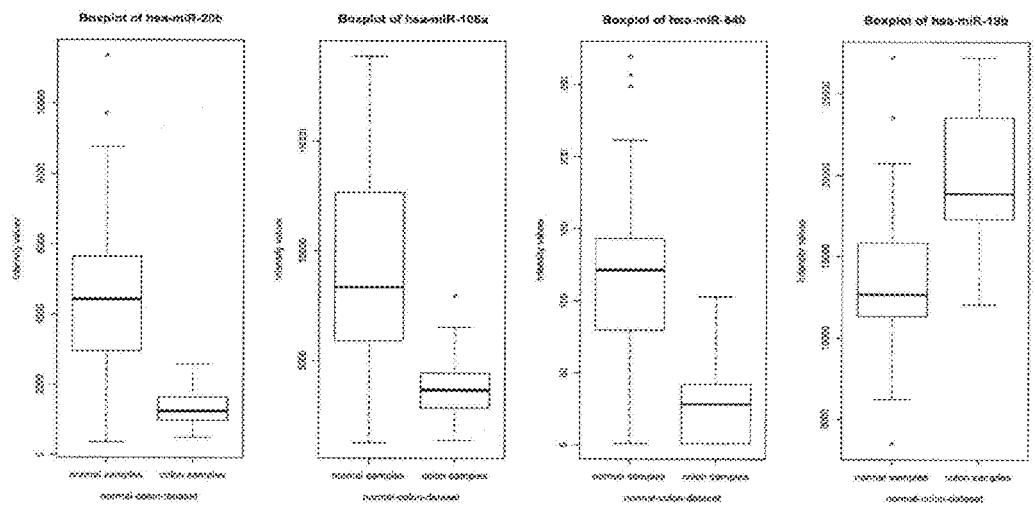
FIG. 4: Boxplot of the experimental data of selected miRNAs suitable for diagnosis or prognosis of colon cancer. Y-axis: intensity values corresponding to the expression level of the miRNAs, x-axis left: normal samples (healthy controls), right: colon cancer samples (patients with colon cancer)

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and in the appended claims, the singular forms "a", "an", and "the" include plural referents, unless the content clearly dictates otherwise. For example, the term "a test compound" also includes "test compounds".

The terms "microRNA" or "miRNA" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The miRNAs regulate gene expression and are encoded by genes from whose DNA they are transcribed but miRNAs are not translated into protein (i.e. miRNAs are non-coding RNAs). The genes encoding miRNAs are longer than the processed mature miRNA molecules. The miRNAs are first transcribed as primary transcripts or pri-miRNAs with a cap and poly-A tail and processed to short, 70 nucleotide stem-loop structures known as pre-miRNAs in the cell nucleus. This processing is performed in animals by a protein complex known as the Microprocessor complex consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide (anti-strand), or passenger strand, is degraded as a RISC substrate. Therefore, the miRNA*s are derived from the same hairpin structure like the "normal" miRNAs. So if the "normal" miRNA is then later called the "mature miRNA" or "guide strand", the miRNA* is the "anti-guide strand" or "passenger strand".

The terms "microRNA*" or "miRNA*" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The "miRNA*s", also known as the "anti-guide strands" or "passenger strands", are mostly complementary to the "mature miRNAs" or "guide strands", but have usually single-stranded overhangs on each end. There are usually one or more mispairs and there are sometimes extra or missing bases causing single-stranded "bubbles". The miRNA*s are likely to act in a regulatory fashion as the miRNAs (see also above). In the context of the present invention, the terms "miRNA" and "miRNA*" are interchangeable used. The present invention encompasses (target) miRNAs which are dysregulated in biological samples such as blood or tissue of colon cancer patients in comparison to healthy controls. Said (target) miRNAs are preferably selected from the group consisting of SEQ ID NO: 1 to 588.

The term "miRBase" refers to a well-established repository of validated miRNAs. The miRBase is a searchable database of published miRNA sequences and annotation.

Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download.

As used herein, the term "nucleotides" refers to structural components, or building blocks, of DNA and RNA. Nucleotides consist of a base (one of four chemicals: adenine, thymine, guanine, and cytosine) plus a molecule of sugar and one of phosphoric acid. The term "nucleosides" refers to glycosylamine consisting of a nucleobase (often referred to simply base) bound to a ribose or deoxyribose sugar. Examples of nucleosides include cytidine, uridine, adenosine, guanosine, thymidine and inosine. Nucleosides can be phosphorylated by specific kinases in the cell on the sugar's primary alcohol group (—CH2-OH), producing nucleotides, which are the molecular building blocks of DNA and RNA.

The term "polynucleotide", as used herein, means a molecule of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally spacer elements and/or elongation elements described below. The depiction of a single strand of a polynucleotide also defines the sequence of the complementary strand. Polynucleotides may be single stranded or double stranded, or may contain portions of both double stranded and single stranded sequences. The term "polynucleotide" means a polymer of deoxyribonucleotide or ribonucleotide bases and includes DNA and RNA molecules, both sense and anti-sense strands. In detail, the polynucleotide may be DNA, both cDNA and genomic DNA, RNA, cRNA or a hybrid, where the polynucleotide sequence may contain combinations of deoxyribonucleotide or ribonucleotide bases, and combinations of bases including uracil, adenine, thymine, cytosine, guanine, inosine, xanthine, hypoxanthine, isocytosine and isoguanine. Polynucleotides may be obtained by chemical synthesis methods or by recombinant methods.

In the context of the present invention, a polynucleotide as a single polynucleotide strand provides a probe (e.g. miRNA capture probe) that is capable of binding to, hybridizing with, or detecting a target of complementary sequence, such as a nucleotide sequence of a miRNA or miRNA*, through one or more types of chemical bonds, usually through complementary base pairing, usually through hydrogen bond formation. Polynucleotides in their function as probes may bind target sequences, such as nucleotide sequences of miRNAs or miRNAs*, lacking complete complementarity with the polynucleotide sequences depending upon the stringency of the hybridization condition. There may be any number of base pair mismatches which will interfere with hybridization between the target sequence, such as a nucleotide sequence of a miRNA or miRNA*, and the single stranded polynucleotide described herein. However, if the number of mutations is so great that no hybridization can occur under even the least stringent hybridization conditions, the sequences are no complementary sequences. The present invention encompasses polynucleotides in form of single polynucleotide strands as probes for binding to, hybridizing with or detecting complementary sequences of (target) miRNAs for diagnosing and/or prognosing of colon cancer. Said (target) miRNAs are preferably selected from the group consisting of SEQ ID NO: 1 to 588.

Because of the conservation of miRNAs among species, for example between humans and other mammals, e.g. animals such as mice, monkey or rat, the polynucleotide(s) of the invention may not only be suitable for detecting a miRNA(s) of a specific species, e.g. a human miRNA, but may also be suitable for detecting the respective miRNA orthologue(s) in another species, e.g. in another mammal, e.g. animal such as mouse or rat.

The term "antisense", as used herein, refers to nucleotide sequences which are complementary to a specific DNA or RNA sequence. The term "antisense strand" is used in reference to a nucleic acid strand that is complementary to the "sense" strand.

The term "label", as used herein, means a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and other entities which can be made detectable. A label may be incorporated into nucleic acids at any position, e.g. at the 3' or 5' end or internally. The polynucleotide for detecting a miRNA (polynucleotide probe) and/or the miRNA itself may be labeled. For detection purposes, the miRNA(s) or miRNA*(s) may be employed unlabeled, directly labeled, or indirectly labeled, such as with biotin to which a streptavidin complex may later bind.

The term "stringent hybridization conditions", as used herein, means conditions under which a first nucleotide sequence (e.g. polynucleotide in its function as a probe for detecting a miRNA or miRNA*) will hybridize to a second nucleotide sequence (e.g. target sequence such as nucleotide sequence of a miRNA or miRNA*), such as in a complex mixture of nucleotide sequences. Stringent conditions are sequence-dependent and will be different in different circumstances. Stringent conditions may be selected to be about 5 to 10° C. lower than the thermal melting point (Tm) for the specific sequence at a defined ionic strength, pH. The Tm may be the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01 to 1.0 M sodium ion concentration (or other salts) at pH 7.0 to 8.3 and the temperature is at least about 20° C. for short probes (e.g. about 10-35 nucleotides) and up to 60° C. for long probes (e.g. greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 05×SSPE and 6×SSPE at 45° C.

The term "sensitivity", as used herein, means a statistical measure of how well a binary classification test correctly identifies a condition, for example how frequently it correctly classifies a heart and cardiovascular system disease into the correct type out of two or more possible types (e.g. heart and cardiovascular system disease type and healthy type). The sensitivity for class A is the proportion of cases that are determined to belong to class "A" by the test out of the cases that are in class "A". A theoretical, optimal prediction can achieve 100% sensitivity (i.e. predict all patients from the sick group as sick).

The term "specificity", as used herein, means a statistical measure of how well a binary classification test correctly identifies a condition, for example how frequently it correctly classifies a heart and cardiovascular system disease into the correct type out of two or more possible types. The specificity for class A is the proportion of cases that are determined to belong to class "not A" by the test out of the cases that are in class "not A". A theoretical, optimal prediction can achieve 100% specificity (i.e. not predict anyone from the healthy group as sick).

The term "accuracy", as used herein, means a statistical measure for the correctness of classification or identification of sample types. The accuracy is the proportion of true results (both true positives and true negatives).

The term "Receiver operating characteristic (ROC) curves" means a graphical measure of sensitivity (y-axis) vs. 1—specificity (x-axis) for a clinical test. An important measure of the accuracy of the clinical test is the area under the ROC curve value (AUC value). If this area is equal to 1.0 then this test is 100% accurate because both the sensitivity and specificity are 1.0 so there are no false positives and no false negatives. On the other hand a test that cannot discriminate that is the diagonal line from 0,0 to 1,1. The ROC area for this line is 0.5. ROC curve areas (AUC-values) are typically between 0.5 and 1.0, but also ROC values below 0.5 can—according to information theory—be as good, if the result is interpreted inversely. Therefore, according to the present invention an AUC-value close to 1 (e.g. 0.95) represents the same good measure for a clinical test as an AUC-value close to 0 (e.g. 0.05).

The term "biological sample", as used in the context of the present invention, refers to any biological sample containing miRNA(s). Said biological sample may be a biological fluid, tissue, cell(s) or mixtures thereof. For example, biological samples encompassed by the present invention are body fluids, tissue (e.g. section or explant) samples, cell culture samples, cell colony samples, single cell samples, collection of single cell samples, blood samples (e.g. whole blood or a blood fraction such as serum or plasma), urine samples, or samples from other peripheral sources. Said biological samples may be mixed or pooled, e.g. a biological sample may be a mixture of blood and urine samples. A "biological sample" may be provided by removing cell(s), cell colonies, an explant, or a section from a subject suspected to be affected by colon cancer, but may also be provided by using a previously isolated sample. For example, a tissue sample may be removed from a subject suspected to be affected by colon cancers by conventional biopsy techniques or a blood sample may be taken from a subject suspected to be affected by colon cancer by conventional blood collection techniques. The biological sample, e.g. tissue or blood sample, may be obtained from a subject suspected to be affected by colon cancer prior to initiation of the therapeutic treatment, during the therapeutic treatment and/or after the therapeutic treatment.

The term "body fluid sample", as used in the context of the present invention, refers to liquids originating from the body of a subject. Said body fluid samples include, but are not limited to, blood, urine, sputum, breast milk, cerebrospinal fluid, amniotic fluid, bronchial lavage, colostrum, seminal fluid, cerumen (earwax), endolymph, perilymph, gastric juice, mucus, peritoneal fluid, pleural fluid, saliva, sebum (skin oil), semen, sweat, tears, vaginal secretion, vomit including components or fractions thereof. Said body fluid samples may be mixed or pooled, e.g. a body fluid sample may be a mixture of blood and urine samples or blood and tissue material. A "body fluid sample" may be provided by removing a body liquid from a subject, but may also be provided by using previously isolated sample material.

Preferably, the body fluid sample from a subject (e.g. human or animal) has a volume of between 0.1 and 20 ml, more preferably of between 0.5 and 10 ml, more preferably between 1 and 8 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

In the context of the present invention said "body fluid sample" allows for a non-invasive diagnosis/and or prognosis of a subject.

The term "blood sample", as used in the context of the present invention, refers to a blood sample originating from a subject. The "blood sample" may be derived by removing blood from a subject by conventional blood collecting techniques, but may also be provided by using previously isolated and/or stored blood samples. For example a blood sample may be whole blood, plasma, serum, blood cells, PBMC (peripheral blood mononuclear cells), blood cellular fractions including or comprising red blood cells (erythrocytes), white blood cells (leukocytes), platelets (thrombocytes), or blood collected in blood collection tubes (e.g. EDTA-, heparin-, citrate-, PAXgene-, Tempus-tubes) including components or fractions thereof. For example, a blood sample may be taken from a subject suspected to be affected or to be suspected to be affected by colon cancer, prior to initiation of a therapeutic treatment, during the therapeutic treatment and/or after the therapeutic treatment.

Preferably, the blood sample from a subject (e.g. human or animal) has a volume of between 0.1 and 20 ml, more preferably of between 0.5 and 10 ml, more preferably between 1 and 8 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

In the context of the present invention said "body fluid sample" or "blood sample" allows for a non-invasive diagnosis/and or prognosis of a subject.

Preferably, when the blood sample is collected from the subject the RNA-fraction, especially the miRNA fraction, is guarded against degradation. For this purpose special collection tubes (e.g. PAXgene RNA tubes from Preanalytix, Tempus Blood RNA tubes from Applied Biosystems) or additives (e.g. RNAlater from Ambion, RNAsin from Promega) that stabilize the RNA fraction and/or the miRNA fraction are employed.

The biological sample, preferably the body fluid sample may be from a subject (e.g. human or mammal) that has been therapeutically treated or that has not been therapeutically treated. In one embodiment, the therapeutical treatment is monitored on the basis of the detection of the miRNA or set of miRNAs by the polynucleotide or set of polynucleotides of the invention. It is also preferred that total RNA or a subfraction thereof, isolated (e.g. extracted) from a biological sample of a subject (e.g. human or animal), is used for detecting the miRNA or set of miRNAs by the polynucleotide or set of polynucleotides or primer pairs of the invention.

The term "non-invasive", as used in the context of the present invention, refers to methods for obtaining a biological sample, particularly a body fluid sample, without the need for an invasive surgical intervention or invasive medical procedure. In the context of the present invention, a blood drawn represents a non-invasive procedure, therefore a blood-based test (utilizing blood or fractions thereof) is a non-invasive test. Other body fluid samples for non-invasive tests are e.g. urine, sputum, tears, mothers mild, cerumen, sweat, saliva, vaginal secretion, vomit, etc.

The term "minimal invasive", as used in the context of the present invention, refers to methods for obtaining a biological sample, particularly a body fluid sample, with a minimal need for an invasive surgical intervention or invasive medical procedure.

The term "biomarker", as used in the context of the present invention, represents a characteristic that can be objectively measured and evaluated as an indicator of normal and disease processes or pharmacological responses. A biomarker is a parameter that can be used to measure the onset or the progress of disease or the effects of treatment. The parameter can be chemical, physical or biological.

The term "surrogate biomarker", as used in the context of the present invention, represents biomarker intended to substitute for a clinical endpoint. It is a measure of a clinical condition or a measure of effect of a certain treatment that may correlate with the real clinical condition (e.g. healthy, diseased) but doesn't necessarily have a guaranteed relationship. An ideal surrogate biomarker is a laboratory substitute for a clinically meaningful result, and should lie directly in the causal pathway linking disease to outcome. Surrogate biomarkers are used when the primary endpoint is undesired (e.g. death). A commonly used example is cholesterol: while elevated cholesterol levels increase the likelihood for heart disease, the relationship is not linear—many people with normal cholesterol develop heart disease, and many with high cholesterol do not. "Death from heart disease" is the endpoint of interest, but "cholesterol" is the surrogate biomarker.

The term "diagnosis" as used in the context of the present invention refers to the process of determining a possible disease or disorder and therefore is a process attempting to define the (clinical) condition of a subject. The determination of the expression level of a set of miRNAs according to the present invention correlates with the (clinical) condition of a subject. Preferably, the diagnosis comprises (i) determining the occurrence/presence of colon cancer, (ii) monitoring the course of colon cancer, (iii) staging of colon cancer, (iv) measuring the response of a patient with colon cancer to therapeutic intervention, and/or (v) segmentation of a subject suffering from colon cancer.

The term "prognosis" as used in the context of the present invention refers to describing the likelihood of the outcome or course of a disease or a disorder. Preferably, the prognosis comprises (i) identifying of a subject who has a risk to develop colon cancer, (ii) predicting/estimating the occurrence, preferably the severity of occurrence of colon cancer, and/or (iii) predicting the response of a subject with colon cancer to therapeutic intervention.

The term "(clinical) condition" (biological state or health state), as used herein, means a status of a subject that can be described by physical, mental or social criteria. It includes so-called "healthy" and "diseased" conditions. For the definition of "healthy" and "diseased" conditions it is referred to the international classification of diseases (ICD) of the WHO (int/classifications/icd/en/index). When one condition is compared according to a preferred embodiment of the method of the present invention, it is understood that said condition is colon cancer or a specific form of colon cancer.

When two or more conditions are compared according to another preferred embodiment of the method of the present invention, it is understood that this is possible for all conditions that can be defined and is not limited to a comparison of a diseased versus healthy comparison and extends to multiway comparison, under the proviso that at least one condition is colon cancers, preferably a specific form of colon cancer.

The term "miRNA expression profile" as used in the context of the present invention, represents the determination of the miRNA expression level or a measure that correlates with the miRNA expression level in a biological sample. The miRNA expression profile may be generated by any convenient means, e.g. nucleic acid hybridization (e.g. to a microarray, bead-based methods), nucleic acid amplification (PCR, RT-PCR, qRT-PCR, high-throughput RT-PCR), ELISA for quantitation, next generation sequencing (e.g. ABI SOLID, Illumina Genome Analyzer, Roche/454 GS FLX), flow cytometry (e.g. LUMINEX, Firefly Bioworks) and the like, that allow the analysis of differential miRNA expression levels between samples of a subject (e.g. diseased) and a control subject (e.g. healthy, reference sample). The sample material measure by the aforementioned means may be total RNA, labeled total RNA, amplified total RNA, cDNA, labeled cDNA, amplified cDNA, miRNA, labeled miRNA, amplified miRNA or any derivatives that may be generated from the aforementioned RNA/DNA species. By determining the miRNA expression profile, each miRNA is represented by a numerical value. The higher the value of an individual miRNA, the higher is the expression level of said miRNA, or the lower the value of an individual miRNA, the lower is the expression level of said miRNA.

The "miRNA expression profile", as used herein, represents the expression level/expression data of a single miRNA or a collection of expression levels of at least two miRNAs, preferably of least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more, or up to all known miRNAs.

The term "differential expression" of miRNAs as used herein, means qualitative and/or quantitative differences in the temporal and/or local miRNA expression patterns, e.g. within and/or among biological samples, body fluid samples, cells, or within blood. Thus, a differentially expressed miRNA may qualitatively have its expression altered, including an activation or inactivation in, for example, blood from a diseases subject versus blood from a healthy subject. The difference in miRNA expression may also be quantitative, e.g. in that expression is modulated, i.e. either up-regulated, resulting in an increased amount of miRNA, or down-regulated, resulting in a decreased amount of miRNA. The degree to which miRNA expression differs need only be large enough to be quantified via standard expression characterization techniques, e.g. by quantitative hybridization (e.g. to a microarray, to beads), amplification (PCR, RT-PCR, qRT-PCR, high-throughput RT-PCR), ELISA for quantitation, next generation sequencing (e.g. ABI SOLID, Illumina Genome Analyzer, Roche 454 GS FL), flow cytometry (e.g. LUMINEX, Firefly Bioworks) and the like.

Nucleic acid hybridization may be performed using a microarray/biochip or in situ hybridization. In situ hybridization is preferred for the analysis of a single miRNA or a set comprising a low number of miRNAs (e.g. a set of at least 2 to 50 miRNAs such as a set of 2, 5, 10, 20, 30, or 40 miRNAs). The microarray/biochip, however, allows the analysis of a single miRNA as well as a complex set of miRNAs (e.g. all known miRNAs or subsets thereof).

For nucleic acid hybridization, for example, the polynucleotides (probes) according to the present invention with complementarity to the corresponding miRNAs to be detected are attached to a solid phase to generate a microarray/biochip (e.g. 484 (588) polynucleotides (probes) which are complementary to the 484 (588) miRNAs having SEQ ID NO: 1 to 484 (588)). Said microarray/biochip is then incubated with a biological sample containing miRNAs, isolated (e.g. extracted) from the body fluid sample such as blood sample from a subject such as a human or an animal, which may be labelled, e.g. fluorescently labelled, or unlabelled. Quantification of the expression level of the miRNAs may then be carried out e.g. by direct read out of a label or by additional manipulations, e.g. by use of a polymerase reaction (e.g. template directed primer extension, MPEA-Assay, RAKE-assay) or a ligation reaction to incorporate or add labels to the captured miRNAs.

Alternatively, the polynucleotides which are at least partially complementary (e.g. a set of chimeric polynucleotides with each a first stretch being complementary to a set of miRNA sequences and a second stretch complementary to capture probes bound to a solid surface (e.g. beads, Luminex beads)) to miRNAs having SEQ ID NO: 1 to 588 are contacted with the biological sample containing miRNAs (e.g. a body fluid sample, preferably a blood sample) in solution to hybridize. Afterwards, the hybridized duplexes are pulled down to the surface (e.g. a plurality of beads) and successfully captured miRNAs are quantitatively determined (e.g. FlexmiR-assay, FlexmiR v2 detection assays from Luminex, Firefly Bioworks).

Nucleic acid amplification may be performed using real time polymerase chain reaction (RT-PCR) such as real time quantitative polymerase chain reaction (RT qPCR). The standard real time polymerase chain reaction (RT-PCR) is preferred for the analysis of a single miRNA or a set comprising a low number of miRNAs (e.g. a set of at least 2 to 50 miRNAs such as a set of 2, 5, 10, 20, 30, or 40 miRNAs), whereas high-throughput RT-PCR technologies (e.g. OpenArray from Applied Biosystems, SmartPCR from Wafergen, Biomark System from Fluidigm) are also able to measure large sets (e.g. a set of 10, 20, 30, 50, 80, 100, 200 or more) to all known miRNAs in a high parallel fashion. RT-PCR is particularly suitable for detecting low abandoned miRNAs.

The aforesaid real time polymerase chain reaction (RT-PCR) may include the following steps:
(i) extracting the total RNA from a biological sample or body fluid sample such as a blood sample (e.g. whole blood, serum, or plasma) of a subjects such as human or animal, and obtaining cDNA samples by RNA reverse transcription (RT) reaction using universal or miRNA-specific primers; or collecting a body fluid sample such as urine or blood sample (e.g. whole blood, serum, or plasma) of a patient such as human or animal, and conducting reverse transcriptase reaction using universal or miRNA-specific primers (e.g. looped RT-primers) within the body fluid sample such as urine or blood sample (e.g. whole blood, serum, or plasma) being a buffer so as to prepare directly cDNA samples,
(ii) designing miRNA-specific cDNA forward primers and providing universal reverse primers to amplify the cDNA via polymerase chain reaction (PCR),
(iii) adding a fluorescent dye (e.g. SYBR Green) or a fluorescent probe (e.g. Taqman probe) probe to conduct PCR, and
(iv) detecting the miRNA(s) level in the body fluid sample such as urine or blood sample (e.g. whole blood, serum, or plasma).

A variety of kits and protocols to determine an expression profile by real time polymerase chain reaction (RT-PCR) such as real time quantitative polymerase chain reaction (RT qPCR) are available. For example, reverse transcription of miRNAs may be performed using the TaqMan MicroRNA Reverse Transcription Kit (Applied Biosystems) according to manufacturer's recommendations. Briefly, miRNA may be combined with dNTPs, MultiScribe reverse transcriptase and the primer specific for the target miRNA. The resulting cDNA may be diluted and may be used for PCR reaction. The PCR may be performed according to the manufacturer's recommendation (Applied Biosystems). Briefly, cDNA may be combined with the TaqMan assay specific for the target miRNA and PCR reaction may be performed using ABI7300. Alternative kits are available from Ambion, Roche, Qiagen, Invitrogen, SABiosciences, Exiqon etc.

The term "subject", as used in the context of the present invention, means a patient or individual or mammal suspected to be affected by colon cancer. The patient may be diagnosed to be affected by colon cancer, i.e. diseased, or may be diagnosed to be not affected by colon cancer, i.e. healthy. The subject may also be diagnosed to be affected by a specific form of colon cancer. The subject may further be diagnosed to develop colon cancer or a specific form of colon cancer as the inventors of the present invention surprisingly found that miRNAs representative for colon cancer are already present in the biological sample, e.g. blood sample, before colon cancer occurs or during the early stage of colon cancer. It should be noted that a subject that is diagnosed as being healthy, i.e. not suffering from colon cancer or from a specific form of colon cancer, may possibly suffer from another disease not tested/known. The subject may be any mammal, including both a human and another mammal, e.g. an animal such as a rabbit, mouse, rat, or monkey. Human subjects are particularly preferred. Therefore, the miRNA from a subject may be a human miRNA or a miRNA from another mammal, e.g. an animal miRNA such as a mouse, monkey or rat miRNA, or the miRNAs comprised in a set may be human miRNAs or miRNAs from another mammal, e.g. animal miRNAs such as mouse, monkey or rat miRNAs.

The term "control subject", as used in the context of the present invention, may refer to a subject known to be affected with colon cancer (positive control), i.e. diseased, or to a subject known to be not affected with colon cancer (negative control), i.e. healthy. It may also refer to a subject known to be effected by another disease/condition (see definition "(clinical) condition"). It should be noted that a control subject that is known to be healthy, i.e. not suffering from colon cancer, may possibly suffer from another disease not tested/known. The control subject may be any mammal, including both a human and another mammal, e.g. an animal such as a rabbit, mouse, rat, or monkey. Human "control subjects" are particularly preferred.

The term "set comprising at least two miRNAs representative for colon cancer", as used herein, refers to refers to at least two fixed defined miRNAs comprised in a set which are known to be differential (differentially expressed) between subjects (e.g. humans or other mammals such as animals) suffering from colon cancer (diseased state) and control subjects (e.g. humans or other mammals such as animals and are, thus, representative for colon cancer. Said "set comprising at least two miRNAs representative for colon cancer" are preferably selected from the group consisting of SEQ ID NO: 1 to 588, a fragment thereof, and a sequence having at least 80% sequence identity thereto.

The term "colon cancer", as used herein refers to cancer that forms in the colon. Colon cancers start in the lining of the bowel. If left untreated, it can grow into the muscle layers underneath, and then through the bowel wall. Most begin as a small growth on the bowel wall: a colon polyp or adenoma. These mushroom-shaped growths are usually benign, but some develop into cancer over time. Localized bowel cancer is usually diagnosed through colonoscopy. Invasive cancers that are confined within the wall of the colon (TNM stages I and II) are often curable with surgery-tients. Colon cancer can take many years to develop and early detection of colon cancer greatly improves the chances of a cure. Despite this, colon cancer screening rates remain low. There are several different tests available for diagnosis: Digital rectal exam (DRE): The doctor inserts a lubricated, gloved finger into the rectum to feel for abnormal areas. It only detects tumors large enough to be felt in the distal part of the rectum but is useful as an initial screening test/Fecal occult blood test (FOBT): a test for blood in the stool./ Sigmoidoscopy: A lighted probe (sigmoidoscope) is inserted into the rectum and lower colon to check for polyps and other abnormalities./Colonoscopy: A lighted probe called a colonoscope is inserted into the rectum and the entire colon to look for polyps and other abnormalities that may be caused by cancer. A colonoscopy has the advantage that if polyps are found during the procedure they can be removed immediately. Tissue can also be taken for biopsy.

Due to the shortcomings of current state of the art diagnosis for colon cancer, there is an urgent need for better, non-invasive tests to further diagnosis and prognosis options for patients.

Due to the shortcomings of current state of the art diagnosis for colon cancer, there is an urgent need for better, non-invasive tests to further diagnosis and prognosis options for patients.

The inventors of the present invention surprisingly found that miRNAs are significantly dysregulated in body fluid samples such as blood of colon cancer subjects in comparison to a cohort of controls (healthy subjects) and thus, miRNAs are appropriated biomarkers for diagnosing and/or prognosing of colon cancer in a non-invasive fashion or minimal-invasive fashion. Furthermore, the sets of miRNAs of the present invention lead to high performance in diagnosing and/or prognosing of colon cancer, thus expose very high specificity, sensitivity and accuracy. They succeeded in determining the miRNAs that are differentially regulated in body fluid samples from patients having colon cancer compared to a cohort of controls (healthy subjects) (see experimental section for experimental details). Additionally, the inventors of the present invention performed hypothesis tests (e.g. t-test, limma-test) or other measurements (e.g. AUC, mutual information) on the expression level of the found miRNAs, in all controls (healthy subjects) and subjects suffering from colon cancer. These tests resulted in a significance value (p-value) for each miRNA. This p-value is a measure for the diagnostic power of each of these single miRNAs to discriminate, for example, between the two clinical conditions: controls (healthy subjects), i.e. not suffering from colon cancer, or diseased, i.e. suffering from colon cancer. Since a manifold of tests are carried out, one for each miRNA, the p-values may be too optimistic and, thus, over-estimate the actual discriminatory power. Hence, the p-values are corrected for multiple testing by the Benjamini Hochberg approach.

An overview of the miRNAs that are found to be significantly differentially regulated in biological samples of colon cancer and that performed best according to t-test, limma-test or AUC is provided in FIG. 1 or FIG. 6 (Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with colon cancer, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.). The miRNAs, i.e. miRNAs according to SEQ ID NO: 1 to 484 (FIG. 1) or SEQ ID NO: 1 to 588 (FIG. 6), are sorted in order of their t-test significance as described in more detail in the experimental section (see ttest_adjp=adjusted p-value calculated according to ttest). It should be noted that the lower the ttest_adjp value of a single miRNA, the higher is the diagnostic power of said miRNA for diagnosing and/or prognosing of colon cancer.

The significantly differentially regulated miRNAs are either up-regulated (see FIG. 8a) or strong up-regulated (see FIG. 8b) or even very strong up-regulated (see FIG. 8c) or alternatively down-regulated (see FIG. 9a) or strong down-regulated (see FIG. 9b) or even very strong down-regulated (see FIG. 9c) in biological samples of colon cancer as compared to healthy controls.

Usually the diagnostic power of a single miRNA biomarker is not sufficient to reach high accuracy, specificity and sensitivity for discrimination between healthy subjects (controls) and subjects suffering from colon cancer, hence no simple threshold method can be used for diagnosis and/or prognosis.

Therefore, the inventors of the present invention employed more than one miRNA biomarker, i.e. sets of miRNA biomarkers (signatures), to further increase and/or improve the performance for diagnosing and/or prognosing of subjects suffering from colon cancer. This leads to a significant increase in sensitivity, specificity and accuracy when compared to the prior art.

In order to be able to discriminate, for example, between two or more clinical conditions, e.g. healthy and suffering from colon cancer, for a defined set of miRNA biomarkers, the inventors of the present invention applied a machine learning approach (e.g. t-test, AUC, support vector machine, hierarchical clustering, or k-means) which leads to an algorithm that is trained by reference data (i.e. data of reference miRNA expression profiles from the two clinical conditions, e.g. healthy and suffering from colon cancer, for the defined set of miRNA markers) to discriminate between the two statistical classes (i.e. two clinical conditions, e.g. healthy or suffering from colon cancer).

Figure 5A:
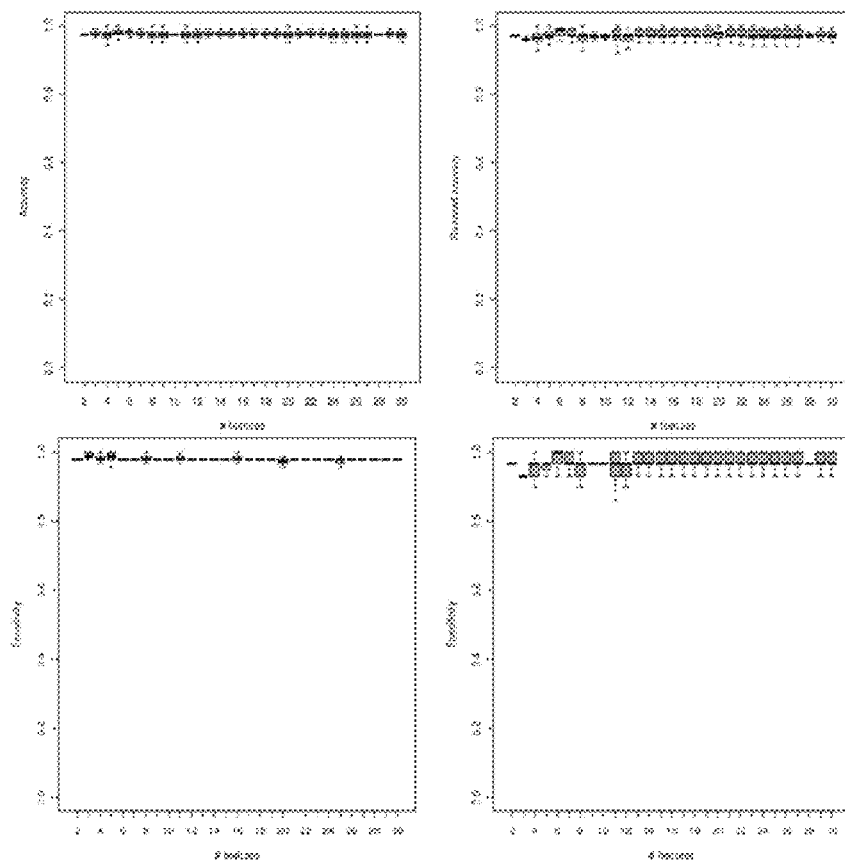

The inventors of the present invention surprisingly found that this approach yields in miRNA sets (signatures) that provide high diagnostic accuracy, specificity and sensitivity in the determination of colon cancer in patients (see FIG. 2 or FIG. 5b or FIG. 7). Said miRNA sets (signatures) comprise at least two miRNAs, wherein the nucleotide sequences of said miRNAs are preferably selected from the group consisting of SEQ ID NO: 1 to 484 (see FIG. 1) or SEQ ID NO: 1 to 588 (see FIG. 6).

An exemplarily approach to arrive at miRNA sets/signatures that correlate with colon cancer is summarized below:

Step 1: Total RNA (or subfractions thereof) is extracted from the biological sample, e.g. a body fluid sample, preferably a blood sample (including but not limited to plasma, serum, PBMC or other blood fractions), using suitable kits and/or purification methods.

Step 2: From the respective samples the quantity (expression level) of one miRNA or sets of at least two miRNAs, e.g. selected from the group consisting of SEQ ID NO: 1 to SEQ ID NO: 588, is measured using experimental techniques. These techniques include but are not restricted to array based approaches, amplification methods (PCR, RT-PCR, qPCR), sequencing, next generation sequencing, flow cytometry and/or mass spectroscopy.

Step 3: In order to gather information on the diagnostic/prognostic value and the redundancy of each of the single miRNA biomarkers, mathematical methods are applied. These methods include, but are not restricted to, basic mathematic approaches (e.g. Fold Quotients, Signal to Noise ratios, Correlation), statistical methods as hypothesis tests (e.g. t-test, Wilcoxon-Mann-Whitney test), the Area under the Receiver operator Characteristics Curve, information theory approaches, (e.g. the Mutual Information, Cross-entropy), probability theory (e.g. joint and conditional probabilities) or combinations and modifications of the previously mentioned methods.

Step 4: The information gathered in step 3) is used to estimate for each miRNA biomarker the diagnostic content or value. Usually, however, this diagnostic value is too small to get a highly accurate diagnosis with accuracy rates, specificities and sensitivities beyond the 90% barrier.

i. The diagnostic content of the miRNAs suitable for diagnosing/prognosing colon cancer is exemplarily listed in FIG. 1 or FIG. 6 (Experimental details: SEQ ID NO: sequence identification number, miRNA: identifier of the miRNA according to miRBase, median g1: median intensity obtained from microarray analysis for healthy controls, median g2: median intensity obtained from microarray analysis for subjects with colon cancer, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.). These Figures include the miRNAs according to SEQ ID NO: 1 to 484 or SEQ ID NO: 1 to 588.

Step 5: In order to increase the performance for diagnosing/prognosing of subjects suffering from colon cancer, more than one miRNA biomarker needs to be employed. Thus statistical learning/machine learning/bioinformatics/computational approaches are applied for set selection in order to select/define sets of miRNA biomarkers (e.g. comprising miRNAs SEQ ID NO: 1 to 588) that are tailored for the detection of colon cancer. These techniques include, but are not restricted to, Wrapper subset selection techniques (e.g. forward step-wise, backward step-wise, combinatorial approaches, optimization approaches), filter subset selection methods (e.g. the methods mentioned in Step 3), principal component analysis, or combinations and modifications of such methods (e.g. hybrid approaches).

Step 6: The subsets, selected/defined in Step 5, which may range from only a small number (at least two for the set) to all measured biomarkers is then used to carry out a diagnosis/prognosis of colon cancer. To this end, statistical learning/machine learning/bioinformatics/computational approaches are applied that include but are not restricted to any type of supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

Step 7: By combination of subset selection (Step 5) and machine learning (Step 6) an algorithm or mathematical function for diagnosing/prognosing colon cancer is obtained. This algorithm or mathematical function is applied to a miRNA expression profile of a subject to be diagnosed for colon cancer.

In a first aspect, the present invention relates to a method for diagnosing and/or prognosing of colon cancer comprising the steps of:
(i) determining an expression profile of a set comprising at least two miRNAs representative for colon cancer in a body fluid sample from a subject, and
(ii) comparing said expression profile to a reference, wherein the comparison of said expression profile to said reference allows for the diagnosis and/or prognosis of colon cancer, It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

Preferably, the set comprising at least two miRNAs is from the group consisting of SEQ ID NO: 1 to 484 or SEQ ID NO: 1 to 588.

It is preferred that the set comprising at least two miRNAs is selected from the set of miRNAs listed in FIG. 2 or FIG. 5b or FIG. 7.

It is preferred that the set comprising at least two miRNAs comprises at least one set of miRNAs listed in FIG. 2 or FIG. 5b or FIG. 7.

Preferably, the set comprising at least two miRNAs comprises at least one up-regulated miRNA listed in FIG. 8a or comprises at least one down-regulated miRNAs listed in FIG. 9a. More preferably, the set comprising at least two miRNAs comprises at least one up-regulated miRNA listed in FIG. 8b or comprises at least one down-regulated miRNAs listed in FIG. 9b. Most preferably, the set comprising at least two miRNAs comprises at least one up-regulated miRNA listed in FIG. 8c or comprises at least one down-regulated miRNAs listed in FIG. 9c. It is further preferred, that the set comprising at least two miRNAs comprises at least one up-regulated miRNA listed in FIG. 8a and further comprises at least one down-regulated miRNAs listed in FIG. 9a.

It is preferred that the determining the expression profile of a set comprising at least two miRNAs is for or is representative for assessing the response of the immune system in a body fluid sample, preferably in a blood sample, of the subject having of suspected of having colon cancer.

Thus, it is preferred that the method for diagnosing and/or prognosing of colon cancer comprises the steps of:
(i) determining an expression profile (expression profile data) of a set comprising, essentially consisting of, or consisting of at least two miRNAs representative for colon cancer in a blood sample from a subject (e.g. a human or another mammal such as an animal), and
(ii) comparing said expression profile (expression profile data) to a reference, wherein the comparison of said expression profile (expression profile data) to said reference allows for the diagnosis and/or prognosis of colon cancer.

Thus, for analysis of a body fluid sample (e.g. blood sample) in step (i) of the method of the present invention, an expression profile of a set comprising at least two miRNAs which are known to be differential between subjects (e.g. humans or other mammals such as animals) having or being suspected to have colon cancer or a special form of colon cancer (diseased state) and subjects (e.g. humans or other mammals such as animals) not having colon cancer or a special form of colon cancer (healthy/control state) and are, thus, representative for colon cancer, is determined, wherein the nucleotide sequences of said miRNAs are) preferably selected from the group consisting of SEQ ID NO: 1 to 588, a fragment thereof, and a sequence having at least 80% sequence identity thereto.

It is more particularly preferred that an expression profile of a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more, or comprising/consisting of 484 (588) miRNAs, representative for colon cancer in a body fluid sample (e.g. a blood sample) from a subject (e.g. a human or another mammal such as an animal) is determined in the step (i) of the method of the present invention, wherein the nucleotide sequences of said miRNAs are selected from the group consisting of
(i) a nucleotide sequence according to SEQ ID NO: 1 to SEQ ID NO: 588,
a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and
a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

Additionally, it is more particularly preferred that an expression profile of a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more, or comprising/consisting of 484 (588) miRNAs, representative for colon cancer in a body fluid sample (e.g. a blood sample) from a subject (e.g. a human or another mammal such as an animal) is determined in the step (i) of the method of the present invention, wherein the set comprising at least two miRNAs is selected from the group consisting of a set of miRNAs listed in FIG. 2 or FIG. 5b or FIG. 7
a combination of at least 2 sets of miRNAs listed in FIG. 2 or FIG. 5b or FIG. 7
nucleotide sequences that are fragments of the nucleotide sequence according to (i) or (ii), preferably, nucleotide sequences that are fragments which are between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequences according to (i) or (ii), and
nucleotide sequences that have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequences according to (i) or (ii) or nucleotide sequence fragments according to (iii).

It is particularly preferred that the nucleotide sequences as defined in (iv) have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequences of the nucleotides according to (i) or (ii) or nucleotide fragments according to (iii).

Furthermore, according to the present invention, a first diagnosis and/or prognosis of colon cancer can be performed employing, as disclosed, miRNA-detection in a body fluid sample, e.g. in blood, followed by a second diagnosis and/or prognosis that is based on other methods (e.g. other biomarkers and/or imaging methods).

Furthermore, according to the present invention, the set comprising at least two miRNAs for diagnosing and/or prognosing colon cancer in a body fluid sample, e.g. blood sample, from a patient, e.g. human or animal, may be established on one experimental platform (e.g. microarray/biochip), while for routine diagnosis/prognosis another experimental platform (e.g. qPCR) may be chosen.

Subsequent to the determination of an expression profile (of expression profile data) of a set comprising at least two miRNAs representative for colon cancer as defined above in a body fluid sample (e.g. blood sample) from a patient (e.g. human or animal) in step (i) of the method for diagnosing and/or prognosing of colon cancer of the present invention, said method further comprises the step (ii) of comparing said expression profile (expression profile data) to a reference, wherein the comparison of said expression profile (expression profile data) to said reference allows for the diagnosis and/or prognosis of colon cancer.

The subject (e.g. human or another mammal (e.g. animal)) to be diagnosed with the method of the present invention may suffer, may be suspected to suffer or may not suffer from colon cancer. The subject (e.g. human or another mammal (e.g. animal)) to be diagnosed with the method of the present invention may suffer from a specific type of colon cancer. It is also possible to determine, whether the subject (e.g. human or another mammal (e.g. animal) to be diagnosed will develop colon cancer as the inventors of the present invention surprisingly found that miRNAs representative for colon cancer are already present in the body fluid sample, e.g. blood sample, before colon cancer occurs or during the early stage of colon cancer.

The reference may be the reference (e.g. reference expression profile (data)) of a healthy condition (i.e. not colon cancer), may be the reference (e.g. reference expression profile (data)) of a diseased condition (i.e. colon cancer) or may be the reference (e.g. reference expression profiles (data)) of at least two conditions from which at least one condition is a diseased condition (i.e. colon cancer). For example, (i) one condition may be a healthy condition (i.e. not colon cancer) and one condition may be a diseased condition (i.e. colon cancer), or (ii) one condition may be a diseased condition (e.g. a specific form of colon cancer) and one condition may be another diseased condition (i.e. specific form of colon cancer, or other timepoint of treatment, other therapeutic treatment).

Further, the reference may be the reference expression profiles (data) of essentially the same, preferably the same, set of miRNAs of step (i), preferably in a body fluid sample originated from the same source (e.g. urine, or blood such as serum, plasma, or blood cells) as the body fluid sample from the subject (e.g. human or animal) to be tested, but obtained from subjects (e.g. human or animal) known to not suffer from colon cancer and from subjects (e.g. human or animal) known to suffer from colon cancer (e.g. colon cancer, e.g. colon cancer that has been therapeutically treated).

Preferably, both the reference expression profile and the expression profile of step (i) are determined in the same body fluid sample, e.g. urine, or blood sample including a whole blood, a blood serum sample, blood plasma sample or a blood cell sample (e.g. erythrocytes, leukocytes and/or thrombocytes). It is understood that the reference expression profile is not necessarily obtained from a single subject known to be affected by colon cancer or known to be not affected by colon cancer (e.g. healthy subject, such as healthy human or animal, or diseased subject, such as diseased human or animal) but may be an average reference expression profile of a plurality of subjects known to be affected by colon cancer or known to be not affected by colon cancer (e.g. healthy subjects, such as healthy humans or animals, or diseased subjects, such as diseased humans or animals), e.g. at least 2 to 200 subjects, more preferably at least 10 to 150 subjects, and most preferably at least 20 to 100 subjects, (e.g. healthy subject, such as healthy human or animal, or diseased subject, such as diseased human or animal). The expression profile and the reference expression profile may be obtained from a subject/patient of the same species (e.g. human or animal), or may be obtained from a subject/patient of a different species (e.g. human or animal). Preferably, the expression profile is obtained from a subject known to be affected by colon cancer or known to be not affected by colon cancer of the same species (e.g. human or animal), of the same gender (e.g. female or male) and/or of a similar age/phase of life (e.g. infant, young child, juvenile, adult) as the subject (e.g. human or animal) to be tested or diagnosed.

Thus, in a preferred embodiment of the method of the present invention, the reference is a reference expression profile (data) of at least one subject, preferably the reference is an average expression profile (data) of at least 2 to 200 subjects, more preferably of at least 10 to 150 subjects, and most preferably of at least 20 to 100 subjects, with one known clinical condition which is colon cancer or a specific form of colon cancer, or which is not colon cancer or a specific form of colon cancer (i.e. healthy/healthiness), wherein the reference expression profile is the profile of a set comprising at least two miRNAs that have nucleotide sequences that essentially correspond (are essentially identical), preferably that correspond (are identical), to the nucleotide sequences of the miRNAs of step (i). Preferably, the reference expression profile is the profile of a set comprising at least two miRNAs that have nucleotide sequences that essentially correspond (are essentially identical), preferably that correspond (are identical), to the nucleotide sequences of the miRNAs selected from the group consisting of SEQ ID NO: 1 to 588, a fragment thereof, and a sequence having at least 80% sequence identity thereto of step (i).

The comparison of the expression profile of the patient to be diagnosed (e.g. human or animal) to the (average) reference expression profile may then allow for diagnosing and/or prognosing of colon cancer or a specific form of colon cancer (step (ii)), either the subject/patient (e.g. human or animal) to be diagnosed is healthy, i.e. not suffering from colon cancer, or diseased, i.e. suffering from colon cancer or a specific form of colon cancer.

The comparison of the expression profile of the subject (e.g. human or animal) to be diagnosed to said reference expression profile(s) may then allow for the diagnosis and/or prognosis of colon cancer (step (ii)), either the subject (e.g. human or animal) to be diagnosed is healthy, i.e. not suffering from colon cancer, or the subject (e.g. human or animal) is diseased, i.e. suffering from colon cancer.

The comparison of the expression profile of the patient (e.g. human or animal) to be diagnosed to said reference expression profiles may then allow for the diagnosis/prognosis of a specific form of colon cancer (step (ii)), e.g. whether the patient to be diagnosed suffers from colon cancer.

In a particularly preferred embodiment of the method of the present invention, the reference is an algorithm or mathematical function. Preferably, the algorithm or mathematical function is obtained on the basis of reference expression profiles (data) of at least 2 to 200 subjects, more preferably of at least 10 to 150 subjects, and most preferably of at least 20 to 100 subjects, with two known clinical conditions from which one is colon cancer, wherein the reference expression profiles is the profile of a set comprising at least two miRNAs that have nucleotide sequences that essentially correspond (are essentially identical), preferably that correspond (are identical), to the nucleotide sequences of the miRNAs of step (i). Preferably, is the profile of a set comprising at least two miRNAs that have nucleotide sequences that essentially correspond (are essentially identical), preferably that correspond (are identical), to the nucleotide sequences of the miRNAs selected from the group consisting of SEQ ID NO: 1 to 588, a fragment thereof, and a sequence having at least 80% sequence identity thereto of step (i).

It is preferred that the algorithm or mathematical function is obtained using a machine learning approach.

Machine learning approaches may include but are not limited to supervised or unsupervised analysis: classification techniques (e.g. naive Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

The inventors of the present invention surprisingly found that the application/use of a machine learning approach (e.g. t-test, AUC, support vector machine, hierarchical clustering, or k-means) leads to the obtainment of an algorithm or mathematical function that is trained by the reference expression profile(s) or reference expression profile data mentioned above (e.g. trained by the miRNA reference expression profile (data) of a diseased condition (i.e. colon cancer or a specific form of colon cancer), for example, obtained from subjects (e.g. humans or animals) known to suffer from colon cancer or from a specific form of colon cancer (i.e. being diseased) and/or a trained by the miRNA reference expression profile (data) of a healthy condition (i.e. not colon cancer or a specific form of colon cancer), for example, obtained from subjects (e.g. humans or animals) known to not suffer from colon cancer or from a specific form of colon cancer and that this allows a better (i) discrimination between the at least two (e.g. 2 or 3) clinical conditions (the at least two statistical classes, e.g. the two conditions healthy or suffering from colon cancer or the two clinical conditions suffering from a specific form of colon cancer or suffering from another specific form of colon cancer or at least three clinical conditions, e.g. the three clinical conditions healthy, suffering from a specific form of colon cancer or suffering from another specific form of colon cancer or (ii) decision whether the at least one clinical condition (the one condition healthy or suffering from colon cancer is present. In this way, the performance for diagnosing/prognosing of individuals suffering from colon cancer can be increased (see also experimental section for details).

Thus, in a preferred embodiment of the method of the present invention, the algorithm or mathematical function is obtained using a machine learning approach, wherein said algorithm or mathematical function is trained by a reference expression profile (data) of at least 2 to 200 subjects, more preferably of at least 10 to 150 subjects, and most preferably of at least 20 to 100 subjects with two known clinical condition for which one is colon cancer or a specific form of colon cancer, wherein the reference expression profile is the profile of a set comprising at least two miRNAs that have nucleotide sequences that essentially correspond (are essentially identical), preferably that correspond (are identical), to the nucleotide sequences of the miRNAs of step (i), preferably to decide whether the at least one clinical condition which is colon cancer or a specific form of colon cancer.

Further, for instance, the machine learning approach may be applied to the reference expression profiles (data) of a set comprising at least 2 miRNAs (e.g. 10 miRNAs such as miRNAs according to SEQ ID NO: 1 to 10) of at least one subject (e.g. human or animal) known to suffer from colon cancer and of at least one subject (e.g. human or animal) known to be healthy and may led to the obtainment of an algorithm or mathematical function. This algorithm or mathematical function may then be applied to a miRNA expression profile of the same at least 2 miRNAs as mentioned above (e.g. 10 miRNAs such as miRNAs according to SEQ ID NO: 1 to 10) of a subject (e.g. human or animal) to be diagnosed for colon cancer and, thus, may then allow to discriminate whether the subject (e.g. human or animal) tested is healthy, i.e. not suffering from colon cancer, or diseased, i.e. suffering from colon cancer.

Additionally the algorithm may be trained to discriminate between more than 2 (e.g. 3, 4, 5 or more) clinical conditions from which at least one is colon cancer.

Preferably, the reference and optionally the expression profile (data) of the miRNA(s) representative for colon cancer is (are) stored in a database, e.g. an internet database, a centralized, and/or a decentralized database. It is preferred that the reference, e.g. mathematical function or algorithm, is comprised in a computer program, e.g. saved on a data carrier.

The above mentioned method is for diagnosing colon cancer in a subject, e.g. a human or another mammal such as an animal. Preferably, the diagnosis comprises (i) determining the occurrence/presence of colon cancer, (ii) monitoring the course of colon cancer, (iii) staging of colon cancer, (iv) measuring the response of a patient with colon cancer to therapeutic intervention, and/or (v) segmentation of a subject suffering from colon cancer.

Further, the above mentioned method is for prognosis of colon cancer in a subject, a human or another mammal such as an animal. Preferably, the prognosis comprises (i) identifying of a subject who has a risk to develop colon cancer, (ii) predicting/estimating the occurrence, preferably the severity of occurrence of colon cancer, and/or (iii) predicting the response of a subject with colon cancer to therapeutic intervention.

Further, in a preferred embodiment of the method of the present invention, for determining an expression profile of the set comprising at least two miRNAs representative for colon cancer in a body fluid sample from a subject comprises a set of miRNAs listed in FIG. 2 or FIG. 5*b* or FIG. 7.

For example, said set comprising 30 miRNAs representative for colon cancer in a body fluid sample from a subject comprises a set of miRNAs listed in FIG. 2 or FIG. 5*b* or FIG. 7. Alternatively, said set comprising 29, 28, 27, 26, 25, 24, 23, 22, 21, 20, 19, 18, 17, 16, 15, 14, 13, 12, 11, 10, 9, 8, 7, 6, 5, 4 or 3 miRNAs comprises a set of miRNAs listed in FIG. 2 or FIG. 5*b* or FIG. 7.

For example, said set comprising 30 miRNAs representative for colon cancer in a body fluid sample from a subject comprises a set of miRNAs listed in FIG. 2 or FIG. 5*b* or FIG. 7. For example, said set comprising 25 miRNAs representative for colon cancer in a body fluid sample from a subject comprises a set of miRNAs listed in FIG. 2 or FIG. 5*b* or FIG. 7. For example, said set comprising 20 miRNAs representative for colon cancer in a body fluid sample from a subject comprises a set of miRNAs listed in FIG. 2 or FIG. 5*b* or FIG. 7. For example, said set comprising 15 miRNAs representative for colon cancer in a body fluid sample from a subject comprises a set of miRNAs listed in FIG. 2 or FIG. 5*b* or FIG. 7. For example, said set comprising 10 miRNAs representative for colon cancer in a body fluid sample from a subject comprises a set of miRNAs listed in FIG. 2 or FIG. 5*b* or FIG. 7. For example, said set comprising 5 miRNAs representative for colon cancer in a body fluid sample from a subject comprises a set of miRNAs listed in FIG. 2 or FIG. 5*b* or FIG. 7.

Further, in another preferred embodiment of the method of the present invention, for determining an expression profile of the set comprising at least two miRNAs representative for colon cancer in a body fluid sample from a subject comprises combinations of sets of miRNAs listed in FIG. 2 or FIG. 5*b* or FIG. 7.

For example, said set comprising 30 miRNAs representative for colon cancer in a body fluid sample from a subject comprises at least 2 sets of miRNAs listed in FIG. 2 or FIG. 5*b* or FIG. 7. Alternatively, said set comprising 29, 28, 27, 26, 25, 24, 23, 22, 21, 20, 19, 18, 17, 16, 15, 14, 13, 12, 11, 10, 9, 8, 7, 6, 5 or 4 miRNAs comprises a least 2 sets of miRNAs listed in FIG. 2 or FIG. 5*b* or FIG. 7.

For example, said set comprising 30 miRNAs representative for colon cancer in a body fluid sample from a subject comprises a least 2 sets of miRNAs listed in FIG. 2 or FIG. 5*b* or FIG. 7. For example, said set comprising 25 miRNAs representative for colon cancer in a body fluid sample from a subject comprises a least 2 sets of miRNAs listed in FIG. 2 or FIG. 5*b* or FIG. 7. For example, said set comprising 20 miRNAs representative for colon cancer in a body fluid sample from a subject comprises a least 2 sets of miRNAs listed in FIG. 2 or FIG. 5b or FIG. 7. For example, said set comprising 15 miRNAs representative for colon cancer in a body fluid sample from a subject comprises a least 2 sets of miRNAs listed in FIG. 2 or FIG. 5b or FIG. 7. For example, said set comprising 10 miRNAs representative for colon cancer in a body fluid sample from a subject comprises a least 2 sets of miRNAs listed in FIG. 2 or FIG. 5b or FIG. 7. For example, said set comprising 5 miRNAs representative for colon cancer in a body fluid sample from a subject comprises a least 2 sets of miRNAs listed in FIG. 2 or FIG. 5b or FIG. 7.

In a second aspect, the invention relates to a set comprising polynucleotides for detecting a set comprising at least two miRNAs for diagnosing and/or prognosing of colon cancer in a body fluid sample from a subject.

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

Preferably, the nucleotide sequences of the set comprising at least two miRNAs for diagnosing and/or prognosing of colon cancer in a body fluid sample, e.g. blood sample, from a patient, e.g. human or animal, are selected from the group consisting of SEQ ID NO: 1 to 484 or SEQ ID NO: 1 to 588.

It is preferred that the set comprising at least two miRNAs is selected from or comprises the sets of miRNAs listed in FIG. 2 or FIG. 5b or FIG. 7.

Preferably, the set comprising polynucleotides for detecting a set comprising at least two miRNAs for diagnosing and/or prognosing of colon cancer comprises polynucleotides for detecting at least one up-regulated miRNA listed in FIG. 8a or for detecting at least one down-regulated miRNAs listed in FIG. 9a. More preferably, the set comprises polynucleotides for detecting at least one up-regulated miRNA listed in FIG. 8b or comprises polynucleotides for detecting at least one down-regulated miRNAs listed in FIG. 9b. Most preferably, the set comprises polynucleotides for detecting at least one up-regulated miRNA listed in FIG. 8c or comprises polynucleotides for detecting at least one down-regulated miRNAs listed in FIG. 9c. It is further preferred, that the set comprises polynucleotides for detecting at least one up-regulated miRNA listed in FIG. 8a and further comprises polynucleotides for detecting at least one down-regulated miRNAs listed in FIG. 9a.

It is preferred that
(i) the polynucleotides comprised in the set of the present invention are complementary to the miRNAs comprised in the set, wherein the nucleotide sequences of said miRNAs are preferably selected from the group consisting of SEQ ID NO: 1 to 588,
(ii) the polynucleotides comprised in the set are fragments of the polynucleotides comprised in the set according to (i), preferably the polynucleotides comprised in the set are fragments which are between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the polynucleotides comprised in the set according to (i), or
(iii) the polynucleotides comprised in the set have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the polynucleotide sequences of the polynucleotides comprised in the set according to (i) or polynucleotide fragments comprised in the set according to (ii).

It is preferred that the polynucleotides of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or more miRNAs, or comprising/consisting of 484 (588) miRNAs and wherein the nucleotide sequences of said miRNAs are selected from the group consisting of SEQ ID NO: 1 to 484 (588).

It is preferred that the polynucleotides of the present invention are for detecting a set comprising, essentially consisting of, or consisting of at least 2 miRNAs, wherein the set comprising, miRNAs is selected from the set listed in FIG. 2 or FIG. 5b or FIG. 7.

It is preferred that the polynucleotides of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or more miRNAs, or comprising/consisting of 484 (588) miRNAs and wherein the set of miRNAs comprises at least one of the sets listed in FIG. 2 or FIG. 5b or FIG. 7.

For the body fluid sample (e.g. blood sample) analysis, it may be required that a set of polynucleotides (probes) capable of detecting a fixed defined set of miRNAs are attached to a solid support, bead, substrate, surface, platform, or matrix, e.g. biochip, which may be used for body fluid sample (e.g. blood sample) analysis. For example, if the fixed defined set of miRNAs for diagnosing colon cancer comprises or consists of 20 miRNAs, polynucleotides capable of detecting these 20 miRNAs are attached to a solid support, substrate, surface, platform or matrix, e.g. biochip, in order to perform the diagnostic sample analysis.

Alternatively, it may be required that a set of chimeric polynucleotides (probes) capable of detecting a fixed defined set of miRNAs it contacted in solution with a sample containing miRNAs derived from a body fluid sample. The chimeric polynucleotide may comprise of a first sequence stretch that is complementary to a miRNA and a second sequence stretch that allows to pull down the chimeric polynucleotide-miRNA-duplexes to one or more solid supports (e.g. a set of beads for determining the set of miRNAs). For example, a set of 20 chimeric polynucleotides capable of detecting 20 miRNAs are contacted with sample containing miRNAs derived from a body fluid sample in order to form duplexes that can be pulled down to 20 different species of beads and detected thereon.

For example, the polynucleotides of the present invention are for detecting a set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 miRNAs wherein the set of miRNAs comprises at least one of the set of miRNAs listed in FIG. 2 or FIG. 5b or FIG. 7.

For example, the polynucleotides of the present invention are for detecting a set of 30 miRNAs wherein the set of miRNAs comprises at least one of the sets of miRNAs listed in FIG. 2 or FIG. 5b or FIG. 7.

For example, the polynucleotides of the present invention are for detecting a set of 25 miRNAs wherein the set of miRNAs comprises at least one of the sets of miRNAs listed in FIG. 2 or FIG. 5b or FIG. 7.

For example, the polynucleotides of the present invention are for detecting a set of 20 miRNAs wherein the set of miRNAs comprises at least one of the sets of miRNAs listed in FIG. 2 or FIG. 5b or FIG. 7.

For example, the polynucleotides of the present invention are for detecting a set of 15 miRNAs wherein the set of miRNAs comprises at least one of the sets of miRNAs listed in FIG. 2 or FIG. 5b or FIG. 7.

For example, the polynucleotides of the present invention are for detecting a set of 10 miRNAs wherein the set of miRNAs comprises at least one of the sets of miRNAs listed in FIG. 2 or FIG. 5b or FIG. 7.

For example, the polynucleotides of the present invention are for detecting a set of 5 miRNAs wherein the set of miRNAs comprises at least one of the sets of miRNAs listed in FIG. 2 or FIG. 5b or FIG. 7.

In a third aspect, the invention relates to the use of set of polynucleotides according to the second aspect of the invention for diagnosing and/or prognosing colon cancer in a subject In a fourth aspect, the invention relates to a set of at least two primer pairs for determining the expression level of a set of miRNAs in a body fluid sample of a subject suffering or suspected of suffering from colon cancer.

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is preferred that the subject is a mammal including both a human and another mammal, e.g. an animal such as a mouse, a rat, a rabbit, or a monkey. It is particularly preferred that the subject is a human.

Preferably, that the set comprising at least two miRNAs for diagnosing and/or prognosing of colon cancer in a body fluid sample, e.g. blood sample, from a subject, e.g. patient, human or animal, are selected from the group consisting of SEQ ID NO: 1 to 484 or SEQ ID NO: 1 to 588.

It is preferred that the set comprising at least two miRNAs is selected from or comprises the sets of miRNAs listed in FIG. 2 or FIG. 5b or FIG. 7.

It is preferred that the set of at least two primer pairs for determining the expression level of a set of miRNAs in a body fluid sample of a subject suffering or suspected of suffering from colon cancer are primer pairs that are specific for at least one miRNA selected from the group consisting of SEQ ID NO: 1 to 588.

It is preferred that the set of at least two primer pairs for determining the expression level of a set of miRNAs in a body fluid sample of a subject suffering or suspected of suffering from colon cancer are primer pairs that are specific for at least one set of miRNAs listed in FIG. 2 or FIG. 5b or FIG. 7.

Preferably, the set of least two primer pairs for determining the expression level comprises primer pairs for determining at least one up-regulated miRNA listed in FIG. 8a or comprises primer pairs for determining at least one down-regulated miRNAs listed in FIG. 9a. More preferably, the set of least two primer pairs for determining the expression level comprises primer pairs for determining at least one up-regulated miRNA listed in FIG. 8b or comprises at least one down-regulated miRNAs listed in FIG. 9b. Most preferably, the set comprising at least two miRNAs comprises at least one up-regulated miRNA listed in FIG. 8c or comprises primer pairs for determining at least one down-regulated miRNAs listed in FIG. 9c. It is further preferred, that the set comprises primer pairs for determining at least one up-regulated miRNA listed in FIG. 8a and further comprises primer pairs for determining at least one down-regulated miRNAs listed in FIG. 9a.

It is preferred that the set of at least two primer pairs of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 36, 37, 38, 39, 40 or more miRNAs, or comprising/consisting of 484 (588) miRNAs and wherein the nucleotide sequences of said miRNAs are selected from the group consisting of SEQ ID NO: 1 to 484 (588).

It is preferred that the set of at least two primer pairs of the present invention are for detecting a set comprising, essentially consisting of, or consisting of at least 2 miRNAs, wherein the set comprising, miRNAs is selected from or comprises the sets listed in FIG. 2 or FIG. 5b or FIG. 7.

It is preferred that the set of at least two primer pairs of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 36, 37, 38, 39, 40 or more miRNAs, or comprising/consisting of 484 (588) miRNAs and wherein the set of miRNAs comprises at least one of the sets listed in FIG. 2 or FIG. 5b or FIG. 7.

For example, the set of at least two primer pairs of the present invention are for detecting a set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 or 2 miRNAs wherein the set of miRNAs comprises at least one of the set of miRNAs listed in FIG. 2 or FIG. 5b or FIG. 7.

For example, the set of primer pairs of the present invention are for detecting a set of 30 miRNAs wherein the set of miRNAs comprises at least one of the sets of miRNAs listed in FIG. 2 or FIG. 5b or FIG. 7. For example, the set of primer pairs of the present invention are for detecting a set of 25 miRNAs wherein the set of miRNAs comprises at least one of the sets of miRNAs listed in FIG. 2 or FIG. 5b or FIG. 7. For example, the set of primer pairs of the present invention are for detecting a set of 20 miRNAs wherein the set of miRNAs comprises at least one of the sets of miRNAs listed in FIG. 2 or FIG. 5b or FIG. 7. For example, the set of primer pairs of the present invention are for detecting a set of 15 miRNAs wherein the set of miRNAs comprises at least one of the sets of miRNAs listed in FIG. 2 or FIG. 5b or FIG. 7. For example, the set of primer pairs of the present invention are for detecting a set of 10 miRNAs wherein the set of miRNAs comprises at least one of the sets of miRNAs listed in FIG. 2 or FIG. 5b or FIG. 7.

Preferably, the said primer pairs may be used for amplifying cDNA transcripts of the set of miRNAs selected from the group consisting of SEQ ID 1 to 588. Furthermore, the said primer pairs may be used for amplifying cDNA transcripts of the set of miRNAs listed in FIG. 2 or FIG. 5b or FIG. 7

It is understood that the primer pairs for detecting a set of miRNAs may consist of specific and or non-specific primers. Additionally, the set of primer pairs may be complemented by other substances or reagents (e.g. buffers, enzymes, dye, labelled probes) known to the skilled in the art for conducting real time polymerase chain reaction (RT-PCR)

In a fifth aspect, the invention relates to the use of a set of primer pairs according to the fourth aspect of the invention for diagnosing and/or prognosing colon cancer in a subject In a sixth aspect, the invention relates to means for diagnosing and/or prognosing of colon cancer in a body fluid sample of a subject.

Preferably, the invention relates to means for diagnosing and/or prognosing of colon cancer in a body fluid sample of a subject comprising a set of at least two polynucleotides according to the second aspect of the invention or a set of at least two primer pairs according the fourth aspect of the invention.

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

Preferably, that the set of at least two polynucleotides or the set of at least 2 primer pairs are for detecting a set comprising at least two miRNAs for diagnosing and/or prognosing of colon cancer in a body fluid sample, e.g. blood sample, from a subject, e.g. patient, human or animal, wherein the set of miRNAs is selected from the group consisting of SEQ ID NO: 1 to 484 or SEQ ID NO: 1 to 588.

It is preferred that the set of at least two polynucleotides or the set of at least 2 primer pairs are for detecting a set comprising at least two miRNAs for diagnosing and/or prognosing of colon cancer in a body fluid sample, e.g. blood sample, from a subject, e.g. patient, human or animal, wherein the set of miRNAs is selected from the sets of miRNAs listed in FIG. 2 or FIG. 5b or FIG. 7.

It is preferred that the set of at least two primer pairs for determining the expression level of a set of miRNAs in a body fluid sample of a subject suffering or suspected of suffering from colon cancer are primer pairs that are specific for at least two miRNAs selected from the group consisting of SEQ ID NO: 1 to 588.

It is preferred that the set of at least two primer pairs for determining the expression level of a set of miRNAs in a body fluid sample of a subject suffering or suspected of suffering from colon cancer are primer pairs that are specific for at least one set of miRNAs listed in FIG. 2 or FIG. 5b or FIG. 7.

It is preferred that the subject is a mammal including both a human and another mammal, e.g. an animal such as a mouse, a rat, a rabbit, or a monkey. It is particularly preferred that the subject is a human.

The present invention provides means for diagnosing and/or prognosing of colon cancer comprising a set comprising, essentially consisting of, or consisting of at least two polynucleotides (probes) according to the second aspect of the present invention, e.g. a polynucleotide for detecting a set comprising, essentially consisting of, or consisting of at least 2 polynucleotides, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or up to 484 (588) or more polynucleotides for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or 484 miRNAs or all known miRNAs, wherein the nucleotide sequence of said miRNAs are preferably selected from the group consisting of SEQ ID NO: 1 to 484 (588), a fragment thereof, and a sequence having at least 80% sequence identity thereto.

The means for diagnosing and/or prognosing of colon cancer comprises, essentially consists of, or consists of a solid support, substrate, surface, platform or matrix comprising a set comprising, essentially consisting of, or consisting of at least two polynucleotides (probes) according to the second aspect of the present invention, e.g. a solid support, substrate, surface, platform or matrix comprising at least 2 polynucleotides, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more polynucleotides, or comprising/consisting of 484 (588) polynucleotides for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more miRNAs, or comprising/consisting of 484 miRNAs, wherein the nucleotide sequence said miRNAs are preferably selected from the group consisting of SEQ ID NO: 1 to 484 (588), a fragment thereof, and a sequence having at least 80% sequence identity thereto. Preferably, the above mentioned polynucleotide(s) is (are) attached or immobilized to the solid support, substrate, surface, platform or matrix. It is possible to include appropriate controls for non-specific hybridization on the solid support, substrate, surface, platform or matrix.

Additionally, the means for diagnosing and/or prognosing of colon cancer comprises, essentially consists of, or consists of a solid support, substrate, surface, platform or matrix comprising a set comprising, essentially consisting of, or consisting of at least two polynucleotides (probes) according to the second aspect of the present invention, e.g. a solid support, substrate, surface, platform or matrix comprising at least 2 polynucleotides, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more polynucleotides, or comprising/consisting of 484 (588) polynucleotides for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more miRNAs, or comprising/consisting of 484 (588) miRNAs, wherein the set of miRNAs comprises at least one set of miRNAs listed in FIG. 2 or FIG. 5b or FIG. 7. Preferably, the above mentioned polynucleotides are attached or immobilized to the solid support, substrate, surface, platform or matrix. It is possible to include appropriate controls for non-specific hybridization on the solid support, substrate, surface, platform or matrix.

It is particularly preferred that said means for diagnosing and/or prognosing of colon cancer comprise, essentially consists of, or consists of a microarray/biochip comprising at least two polynucleotides according to the second aspect of the present invention.

It is also preferred that said means for diagnosing and/or prognosing of colon cancer comprise, essentially consists of, or consists of a set of beads comprising a at least two polynucleotides according to the second aspect of the present invention. It is especially preferred that the beads are employed within a flow cytometer setup or a setup for analysing magnetic beads for diagnosing and/or prognosing of colon cancer, e.g. in a LUMINEX system (luminexcorp.com)

Additionally, the present invention provides means for diagnosing and/or prognosing of colon cancer comprising a set comprising, essentially consisting of, or consisting of at least two primer pairs according to the fourth aspect of the present invention, e.g. of at least 2 primer pairs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or up to 484 (588) or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 484 (588) miRNAs or all known miRNAs, wherein the nucleotide sequence of said miRNA or the nucleotide sequences of said miRNAs is (are) preferably selected from the group consisting of SEQ ID NO: 1 to 484 (588), a fragment thereof, and a sequence having at least 80% sequence identity thereto.

Also, the present invention provides means for diagnosing and/or prognosing of colon cancer comprising a set comprising, essentially consisting of, or consisting of at least two primer pairs according to the fourth aspect of the present invention, e.g. of at least 2 primer pairs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or up to 484 (588) or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 484 (588) miRNAs or all known miRNAs, wherein the set of miRNAs comprises at least one set of miRNAs listed in FIG. 2 or FIG. 5b or FIG. 7.

In a seventh aspect, the invention relates to a kit for diagnosing and/or prognosing of colon cancer in a subject.

Preferably, the invention relates to a kit for diagnosing and/or prognosing of colon cancer comprising
(i) means for determining an expression profile of a set comprising at least two miRNAs representative for colon cancer in a body fluid sample from a subject, and
(ii) at least one reference.

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

The present invention provides a kit for diagnosing and/or prognosing of colon cancer comprising
(i) means for determining an expression profile of a set comprising, essentially consisting of, or consisting of at least two miRNAs (e.g. human miRNAs or miRNAs from another mammal such as an animal (e.g. mouse miRNA or rat miRNAs)), preferably comprising, essentially consisting of, or consisting of at least 2 or up to 484 (588) or more polynucleotides or alternatively a set of at least 2 or up to 484 (588) or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more or 484 miRNAs or all known miRNAs, representative for colon cancer in a biological sample (e.g. a body fluid samples or a blood sample) from a subject (e.g. human or animal), wherein the nucleotide sequence of said miRNA or the nucleotide sequences of said miRNAs is (are) preferably selected from the group consisting of SEQ ID NO: 1 to 484 (588), a fragment thereof, and a sequence having at least 80% sequence identity thereto; and
(ii) at least one reference.

The present invention provides a kit for diagnosing and/or prognosing of colon cancer comprising
(i) means for determining an expression profile of a set comprising, essentially consisting of, or consisting of at least two miRNAs (e.g. human miRNAs or miRNAs from another mammal such as an animal (e.g. mouse miRNA or rat miRNAs)), preferably comprising, essentially consisting of, or consisting of at least 2 or up to 484 (588) or more polynucleotides or alternatively a set of at least 2 or up to 484 (588) or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more or 484 (588) miRNAs or all known miRNAs, representative for colon cancer in a biological sample (e.g. a body fluid samples or a blood sample) from a subject (e.g. human or animal), wherein the set of miRNAs comprises at least one of the set of miRNAs listed in FIG. 2 or FIG. 5b or FIG. 7.
(ii) at least one reference.

Said means may comprise a set comprising, essentially consisting of, or consisting of at least two polynucleotides according to the second aspect of the present invention, a set of at least 2 primer pairs according to the fourth aspect of the invention; means according to the sixth aspect of the present invention; primers suitable to perform reverse transcriptase reaction and/or real time polymerase chain reaction such as quantitative polymerase chain reaction; and/or means for conducting next generation sequencing.

It is particularly preferred that said kit comprises
(ia) a set comprising, essentially consisting of, or consisting of at least two polynucleotides according to the second aspect of the present invention, or a set of primer pairs according to the fourth aspect of the invention and (ib) optionally at least one of the means selected from the group consisting of: at least one biological sample, for example, tissue sample or body fluid sample, e.g. a blood sample, e.g. whole blood, serum, plasma, or blood cells, of a subject (e.g. human or animal), at least one sample of total RNA extracted from said biological sample, for example, body fluid sample, tissue sample or blood sample, e.g. whole blood, serum, plasma, or blood cells, of a patient (e.g. human or animal), and means to extract RNA from a body fluid sample, e.g. blood sample, e.g. for determining an expression profile of a set comprising, essentially consisting of, or consisting of at least two miRNAs representative for colon cancer in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 588, a fragment thereof, and a sequence having at least 80% sequence identity thereto.

It is more particularly preferred that said kit comprises (ia) a solid support, substrate, surface, platform or matrix (e.g. a microarray of a set of beads) according to the third aspect of the present invention comprising a polynucleotide or a set comprising, essentially consisting of, or consisting of at least two polynucleotides according of the first aspect of the present invention, and (ib) optionally at least one of the means selected from the group consisting of: at least one body fluid sample, for example, tissue or blood sample, e.g. serum, plasma, or blood cells, from a patient (e.g. human or animal), at least one sample of total RNA (or fractions thereof, e.g. miRNA) extracted from a body fluid sample, for example, tissue or blood sample, e.g. serum, plasma, or blood cells, from a patient (e.g. human or animal), means to extract total RNA (or fractions thereof, e.g. miRNA) from a body fluid sample (e.g. blood sample), means for input/injection of a body fluid sample (e.g. blood sample), positive controls for the hybridization experiment, means for holding the solid support, substrate, platform or matrix comprising the polynucleotide(s) (probe(s)), means for labelling the isolated miRNA (e.g. NTP/biotin-NTP), means for hybridization, means to carry out enzymatic reactions (e.g. exonuclease I and/or Klenow enzyme) means for washing steps, means for detecting the hybridization signal, and mean for analysing the detected hybridization signal, e.g. for determining an expression profile of a miRNA or a set comprising, essentially consisting of, or consisting of at least two miRNAs representative for colon cancer in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 588, a fragment thereof, and a sequence having at least 80% sequence identity thereto.

Preferably, the above mentioned set comprising, essentially consisting of, or consisting of at least two polynucleotides are attached or immobilized to the solid support, substrate, surface, platform or matrix, e.g. to a microarray or to a set of beads.

Preferably, the above mentioned set comprising, essentially consisting of, or consisting of at least two polynucleotides is (are) attached or immobilized to microarray/biochip.

It is particularly preferred that said kit comprises (ia) a miRNA-specific primer for reverse transcription of miRNA in miRNA-specific cDNA for a single miRNA (e.g. human miRNA or miRNA from another mammal such as an animal (e.g. mouse or rat miRNA)) or at least two miRNA-specific primers for reverse transcription of miRNAs in miRNA-specific cDNAs for at least 2 miRNAs (e.g. human miRNAs or miRNAs from another mammal such as an animal (e.g. mouse or rat miRNAs)), preferably for at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more, or 484 (588) miRNAs (e.g. human miRNAs or miRNAs from another mammal such as an animal (e.g. mouse or rat miRNAs)), comprised in a set of miRNAs, wherein the nucleotide sequence of said miRNA or the nucleotide sequences of said miRNAs is (are) preferably selected from the group consisting of SEQ ID NO: 1 to 588, and (ib) preferably, a primer set comprising a forward primer which is specific for the cDNA obtained from the miRNA and an universal reverse primer for amplifying the cDNA obtained from the miRNA via real time polymerase chain reaction (RT-PCR) such as real time quantitative polymerase chain reaction (RT qPCR) for the single cDNA obtained from the miRNA or at least two primer sets comprising a forward primer which is specific for the single cDNA obtained from the miRNA and an universal reverse primer for amplifying the cDNA obtained from the miRNA via real time polymerase chain reaction (RT-PCR) such as real time quantitative polymerase chain reaction (RT qPCR) for at least 2, preferably for at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more or 484 (588) cDNAs obtained from the miRNAs comprised in the set of miRNAs, wherein preferably said cDNA is complementary to the nucleotide sequence of the miRNA or said cDNAs are complementary to the nucleotide sequences of the miRNAs selected from the group consisting of SEQ ID NO: 1 to 588, and (ic) optionally at least one of the means selected from the group consisting of: at least one body fluid sample, for example, tissue or blood sample, e.g. serum, plasma, or blood cells, from a patient (e.g. human or animal), at least one sample of total RNA (or fractions thereof, e.g. miRNA) extracted from a body fluid sample, for example, tissue or blood sample, e.g. serum, plasma, or blood cells, form a patient (e.g. human or animal), means to extract total RNA (or fractions thereof, e.g. miRNA) from a body fluid sample (e.g. blood sample), additional means to carry out the reverse transcriptase reaction (miRNA in cDNA) (e.g. reverse transcriptase (RT) enzyme, puffers, dNTPs, RNAse inhibitor), additional means to carry out real time polymerase chain reaction (RT-PCR) such as real time quantitative PCR (RT qPCR) (e.g. enzymes, puffers, water), means for labelling (e.g. fluorescent label and/or quencher), positive controls for reverse transcriptase reaction and real time PCR, and means for analysing the real time polymerase chain reaction (RT-PCR) result, e.g. for determining an expression profile of a miRNA or a set comprising, essentially consisting of, or consisting of at least 2, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more, or 484 (588) miRNAs representative for colon cancer in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 588, a fragment thereof, and a sequence having at least 80% sequence identity thereto.

The primer as defined above may also be an oligo-dT primer, e.g. if the miRNA comprises a polyA tail (e.g. as a result of a miRNA elongation, for example, subsequent to RNA extraction) or a miRNA specific looped RT primer (Please amend/adapted if required).

It is also preferred that said kit comprises means for conducting next generation sequencing in order to determine an expression profile of a (single) miRNA or a set comprising, essentially consisting of, or consisting of at least 2 miRNAs representative for colon cancer in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 588, a fragment thereof, and a sequence having at least 80% sequence identity thereto. Preferably, said kit further comprises means selected from the group consisting of: at least one body fluid sample, for example, tissue or blood sample, e.g. blood serum, blood plasma, or blood cells from a patient (e.g. human or animal), at least one sample of total RNA (or fractions thereof, e.g. miRNA) extracted from the body fluid sample (e.g. tissue or blood sample) of a patient (e.g. human or animal), and means to extract total RNA (or fractions thereof, e.g. miRNA) from a body fluid sample (e.g. blood sample).

The above mentioned kits further comprise at least one reference (ii). A comparison to said reference may allow for the diagnosis and/or prognosis of colon cancer. Said reference may be the reference (e.g. reference expression profile (data)) of a healthy condition (i.e. not colon cancer or a specific form of colon cancer), may be the reference (e.g. reference expression profile (data)) of a diseased condition (i.e. colon cancer), or may be the reference (e.g. reference expression (data)) of at least two conditions from which at least one condition is a diseased condition (i.e. colon cancer).

It is preferred that said reference is a reference expression profile (data) of at least one subject (e.g. human or animal), preferably the reference is an average expression profile (data) of at least 2 to 200 subjects, more preferably at least 10 to 150 subjects, and most preferably at least 20 to 100 subjects, with one known clinical condition which is colon cancer or a specific form of colon cancer, or which is not colon cancer or not a specific form of colon cancer (i.e. healthy/healthiness), wherein the reference expression profile of a set comprising at least two miRNAs that have nucleotide sequences that essentially correspond (are essentially identical), preferably that correspond (are identical), to the nucleotide sequences of the miRNAs which expression profile is determined by the means of (i).

It is also preferred that said reference are (average) reference expression profiles (data) of at least two subjects, preferably of at least 2 to 200 subjects, more preferably of at least 10 to 150 subjects, and most preferably of at least 20 to 100 subjects, with at least two known clinical conditions, preferably at least 2 to 5, more preferably at least 2 to 4 (i.e. at least 2, 3, 4, or 5) known clinical conditions, from which at least one is colon cancer), wherein the reference expression profiles are the profiles of a set comprising at least two miRNAs that have nucleotide sequences that essentially correspond (are essentially identical), preferably that correspond (are identical), to the nucleotide sequences of the miRNAs which expression profile is determined by the means of (i).

It is preferred that the reference is generated from expression profiles (data) obtained from 2 clinical conditions, which are colon cancer and healthy control.

Preferably, (i) the (average) reference expression profile (data), which is provided with the kit, is determined in the same type of body fluid sample (e.g. blood and/or urine sample) and/or obtained from (control) subject(s) of the same species, gender and/or of similar age/stage of life, or (ii) the (average) reference expression profiles (data), which are provided with the kit, are determined in the same type of body fluid sample (e.g. blood and/or urine sample) and/or are obtained from (control) subject(s) of the same species, gender and/or of similar age/stage of life.

Said reference, preferably said (average) reference expression profile(s) (data) may be comprised in an information leaflet (e.g. for comparing tested single reference miRNA biomarkers with the expression profile data of a patient to be diagnosed) or saved on a data carrier (e.g. for comparing tested sets of miRNA biomarkers with the expression profile data of a patient to be diagnosed). Said reference, preferably said (average) reference expression profile(s) (data) may also be comprised in a computer program which is saved on a data carrier. The kit may alternatively comprise an access code which allows the access to a database, e.g. an internet database, a centralized or a decentralized database, where said reference, preferably said (average) reference expression profile(s) (data) is (are) comprised.

It is particularly preferred that the reference is an algorithm or mathematical function.

Preferably the algorithm or mathematical function is obtained from a reference expression profile (data) of at least one subject, preferably the algorithm or mathematical function is obtained from an average reference expression profile (data) of at least 2 to 200 subjects, more preferably of at least 10 to 150 subjects, and most preferably of at least 20 to 100 subjects, i.e. of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with one known clinical condition which is colon cancer or a specific form of colon cancer, or which is not colon cancer or a specific form of colon cancer (i.e. healthy/healthiness), wherein the reference expression profile is the profile of a single miRNA that has a nucleotide sequence that essentially corresponds (is essentially identical), preferably that corresponds (is identical), to the nucleotide sequence of the miRNA which expression profile is determined by the means of (i), or is the profile of a set comprising at least two miRNAs that have nucleotide sequences that essentially correspond (are essentially identical), preferably that correspond (are identical), to the nucleotide sequences of the miRNAs which expression profile is determined by the means of (i).

It is also preferred that the algorithm or mathematical function is obtained from (average) reference expression profiles (data) of at least two subjects, preferably of at least 2 to 200 subjects, more preferably of at least 10 to 150 subjects, and most preferably of at least 20 to 100 subjects, i.e. of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with at least two known clinical conditions, preferably at least 2 to 5, more preferably at least 2 to 4 (i.e. at least 2, 3, 4, or 5) known clinical conditions, from which at least one is colon cancer, wherein the reference expression profiles are the profiles of a single miRNA that has a nucleotide sequence that essentially corresponds (is essentially identical), preferably that corresponds (is identical), to the nucleotide sequence of the miRNA which expression profile is determined by the means of (i) or are the profiles of a set comprising at least two miRNAs that have nucleotide sequences that essentially correspond (are essentially identical), preferably that correspond (are identical), to the nucleotide sequences of the miRNAs which expression profile is determined by the means of (i).

It is preferred that the algorithm or mathematical function is obtained using a machine learning approach (see second aspect of the present invention).

Preferably, the algorithm or mathematical function is saved on a data carrier comprised in the kit or the computer program, wherein the algorithm or mathematical function is comprised, is saved on a data carrier comprised in the kit. Said kit may alternatively comprise an access code which allows the access to an internet page, where the algorithm or mathematical function is saved or where the computer program, wherein the algorithm or mathematical function is comprised, can be downloaded.

Preferably, the algorithm or mathematical function is saved on a data carrier or the algorithm or mathematical function is comprised in a computer program which is saved on a data carrier. Said kit may alternatively comprise an access code which allows the access to a database or an internet page, where the algorithm or mathematical function is comprised, or where a computer program comprising the algorithm or mathematical function can be downloaded.

More than one reference may be comprised in the kit, e.g. 2, 3, 4, 5, or more references. For example, the kit may comprise reference data, preferably (average) reference expression profile(s) (data), which may be comprised in an information leaflet or saved on a data carrier. In addition, the kit may comprise more than one algorithm or mathematical function, e.g. two algorithms or mathematical functions, e.g. one trained to discriminate between a healthy condition and colon cancer and one trained to discriminate between specific forms of colon cancer, e.g. comprised in a computer program, preferably stored on a data carrier.

In an eighth aspect, the invention relates to a set of miRNAs isolated from a body fluid sample from a subject for diagnosing and/or prognosing of colon cancer, wherein the miRNAs are selected from the group consisting of SEQ ID NO: 1 to 484 or SEQ ID NO: 1 to 588.

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

It is preferred that the predetermined set of miRNAs comprises miRNAs that are differentially regulated in blood samples from colon cancer patients as compared to healthy controls. Preferably, the predetermined set of miRNAs comprises miRNAs selected from the group consisting of SEQ ID NO: 1 to 484 or SEQ ID NO: 1 to 588.

Preferably, the predetermined set comprising at least two miRNAs that are differentially regulated in blood samples from colon cancer patients as compared to healthy controls is selected from the set of miRNAs listed in FIG. 2 or FIG. 5b or FIG. 7.

It is preferred that the predetermined set comprising at least two miRNAs that are differentially regulated in blood samples from colon cancer patients as compared to healthy controls comprises at least one set of miRNAs listed in FIG. 2 or FIG. 5b or FIG. 7.

Preferably, the set of miRNAs isolated from a body fluid sample comprises at least one up-regulated miRNA listed in FIG. 8a or comprises at least one down-regulated miRNAs listed in FIG. 9a. More preferably, the of miRNAs isolated from a body fluid sample comprises at least one up-regulated miRNA listed in FIG. 8b or comprises at least one down-regulated miRNAs listed in FIG. 9b. Most preferably, the of miRNAs isolated from a body fluid sample comprises at least one up-regulated miRNA listed in FIG. 8c or comprises at least one down-regulated miRNAs listed in FIG. 9c. It is further preferred, that of miRNAs isolated from a body fluid sample at least two miRNAs comprises at least one up-regulated miRNA listed in FIG. 8a and further comprises at least one down-regulated miRNAs listed in FIG. 9a.

In a ninth aspect, the invention relates to the use of a set of miRNAs according to the eighth aspect of the invention for diagnosing and/or prognosing of colon cancer in a subject, In a further aspect, the present invention relates to a method for determining the status and/or the response of the immune system in a subject having or suspected of having colon cancer, comprising the steps of:

(i) determining an expression profile of a set comprising at least two miRNAs representative for the status and/or the response of the immune system in a body fluid sample from a subject, and (ii) comparing said expression profile to a reference, wherein the comparison of said expression profile to said reference allows for determining the status and/or the response of the immune system in said subject It is preferred that the body fluid sample is a blood sample, particularly preferred it is a whole blood, PBMC, serum, plasma or leukocyte sample, more particularly preferred it is a blood cell sample, preferably a leukocyte-, erythrocyte- and/or platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

Preferably, the set comprising at least two miRNAs is from the group consisting of SEQ ID NO: 1 to 588.

It is preferred that the set comprising at least two miRNAs is selected from the set of miRNAs listed in FIG. 2 or FIG. 5b or FIG. 7.

It is preferred that the set comprising at least two miRNAs comprises at least one set of miRNAs listed in FIG. 2 or FIG. 5b or FIG. 7.

Preferably, the set comprising at least two miRNAs in the method for determining the status and/or the response of the immune system in a subject having or suspected of having colon cancer comprises at least one up-regulated miRNA listed in FIG. 8a or comprises at least one down-regulated miRNAs listed in FIG. 9a. More preferably, the set comprising at least two miRNAs comprises at least one up-regulated miRNA listed in FIG. 8b or comprises at least one down-regulated miRNAs listed in FIG. 9b. Most preferably, the set comprising at least two miRNAs comprises at least one up-regulated miRNA listed in FIG. 8c or comprises at least one down-regulated miRNAs listed in FIG. 9c. It is further preferred, that the set comprising at least two miRNAs comprises at least one up-regulated miRNA listed in FIG. 8a and further comprises at least one down-regulated miRNAs listed in FIG. 9a.

It is preferred that the determining the expression profile of a set comprising at least two miRNAs selected from the group consisting of SEQ ID NO: 1 to 588 is for or is representative for determining the status and/or the response of the immune system in a body fluid sample, preferably in a blood sample, of the subject having of suspected of having colon cancer.

It is further preferred that the determination of the status and/or the response of the immune system in a body fluid sample or blood sample, allows for a diagnosis in the subject having or suspected of having colon cancer.

Preferably, the determination of the status and/or the response of the immune system in a body fluid sample or blood sample, allows for a treatment decision in said subject.

In a further aspect, the present invention relates to a method for diagnosing and/or prognosing of colon cancer comprising the steps of:
(i) providing a set comprising at least two polynucleotides according to the second aspect of the present invention for detecting a set comprising at least two miRNAs representative for colon cancer in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 588, a fragment thereof, and a sequence having at least 80% sequence identity thereto,
(ii) using the polynucleotide(s) provided in (i) for determining an miRNA expression profile in a body fluid sample (e.g. blood sample) from a patient (e.g. human or animal) with an unknown clinical condition,
comparing said expression profile to a reference,
diagnosing or prognosing the clinical condition of the patient (e.g. human or animal) on the basis of said comparison.

The term "patient with an unknown clinical condition" refers to a patient (e.g. human or animal) which may suffer from colon cancer (i.e. diseased patient) or may not suffer from colon cancer (i.e. healthy patient). The patient (e.g. human or animal) to be diagnosed may further suffer from a specific type of colon cancer. It is also possible to determine, whether the patient (e.g. human or animal) to be diagnosed will develop the above mentioned disease as the inventors of the present invention surprisingly found that miRNAs representative for colon cancer are already present in the body fluid sample, e.g. blood sample, before colon cancer occurs or during the early stage of colon cancer. It should be noted that a patient that is diagnosed as being healthy, i.e. not suffering from colon cancer, may possibly suffer from another disease not tested/known.

In summary, the present invention is composed of the following items:

A method for diagnosing and/or prognosing of colon cancer comprising the steps of:
(i) determining an expression profile of a set comprising at least two miRNAs representative for colon cancer in a body fluid sample from a subject, and
(ii) comparing said expression profile to a reference, wherein the comparison of said expression profile to said reference allows for the diagnosis and/or prognosis of colon cancer,
(iii) wherein the nucleotide sequences of the miRNAs comprised in the set are selected from the group consisting of SEQ ID NO: 1 to 484 or SEQ ID NO: 1 to 588, a fragment thereof, and a sequence having at least 80% sequence identity thereto.

The method of item 1, wherein the body fluid sample is a blood sample.

The method of item 2, wherein the blood sample is selected from whole blood, PBMC, serum, plasma, a leukocyte sample, a blood cell sample, a leukocyte-, erythrocyte- and/or platelet-containing sample.

The method of any of the items 1 to 3, wherein the set of miRNAs comprises at least one of the sets of miRNAs listed in FIG. 2 or FIG. 5b or FIG. 7.

The method of any of the items 1 to 4, wherein the set of miRNAs comprises at least one up-regulated miRNA listed in FIG. 8a or 8b or 8c.

The method of any of the items 1 to 4, wherein the set of miRNAs comprises at least one down-regulated miRNA listed in FIG. 9a or 9b or 9c.

The method of any of the items 1 to 4, wherein the set of miRNAs comprises at least one up-regulated miRNA listed in FIG. 8a or 8b or 8c and at least one down-regulated miRNA listed in FIG. 9a or 9b or 9c.

The method according to any of the items 1 to 7, wherein the reference are reference expression profiles of at least two subjects with at least two known clinical conditions from which at least one is colon cancer, wherein the reference expression profiles are the profiles of a set comprising at least two miRNAs that have nucleotide sequences that correspond to the nucleotide sequences of the miRNAs of step (i).

The method according to any of the items 1 to 7, wherein the reference is an algorithm or mathematical function that is obtained from reference expression profiles of at least two subjects with at least two known clinical conditions from which at least one is colon cancer, wherein the reference expression profiles are the profiles of a set comprising at least two miRNAs that have nucleotide sequences that correspond to the nucleotide sequences of the miRNAs of step (i).

A set comprising polynucleotides for detecting a set comprising at least two miRNAs for diagnosing and/or prognosing of colon cancer in a body fluid sample from a subject, wherein the nucleotide sequences of the miRNAs comprised in the set are selected from the group consisting of SEQ ID NO: 1 to 484 or SEQ ID NO: 1 to 588.

The set comprising polynucleotides of item 10, wherein the body fluid sample is a blood sample.

The set comprising polynucleotides of item 11, wherein the blood sample is selected from whole blood, PBMC, serum, plasma, a leukocyte sample, a blood cell sample, a leukocyte-, erythrocyte- and/or platelet-containing sample.

The set comprising polynucleotides of any of the items 10 to 12, wherein set comprising at least two miRNAs is selected from the set of miRNAs listed in FIG. 2 or FIG. 5b or FIG. 7.

The set comprising polynucleotides of any of the items 10 to 12, wherein the nucleotide sequences of the miRNAs comprised in the set are selected from the set of miRNAs listed in FIG. 2 or FIG. 5b or FIG. 7.

The set comprising polynucleotides of any of the items 10 to 14, wherein the set of miRNAs comprises at least one up-regulated miRNA listed in FIG. 8a or 8b or 8c.

The set comprising polynucleotides of any of the items 10 to 14, wherein the set of miRNAs comprises at least one down-regulated miRNA listed in FIG. 9a or 9b or 9c.

The set comprising polynucleotides of any of the items 10 to 14, wherein the set of miRNAs comprises at least one up-regulated miRNA listed in FIG. 8a or 8b or 8c and at least one down-regulated miRNA listed in FIG. 9a or 9b or 9c.

The set comprising polynucleotides according to any of the items 10 to 17, wherein
(i) the polynucleotides comprised in the set are complementary to the miRNAs comprised in the set according to items 10 or 17,
(ii) the polynucleotides comprised in the set are fragments of the polynucleotides comprised in the set according to (i), or
(iii) the polynucleotides comprised in the set have at least 80% sequence identity to the polynucleotide sequences of the polynucleotides comprised in the set according to (i) or polynucleotide fragments comprised in the set according to (ii).

Use of set of polynucleotides according to any of the items 10 to 18 for diagnosing and/or prognosing colon cancer in a subject A set of at least two primer pairs for determining the expression level of a set of miRNAs in a body fluid sample of a subject suffering or suspected of suffering from colon cancer, wherein the primer pairs are specific for at least two miRNAs selected from the group consisting of SEQ ID NO: 1 to 484 or SEQ ID NO: 1 to 588.

The set of primer pairs of item 20, wherein the body fluid sample is a blood sample.

The set of primer pairs of item 21, wherein the blood sample is selected from whole blood, PBMC, serum, plasma, a leukocyte sample, a blood cell sample, a leukocyte-, erythrocyte- and/or platelet-containing sample.

The set of primer pairs of any of the items 20 to 22, wherein the sets of miRNAs comprises at least one of the sets of miRNAs listed in FIG. 2 or FIG. 5b or FIG. 7.

The set of primer pairs of any of the items 20 to 23, wherein the set of miRNAs comprises at least one up-regulated miRNA listed in FIG. 8a or 8b or 8c.

The set of primer pairs of any of the items 20 to 23, wherein the set of miRNAs comprises at least one down-regulated miRNA listed in FIG. 9a or 9b or 9c.

The set of primer pairs of any of the items 20 to 23, wherein the set of miRNAs comprises at least one up-regulated miRNA listed in FIG. 8a or 8b or 8c and at least one down-regulated miRNA listed in FIG. 9a or 9b or 9c.

Use of set of primer pairs according to any of the items 20 to 26 for diagnosing and/or prognosing colon cancer in a subject Means for diagnosing and/or prognosing of colon cancer in a body fluid sample of a subject comprising:
(i) a set of at least two polynucleotides according to any of the items 10 to 18 or
(ii) a set of primer pairs according to any of the items 20 to 26.

The means of item 28, wherein said means comprise a biochip, a RT-PCT system, a PCR-system, a flow cytometer or a next generation sequencing system.

The means of items 28 or 29, wherein the body fluid sample is a blood sample.

The means of item 30, wherein the blood sample is selected from whole blood, PBMC, serum, plasma, a leukocyte sample, a blood cell sample, a leukocyte-, erythrocyte- and/or platelet-containing sample.

A kit for diagnosing and/or prognosing of colon cancer comprising
(i) means for determining an expression profile of a set comprising at least two miRNAs representative for colon cancer in a body fluid sample from a subject, and
(ii) at least one reference.

The kit of item 32, wherein the nucleotide sequences of said miRNAs are selected from the group consisting of SEQ ID NO: 1 to 484 or SEQ ID NO: 1 to 588, a fragment thereof, and a sequence having at least 80% sequence identity thereto.

The kit of items 32 or 33, wherein said kit comprises the means according to any of the items 28 to 31.

A set of miRNAs isolated from a body fluid sample from a subject for diagnosing and/or prognosing of colon cancer, wherein the miRNAs are selected from the group consisting of SEQ ID SEQ ID NO: 1 to 484 or SEQ ID NO: 1 to 588.

The set of miRNAs of item 35, wherein the body fluid sample is a blood sample.

The set of miRNAs of item 36, wherein the blood sample is selected from whole blood, PBMC, serum, plasma, a leukocyte sample, a blood cell sample, a leukocyte-, erythrocyte- and/or platelet-containing sample.

The set of miRNAs of any of the items 35 to 37, wherein the set of miRNAs comprises at least one of the sets of miRNAs listed in FIG. 2 or FIG. 5b or FIG. 7.

The set of miRNAs of any of the items 35 to 38, wherein the set of miRNAs comprises at least one up-regulated miRNA listed in FIG. 8a or 8b or 8c.

The set of miRNAs of any of the items 35 to 38, wherein the set of miRNAs comprises at least one down-regulated miRNA listed in FIG. 9a or 9b or 9c.

The set of miRNAs of any of the items 35 to 38, wherein the set of miRNAs comprises at least one up-regulated miRNA listed in FIG. 8a or 8b or 8c and at least one down-regulated miRNA listed in FIG. 9a or 9b or 9c

Use of a set of miRNAs according to any of the items 35 to 41 for diagnosing and/or prognosing of colon cancer in a subject.

A method for determining the status and/or the response of the immune system in a subject having or suspected of having colon cancer, comprising the steps of:
determining an expression profile of a set comprising at least two miRNAs representative for the status and/or the response of the immune system in a body fluid sample from a subject, and
comparing said expression profile to a reference, wherein the comparison of said expression profile to said reference allows for determining the status and/or the response of the immune system in said subject
(i) wherein the miRNAs comprised in the set are selected from the group consisting of SEQ ID NO: 1 588, a fragment thereof, and a sequence having at least 80% sequence identity thereto.

The method of item 43, wherein the body fluid sample is a blood sample.

The method of item 44, wherein the blood sample is selected from whole blood, PBMC, serum, plasma, a leukocyte sample, a blood cell sample, a leukocyte-, erythrocyte- and/or platelet-containing sample.

The method of any of the items 43 to 45, wherein the set of miRNAs comprises at least one of the sets of miRNAs listed in FIG. 2 or FIG. 5b or FIG. 7.

The method of any of the items 43 to 45, wherein the set of miRNAs comprises at least one up-regulated miRNA listed in FIG. 8a or 8b or 8c.

The method of any of the items 43 to 45, wherein the set of miRNAs comprises at least one down-regulated miRNA listed in FIG. 9a or 9b or 9c.

The method of any of the items 43 to 45, wherein the set of miRNAs comprises at least one up-regulated miRNA listed in FIG. 8a or 8b or 8c and at least one down-regulated miRNA listed in FIG. 9a or 9b or 9c.

The method according to any of the items 43 to 49, wherein the reference are reference expression profiles of at least two subjects with at least two known clinical conditions from which at least one is colon cancer, wherein the reference expression profiles are the profiles of a set comprising at least two miRNAs that have nucleotide sequences that correspond to the nucleotide sequences of the miRNAs of step (i).

The method according to any of the items 43 to 49 wherein the reference is an algorithm or mathematical function that is obtained from reference expression profiles of at least two subjects with at least two known clinical conditions from which at least one is colon cancer, wherein the reference expression profiles are the profiles of a set comprising at least two miRNAs that have nucleotide sequences that correspond to the nucleotide sequences of the miRNAs of step (i).

EXAMPLES

The Examples are designed in order to further illustrate the present invention and serve a better understanding. They are not to be construed as limiting the scope of the invention in any way.

Materials and Methods

Samples

All blood donors participating in this study have given their written informed consent. The patient samples have been prepared at the Institute for Human Genetics at University Saarland (Homburg,/Saar, Germany). Besides the samples of diseased patients, also normal (healthy) control samples were provided. Further normal control samples were provided by 3 other institutions. Altogether, 28 colon cancer samples and 70 healthy control samples were analyzed. The colon cancer samples were characterized with clinical progression MA (2 samples) and IIIB (26 samples) or according to TNM-status with T2N1M0 (3×), T3N1M0 (13×), T3N2M0 (2×) T4N1M0 (8×), T4N2M0 (2×).

miRNA Extraction and Microarray Screening

Blood of patients has been extracted as previously described [1]. In brief, 2.5 to 5 ml blood was extracted in PAXgene Blood RNA tubes (BD, Franklin Lakes, N.J. USA) and centrifuged at 5000×g for 10 min at room temperature. The miRNeasy kit (Qiagen GmbH, Hilden) was used to isolate total RNA including miRNA from the resuspended pellet according to manufacturer's instructions. The eluted RNA was stored at −70° C.

All samples were shipped overnight on dry ice and analyzed with the Geniom RT Analyzer (febit biomed GmbH, Heidelberg, Germany) at the in-house genomic service department using the Geniom Biochip miRNA Homo sapiens. Each array contains 7 replicates of about 863 miRNAs and miRNA* sequences as annotated in the Sanger miRBase releases 14.0. On-chip sample labeling with biotin was carried out by microfluidic-based primer extension labeling of miRNAs (MPEA [2]). Following hybridization for 16 hours at 42° C., the biochip was washed and a program for signal enhancement was carried out. All steps from sample loading to miRNA detection were processed without any manual intervention and inside the machine. The detection pictures were evaluated using the Geniom Wizard Software. For each feature, the median signal intensity was calculated. Following a background correction step, the median of the 7 replicates of each miRNA was computed. To normalize the data across different arrays, quantile normalization [3] was applied and all further analyses were carried out using the normalized and background subtracted intensity values.

Statistical Analysis

To estimate the value of single miRNAs, t-tests (unpaired, two-tailed) were carried out. The resulting p-values have been adjusted for multiple testing by Benjamini-Hochberg adjustment [4, 5]. In addition to this single biomarker analysis, we performed supervised classification of samples by using Support Vector Machines (SVM [6]) as implemented in the R e1071 package [7]. As parameters, we evaluated different kernel methods including linear, polynomial (degree 2 to 5), sigmoid and radial basis function kernels. The cost parameter was sampled from 0.01 to 10 in decimal powers. As subset selection technique, a filter approach based on t-test was carried out. In each iteration, the s miRNAs with lowest p-values were computed on the training set in each fold of a standard 10-fold cross validation, where s was sampled in regular intervals between 2 and 300. The respective subset was used to train the SVM and to carry out the prediction of the test samples in the cross validation. To compute probabilities for classes instead of class labels, a regression approach based on the output of the support vectors has been applied. To test for overtraining, non-parametric permutation tests have been applied. All computations were carried out using R [7], a freely available language for statistical tasks.

REFERENCES

1. Keller A, Leidinger P, Borries A, Wendschlag A, Wucherpfennig F, Scheffler M, Huwer H, Lenhof H P, Meese E: miRNAs in lung cancer—studying complex fingerprints in patient's blood cells by microarray experiments. BMC Cancer 2009, 9:353.
2. Vorwerk S, Ganter K, Cheng Y, Hoheisel J, Stabler P F, Beier M: Microfluidic-based enzymatic on-chip labeling of miRNAs. N Biotechnol 2008, 25(2-3):142-149.
3. Bolstad B M, Irizarry R A, Astrand M, Speed T P: A comparison of normalization methods for high density oligonucleotide array data based on variance and bias. Bioinformatics 2003, 19(2): 185-193.
4. Benjamini Y, Drai D, Elmer G, Kafkafi N, Golani I: Controlling the false discovery rate in behavior genetics research. Behav Brain Res 2001, 125(1-2):279-284.
5. Hochberg Y: A sharper bonferroni procedure for multiple tests of significance. Biometrica 1988, 75:185-193.
6. Vapnik V: The nature of statistical learning theory, 2nd edition edn. New York: Springer; 2000.
7. Team R: R: A Language and Environment for Statistical Computing. In. Vienna: R Foundation for Statistical Computing; 2008.

What is claimed is:

1. A method for detecting altered levels of miRNA expression in a human subject having, or suspected of having, colon cancer comprising the steps of:
   (i) determining an expression profile of a set comprising at least two miRNAs representative for colon cancer in a blood cell sample from the human subject,
   wherein the blood cell sample consists of a mixture of erythrocytes, leukocytes, and thrombocytes,
   wherein the miRNAs comprised in the set comprising at least two miRNAs are selected from the group consisting of:
   hsa-miR-20a, hsa-miR-144*, hsa-miR-183, hsa-miR-499-3p, hsa-miR-658, hsa-miR-208b, hsa-miR-145, hsa-miR-28-3p, hsa-miR-18a, hsa-miR-646, hsa-miR-17, hsa-miR-19b, hsa-miR-596, hsa-miR-664, hsa-miR-1180, hsa-miR-20b, hsa-miR-106a, hsa-miR-564, hsa-miR-93, hsa-miR-183*, hsa-miR-1260, hsa-miR-373, hsa-miR-1227, hsa-miR-483-5p, hsa-miR-621, hsa-miR-1908, hsa-miR-106b, hsa-miR-607, hsa-miR-374a, hsa-miR-224, hsa-miR-17*, hsa-miR-130b, hsa-miR-1246, hsa-miR-635, hsa-miR-146a, hsa-miR-144, hsa-miR-523, hsa-miR-454, hsa-miR-296-5p, hsa-miR-1226*, hsa-miR-496, hsa-miR-216a, hsa-miR-613, hsa-miR-200a*, hsa-miR-1225-5p, hsa-miR-328, hsa-miR-556-5p, hsa-miR-1247, hsa-miR-1294, hsa-miR-609, hsa-miR-1282, hsa-miR-485-5p, hsa-miR-520d-3p, hsa-miR-1251, hsa-miR-151-3p, hsa-miR-593*, hsa-miR-361-5p, hsa-miR-720, hsa-miR-452*, hsa-miR-216b, hsa-miR-32, hsa-miR-934, hsa-miR-640, hsa-miR-34a*, hsa-let-7d*, hsa-miR-197, hsa-miR-423-5p, hsa-miR-214*, hsa-miR-574-3p, hsa-miR-604, hsa-miR-1324, hsa-miR-320d, hsa-miR-151-5p, hsa-miR-744, hsa-miR-33b, hsa-miR-455-3p, hsa-miR-483-3p, hsa-miR-891b, hsa-miR-219-2-3p, hsa-miR-892a, hsa-miR-1272, hsa-miR-153, hsa-miR-31*, hsa-miR-654-5p, hsa-miR-125a-3p, and hsa-miR-545, and
   wherein the set comprising at least two miRNAs comprises at least one of the sets of miRNAs listed in FIG. 2, FIG. 5b or FIG. 7; and
   (ii) comparing said expression profile to a reference expression profile obtained from at least one healthy human subject, or a human subject not having, or being suspected of having colon cancer;
   (iii) detecting at least one of the following up-regulations relative to the reference expression profile of:
   hsa-miR-183, hsa-miR-658, hsa-miR-145, hsa-miR-28-3p, hsa-miR-19b, hsa-miR-664, hsa-miR-1180, hsa-miR-183*, hsa-miR-1260, hsa-miR-373, hsa-miR-1227, hsa-miR-483-5p, hsa-miR-1908, hsa-miR-224, hsa-miR-130b, hsa-miR-1246, hsa-miR-146a, hsa-miR-296-5p, hsa-miR-613, hsa-miR-1225-5p, hsa-miR-328, hsa-miR-1294, hsa-miR-609, hsa-miR-520d-3p, hsa-miR-151-3p, hsa-miR-361-5p, hsa-miR-720, hsa-let-7d*, hsa-miR-197, hsa-miR-423-5p, hsa-miR-574-3p, hsa-miR-320d, hsa-miR-151-5p, hsa-miR-483-3p, hsa-miR-219-2-3p, hsa-miR-892a, hsa-miR-125a-3p, hsa-miR-1282, or hsa-miR-744, and/or
   at least one of the following down-regulations relative to the reference expression profile of:
   hsa-miR-20a, hsa-miR-144*, hsa-miR-499-3p, hsa-miR-208b, hsa-miR-18a, hsa-miR-646, hsa-miR-17, hsa-miR-596, hsa-miR-20b, hsa-miR-106a, hsa-miR-564, hsa-miR-93, hsa-miR-621, hsa-miR-106b, hsa-miR-607, hsa-miR-374a, hsa-miR-17*, hsa-miR-635, hsa-miR-144, hsa-miR-523, hsa-miR-454, hsa-miR-1226*, hsa-miR-496, hsa-miR-216a, hsa-miR-200a*, hsa-miR-556-5p, hsa-miR-1247, hsa-miR-485-5p, hsa-miR-1251, hsa-miR-593*, hsa-miR-452*, hsa-miR-216b, hsa-miR-32, hsa-miR-934, hsa-miR-640, hsa-miR-34a*, hsa-miR-214*, hsa-miR-604, hsa-miR-1324, hsa-miR-33b, hsamiR-455-3p, hsa-miR-891b, hsa-miR-1272, hsa-miR-153, hsa-miR-31*, hsa-miR-654-5p, or hsa-miR-545, and (iv) determining whether the subject has colon cancer or will develop colon cancer by transforming the individual expression levels of the miRNAs in the individual blood cells of the blood cell sample to one numerical value which represents the mathematical average of the miRNA expression levels of the individual blood cells, wherein the individual blood cells are erythrocytes, leukocytes, and thrombocytes.

2. The method of claim 1, wherein the expression profile of the miRNAs is determined comprising the steps:
(a) extracting total RNA from said blood sample,
(b) reverse-transcribing the total RNA into cDNA, and
(c) amplifying the cDNA and thereby detecting the miRNA levels in said blood sample.

3. A kit for diagnosing and/or prognosing colon cancer according to the method of claim 1, comprising
(i) means for determining the expression profile of the set comprising at least two miRNAs representative for colon cancer in the blood sample from the subject, and
(ii) at least one reference,
wherein the reference is determined from reference expression profiles of at least 2 control subjects with at least 2 clinical conditions, from which at least one is colon cancer.

4. The kit according to claim 3, wherein the reference is determined in the same type of blood sample as the subject to be diagnosed and/or prognosed.

5. The kit according to claim 4, wherein the means comprise:
(i) a set of at least two polynucleotides or a set of at least two primer pairs for detecting the set comprising at least two miRNAs for diagnosing and/or prognosing colon cancer in the blood sample from a subject, wherein the nucleotide sequences of the miRNAs comprised in the set are selected from the group consisting of SEQ ID NOs: 1 to 588, and
(ii) a biochip, a RT-PCT system, a PCR-system, a flow cytometer, a bead-based multiplex system or a next generation sequencing system.

6. A method of detecting an expression profile for colon cancer in a subject comprising the steps of:
(i) providing a blood cell sample consisting of a mixture of erythrocytes, leukocytes, and thrombocytes obtained from the subject, and
(i.) detecting whether the expression profile for colon cancer is present in the blood cell sample obtained from the subject by contacting the blood cell sample with probes for a miRNA expression profile and detecting binding between the probes and the miRNAs,
wherein the expression profile comprises a set of at least two miRNAs representative for colon cancer in the blood cell sample,
wherein the set of at least two miRNAs comprises at least one of the sets of miRNAs listed in FIG. 2, FIG. 5b or FIG. 7; and,
determinin whether the subject has colon cancer or will develop colon cancer by transforming the individual expression levels of the miRNAs in the individual blood cells of the blood cell sample to one numerical value which represents the mathematical average of the miRNA expression levels of the individual blood cells, wherein the individual blood cells are erythrocytes, leukocytes, and thrombocytes.

* * * * *

UNITED STATES PATENT AND TRADEMARK OFFICE
CERTIFICATE OF CORRECTION

PATENT NO. : 9,631,241 B2
APPLICATION NO. : 15/002725
DATED : April 25, 2017
INVENTOR(S) : Andreas Keller et al.

It is certified that error appears in the above-identified patent and that said Letters Patent is hereby corrected as shown below:

In the Claims

Column 196, Claim 6, Line 25, Change "determinin" to -- determining --.

Signed and Sealed this
Sixth Day of June, 2017

Michelle K. Lee
*Director of the United States Patent and Trademark Office*

SEQUENCE LISTING

<160> NUMBER OF SEQ ID NOS: 588

<210> SEQ ID NO 1
<211> LENGTH: 21

```
<212> TYPE: RNA
<213> ORGANISM: Homo sapiens

<400> SEQUENCE: 1
acucuagcug ccaaaggcgc u                                              21

<210> SEQ ID NO 2
<211> LENGTH: 21
<212> TYPE: RNA
<213> ORGANISM: Homo sapiens

<400> SEQUENCE: 2
cuagacugaa gcuccuugag g                                              21

<210> SEQ ID NO 3
<211> LENGTH: 23
<212> TYPE: RNA
<213> ORGANISM: Homo sapiens

<400> SEQUENCE: 3
ugugcaaauc caugcaaaac uga                                            23

<210> SEQ ID NO 4
<211> LENGTH: 22
<212> TYPE: RNA
<213> ORGANISM: Homo sapiens

<400> SEQUENCE: 4
uuaucagaau cuccaggggu ac                                             22

<210> SEQ ID NO 5
<211> LENGTH: 23
<212> TYPE: RNA
<213> ORGANISM: Homo sapiens

<400> SEQUENCE: 5
aaaagugcuu acagugcagg uag                                            23

<210> SEQ ID NO 6
<211> LENGTH: 21
<212> TYPE: RNA
<213> ORGANISM: Homo sapiens

<400> SEQUENCE: 6
augauccagg aaccugccuc u                                              21

<210> SEQ ID NO 7
<211> LENGTH: 23
<212> TYPE: RNA
<213> ORGANISM: Homo sapiens

<400> SEQUENCE: 7
caaagugcuc auagugcagg uag                                            23

<210> SEQ ID NO 8
<211> LENGTH: 22
<212> TYPE: RNA
<213> ORGANISM: Homo sapiens

<400> SEQUENCE: 8
cacuagauug ugagcuccug ga                                             22

<210> SEQ ID NO 9
```

-continued

```
<211> LENGTH: 22
<212> TYPE: RNA
<213> ORGANISM: Homo sapiens

<400> SEQUENCE: 9
auaagacgaa caaaagguuu gu                                               22

<210> SEQ ID NO 10
<211> LENGTH: 23
<212> TYPE: RNA
<213> ORGANISM: Homo sapiens

<400> SEQUENCE: 10
guccaguuuu cccaggaauc ccu                                              23

<210> SEQ ID NO 11
<211> LENGTH: 22
<212> TYPE: RNA
<213> ORGANISM: Homo sapiens

<400> SEQUENCE: 11
cuauacgacc ugcugccuuu cu                                               22

<210> SEQ ID NO 12
<211> LENGTH: 22
<212> TYPE: RNA
<213> ORGANISM: Homo sapiens

<400> SEQUENCE: 12
ugucuacuac uggagacacu gg                                               22

<210> SEQ ID NO 13
<211> LENGTH: 23
<212> TYPE: RNA
<213> ORGANISM: Homo sapiens

<400> SEQUENCE: 13
caaagugcuu acagugcagg uag                                              23

<210> SEQ ID NO 14
<211> LENGTH: 21
<212> TYPE: RNA
<213> ORGANISM: Homo sapiens

<400> SEQUENCE: 14
aagccugccc ggcuccucgg g                                                21

<210> SEQ ID NO 15
<211> LENGTH: 22
<212> TYPE: RNA
<213> ORGANISM: Homo sapiens

<400> SEQUENCE: 15
uuuccggcuc gcguggugu gu                                                22

<210> SEQ ID NO 16
<211> LENGTH: 23
<212> TYPE: RNA
<213> ORGANISM: Homo sapiens

<400> SEQUENCE: 16
uauucauuua uccccagccu aca                                              23
```

```
<210> SEQ ID NO 17
<211> LENGTH: 23
<212> TYPE: RNA
<213> ORGANISM: Homo sapiens

<400> SEQUENCE: 17
uaaagugcuu auagugcagg uag                                              23

<210> SEQ ID NO 18
<211> LENGTH: 21
<212> TYPE: RNA
<213> ORGANISM: Homo sapiens

<400> SEQUENCE: 18
caagucacua ugguuccgu u                                                 21

<210> SEQ ID NO 19
<211> LENGTH: 23
<212> TYPE: RNA
<213> ORGANISM: Homo sapiens

<400> SEQUENCE: 19
gaacgcgcuu cccuauagag ggu                                              23

<210> SEQ ID NO 20
<211> LENGTH: 22
<212> TYPE: RNA
<213> ORGANISM: Homo sapiens

<400> SEQUENCE: 20
gugaauuacc gaagggccau aa                                               22

<210> SEQ ID NO 21
<211> LENGTH: 22
<212> TYPE: RNA
<213> ORGANISM: Homo sapiens

<400> SEQUENCE: 21
aacaucacag caagucugug cu                                               22

<210> SEQ ID NO 22
<211> LENGTH: 18
<212> TYPE: RNA
<213> ORGANISM: Homo sapiens

<400> SEQUENCE: 22
aucccaccuc ugccacca                                                    18

<210> SEQ ID NO 23
<211> LENGTH: 22
<212> TYPE: RNA
<213> ORGANISM: Homo sapiens

<400> SEQUENCE: 23
ugaguauuac auggccaauc uc                                               22

<210> SEQ ID NO 24
<211> LENGTH: 22
<212> TYPE: RNA
<213> ORGANISM: Homo sapiens

<400> SEQUENCE: 24
ggauaucauc auauacugua ag                                               22
```

```
<210> SEQ ID NO 25
<211> LENGTH: 20
<212> TYPE: RNA
<213> ORGANISM: Homo sapiens

<400> SEQUENCE: 25
aggaauguuc cuucuuugcc                                               20

<210> SEQ ID NO 26
<211> LENGTH: 19
<212> TYPE: RNA
<213> ORGANISM: Homo sapiens

<400> SEQUENCE: 26
aggcacggug ucagcaggc                                                19

<210> SEQ ID NO 27
<211> LENGTH: 22
<212> TYPE: RNA
<213> ORGANISM: Homo sapiens

<400> SEQUENCE: 27
acugcaguga aggcacuugu ag                                            22

<210> SEQ ID NO 28
<211> LENGTH: 21
<212> TYPE: RNA
<213> ORGANISM: Homo sapiens

<400> SEQUENCE: 28
guucaaaucc agaucuauaa c                                             21

<210> SEQ ID NO 29
<211> LENGTH: 20
<212> TYPE: RNA
<213> ORGANISM: Homo sapiens

<400> SEQUENCE: 29
ucacuguuca gacaggcgga                                               20

<210> SEQ ID NO 30
<211> LENGTH: 21
<212> TYPE: RNA
<213> ORGANISM: Homo sapiens

<400> SEQUENCE: 30
uaaagugcug acagugcaga u                                             21

<210> SEQ ID NO 31
<211> LENGTH: 22
<212> TYPE: RNA
<213> ORGANISM: Homo sapiens

<400> SEQUENCE: 31
ccuguucucc auuacuuggc uc                                            22

<210> SEQ ID NO 32
<211> LENGTH: 22
<212> TYPE: RNA
<213> ORGANISM: Homo sapiens

<400> SEQUENCE: 32
uuuugcaaua uguuccugaa ua                                            22
```

```
<210> SEQ ID NO 33
<211> LENGTH: 22
<212> TYPE: RNA
<213> ORGANISM: Homo sapiens

<400> SEQUENCE: 33
uauggcacug guagaauuca cu                                              22

<210> SEQ ID NO 34
<211> LENGTH: 21
<212> TYPE: RNA
<213> ORGANISM: Homo sapiens

<400> SEQUENCE: 34
aggaggcagc gcucucagga c                                               21

<210> SEQ ID NO 35
<211> LENGTH: 22
<212> TYPE: RNA
<213> ORGANISM: Homo sapiens

<400> SEQUENCE: 35
uucaccaccu ucuccaccca gc                                              22

<210> SEQ ID NO 36
<211> LENGTH: 21
<212> TYPE: RNA
<213> ORGANISM: Homo sapiens

<400> SEQUENCE: 36
ucuaguaaga guggcagucg a                                               21

<210> SEQ ID NO 37
<211> LENGTH: 21
<212> TYPE: RNA
<213> ORGANISM: Homo sapiens

<400> SEQUENCE: 37
caaagguauu ugugguuuuu g                                               21

<210> SEQ ID NO 38
<211> LENGTH: 22
<212> TYPE: RNA
<213> ORGANISM: Homo sapiens

<400> SEQUENCE: 38
ugagaacuga auuccauggg uu                                              22

<210> SEQ ID NO 39
<211> LENGTH: 23
<212> TYPE: RNA
<213> ORGANISM: Homo sapiens

<400> SEQUENCE: 39
gaagugcuuc gauuuugggg ugu                                             23

<210> SEQ ID NO 40
<211> LENGTH: 22
<212> TYPE: RNA
<213> ORGANISM: Homo sapiens

<400> SEQUENCE: 40
```

| | |
|---|---|
| uuauaaagca augagacuga uu | 22 |

<210> SEQ ID NO 41
<211> LENGTH: 22
<212> TYPE: RNA
<213> ORGANISM: Homo sapiens

<400> SEQUENCE: 41

| | |
|---|---|
| acccgucccg uucguccccg ga | 22 |

<210> SEQ ID NO 42
<211> LENGTH: 22
<212> TYPE: RNA
<213> ORGANISM: Homo sapiens

<400> SEQUENCE: 42

| | |
|---|---|
| cgucaacacu ugcugguuuc cu | 22 |

<210> SEQ ID NO 43
<211> LENGTH: 22
<212> TYPE: RNA
<213> ORGANISM: Homo sapiens

<400> SEQUENCE: 43

| | |
|---|---|
| caaucagcaa guauacugcc cu | 22 |

<210> SEQ ID NO 44
<211> LENGTH: 22
<212> TYPE: RNA
<213> ORGANISM: Homo sapiens

<400> SEQUENCE: 44

| | |
|---|---|
| ugccugucua cacuugcugu gc | 22 |

<210> SEQ ID NO 45
<211> LENGTH: 20
<212> TYPE: RNA
<213> ORGANISM: Homo sapiens

<400> SEQUENCE: 45

| | |
|---|---|
| cgugccaccc uuuucccag | 20 |

<210> SEQ ID NO 46
<211> LENGTH: 19
<212> TYPE: RNA
<213> ORGANISM: Homo sapiens

<400> SEQUENCE: 46

| | |
|---|---|
| aauggauuuu uggagcagg | 19 |

<210> SEQ ID NO 47
<211> LENGTH: 23
<212> TYPE: RNA
<213> ORGANISM: Homo sapiens

<400> SEQUENCE: 47

| | |
|---|---|
| acuugggcac ugaaacaaug ucc | 23 |

<210> SEQ ID NO 48
<211> LENGTH: 22
<212> TYPE: RNA
<213> ORGANISM: Homo sapiens

<400> SEQUENCE: 48
aaucguacag ggucauccac uu                                    22

<210> SEQ ID NO 49
<211> LENGTH: 22
<212> TYPE: RNA
<213> ORGANISM: Homo sapiens

<400> SEQUENCE: 49
aaggagcuca cagucuauug ag                                    22

<210> SEQ ID NO 50
<211> LENGTH: 17
<212> TYPE: RNA
<213> ORGANISM: Homo sapiens

<400> SEQUENCE: 50
ucucgcuggg gccucca                                          17

<210> SEQ ID NO 51
<211> LENGTH: 22
<212> TYPE: RNA
<213> ORGANISM: Homo sapiens

<400> SEQUENCE: 51
caaccuggag gacuccaugc ug                                    22

<210> SEQ ID NO 52
<211> LENGTH: 21
<212> TYPE: RNA
<213> ORGANISM: Homo sapiens

<400> SEQUENCE: 52
aucacauugc cagggauuac c                                     21

<210> SEQ ID NO 53
<211> LENGTH: 23
<212> TYPE: RNA
<213> ORGANISM: Homo sapiens

<400> SEQUENCE: 53
caaagugcug uucgugcagg uag                                   23

<210> SEQ ID NO 54
<211> LENGTH: 22
<212> TYPE: RNA
<213> ORGANISM: Homo sapiens

<400> SEQUENCE: 54
augguuccgu caagcaccau gg                                    22

<210> SEQ ID NO 55
<211> LENGTH: 21
<212> TYPE: RNA
<213> ORGANISM: Homo sapiens

<400> SEQUENCE: 55
ucacuccucu ccucccgucu u                                     21

<210> SEQ ID NO 56
<211> LENGTH: 22
<212> TYPE: RNA
<213> ORGANISM: Homo sapiens

<400> SEQUENCE: 56
acaggugagg uucuugggag cc					22

<210> SEQ ID NO 57
<211> LENGTH: 22
<212> TYPE: RNA
<213> ORGANISM: Homo sapiens

<400> SEQUENCE: 57
guggguacgg cccagugggg gg					22

<210> SEQ ID NO 58
<211> LENGTH: 21
<212> TYPE: RNA
<213> ORGANISM: Homo sapiens

<400> SEQUENCE: 58
uacaguacug ugauaacuga a						21

<210> SEQ ID NO 59
<211> LENGTH: 25
<212> TYPE: RNA
<213> ORGANISM: Homo sapiens

<400> SEQUENCE: 59
ggcggaggga aguagguccg uuggu					25

<210> SEQ ID NO 60
<211> LENGTH: 22
<212> TYPE: RNA
<213> ORGANISM: Homo sapiens

<400> SEQUENCE: 60
caucuuaccg gacagugcug ga					22

<210> SEQ ID NO 61
<211> LENGTH: 21
<212> TYPE: RNA
<213> ORGANISM: Homo sapiens

<400> SEQUENCE: 61
agggcccccc cucaauccug u						21

<210> SEQ ID NO 62
<211> LENGTH: 22
<212> TYPE: RNA
<213> ORGANISM: Homo sapiens

<400> SEQUENCE: 62
uggugggccg cagaacaugu gc					22

<210> SEQ ID NO 63
<211> LENGTH: 23
<212> TYPE: RNA
<213> ORGANISM: Homo sapiens

<400> SEQUENCE: 63
uauggcuuuu uauuccuaug uga					23

<210> SEQ ID NO 64
<211> LENGTH: 21
<212> TYPE: RNA
<213> ORGANISM: Homo sapiens

```
<400> SEQUENCE: 64
uugaaaggcu auucuuggu c                                              21

<210> SEQ ID NO 65
<211> LENGTH: 22
<212> TYPE: RNA
<213> ORGANISM: Homo sapiens

<400> SEQUENCE: 65
cuggcccucu cugcccuucc gu                                            22

<210> SEQ ID NO 66
<211> LENGTH: 22
<212> TYPE: RNA
<213> ORGANISM: Homo sapiens

<400> SEQUENCE: 66
gaugagcuca uuguaauaug ag                                            22

<210> SEQ ID NO 67
<211> LENGTH: 20
<212> TYPE: RNA
<213> ORGANISM: Homo sapiens

<400> SEQUENCE: 67
uacaguauag augauguacu                                               20

<210> SEQ ID NO 68
<211> LENGTH: 22
<212> TYPE: RNA
<213> ORGANISM: Homo sapiens

<400> SEQUENCE: 68
acuguugcua auaugcaacu cu                                            22

<210> SEQ ID NO 69
<211> LENGTH: 25
<212> TYPE: RNA
<213> ORGANISM: Homo sapiens

<400> SEQUENCE: 69
aggcaccagc caggcauugc ucagc                                         25

<210> SEQ ID NO 70
<211> LENGTH: 22
<212> TYPE: RNA
<213> ORGANISM: Homo sapiens

<400> SEQUENCE: 70
accguggcuu ucgauuguua cu                                            22

<210> SEQ ID NO 71
<211> LENGTH: 22
<212> TYPE: RNA
<213> ORGANISM: Homo sapiens

<400> SEQUENCE: 71
uaaucucagc uggcaacugu ga                                            22

<210> SEQ ID NO 72
<211> LENGTH: 22
<212> TYPE: RNA
```

```
<213> ORGANISM: Homo sapiens

<400> SEQUENCE: 72
acaguagagg gaggaaucgc ag                                              22

<210> SEQ ID NO 73
<211> LENGTH: 22
<212> TYPE: RNA
<213> ORGANISM: Homo sapiens

<400> SEQUENCE: 73
aaaucucugc aggcaaaugu ga                                              22

<210> SEQ ID NO 74
<211> LENGTH: 22
<212> TYPE: RNA
<213> ORGANISM: Homo sapiens

<400> SEQUENCE: 74
uguaacagca acuccaugug ga                                              22

<210> SEQ ID NO 75
<211> LENGTH: 18
<212> TYPE: RNA
<213> ORGANISM: Homo sapiens

<400> SEQUENCE: 75
gucccuguuc aggcgcca                                                   18

<210> SEQ ID NO 76
<211> LENGTH: 22
<212> TYPE: RNA
<213> ORGANISM: Homo sapiens

<400> SEQUENCE: 76
uugcauaguc acaaaaguga uc                                              22

<210> SEQ ID NO 77
<211> LENGTH: 21
<212> TYPE: RNA
<213> ORGANISM: Homo sapiens

<400> SEQUENCE: 77
aggggugcua ucugugauug a                                               21

<210> SEQ ID NO 78
<211> LENGTH: 21
<212> TYPE: RNA
<213> ORGANISM: Homo sapiens

<400> SEQUENCE: 78
guguugaaac aaucucuacu g                                               21

<210> SEQ ID NO 79
<211> LENGTH: 23
<212> TYPE: RNA
<213> ORGANISM: Homo sapiens

<400> SEQUENCE: 79
uaaggugcau cuagugcaga uag                                             23

<210> SEQ ID NO 80
<211> LENGTH: 23
```

```
<212> TYPE: RNA
<213> ORGANISM: Homo sapiens

<400> SEQUENCE: 80
uagugcaaua uugcuuauag ggu                                     23

<210> SEQ ID NO 81
<211> LENGTH: 21
<212> TYPE: RNA
<213> ORGANISM: Homo sapiens

<400> SEQUENCE: 81
caucccuugc augguggagg g                                       21

<210> SEQ ID NO 82
<211> LENGTH: 23
<212> TYPE: RNA
<213> ORGANISM: Homo sapiens

<400> SEQUENCE: 82
cuggagauau ggaagagcug ugu                                     23

<210> SEQ ID NO 83
<211> LENGTH: 22
<212> TYPE: RNA
<213> ORGANISM: Homo sapiens

<400> SEQUENCE: 83
aagacgggag gaaagaaggg ag                                      22

<210> SEQ ID NO 84
<211> LENGTH: 22
<212> TYPE: RNA
<213> ORGANISM: Homo sapiens

<400> SEQUENCE: 84
cagugcaaug augaaagggc au                                      22

<210> SEQ ID NO 85
<211> LENGTH: 22
<212> TYPE: RNA
<213> ORGANISM: Homo sapiens

<400> SEQUENCE: 85
ggugcagugc ugcaucucug gu                                      22

<210> SEQ ID NO 86
<211> LENGTH: 18
<212> TYPE: RNA
<213> ORGANISM: Homo sapiens

<400> SEQUENCE: 86
cagggaggug aaugugau                                           18

<210> SEQ ID NO 87
<211> LENGTH: 22
<212> TYPE: RNA
<213> ORGANISM: Homo sapiens

<400> SEQUENCE: 87
uuauaauaca accugauaag ug                                      22

<210> SEQ ID NO 88
```

```
<211> LENGTH: 21
<212> TYPE: RNA
<213> ORGANISM: Homo sapiens

<400> SEQUENCE: 88
ugaguuggcc aucugaguga g                                              21

<210> SEQ ID NO 89
<211> LENGTH: 23
<212> TYPE: RNA
<213> ORGANISM: Homo sapiens

<400> SEQUENCE: 89
cggcccgggc ugcugcuguu ccu                                            23

<210> SEQ ID NO 90
<211> LENGTH: 22
<212> TYPE: RNA
<213> ORGANISM: Homo sapiens

<400> SEQUENCE: 90
ggguggggau uuguugcauu ac                                             22

<210> SEQ ID NO 91
<211> LENGTH: 21
<212> TYPE: RNA
<213> ORGANISM: Homo sapiens

<400> SEQUENCE: 91
ggcuagcaac agcgcuuacc u                                              21

<210> SEQ ID NO 92
<211> LENGTH: 24
<212> TYPE: RNA
<213> ORGANISM: Homo sapiens

<400> SEQUENCE: 92
uuuggcaaug guagaacuca cacu                                           24

<210> SEQ ID NO 93
<211> LENGTH: 23
<212> TYPE: RNA
<213> ORGANISM: Homo sapiens

<400> SEQUENCE: 93
aggaccugcg ggacaagauu cuu                                            23

<210> SEQ ID NO 94
<211> LENGTH: 22
<212> TYPE: RNA
<213> ORGANISM: Homo sapiens

<400> SEQUENCE: 94
agaauugugg cuggacaucu gu                                             22

<210> SEQ ID NO 95
<211> LENGTH: 19
<212> TYPE: RNA
<213> ORGANISM: Homo sapiens

<400> SEQUENCE: 95
auggauaagg cuuuggcuu                                                 19
```

```
<210> SEQ ID NO 96
<211> LENGTH: 22
<212> TYPE: RNA
<213> ORGANISM: Homo sapiens

<400> SEQUENCE: 96 ugugcacuc gaugaccacu gu                                              22

<210> SEQ ID NO 97
<211> LENGTH: 21
<212> TYPE: RNA
<213> ORGANISM: Homo sapiens

<400> SEQUENCE: 97
gcgacccacu cuugguuucc a                                              21

<210> SEQ ID NO 98
<211> LENGTH: 22
<212> TYPE: RNA
<213> ORGANISM: Homo sapiens

<400> SEQUENCE: 98
ugcaacuuac cugagucauu ga                                             22

<210> SEQ ID NO 99
<211> LENGTH: 18
<212> TYPE: RNA
<213> ORGANISM: Homo sapiens

<400> SEQUENCE: 99
uccagugccc uccucucc                                                  18

<210> SEQ ID NO 100
<211> LENGTH: 17
<212> TYPE: RNA
<213> ORGANISM: Homo sapiens

<400> SEQUENCE: 100 guggggaga ggcuguc                                                    17

<210> SEQ ID NO 101
<211> LENGTH: 21
<212> TYPE: RNA
<213> ORGANISM: Homo sapiens

<400> SEQUENCE: 101
cggcggggac ggcgauuggu c                                              21

<210> SEQ ID NO 102
<211> LENGTH: 21
<212> TYPE: RNA
<213> ORGANISM: Homo sapiens

<400> SEQUENCE: 102
gcuaguccug acucagccag u                                              21

<210> SEQ ID NO 103
<211> LENGTH: 24
<212> TYPE: RNA
<213> ORGANISM: Homo sapiens

<400> SEQUENCE: 103
uugcagcugc cugggaguga cuuc                                           24
```

```
<210> SEQ ID NO 104
<211> LENGTH: 23
<212> TYPE: RNA
<213> ORGANISM: Homo sapiens

<400> SEQUENCE: 104
uuuggcacua gcacauuuuu gcu                                              23

<210> SEQ ID NO 105
<211> LENGTH: 19
<212> TYPE: RNA
<213> ORGANISM: Homo sapiens

<400> SEQUENCE: 105
aagcagcugc cucugaggc                                                   19

<210> SEQ ID NO 106
<211> LENGTH: 22
<212> TYPE: RNA
<213> ORGANISM: Homo sapiens

<400> SEQUENCE: 106
aucauagagg aaaauccaug uu                                               22

<210> SEQ ID NO 107
<211> LENGTH: 26
<212> TYPE: RNA
<213> ORGANISM: Homo sapiens

<400> SEQUENCE: 107
gaugaugaug gcagcaaauu cugaaa                                           26

<210> SEQ ID NO 108
<211> LENGTH: 23
<212> TYPE: RNA
<213> ORGANISM: Homo sapiens

<400> SEQUENCE: 108
cccaguguuu agacuaucug uuc                                              23

<210> SEQ ID NO 109
<211> LENGTH: 21
<212> TYPE: RNA
<213> ORGANISM: Homo sapiens

<400> SEQUENCE: 109
gugcauugua guugcauugc a                                                21

<210> SEQ ID NO 110
<211> LENGTH: 22
<212> TYPE: RNA
<213> ORGANISM: Homo sapiens

<400> SEQUENCE: 110
accuggcaua caauguagau uu                                               22

<210> SEQ ID NO 111
<211> LENGTH: 24
<212> TYPE: RNA
<213> ORGANISM: Homo sapiens

<400> SEQUENCE: 111
ccagacagaa uucuaugcac uuuc                                             24
```

```
<210> SEQ ID NO 112
<211> LENGTH: 22
<212> TYPE: RNA
<213> ORGANISM: Homo sapiens

<400> SEQUENCE: 112
ugggucuuug cgggcgagau ga                                              22

<210> SEQ ID NO 113
<211> LENGTH: 22
<212> TYPE: RNA
<213> ORGANISM: Homo sapiens

<400> SEQUENCE: 113
ucaccagccc uguguucccu ag                                              22

<210> SEQ ID NO 114
<211> LENGTH: 22
<212> TYPE: RNA
<213> ORGANISM: Homo sapiens

<400> SEQUENCE: 114
cgggguuuug agggcgagau ga                                              22

<210> SEQ ID NO 115
<211> LENGTH: 19
<212> TYPE: RNA
<213> ORGANISM: Homo sapiens

<400> SEQUENCE: 115
gugucugcuu ccuguggga                                                  19

<210> SEQ ID NO 116
<211> LENGTH: 22
<212> TYPE: RNA
<213> ORGANISM: Homo sapiens

<400> SEQUENCE: 116
aaucaugugc agugccaaua ug                                              22

<210> SEQ ID NO 117
<211> LENGTH: 21
<212> TYPE: RNA
<213> ORGANISM: Homo sapiens

<400> SEQUENCE: 117
aggcggagac uugggcaauu g                                               21

<210> SEQ ID NO 118
<211> LENGTH: 21
<212> TYPE: RNA
<213> ORGANISM: Homo sapiens

<400> SEQUENCE: 118
uggguuuacg uugggagaac u                                               21

<210> SEQ ID NO 119
<211> LENGTH: 22
<212> TYPE: RNA
<213> ORGANISM: Homo sapiens

<400> SEQUENCE: 119
```
gaaguuguuc gugguggauu cg                                              22

<210> SEQ ID NO 120
<211> LENGTH: 22
<212> TYPE: RNA
<213> ORGANISM: Homo sapiens

<400> SEQUENCE: 120
ugguugacca uagaacaugc gc                                              22

<210> SEQ ID NO 121
<211> LENGTH: 23
<212> TYPE: RNA
<213> ORGANISM: Homo sapiens

<400> SEQUENCE: 121
ugaggggcag agagcgagac uuu                                             23

<210> SEQ ID NO 122
<211> LENGTH: 21
<212> TYPE: RNA
<213> ORGANISM: Homo sapiens

<400> SEQUENCE: 122
ccuguugaag uguaaucccc a                                               21

<210> SEQ ID NO 123
<211> LENGTH: 18
<212> TYPE: RNA
<213> ORGANISM: Homo sapiens

<400> SEQUENCE: 123
cgggcguggu ggugggggg                                                  18

<210> SEQ ID NO 124
<211> LENGTH: 21
<212> TYPE: RNA
<213> ORGANISM: Homo sapiens

<400> SEQUENCE: 124
ugucuugcag gccgucaugc a                                               21

<210> SEQ ID NO 125
<211> LENGTH: 23
<212> TYPE: RNA
<213> ORGANISM: Homo sapiens

<400> SEQUENCE: 125
agcagcauug uacagggcua uga                                             23

<210> SEQ ID NO 126
<211> LENGTH: 22
<212> TYPE: RNA
<213> ORGANISM: Homo sapiens

<400> SEQUENCE: 126
agggacggga cgcggugcag ug                                              22

<210> SEQ ID NO 127
<211> LENGTH: 20
<212> TYPE: RNA
<213> ORGANISM: Homo sapiens

<400> SEQUENCE: 127

```
ccauggaucu ccaggugggu                                              20

<210> SEQ ID NO 128
<211> LENGTH: 23
<212> TYPE: RNA
<213> ORGANISM: Homo sapiens

<400> SEQUENCE: 128
uggaguccag gaaucugcau uuu                                          23

<210> SEQ ID NO 129
<211> LENGTH: 23
<212> TYPE: RNA
<213> ORGANISM: Homo sapiens

<400> SEQUENCE: 129
uuauugcuua agaauacgcg uag                                          23

<210> SEQ ID NO 130
<211> LENGTH: 22
<212> TYPE: RNA
<213> ORGANISM: Homo sapiens

<400> SEQUENCE: 130
ucacaaguca ggcucuuggg ac                                           22

<210> SEQ ID NO 131
<211> LENGTH: 21
<212> TYPE: RNA
<213> ORGANISM: Homo sapiens

<400> SEQUENCE: 131
aaacuacuga aaaucaaaga u                                            21

<210> SEQ ID NO 132
<211> LENGTH: 22
<212> TYPE: RNA
<213> ORGANISM: Homo sapiens

<400> SEQUENCE: 132
ugcuaugcca acauauugcc au                                           22

<210> SEQ ID NO 133
<211> LENGTH: 22
<212> TYPE: RNA
<213> ORGANISM: Homo sapiens

<400> SEQUENCE: 133
uauugcacuc gucccggccu cc                                           22

<210> SEQ ID NO 134
<211> LENGTH: 23
<212> TYPE: RNA
<213> ORGANISM: Homo sapiens

<400> SEQUENCE: 134
cuaauaguau cuaccacaau aaa                                          23

<210> SEQ ID NO 135
<211> LENGTH: 23
<212> TYPE: RNA
<213> ORGANISM: Homo sapiens
```

<400> SEQUENCE: 135
cacccggcug ugugcacaug ugc                                       23

<210> SEQ ID NO 136
<211> LENGTH: 20
<212> TYPE: RNA
<213> ORGANISM: Homo sapiens

<400> SEQUENCE: 136
gugcauugcu guugcauugc                                           20

<210> SEQ ID NO 137
<211> LENGTH: 22
<212> TYPE: RNA
<213> ORGANISM: Homo sapiens

<400> SEQUENCE: 137
ucucugggcc ugugucuuag gc                                        22

<210> SEQ ID NO 138
<211> LENGTH: 20
<212> TYPE: RNA
<213> ORGANISM: Homo sapiens

<400> SEQUENCE: 138
agagguauag ggcaugggaa                                           20

<210> SEQ ID NO 139
<211> LENGTH: 23
<212> TYPE: RNA
<213> ORGANISM: Homo sapiens

<400> SEQUENCE: 139
ugcaccaugg uugucugagc aug                                       23

<210> SEQ ID NO 140
<211> LENGTH: 22
<212> TYPE: RNA
<213> ORGANISM: Homo sapiens

<400> SEQUENCE: 140
uauagggauu ggagccgugg cg                                        22

<210> SEQ ID NO 141
<211> LENGTH: 22
<212> TYPE: RNA
<213> ORGANISM: Homo sapiens

<400> SEQUENCE: 141
ggagaaauua uccuuggugu gu                                        22

<210> SEQ ID NO 142
<211> LENGTH: 21
<212> TYPE: RNA
<213> ORGANISM: Homo sapiens

<400> SEQUENCE: 142
cucccacaug caggguuugc a                                         21

<210> SEQ ID NO 143
<211> LENGTH: 21
<212> TYPE: RNA
<213> ORGANISM: Homo sapiens

```
<400> SEQUENCE: 143
uggcagggag gcugggaggg g                                        21

<210> SEQ ID NO 144
<211> LENGTH: 23
<212> TYPE: RNA
<213> ORGANISM: Homo sapiens

<400> SEQUENCE: 144
aacauucauu guugucggug ggu                                      23

<210> SEQ ID NO 145
<211> LENGTH: 22
<212> TYPE: RNA
<213> ORGANISM: Homo sapiens

<400> SEQUENCE: 145
acuguaguau gggcacuucc ag                                       22

<210> SEQ ID NO 146
<211> LENGTH: 22
<212> TYPE: RNA
<213> ORGANISM: Homo sapiens

<400> SEQUENCE: 146
accacugacc guugacugua cc                                       22

<210> SEQ ID NO 147
<211> LENGTH: 22
<212> TYPE: RNA
<213> ORGANISM: Homo sapiens

<400> SEQUENCE: 147
caaagaauuc uccuuuuggg cu                                       22

<210> SEQ ID NO 148
<211> LENGTH: 23
<212> TYPE: RNA
<213> ORGANISM: Homo sapiens

<400> SEQUENCE: 148
aaugacacga ucacucccgu uga                                      23

<210> SEQ ID NO 149
<211> LENGTH: 22
<212> TYPE: RNA
<213> ORGANISM: Homo sapiens

<400> SEQUENCE: 149 agugggaac ccuuccauga gg                                        22

<210> SEQ ID NO 150
<211> LENGTH: 20
<212> TYPE: RNA
<213> ORGANISM: Homo sapiens

<400> SEQUENCE: 150
ugagcccugu ccucccgcag                                          20

<210> SEQ ID NO 151
<211> LENGTH: 21
<212> TYPE: RNA
```

```
<213> ORGANISM: Homo sapiens

<400> SEQUENCE: 151
agaccuggcc cagaccucag c                                              21

<210> SEQ ID NO 152
<211> LENGTH: 20
<212> TYPE: RNA
<213> ORGANISM: Homo sapiens

<400> SEQUENCE: 152
uaaggcacgc ggugaaugcc                                                20

<210> SEQ ID NO 153
<211> LENGTH: 22
<212> TYPE: RNA
<213> ORGANISM: Homo sapiens

<400> SEQUENCE: 153
ccaaaacugc aguuacuuuu gc                                             22

<210> SEQ ID NO 154
<211> LENGTH: 22
<212> TYPE: RNA
<213> ORGANISM: Homo sapiens

<400> SEQUENCE: 154
ggagacgcgg cccguuugga gu                                             22

<210> SEQ ID NO 155
<211> LENGTH: 23
<212> TYPE: RNA
<213> ORGANISM: Homo sapiens

<400> SEQUENCE: 155
uaaauuucac cuuucugaga agg                                            23

<210> SEQ ID NO 156
<211> LENGTH: 23
<212> TYPE: RNA
<213> ORGANISM: Homo sapiens

<400> SEQUENCE: 156
agguugggau cgguugcaau gcu                                            23

<210> SEQ ID NO 157
<211> LENGTH: 21
<212> TYPE: RNA
<213> ORGANISM: Homo sapiens

<400> SEQUENCE: 157
aaaacgguga gauuuuguuu u                                              21

<210> SEQ ID NO 158
<211> LENGTH: 18
<212> TYPE: RNA
<213> ORGANISM: Homo sapiens

<400> SEQUENCE: 158
acguuggcuc ugguggug                                                  18

<210> SEQ ID NO 159
<211> LENGTH: 22
```

```
<212> TYPE: RNA
<213> ORGANISM: Homo sapiens

<400> SEQUENCE: 159
ugcccuaaau gccccuucug gc                                              22

<210> SEQ ID NO 160
<211> LENGTH: 22
<212> TYPE: RNA
<213> ORGANISM: Homo sapiens

<400> SEQUENCE: 160
uuaugguuug ccugggacug ag                                              22

<210> SEQ ID NO 161
<211> LENGTH: 22
<212> TYPE: RNA
<213> ORGANISM: Homo sapiens

<400> SEQUENCE: 161
ugauauguuu gauauauuag gu                                              22

<210> SEQ ID NO 162
<211> LENGTH: 23
<212> TYPE: RNA
<213> ORGANISM: Homo sapiens

<400> SEQUENCE: 162
cagugcaaua guauugucaa agc                                             23

<210> SEQ ID NO 163
<211> LENGTH: 22
<212> TYPE: RNA
<213> ORGANISM: Homo sapiens

<400> SEQUENCE: 163
gaaagcgcuu cccuuugcug ga                                              22

<210> SEQ ID NO 164
<211> LENGTH: 21
<212> TYPE: RNA
<213> ORGANISM: Homo sapiens

<400> SEQUENCE: 164
cugaccuaug aauugacagc c                                               21

<210> SEQ ID NO 165
<211> LENGTH: 22
<212> TYPE: RNA
<213> ORGANISM: Homo sapiens

<400> SEQUENCE: 165
aagcugccag uugaagaacu gu                                              22

<210> SEQ ID NO 166
<211> LENGTH: 22
<212> TYPE: RNA
<213> ORGANISM: Homo sapiens

<400> SEQUENCE: 166
auaaagcuag auaaccgaaa gu                                              22

<210> SEQ ID NO 167
```

```
<211> LENGTH: 22
<212> TYPE: RNA
<213> ORGANISM: Homo sapiens

<400> SEQUENCE: 167
aucgugcauc cuuuuagagu gu                                              22

<210> SEQ ID NO 168
<211> LENGTH: 17
<212> TYPE: RNA
<213> ORGANISM: Homo sapiens

<400> SEQUENCE: 168
uaauugcuuc cauguuu                                                    17

<210> SEQ ID NO 169
<211> LENGTH: 22
<212> TYPE: RNA
<213> ORGANISM: Homo sapiens

<400> SEQUENCE: 169
ugagaccucu ngguucugag cu                                              22

<210> SEQ ID NO 170
<211> LENGTH: 26
<212> TYPE: RNA
<213> ORGANISM: Homo sapiens

<400> SEQUENCE: 170
gugagggcau gcaggccugg augggg                                          26

<210> SEQ ID NO 171
<211> LENGTH: 23
<212> TYPE: RNA
<213> ORGANISM: Homo sapiens

<400> SEQUENCE: 171
aacauucauu gcugucggug ggu                                             23

<210> SEQ ID NO 172
<211> LENGTH: 22
<212> TYPE: RNA
<213> ORGANISM: Homo sapiens

<400> SEQUENCE: 172
gggagccagg aaguauugau gu                                              22

<210> SEQ ID NO 173
<211> LENGTH: 22
<212> TYPE: RNA
<213> ORGANISM: Homo sapiens

<400> SEQUENCE: 173
uagcaaaaac ugcaguuacu uu                                              22

<210> SEQ ID NO 174
<211> LENGTH: 22
<212> TYPE: RNA
<213> ORGANISM: Homo sapiens

<400> SEQUENCE: 174
uacugcagac guggcaauca ug                                              22
```

```
<210> SEQ ID NO 175
<211> LENGTH: 21
<212> TYPE: RNA
<213> ORGANISM: Homo sapiens

<400> SEQUENCE: 175
caaagcgcuu cccuuuggag c                                              21

<210> SEQ ID NO 176
<211> LENGTH: 22
<212> TYPE: RNA
<213> ORGANISM: Homo sapiens

<400> SEQUENCE: 176
aggcagcggg guguagugga ua                                             22

<210> SEQ ID NO 177
<211> LENGTH: 23
<212> TYPE: RNA
<213> ORGANISM: Homo sapiens

<400> SEQUENCE: 177
ugucugcccg caugccugcc ucu                                            23

<210> SEQ ID NO 178
<211> LENGTH: 22
<212> TYPE: RNA
<213> ORGANISM: Homo sapiens

<400> SEQUENCE: 178
aagugccucc uuuuagagug uu                                             22

<210> SEQ ID NO 179
<211> LENGTH: 21
<212> TYPE: RNA
<213> ORGANISM: Homo sapiens

<400> SEQUENCE: 179
gcaguccaug ggcauauaca c                                              21

<210> SEQ ID NO 180
<211> LENGTH: 21
<212> TYPE: RNA
<213> ORGANISM: Homo sapiens

<400> SEQUENCE: 180 aggggggaaag uucuauaguc c                                             21

<210> SEQ ID NO 181
<211> LENGTH: 22
<212> TYPE: RNA
<213> ORGANISM: Homo sapiens

<400> SEQUENCE: 181
acagcaggca cagacaggca gu                                             22

<210> SEQ ID NO 182
<211> LENGTH: 22
<212> TYPE: RNA
<213> ORGANISM: Homo sapiens

<400> SEQUENCE: 182
cucaucugca aagaaguaag ug                                             22
```

```
<210> SEQ ID NO 183
<211> LENGTH: 21
<212> TYPE: RNA
<213> ORGANISM: Homo sapiens

<400> SEQUENCE: 183
augaccuaug aauugacaga c                                              21

<210> SEQ ID NO 184
<211> LENGTH: 22
<212> TYPE: RNA
<213> ORGANISM: Homo sapiens

<400> SEQUENCE: 184
acuggacuua gggucagaag gc                                             22

<210> SEQ ID NO 185
<211> LENGTH: 22
<212> TYPE: RNA
<213> ORGANISM: Homo sapiens

<400> SEQUENCE: 185
ucuacaaagg aaagcgcuuu cu                                             22

<210> SEQ ID NO 186
<211> LENGTH: 22
<212> TYPE: RNA
<213> ORGANISM: Homo sapiens

<400> SEQUENCE: 186
gaaggcgcuu cccuuuagag cg                                             22

<210> SEQ ID NO 187
<211> LENGTH: 22
<212> TYPE: RNA
<213> ORGANISM: Homo sapiens

<400> SEQUENCE: 187
ugcaacgaac cugagccacu ga                                             22

<210> SEQ ID NO 188
<211> LENGTH: 22
<212> TYPE: RNA
<213> ORGANISM: Homo sapiens

<400> SEQUENCE: 188
caagcucgcu ucuauggguc ug                                             22

<210> SEQ ID NO 189
<211> LENGTH: 22
<212> TYPE: RNA
<213> ORGANISM: Homo sapiens

<400> SEQUENCE: 189
acugcauuau gagcacuuaa ag                                             22

<210> SEQ ID NO 190
<211> LENGTH: 24
<212> TYPE: RNA
<213> ORGANISM: Homo sapiens

<400> SEQUENCE: 190 acuggggcu uucgggcucu gcgu                                            24
```

<210> SEQ ID NO 191
<211> LENGTH: 23
<212> TYPE: RNA
<213> ORGANISM: Homo sapiens

<400> SEQUENCE: 191
uacugcauca ggaacugauu gga                                               23

<210> SEQ ID NO 192
<211> LENGTH: 24
<212> TYPE: RNA
<213> ORGANISM: Homo sapiens

<400> SEQUENCE: 192
ucccugagac ccuuuaaccu guga                                              24

<210> SEQ ID NO 193
<211> LENGTH: 22
<212> TYPE: RNA
<213> ORGANISM: Homo sapiens

<400> SEQUENCE: 193
uucccuuugu cauccuaugc cu                                                22

<210> SEQ ID NO 194
<211> LENGTH: 22
<212> TYPE: RNA
<213> ORGANISM: Homo sapiens

<400> SEQUENCE: 194
ugccuacuga gcugauauca gu                                                22

<210> SEQ ID NO 195
<211> LENGTH: 21
<212> TYPE: RNA
<213> ORGANISM: Homo sapiens

<400> SEQUENCE: 195
aggcaagaug cuggcauagc u                                                 21

<210> SEQ ID NO 196
<211> LENGTH: 21
<212> TYPE: RNA
<213> ORGANISM: Homo sapiens

<400> SEQUENCE: 196
cuguacaggc cacugccuug c                                                 21

<210> SEQ ID NO 197
<211> LENGTH: 24
<212> TYPE: RNA
<213> ORGANISM: Homo sapiens

<400> SEQUENCE: 197
uggcccugac ugaagaccag cagu                                              24

<210> SEQ ID NO 198
<211> LENGTH: 22
<212> TYPE: RNA
<213> ORGANISM: Homo sapiens

<400> SEQUENCE: 198
caaaccacac ugugguguua ga                                      22

<210> SEQ ID NO 199
<211> LENGTH: 22
<212> TYPE: RNA
<213> ORGANISM: Homo sapiens

<400> SEQUENCE: 199
ucugggcaac aaagugagac cu                                      22

<210> SEQ ID NO 200
<211> LENGTH: 21
<212> TYPE: RNA
<213> ORGANISM: Homo sapiens

<400> SEQUENCE: 200
cacugugucc uuucugcgua g                                       21

<210> SEQ ID NO 201
<211> LENGTH: 23
<212> TYPE: RNA
<213> ORGANISM: Homo sapiens

<400> SEQUENCE: 201
agcagcauug uacagggcua uca                                     23

<210> SEQ ID NO 202
<211> LENGTH: 22
<212> TYPE: RNA
<213> ORGANISM: Homo sapiens

<400> SEQUENCE: 202
cacccguaga accgaccuug cg                                      22

<210> SEQ ID NO 203
<211> LENGTH: 21
<212> TYPE: RNA
<213> ORGANISM: Homo sapiens

<400> SEQUENCE: 203
aucacauugc caggauuuc c                                        21

<210> SEQ ID NO 204
<211> LENGTH: 21
<212> TYPE: RNA
<213> ORGANISM: Homo sapiens

<400> SEQUENCE: 204
ucagugcaug acagaacuug g                                       21

<210> SEQ ID NO 205
<211> LENGTH: 22
<212> TYPE: RNA
<213> ORGANISM: Homo sapiens

<400> SEQUENCE: 205
ucuauacaga cccuggcuuu uc                                      22

<210> SEQ ID NO 206
<211> LENGTH: 22
<212> TYPE: RNA
<213> ORGANISM: Homo sapiens

<400> SEQUENCE: 206

```
cugaagcuca gagggcucug au                                              22

<210> SEQ ID NO 207
<211> LENGTH: 19
<212> TYPE: RNA
<213> ORGANISM: Homo sapiens

<400> SEQUENCE: 207
uggauuuuug gaucaggga                                                  19

<210> SEQ ID NO 208
<211> LENGTH: 22
<212> TYPE: RNA
<213> ORGANISM: Homo sapiens

<400> SEQUENCE: 208
caauuuagug ugugugauau uu                                              22

<210> SEQ ID NO 209
<211> LENGTH: 22
<212> TYPE: RNA
<213> ORGANISM: Homo sapiens

<400> SEQUENCE: 209
ugugcgcagg gagaccucuc cc                                              22

<210> SEQ ID NO 210
<211> LENGTH: 19
<212> TYPE: RNA
<213> ORGANISM: Homo sapiens

<400> SEQUENCE: 210
aggcugcgga auucaggac                                                  19

<210> SEQ ID NO 211
<211> LENGTH: 22
<212> TYPE: RNA
<213> ORGANISM: Homo sapiens

<400> SEQUENCE: 211
cucuagaggg aagcgcuuuc ug                                              22

<210> SEQ ID NO 212
<211> LENGTH: 22
<212> TYPE: RNA
<213> ORGANISM: Homo sapiens

<400> SEQUENCE: 212
aagugcuucc uuuuagaggg uu                                              22

<210> SEQ ID NO 213
<211> LENGTH: 22
<212> TYPE: RNA
<213> ORGANISM: Homo sapiens

<400> SEQUENCE: 213
agagguagua gguugcauag uu                                              22

<210> SEQ ID NO 214
<211> LENGTH: 22
<212> TYPE: RNA
<213> ORGANISM: Homo sapiens
```

<400> SEQUENCE: 214
uucccuuugu cauccuucgc cu                                            22

<210> SEQ ID NO 215
<211> LENGTH: 22
<212> TYPE: RNA
<213> ORGANISM: Homo sapiens

<400> SEQUENCE: 215
uagguuaucc guguugccuu cg                                            22

<210> SEQ ID NO 216
<211> LENGTH: 22
<212> TYPE: RNA
<213> ORGANISM: Homo sapiens

<400> SEQUENCE: 216
aaaaguaauu gcggucuuug gu                                            22

<210> SEQ ID NO 217
<211> LENGTH: 21
<212> TYPE: RNA
<213> ORGANISM: Homo sapiens

<400> SEQUENCE: 217
agagaagaag aucagccugc a                                             21

<210> SEQ ID NO 218
<211> LENGTH: 23
<212> TYPE: RNA
<213> ORGANISM: Homo sapiens

<400> SEQUENCE: 218
ucuuggagua ggucauuggg ugg                                           23

<210> SEQ ID NO 219
<211> LENGTH: 23
<212> TYPE: RNA
<213> ORGANISM: Homo sapiens

<400> SEQUENCE: 219
uaaggugcau cuagugcagu uag                                           23

<210> SEQ ID NO 220
<211> LENGTH: 22
<212> TYPE: RNA
<213> ORGANISM: Homo sapiens

<400> SEQUENCE: 220
uugugucaau augcgaugau gu                                            22

<210> SEQ ID NO 221
<211> LENGTH: 22
<212> TYPE: RNA
<213> ORGANISM: Homo sapiens

<400> SEQUENCE: 221
uauugcacuu gucccggccu gu                                            22

<210> SEQ ID NO 222
<211> LENGTH: 22
<212> TYPE: RNA
<213> ORGANISM: Homo sapiens

```
<400> SEQUENCE: 222
cuuaugcaag auucccuucu ac                                              22

<210> SEQ ID NO 223
<211> LENGTH: 22
<212> TYPE: RNA
<213> ORGANISM: Homo sapiens

<400> SEQUENCE: 223
ucuucucugu uuuggccaug ug                                              22

<210> SEQ ID NO 224
<211> LENGTH: 22
<212> TYPE: RNA
<213> ORGANISM: Homo sapiens

<400> SEQUENCE: 224
acucggcgug gcgucggucg ug                                              22

<210> SEQ ID NO 225
<211> LENGTH: 22
<212> TYPE: RNA
<213> ORGANISM: Homo sapiens

<400> SEQUENCE: 225
cccugugccc ggcccacuuc ug                                              22

<210> SEQ ID NO 226
<211> LENGTH: 22
<212> TYPE: RNA
<213> ORGANISM: Homo sapiens

<400> SEQUENCE: 226
ucguaccgug aguaauaaug cg                                              22

<210> SEQ ID NO 227
<211> LENGTH: 22
<212> TYPE: RNA
<213> ORGANISM: Homo sapiens

<400> SEQUENCE: 227
gugaacgggc gccaucccga gg                                              22

<210> SEQ ID NO 228
<211> LENGTH: 20
<212> TYPE: RNA
<213> ORGANISM: Homo sapiens

<400> SEQUENCE: 228
guagaggaga uggcgcaggg                                                 20

<210> SEQ ID NO 229
<211> LENGTH: 22
<212> TYPE: RNA
<213> ORGANISM: Homo sapiens

<400> SEQUENCE: 229
aagcccuuac cccaaaaagu au                                              22

<210> SEQ ID NO 230
<211> LENGTH: 19
<212> TYPE: RNA
```

```
<213> ORGANISM: Homo sapiens

<400> SEQUENCE: 230
ugagcugcug uaccaaaau                                          19

<210> SEQ ID NO 231
<211> LENGTH: 22
<212> TYPE: RNA
<213> ORGANISM: Homo sapiens

<400> SEQUENCE: 231
acaguagucu gcacauuggu ua                                      22

<210> SEQ ID NO 232
<211> LENGTH: 22
<212> TYPE: RNA
<213> ORGANISM: Homo sapiens

<400> SEQUENCE: 232
auaagacgag caaaaagcuu gu                                      22

<210> SEQ ID NO 233
<211> LENGTH: 22
<212> TYPE: RNA
<213> ORGANISM: Homo sapiens

<400> SEQUENCE: 233
cucuagaggg aagcgcuuuc ug                                      22

<210> SEQ ID NO 234
<211> LENGTH: 17
<212> TYPE: RNA
<213> ORGANISM: Homo sapiens

<400> SEQUENCE: 234
ucauauugcu ucuuucu                                            17

<210> SEQ ID NO 235
<211> LENGTH: 22
<212> TYPE: RNA
<213> ORGANISM: Homo sapiens

<400> SEQUENCE: 235
uugggaucau uuugcaucca ua                                      22

<210> SEQ ID NO 236
<211> LENGTH: 22
<212> TYPE: RNA
<213> ORGANISM: Homo sapiens

<400> SEQUENCE: 236
gcccaaaggu gaauuuuuug gg                                      22

<210> SEQ ID NO 237
<211> LENGTH: 22
<212> TYPE: RNA
<213> ORGANISM: Homo sapiens

<400> SEQUENCE: 237
ccaguggggc ugcuguuauc ug                                      22

<210> SEQ ID NO 238
<211> LENGTH: 22
```

```
<212> TYPE: RNA
<213> ORGANISM: Homo sapiens

<400> SEQUENCE: 238
ucuacagugc acgugucucc ag                                    22

<210> SEQ ID NO 239
<211> LENGTH: 21
<212> TYPE: RNA
<213> ORGANISM: Homo sapiens

<400> SEQUENCE: 239
uguucaugua gauguuuaag c                                     21

<210> SEQ ID NO 240
<211> LENGTH: 23
<212> TYPE: RNA
<213> ORGANISM: Homo sapiens

<400> SEQUENCE: 240
uagcagcggg aacaguucug cag                                   23

<210> SEQ ID NO 241
<211> LENGTH: 22
<212> TYPE: RNA
<213> ORGANISM: Homo sapiens

<400> SEQUENCE: 241
ucagcaaaca uuuauugugu gc                                    22

<210> SEQ ID NO 242
<211> LENGTH: 26
<212> TYPE: RNA
<213> ORGANISM: Homo sapiens

<400> SEQUENCE: 242
aaguaguugg uuuguaugag augguu                                26

<210> SEQ ID NO 243
<211> LENGTH: 22
<212> TYPE: RNA
<213> ORGANISM: Homo sapiens

<400> SEQUENCE: 243
ugagaaccac gucugcucug ag                                    22

<210> SEQ ID NO 244
<211> LENGTH: 21
<212> TYPE: RNA
<213> ORGANISM: Homo sapiens

<400> SEQUENCE: 244
uacugcagac aguggcaauc a                                     21

<210> SEQ ID NO 245
<211> LENGTH: 22
<212> TYPE: RNA
<213> ORGANISM: Homo sapiens

<400> SEQUENCE: 245
cucuagaggg aagcgcuuuc ug                                    22

<210> SEQ ID NO 246
```

```
<211> LENGTH: 22
<212> TYPE: RNA
<213> ORGANISM: Homo sapiens

<400> SEQUENCE: 246
aggggcuggc uuccucugg uc                                              22

<210> SEQ ID NO 247
<211> LENGTH: 21
<212> TYPE: RNA
<213> ORGANISM: Homo sapiens

<400> SEQUENCE: 247
cauuauuacu uuugguacgc g                                              21

<210> SEQ ID NO 248
<211> LENGTH: 22
<212> TYPE: RNA
<213> ORGANISM: Homo sapiens

<400> SEQUENCE: 248
aagugcuguc auagcugagg uc                                             22

<210> SEQ ID NO 249
<211> LENGTH: 21
<212> TYPE: RNA
<213> ORGANISM: Homo sapiens

<400> SEQUENCE: 249
cagcagcaca cugugguuug u                                              21

<210> SEQ ID NO 250
<211> LENGTH: 22
<212> TYPE: RNA
<213> ORGANISM: Homo sapiens

<400> SEQUENCE: 250
acagauucga uucuagggga au                                             22

<210> SEQ ID NO 251
<211> LENGTH: 22
<212> TYPE: RNA
<213> ORGANISM: Homo sapiens

<400> SEQUENCE: 251
uauugcacau uacuaaguug ca                                             22

<210> SEQ ID NO 252
<211> LENGTH: 22
<212> TYPE: RNA
<213> ORGANISM: Homo sapiens

<400> SEQUENCE: 252
aaaaguaauu gugguuuuug cc                                             22

<210> SEQ ID NO 253
<211> LENGTH: 22
<212> TYPE: RNA
<213> ORGANISM: Homo sapiens

<400> SEQUENCE: 253
cugggagagg guuguuuacu cc                                             22
```

```
<210> SEQ ID NO 254
<211> LENGTH: 22
<212> TYPE: RNA
<213> ORGANISM: Homo sapiens

<400> SEQUENCE: 254
cgcaggggcc gggugcucac cg                                              22

<210> SEQ ID NO 255
<211> LENGTH: 23
<212> TYPE: RNA
<213> ORGANISM: Homo sapiens

<400> SEQUENCE: 255
ccucagggcu guagaacagg gcu                                             23

<210> SEQ ID NO 256
<211> LENGTH: 21
<212> TYPE: RNA
<213> ORGANISM: Homo sapiens

<400> SEQUENCE: 256
aggguaagcu gaaccucuga u                                               21

<210> SEQ ID NO 257
<211> LENGTH: 22
<212> TYPE: RNA
<213> ORGANISM: Homo sapiens

<400> SEQUENCE: 257
aaagugcuuc cuuuuagagg gu                                              22

<210> SEQ ID NO 258
<211> LENGTH: 22
<212> TYPE: RNA
<213> ORGANISM: Homo sapiens

<400> SEQUENCE: 258
uagcaccauc ugaaaucggu ua                                              22

<210> SEQ ID NO 259
<211> LENGTH: 23
<212> TYPE: RNA
<213> ORGANISM: Homo sapiens

<400> SEQUENCE: 259
ucaaaugcuc agacuccugu ggu                                             23

<210> SEQ ID NO 260
<211> LENGTH: 22
<212> TYPE: RNA
<213> ORGANISM: Homo sapiens

<400> SEQUENCE: 260
uccgagccug ggucucccuc uu                                              22

<210> SEQ ID NO 261
<211> LENGTH: 22
<212> TYPE: RNA
<213> ORGANISM: Homo sapiens

<400> SEQUENCE: 261
gagugccuuc uuuuggagcg uu                                              22
```

```
<210> SEQ ID NO 262
<211> LENGTH: 25
<212> TYPE: RNA
<213> ORGANISM: Homo sapiens

<400> SEQUENCE: 262
aaaggauucu gcugucgguc ccacu                                         25

<210> SEQ ID NO 263
<211> LENGTH: 23
<212> TYPE: RNA
<213> ORGANISM: Homo sapiens

<400> SEQUENCE: 263
uguaaacauc cuacacucuc agc                                           23

<210> SEQ ID NO 264
<211> LENGTH: 22
<212> TYPE: RNA
<213> ORGANISM: Homo sapiens

<400> SEQUENCE: 264
uucucaagga ggugucguuu au                                            22

<210> SEQ ID NO 265
<211> LENGTH: 22
<212> TYPE: RNA
<213> ORGANISM: Homo sapiens

<400> SEQUENCE: 265
ugccuacuga gcugaaacac ag                                            22

<210> SEQ ID NO 266
<211> LENGTH: 22
<212> TYPE: RNA
<213> ORGANISM: Homo sapiens

<400> SEQUENCE: 266
uuuggucccc uucaaccagc ug                                            22

<210> SEQ ID NO 267
<211> LENGTH: 22
<212> TYPE: RNA
<213> ORGANISM: Homo sapiens

<400> SEQUENCE: 267
uuuaacaugg ggguaccugc ug                                            22

<210> SEQ ID NO 268
<211> LENGTH: 23
<212> TYPE: RNA
<213> ORGANISM: Homo sapiens

<400> SEQUENCE: 268
cccaguguuc agacuaccug uuc                                           23

<210> SEQ ID NO 269
<211> LENGTH: 23
<212> TYPE: RNA
<213> ORGANISM: Homo sapiens

<400> SEQUENCE: 269
aguauguucu uccaggacag aac                                           23
```

```
<210> SEQ ID NO 270
<211> LENGTH: 22
<212> TYPE: RNA
<213> ORGANISM: Homo sapiens

<400> SEQUENCE: 270
uuuucaacuc uaaugggaga ga                                             22

<210> SEQ ID NO 271
<211> LENGTH: 22
<212> TYPE: RNA
<213> ORGANISM: Homo sapiens

<400> SEQUENCE: 271
caucuuccag uacaguguug ga                                             22

<210> SEQ ID NO 272
<211> LENGTH: 22
<212> TYPE: RNA
<213> ORGANISM: Homo sapiens

<400> SEQUENCE: 272
uaugugccuu uggacuacau cg                                             22

<210> SEQ ID NO 273
<211> LENGTH: 24
<212> TYPE: RNA
<213> ORGANISM: Homo sapiens

<400> SEQUENCE: 273 ugggagcug aggcucuggg ggug                                            24

<210> SEQ ID NO 274
<211> LENGTH: 23
<212> TYPE: RNA
<213> ORGANISM: Homo sapiens

<400> SEQUENCE: 274
uacuccagag ggcgucacuc aug                                            23

<210> SEQ ID NO 275
<211> LENGTH: 22
<212> TYPE: RNA
<213> ORGANISM: Homo sapiens

<400> SEQUENCE: 275
ugaaacauac acgggaaacc uc                                             22

<210> SEQ ID NO 276
<211> LENGTH: 20
<212> TYPE: RNA
<213> ORGANISM: Homo sapiens

<400> SEQUENCE: 276
auguauaaau guauacacac                                                20

<210> SEQ ID NO 277
<211> LENGTH: 23
<212> TYPE: RNA
<213> ORGANISM: Homo sapiens

<400> SEQUENCE: 277
```
aggcagugua guuagcugau ugc    23

<210> SEQ ID NO 278
<211> LENGTH: 22
<212> TYPE: RNA
<213> ORGANISM: Homo sapiens

<400> SEQUENCE: 278
aucgggaaug ucguguccgc cc    22

<210> SEQ ID NO 279
<211> LENGTH: 23
<212> TYPE: RNA
<213> ORGANISM: Homo sapiens

<400> SEQUENCE: 279
uccaguacca cgugucaggg cca    23

<210> SEQ ID NO 280
<211> LENGTH: 23
<212> TYPE: RNA
<213> ORGANISM: Homo sapiens

<400> SEQUENCE: 280
uaagugcuuc cauguuuugg uga    23

<210> SEQ ID NO 281
<211> LENGTH: 22
<212> TYPE: RNA
<213> ORGANISM: Homo sapiens

<400> SEQUENCE: 281
cuauacaacc uacugccuuc cc    22

<210> SEQ ID NO 282
<211> LENGTH: 24
<212> TYPE: RNA
<213> ORGANISM: Homo sapiens

<400> SEQUENCE: 282
uucuccaaaa gaaagcacuu ucug    24

<210> SEQ ID NO 283
<211> LENGTH: 22
<212> TYPE: RNA
<213> ORGANISM: Homo sapiens

<400> SEQUENCE: 283
uggaauguaa ggaagugugu gg    22

<210> SEQ ID NO 284
<211> LENGTH: 22
<212> TYPE: RNA
<213> ORGANISM: Homo sapiens

<400> SEQUENCE: 284
gaaaucaagc gugggugaga cc    22

<210> SEQ ID NO 285
<211> LENGTH: 23
<212> TYPE: RNA
<213> ORGANISM: Homo sapiens

<400> SEQUENCE: 285

```
acugcccuaa gugcuccuuc ugg                                        23

<210> SEQ ID NO 286
<211> LENGTH: 23
<212> TYPE: RNA
<213> ORGANISM: Homo sapiens

<400> SEQUENCE: 286
gcaaagcaca cggccugcag aga                                        23

<210> SEQ ID NO 287
<211> LENGTH: 22
<212> TYPE: RNA
<213> ORGANISM: Homo sapiens

<400> SEQUENCE: 287
uggacggaga acugauaagg gu                                         22

<210> SEQ ID NO 288
<211> LENGTH: 22
<212> TYPE: RNA
<213> ORGANISM: Homo sapiens

<400> SEQUENCE: 288
uagcagcaca uaaugguuug ug                                         22

<210> SEQ ID NO 289
<211> LENGTH: 22
<212> TYPE: RNA
<213> ORGANISM: Homo sapiens

<400> SEQUENCE: 289
uacccagagc augcagugug aa                                         22

<210> SEQ ID NO 290
<211> LENGTH: 23
<212> TYPE: RNA
<213> ORGANISM: Homo sapiens

<400> SEQUENCE: 290
uauggcuuuu cauuccuaug uga                                        23

<210> SEQ ID NO 291
<211> LENGTH: 22
<212> TYPE: RNA
<213> ORGANISM: Homo sapiens

<400> SEQUENCE: 291
cucuagaggg aagcgcuuuc ug                                         22

<210> SEQ ID NO 292
<211> LENGTH: 22
<212> TYPE: RNA
<213> ORGANISM: Homo sapiens

<400> SEQUENCE: 292
ccucuagaug gaagcacugu cu                                         22

<210> SEQ ID NO 293
<211> LENGTH: 22
<212> TYPE: RNA
<213> ORGANISM: Homo sapiens
```

<400> SEQUENCE: 293
uggucuagga uuguuggagg ag                                              22

<210> SEQ ID NO 294
<211> LENGTH: 23
<212> TYPE: RNA
<213> ORGANISM: Homo sapiens

<400> SEQUENCE: 294
uaagugcuuc cauguuuuag uag                                             23

<210> SEQ ID NO 295
<211> LENGTH: 22
<212> TYPE: RNA
<213> ORGANISM: Homo sapiens

<400> SEQUENCE: 295
cucuagaggg aagcacuuuc ug                                              22

<210> SEQ ID NO 296
<211> LENGTH: 22
<212> TYPE: RNA
<213> ORGANISM: Homo sapiens

<400> SEQUENCE: 296
cuauacaguc uacugucuuu cc                                              22

<210> SEQ ID NO 297
<211> LENGTH: 22
<212> TYPE: RNA
<213> ORGANISM: Homo sapiens

<400> SEQUENCE: 297
uacccauugc auaucggagu ug                                              22

<210> SEQ ID NO 298
<211> LENGTH: 19
<212> TYPE: RNA
<213> ORGANISM: Homo sapiens

<400> SEQUENCE: 298
aguguggcuu ucuuagagc                                                  19

<210> SEQ ID NO 299
<211> LENGTH: 23
<212> TYPE: RNA
<213> ORGANISM: Homo sapiens

<400> SEQUENCE: 299
cugggaucuc cggggucuug guu                                             23

<210> SEQ ID NO 300
<211> LENGTH: 21
<212> TYPE: RNA
<213> ORGANISM: Homo sapiens

<400> SEQUENCE: 300
auguaugugu gcaugugcau g                                               21

<210> SEQ ID NO 301
<211> LENGTH: 22
<212> TYPE: RNA
<213> ORGANISM: Homo sapiens

```
<400> SEQUENCE: 301
acgcccuucc cccccuucuu ca                                              22

<210> SEQ ID NO 302
<211> LENGTH: 21
<212> TYPE: RNA
<213> ORGANISM: Homo sapiens

<400> SEQUENCE: 302
agggagggac gggggcugug c                                               21

<210> SEQ ID NO 303
<211> LENGTH: 23
<212> TYPE: RNA
<213> ORGANISM: Homo sapiens

<400> SEQUENCE: 303
ugaguaccgc caugucuguu ggg                                             23

<210> SEQ ID NO 304
<211> LENGTH: 22
<212> TYPE: RNA
<213> ORGANISM: Homo sapiens

<400> SEQUENCE: 304
gugacaucac auauacggca gc                                              22

<210> SEQ ID NO 305
<211> LENGTH: 22
<212> TYPE: RNA
<213> ORGANISM: Homo sapiens

<400> SEQUENCE: 305
ccuauucuug guuacuugca cg                                              22

<210> SEQ ID NO 306
<211> LENGTH: 19
<212> TYPE: RNA
<213> ORGANISM: Homo sapiens

<400> SEQUENCE: 306
gggcgccugu gaucccaac                                                  19

<210> SEQ ID NO 307
<211> LENGTH: 22
<212> TYPE: RNA
<213> ORGANISM: Homo sapiens

<400> SEQUENCE: 307
cugcgcaagc uacugccuug cu                                              22

<210> SEQ ID NO 308
<211> LENGTH: 21
<212> TYPE: RNA
<213> ORGANISM: Homo sapiens

<400> SEQUENCE: 308
aauaauacau gguugaucuu u                                               21

<210> SEQ ID NO 309
<211> LENGTH: 23
<212> TYPE: RNA
```

<213> ORGANISM: Homo sapiens

<400> SEQUENCE: 309
ucucuggagg gaagcacuuu cug                                        23

<210> SEQ ID NO 310
<211> LENGTH: 22
<212> TYPE: RNA
<213> ORGANISM: Homo sapiens

<400> SEQUENCE: 310
auauuaccau uagcucaucu uu                                         22

<210> SEQ ID NO 311
<211> LENGTH: 22
<212> TYPE: RNA
<213> ORGANISM: Homo sapiens

<400> SEQUENCE: 311
aucacacaaa ggcaacuuuu gu                                         22

<210> SEQ ID NO 312
<211> LENGTH: 22
<212> TYPE: RNA
<213> ORGANISM: Homo sapiens

<400> SEQUENCE: 312
ucagugcacu acagaacuuu gu                                         22

<210> SEQ ID NO 313
<211> LENGTH: 22
<212> TYPE: RNA
<213> ORGANISM: Homo sapiens

<400> SEQUENCE: 313
aguuuugcag guuugcauuu ca                                         22

<210> SEQ ID NO 314
<211> LENGTH: 22
<212> TYPE: RNA
<213> ORGANISM: Homo sapiens

<400> SEQUENCE: 314
aacccguaga uccgaucuug ug                                         22

<210> SEQ ID NO 315
<211> LENGTH: 23
<212> TYPE: RNA
<213> ORGANISM: Homo sapiens

<400> SEQUENCE: 315
uaauacugcc ggguaaugau gga                                        23

<210> SEQ ID NO 316
<211> LENGTH: 21
<212> TYPE: RNA
<213> ORGANISM: Homo sapiens

<400> SEQUENCE: 316
aauggcgcca cuaggguugu g                                          21

<210> SEQ ID NO 317
<211> LENGTH: 23

```
<212> TYPE: RNA
<213> ORGANISM: Homo sapiens

<400> SEQUENCE: 317
agcucggucu gaggccccuc agu                                          23

<210> SEQ ID NO 318
<211> LENGTH: 24
<212> TYPE: RNA
<213> ORGANISM: Homo sapiens

<400> SEQUENCE: 318
agcagaagca gggagguucu ccca                                         24

<210> SEQ ID NO 319
<211> LENGTH: 22
<212> TYPE: RNA
<213> ORGANISM: Homo sapiens

<400> SEQUENCE: 319
gaauguugcu cggugaaccc cu                                           22

<210> SEQ ID NO 320
<211> LENGTH: 22
<212> TYPE: RNA
<213> ORGANISM: Homo sapiens

<400> SEQUENCE: 320
aguuuugcau aguugcacua ca                                           22

<210> SEQ ID NO 321
<211> LENGTH: 22
<212> TYPE: RNA
<213> ORGANISM: Homo sapiens

<400> SEQUENCE: 321
cuuggcaccu agcaagcacu ca                                           22

<210> SEQ ID NO 322
<211> LENGTH: 21
<212> TYPE: RNA
<213> ORGANISM: Homo sapiens

<400> SEQUENCE: 322
uaguagaccg uauagcguac g                                            21

<210> SEQ ID NO 323
<211> LENGTH: 22
<212> TYPE: RNA
<213> ORGANISM: Homo sapiens

<400> SEQUENCE: 323
uuuagagacg gggucuugcu cu                                           22

<210> SEQ ID NO 324
<211> LENGTH: 23
<212> TYPE: RNA
<213> ORGANISM: Homo sapiens

<400> SEQUENCE: 324
cucuugaggg aagcacuuuc ugu                                          23

<210> SEQ ID NO 325
```

```
<211> LENGTH: 22
<212> TYPE: RNA
<213> ORGANISM: Homo sapiens

<400> SEQUENCE: 325
caaaaaccac aguuucuuuu gc                                              22

<210> SEQ ID NO 326
<211> LENGTH: 22
<212> TYPE: RNA
<213> ORGANISM: Homo sapiens

<400> SEQUENCE: 326
caaagcgcuc cccuuuagag gu                                              22

<210> SEQ ID NO 327
<211> LENGTH: 21
<212> TYPE: RNA
<213> ORGANISM: Homo sapiens

<400> SEQUENCE: 327
uggaggagaa ggaaggugau g                                               21

<210> SEQ ID NO 328
<211> LENGTH: 21
<212> TYPE: RNA
<213> ORGANISM: Homo sapiens

<400> SEQUENCE: 328
ucacagugaa ccggucucuu u                                               21

<210> SEQ ID NO 329
<211> LENGTH: 22
<212> TYPE: RNA
<213> ORGANISM: Homo sapiens

<400> SEQUENCE: 329
ugauugguac gucugugggu ag                                              22

<210> SEQ ID NO 330
<211> LENGTH: 22
<212> TYPE: RNA
<213> ORGANISM: Homo sapiens

<400> SEQUENCE: 330
acuccagccc cacagccuca gc                                              22

<210> SEQ ID NO 331
<211> LENGTH: 22
<212> TYPE: RNA
<213> ORGANISM: Homo sapiens

<400> SEQUENCE: 331
cgaaaacagc aauuaccuuu gc                                              22

<210> SEQ ID NO 332
<211> LENGTH: 22
<212> TYPE: RNA
<213> ORGANISM: Homo sapiens

<400> SEQUENCE: 332
uaguacugug cauaucaucu au                                              22
```

```
<210> SEQ ID NO 333
<211> LENGTH: 22
<212> TYPE: RNA
<213> ORGANISM: Homo sapiens

<400> SEQUENCE: 333
acugauuucu uuggguguuc ag                                          22

<210> SEQ ID NO 334
<211> LENGTH: 22
<212> TYPE: RNA
<213> ORGANISM: Homo sapiens

<400> SEQUENCE: 334
cgaaucauua uuugcugcuc ua                                          22

<210> SEQ ID NO 335
<211> LENGTH: 20
<212> TYPE: RNA
<213> ORGANISM: Homo sapiens

<400> SEQUENCE: 335
aggguguuuc ucucaucucu                                             20

<210> SEQ ID NO 336
<211> LENGTH: 23
<212> TYPE: RNA
<213> ORGANISM: Homo sapiens

<400> SEQUENCE: 336
acuuacagac aagagccuug cuc                                         23

<210> SEQ ID NO 337
<211> LENGTH: 22
<212> TYPE: RNA
<213> ORGANISM: Homo sapiens

<400> SEQUENCE: 337
aaaaguaauu gcggauuuug cc                                          22

<210> SEQ ID NO 338
<211> LENGTH: 22
<212> TYPE: RNA
<213> ORGANISM: Homo sapiens

<400> SEQUENCE: 338
cucuagaggg aagcacuuuc ug                                          22

<210> SEQ ID NO 339
<211> LENGTH: 21
<212> TYPE: RNA
<213> ORGANISM: Homo sapiens

<400> SEQUENCE: 339
gugccagcug caguggggga g                                           21

<210> SEQ ID NO 340
<211> LENGTH: 22
<212> TYPE: RNA
<213> ORGANISM: Homo sapiens

<400> SEQUENCE: 340
cuccugacuc cagguccugu gu                                          22
```

```
<210> SEQ ID NO 341
<211> LENGTH: 22
<212> TYPE: RNA
<213> ORGANISM: Homo sapiens

<400> SEQUENCE: 341
gugagucucu aagaaaagag ga                                           22

<210> SEQ ID NO 342
<211> LENGTH: 21
<212> TYPE: RNA
<213> ORGANISM: Homo sapiens

<400> SEQUENCE: 342
ucgaggagcu cacagucuag u                                            21

<210> SEQ ID NO 343
<211> LENGTH: 22
<212> TYPE: RNA
<213> ORGANISM: Homo sapiens

<400> SEQUENCE: 343
uggugggcac agaaucugga cu                                           22

<210> SEQ ID NO 344
<211> LENGTH: 21
<212> TYPE: RNA
<213> ORGANISM: Homo sapiens

<400> SEQUENCE: 344
uccgguucuc agggcuccac c                                            21

<210> SEQ ID NO 345
<211> LENGTH: 25
<212> TYPE: RNA
<213> ORGANISM: Homo sapiens

<400> SEQUENCE: 345
gcugggcagg gcuucugagc uccuu                                        25

<210> SEQ ID NO 346
<211> LENGTH: 21
<212> TYPE: RNA
<213> ORGANISM: Homo sapiens

<400> SEQUENCE: 346
ccgucgccgc cacccgagcc g                                            21

<210> SEQ ID NO 347
<211> LENGTH: 23
<212> TYPE: RNA
<213> ORGANISM: Homo sapiens

<400> SEQUENCE: 347
uuaaugcuaa ucgugauagg ggu                                          23

<210> SEQ ID NO 348
<211> LENGTH: 21
<212> TYPE: RNA
<213> ORGANISM: Homo sapiens

<400> SEQUENCE: 348
auccuugcua ucugggugcu a                                            21
```

```
<210> SEQ ID NO 349
<211> LENGTH: 20
<212> TYPE: RNA
<213> ORGANISM: Homo sapiens

<400> SEQUENCE: 349
aaaguagcug uaccauuugc                                                    20

<210> SEQ ID NO 350
<211> LENGTH: 22
<212> TYPE: RNA
<213> ORGANISM: Homo sapiens

<400> SEQUENCE: 350
aucaugaugg gcuccucggu gu                                                 22

<210> SEQ ID NO 351
<211> LENGTH: 21
<212> TYPE: RNA
<213> ORGANISM: Homo sapiens

<400> SEQUENCE: 351
gaagugugcc guggugugguc u                                                 21

<210> SEQ ID NO 352
<211> LENGTH: 22
<212> TYPE: RNA
<213> ORGANISM: Homo sapiens

<400> SEQUENCE: 352
cagugguuuu acccuauggu ag                                                 22

<210> SEQ ID NO 353
<211> LENGTH: 21
<212> TYPE: RNA
<213> ORGANISM: Homo sapiens

<400> SEQUENCE: 353
uggacugccc ugaucuggag a                                                  21

<210> SEQ ID NO 354
<211> LENGTH: 22
<212> TYPE: RNA
<213> ORGANISM: Homo sapiens

<400> SEQUENCE: 354
cuuucagucg gauguuugca gc                                                 22

<210> SEQ ID NO 355
<211> LENGTH: 20
<212> TYPE: RNA
<213> ORGANISM: Homo sapiens

<400> SEQUENCE: 355
cuuccucguc ugucugcccc                                                    20

<210> SEQ ID NO 356
<211> LENGTH: 22
<212> TYPE: RNA
<213> ORGANISM: Homo sapiens

<400> SEQUENCE: 356
```
ucaguaaaug uuuauuagau ga                                                 22

<210> SEQ ID NO 357
<211> LENGTH: 22
<212> TYPE: RNA
<213> ORGANISM: Homo sapiens

<400> SEQUENCE: 357
gucauacacg gcucuccucu cu                                                 22

<210> SEQ ID NO 358
<211> LENGTH: 21
<212> TYPE: RNA
<213> ORGANISM: Homo sapiens

<400> SEQUENCE: 358
cuauacaauc uacugucuuu c                                                  21

<210> SEQ ID NO 359
<211> LENGTH: 23
<212> TYPE: RNA
<213> ORGANISM: Homo sapiens

<400> SEQUENCE: 359
aucaacagac auuaauuggg cgc                                                23

<210> SEQ ID NO 360
<211> LENGTH: 22
<212> TYPE: RNA
<213> ORGANISM: Homo sapiens

<400> SEQUENCE: 360
uggaguguga caauguguu ug                                                  22

<210> SEQ ID NO 361
<211> LENGTH: 22
<212> TYPE: RNA
<213> ORGANISM: Homo sapiens

<400> SEQUENCE: 361
cugcccuggc ccgagggacc ga                                                 22

<210> SEQ ID NO 362
<211> LENGTH: 22
<212> TYPE: RNA
<213> ORGANISM: Homo sapiens

<400> SEQUENCE: 362
uguaaacauc cucgacugga ag                                                 22

<210> SEQ ID NO 363
<211> LENGTH: 22
<212> TYPE: RNA
<213> ORGANISM: Homo sapiens

<400> SEQUENCE: 363 uuugguccccc uucaaccagc ua                                                22

<210> SEQ ID NO 364
<211> LENGTH: 22
<212> TYPE: RNA
<213> ORGANISM: Homo sapiens

<400> SEQUENCE: 364

-continued uuagggcccu ggcuccaucu cc                                        22

<210> SEQ ID NO 365
<211> LENGTH: 20
<212> TYPE: RNA
<213> ORGANISM: Homo sapiens

<400> SEQUENCE: 365
gugucugggc ggacagcugc                                           20

<210> SEQ ID NO 366
<211> LENGTH: 22
<212> TYPE: RNA
<213> ORGANISM: Homo sapiens

<400> SEQUENCE: 366
agaguugagu cuggacgucc cg                                        22

<210> SEQ ID NO 367
<211> LENGTH: 22
<212> TYPE: RNA
<213> ORGANISM: Homo sapiens

<400> SEQUENCE: 367
cuggacugag ccgugcuacu gg                                        22

<210> SEQ ID NO 368
<211> LENGTH: 20
<212> TYPE: RNA
<213> ORGANISM: Homo sapiens

<400> SEQUENCE: 368
guccgcucgg cgguggccca                                           20

<210> SEQ ID NO 369
<211> LENGTH: 22
<212> TYPE: RNA
<213> ORGANISM: Homo sapiens

<400> SEQUENCE: 369
auauaauaca accugcuaag ug                                        22

<210> SEQ ID NO 370
<211> LENGTH: 20
<212> TYPE: RNA
<213> ORGANISM: Homo sapiens

<400> SEQUENCE: 370
ccucugggcc cuuccuccag                                           20

<210> SEQ ID NO 371
<211> LENGTH: 22
<212> TYPE: RNA
<213> ORGANISM: Homo sapiens

<400> SEQUENCE: 371
ccuauucuug auuacuuguu uc                                        22

<210> SEQ ID NO 372
<211> LENGTH: 21
<212> TYPE: RNA
<213> ORGANISM: Homo sapiens

```
<400> SEQUENCE: 372
aaagugcuuc cuuuuagagg g                                        21

<210> SEQ ID NO 373
<211> LENGTH: 21
<212> TYPE: RNA
<213> ORGANISM: Homo sapiens

<400> SEQUENCE: 373
aauauaacac agauggccug u                                        21

<210> SEQ ID NO 374
<211> LENGTH: 19
<212> TYPE: RNA
<213> ORGANISM: Homo sapiens

<400> SEQUENCE: 374
gugaggacuc gggaggugg                                           19

<210> SEQ ID NO 375
<211> LENGTH: 21
<212> TYPE: RNA
<213> ORGANISM: Homo sapiens

<400> SEQUENCE: 375
uuuccauagg ugaugaguca c                                        21

<210> SEQ ID NO 376
<211> LENGTH: 22
<212> TYPE: RNA
<213> ORGANISM: Homo sapiens

<400> SEQUENCE: 376
augguacccu ggcauacuga gu                                       22

<210> SEQ ID NO 377
<211> LENGTH: 22
<212> TYPE: RNA
<213> ORGANISM: Homo sapiens

<400> SEQUENCE: 377
uggguggucu ggagauuugu gc                                       22

<210> SEQ ID NO 378
<211> LENGTH: 23
<212> TYPE: RNA
<213> ORGANISM: Homo sapiens

<400> SEQUENCE: 378
caguaacaaa gauucauccu ugu                                      23

<210> SEQ ID NO 379
<211> LENGTH: 22
<212> TYPE: RNA
<213> ORGANISM: Homo sapiens

<400> SEQUENCE: 379
aagaugugga aaauuggaa uc                                        22

<210> SEQ ID NO 380
<211> LENGTH: 23
<212> TYPE: RNA
<213> ORGANISM: Homo sapiens
```

```
<400> SEQUENCE: 380
cacucagccu ugagggcacu uuc                                              23

<210> SEQ ID NO 381
<211> LENGTH: 22
<212> TYPE: RNA
<213> ORGANISM: Homo sapiens

<400> SEQUENCE: 381
uucacaagga ggugucauuu au                                               22

<210> SEQ ID NO 382
<211> LENGTH: 19
<212> TYPE: RNA
<213> ORGANISM: Homo sapiens

<400> SEQUENCE: 382
ugucucugcu gggguuucu                                                   19

<210> SEQ ID NO 383
<211> LENGTH: 22
<212> TYPE: RNA
<213> ORGANISM: Homo sapiens

<400> SEQUENCE: 383
uccauuacac uacccugccu cu                                               22

<210> SEQ ID NO 384
<211> LENGTH: 22
<212> TYPE: RNA
<213> ORGANISM: Homo sapiens

<400> SEQUENCE: 384
agaggcuggc cgugaugaau uc                                               22

<210> SEQ ID NO 385
<211> LENGTH: 21
<212> TYPE: RNA
<213> ORGANISM: Homo sapiens

<400> SEQUENCE: 385
gugggcgggg gcaggugugu g                                                21

<210> SEQ ID NO 386
<211> LENGTH: 22
<212> TYPE: RNA
<213> ORGANISM: Homo sapiens

<400> SEQUENCE: 386
cucuagaggg aagcgcuuuc ug                                               22

<210> SEQ ID NO 387
<211> LENGTH: 22
<212> TYPE: RNA
<213> ORGANISM: Homo sapiens

<400> SEQUENCE: 387
auucugcauu uuuagcaagu uc                                               22

<210> SEQ ID NO 388
<211> LENGTH: 21
<212> TYPE: RNA
```

<213> ORGANISM: Homo sapiens

<400> SEQUENCE: 388
aacaggugac ugguuagaca a                                             21

<210> SEQ ID NO 389
<211> LENGTH: 22
<212> TYPE: RNA
<213> ORGANISM: Homo sapiens

<400> SEQUENCE: 389
cggcaacaag aaacugccug ag                                            22

<210> SEQ ID NO 390
<211> LENGTH: 19
<212> TYPE: RNA
<213> ORGANISM: Homo sapiens

<400> SEQUENCE: 390
aaaagcuggg uugagagga                                                19

<210> SEQ ID NO 391
<211> LENGTH: 22
<212> TYPE: RNA
<213> ORGANISM: Homo sapiens

<400> SEQUENCE: 391
uggagagaaa ggcaguuccu ga                                            22

<210> SEQ ID NO 392
<211> LENGTH: 23
<212> TYPE: RNA
<213> ORGANISM: Homo sapiens

<400> SEQUENCE: 392
cagugcaaug auauugucaa agc                                           23

<210> SEQ ID NO 393
<211> LENGTH: 22
<212> TYPE: RNA
<213> ORGANISM: Homo sapiens

<400> SEQUENCE: 393
aaaaguaauu gugguuuugg cc                                            22

<210> SEQ ID NO 394
<211> LENGTH: 22
<212> TYPE: RNA
<213> ORGANISM: Homo sapiens

<400> SEQUENCE: 394
cuauacggcc uccuagcuuu cc                                            22

<210> SEQ ID NO 395
<211> LENGTH: 22
<212> TYPE: RNA
<213> ORGANISM: Homo sapiens

<400> SEQUENCE: 395
uucuggaauu cugugugagg ga                                            22

<210> SEQ ID NO 396
<211> LENGTH: 22

```
<212> TYPE: RNA
<213> ORGANISM: Homo sapiens

<400> SEQUENCE: 396
agacccuggu cugcacucua uc                                         22

<210> SEQ ID NO 397
<211> LENGTH: 23
<212> TYPE: RNA
<213> ORGANISM: Homo sapiens

<400> SEQUENCE: 397
gacacgggcg acagcugcgg ccc                                        23

<210> SEQ ID NO 398
<211> LENGTH: 23
<212> TYPE: RNA
<213> ORGANISM: Homo sapiens

<400> SEQUENCE: 398
ccuaguaggu guccaguaag ugu                                        23

<210> SEQ ID NO 399
<211> LENGTH: 22
<212> TYPE: RNA
<213> ORGANISM: Homo sapiens

<400> SEQUENCE: 399
uaacacuguc ugguaacgau gu                                         22

<210> SEQ ID NO 400
<211> LENGTH: 22
<212> TYPE: RNA
<213> ORGANISM: Homo sapiens

<400> SEQUENCE: 400
aacccguaga uccgaacuug ug                                         22

<210> SEQ ID NO 401
<211> LENGTH: 22
<212> TYPE: RNA
<213> ORGANISM: Homo sapiens

<400> SEQUENCE: 401
uuccuaugca uauacuucuu ug                                         22

<210> SEQ ID NO 402
<211> LENGTH: 22
<212> TYPE: RNA
<213> ORGANISM: Homo sapiens

<400> SEQUENCE: 402
gaggguuggg uggaggcucu cc                                         22

<210> SEQ ID NO 403
<211> LENGTH: 22
<212> TYPE: RNA
<213> ORGANISM: Homo sapiens

<400> SEQUENCE: 403
aucuggaggu aagaagcacu uu                                         22

<210> SEQ ID NO 404
```

-continued

```
<211> LENGTH: 22
<212> TYPE: RNA
<213> ORGANISM: Homo sapiens

<400> SEQUENCE: 404
cacacacugc aauuacuuuu gc                                              22

<210> SEQ ID NO 405
<211> LENGTH: 21
<212> TYPE: RNA
<213> ORGANISM: Homo sapiens

<400> SEQUENCE: 405
uaccacaggg uagaaccacg g                                               21

<210> SEQ ID NO 406
<211> LENGTH: 22
<212> TYPE: RNA
<213> ORGANISM: Homo sapiens

<400> SEQUENCE: 406
aacgcacuuc ccuuuagagu gu                                              22

<210> SEQ ID NO 407
<211> LENGTH: 22
<212> TYPE: RNA
<213> ORGANISM: Homo sapiens

<400> SEQUENCE: 407
ccaauauugg cugugcugcu cc                                              22

<210> SEQ ID NO 408
<211> LENGTH: 22
<212> TYPE: RNA
<213> ORGANISM: Homo sapiens

<400> SEQUENCE: 408
ucccugagac ccuaacuugu ga                                              22

<210> SEQ ID NO 409
<211> LENGTH: 22
<212> TYPE: RNA
<213> ORGANISM: Homo sapiens

<400> SEQUENCE: 409
aaucacuaac cacacggcca gg                                              22

<210> SEQ ID NO 410
<211> LENGTH: 21
<212> TYPE: RNA
<213> ORGANISM: Homo sapiens

<400> SEQUENCE: 410
ucguggccug gucuccauua u                                               21

<210> SEQ ID NO 411
<211> LENGTH: 21
<212> TYPE: RNA
<213> ORGANISM: Homo sapiens

<400> SEQUENCE: 411
gaacggcuuc auacaggagu u                                               21
```

```
<210> SEQ ID NO 412
<211> LENGTH: 23
<212> TYPE: RNA
<213> ORGANISM: Homo sapiens

<400> SEQUENCE: 412
ugauuguagc cuuuuggagu aga                                              23

<210> SEQ ID NO 413
<211> LENGTH: 22
<212> TYPE: RNA
<213> ORGANISM: Homo sapiens

<400> SEQUENCE: 413
acggauguuu gagcaugugc ua                                               22

<210> SEQ ID NO 414
<211> LENGTH: 22
<212> TYPE: RNA
<213> ORGANISM: Homo sapiens

<400> SEQUENCE: 414
gcccgcgugu ggagccaggu gu                                               22

<210> SEQ ID NO 415
<211> LENGTH: 21
<212> TYPE: RNA
<213> ORGANISM: Homo sapiens

<400> SEQUENCE: 415
cuuuuugcgg ucugggcuug c                                                21

<210> SEQ ID NO 416
<211> LENGTH: 21
<212> TYPE: RNA
<213> ORGANISM: Homo sapiens

<400> SEQUENCE: 416
ugcaggacca agaugagccc u                                                21

<210> SEQ ID NO 417
<211> LENGTH: 22
<212> TYPE: RNA
<213> ORGANISM: Homo sapiens

<400> SEQUENCE: 417
gagcuuauuc auaaaagugc ag                                               22

<210> SEQ ID NO 418
<211> LENGTH: 22
<212> TYPE: RNA
<213> ORGANISM: Homo sapiens

<400> SEQUENCE: 418
caguuaucac agugcugaug cu                                               22

<210> SEQ ID NO 419
<211> LENGTH: 21
<212> TYPE: RNA
<213> ORGANISM: Homo sapiens

<400> SEQUENCE: 419
cacaagguau ugguauuacc u                                                21
```

```
<210> SEQ ID NO 420
<211> LENGTH: 23
<212> TYPE: RNA
<213> ORGANISM: Homo sapiens

<400> SEQUENCE: 420
ugagugugug ugugugagug ugu                                         23

<210> SEQ ID NO 421
<211> LENGTH: 22
<212> TYPE: RNA
<213> ORGANISM: Homo sapiens

<400> SEQUENCE: 421
ucucccaacc cuuguaccag ug                                          22

<210> SEQ ID NO 422
<211> LENGTH: 23
<212> TYPE: RNA
<213> ORGANISM: Homo sapiens

<400> SEQUENCE: 422
uucucgagga aagaagcacu uuc                                         23

<210> SEQ ID NO 423
<211> LENGTH: 22
<212> TYPE: RNA
<213> ORGANISM: Homo sapiens

<400> SEQUENCE: 423
agagguugcc cuuggugaau uc                                          22

<210> SEQ ID NO 424
<211> LENGTH: 22
<212> TYPE: RNA
<213> ORGANISM: Homo sapiens

<400> SEQUENCE: 424
uauacaaggg caagcucucu gu                                          22

<210> SEQ ID NO 425
<211> LENGTH: 21
<212> TYPE: RNA
<213> ORGANISM: Homo sapiens

<400> SEQUENCE: 425
uucaaguaau ucaggauagg u                                           21

<210> SEQ ID NO 426
<211> LENGTH: 24
<212> TYPE: RNA
<213> ORGANISM: Homo sapiens

<400> SEQUENCE: 426
agccuggaag cuggagccug cagu                                        24

<210> SEQ ID NO 427
<211> LENGTH: 22
<212> TYPE: RNA
<213> ORGANISM: Homo sapiens

<400> SEQUENCE: 427
uagguaguuu ccuguuguug gg                                          22
```

```
<210> SEQ ID NO 428
<211> LENGTH: 22
<212> TYPE: RNA
<213> ORGANISM: Homo sapiens

<400> SEQUENCE: 428
aaacaaacau ggugcacuuc uu                                            22

<210> SEQ ID NO 429
<211> LENGTH: 21
<212> TYPE: RNA
<213> ORGANISM: Homo sapiens

<400> SEQUENCE: 429
ugauugucca aacgcaauuc u                                             21

<210> SEQ ID NO 430
<211> LENGTH: 22
<212> TYPE: RNA
<213> ORGANISM: Homo sapiens

<400> SEQUENCE: 430
cuuucaguca gauguuugcu gc                                            22

<210> SEQ ID NO 431
<211> LENGTH: 22
<212> TYPE: RNA
<213> ORGANISM: Homo sapiens

<400> SEQUENCE: 431
acggguuagg cucuugggag cu                                            22

<210> SEQ ID NO 432
<211> LENGTH: 22
<212> TYPE: RNA
<213> ORGANISM: Homo sapiens

<400> SEQUENCE: 432
cacgcucaug cacacaccca ca                                            22

<210> SEQ ID NO 433
<211> LENGTH: 22
<212> TYPE: RNA
<213> ORGANISM: Homo sapiens

<400> SEQUENCE: 433
aaaaugguuc ccuuuagagu gu                                            22

<210> SEQ ID NO 434
<211> LENGTH: 22
<212> TYPE: RNA
<213> ORGANISM: Homo sapiens

<400> SEQUENCE: 434
uggauuucuu ugugaaucac ca                                            22

<210> SEQ ID NO 435
<211> LENGTH: 22
<212> TYPE: RNA
<213> ORGANISM: Homo sapiens

<400> SEQUENCE: 435
```

```
cucaguagcc aguguagauc cu                                            22

<210> SEQ ID NO 436
<211> LENGTH: 22
<212> TYPE: RNA
<213> ORGANISM: Homo sapiens

<400> SEQUENCE: 436
cacuggcucc uuucugggua ga                                            22

<210> SEQ ID NO 437
<211> LENGTH: 22
<212> TYPE: RNA
<213> ORGANISM: Homo sapiens

<400> SEQUENCE: 437
gcuauuucac gacaccaggg uu                                            22

<210> SEQ ID NO 438
<211> LENGTH: 21
<212> TYPE: RNA
<213> ORGANISM: Homo sapiens

<400> SEQUENCE: 438
uaaaguaaau augcaccaaa a                                             21

<210> SEQ ID NO 439
<211> LENGTH: 19
<212> TYPE: RNA
<213> ORGANISM: Homo sapiens

<400> SEQUENCE: 439
gagccaguug gacaggagc                                                19

<210> SEQ ID NO 440
<211> LENGTH: 23
<212> TYPE: RNA
<213> ORGANISM: Homo sapiens

<400> SEQUENCE: 440
caagucuuau uugagcaccu guu                                           23

<210> SEQ ID NO 441
<211> LENGTH: 22
<212> TYPE: RNA
<213> ORGANISM: Homo sapiens

<400> SEQUENCE: 441
aacuggauca auuauaggag ug                                            22

<210> SEQ ID NO 442
<211> LENGTH: 23
<212> TYPE: RNA
<213> ORGANISM: Homo sapiens

<400> SEQUENCE: 442
ucaagagcaa uaacgaaaaa ugu                                           23

<210> SEQ ID NO 443
<211> LENGTH: 22
<212> TYPE: RNA
<213> ORGANISM: Homo sapiens

<400> SEQUENCE: 443
```
uauacaaggg cagacucucu cu          22

<210> SEQ ID NO 444
<211> LENGTH: 22
<212> TYPE: RNA
<213> ORGANISM: Homo sapiens

<400> SEQUENCE: 444
gugaaauguu uaggaccacu ag          22

<210> SEQ ID NO 445
<211> LENGTH: 22
<212> TYPE: RNA
<213> ORGANISM: Homo sapiens

<400> SEQUENCE: 445
gguccagagg ggagauaggu uc          22

<210> SEQ ID NO 446
<211> LENGTH: 22
<212> TYPE: RNA
<213> ORGANISM: Homo sapiens

<400> SEQUENCE: 446
uucauucggc uguccagaug ua          22

<210> SEQ ID NO 447
<211> LENGTH: 18
<212> TYPE: RNA
<213> ORGANISM: Homo sapiens

<400> SEQUENCE: 447
ugcuuccuuu cagagggu               18

<210> SEQ ID NO 448
<211> LENGTH: 22
<212> TYPE: RNA
<213> ORGANISM: Homo sapiens

<400> SEQUENCE: 448
uaacagucua cagccauggu cg          22

<210> SEQ ID NO 449
<211> LENGTH: 22
<212> TYPE: RNA
<213> ORGANISM: Homo sapiens

<400> SEQUENCE: 449
cuuaucagau uguauuguaa uu          22

<210> SEQ ID NO 450
<211> LENGTH: 19
<212> TYPE: RNA
<213> ORGANISM: Homo sapiens

<400> SEQUENCE: 450
gaugaugcug cugaugcug              19

<210> SEQ ID NO 451
<211> LENGTH: 22
<212> TYPE: RNA
<213> ORGANISM: Homo sapiens

```
<400> SEQUENCE: 451
cuuucagucg gauguuuaca gc                                          22

<210> SEQ ID NO 452
<211> LENGTH: 22
<212> TYPE: RNA
<213> ORGANISM: Homo sapiens

<400> SEQUENCE: 452
cguguucaca gcggaccuug au                                          22

<210> SEQ ID NO 453
<211> LENGTH: 20
<212> TYPE: RNA
<213> ORGANISM: Homo sapiens

<400> SEQUENCE: 453
auuccuagaa auuguucaua                                             20

<210> SEQ ID NO 454
<211> LENGTH: 22
<212> TYPE: RNA
<213> ORGANISM: Homo sapiens

<400> SEQUENCE: 454
agucauugga ggguuugagc ag                                          22

<210> SEQ ID NO 455
<211> LENGTH: 20
<212> TYPE: RNA
<213> ORGANISM: Homo sapiens

<400> SEQUENCE: 455
auggagauag auauagaaau                                             20

<210> SEQ ID NO 456
<211> LENGTH: 22
<212> TYPE: RNA
<213> ORGANISM: Homo sapiens

<400> SEQUENCE: 456
cuccuacaua uuagcauuaa ca                                          22

<210> SEQ ID NO 457
<211> LENGTH: 22
<212> TYPE: RNA
<213> ORGANISM: Homo sapiens

<400> SEQUENCE: 457
auaauacaug guuaaccucu uu                                          22

<210> SEQ ID NO 458
<211> LENGTH: 22
<212> TYPE: RNA
<213> ORGANISM: Homo sapiens

<400> SEQUENCE: 458
uauguaacac gguccacuaa cc                                          22

<210> SEQ ID NO 459
<211> LENGTH: 22
<212> TYPE: RNA
<213> ORGANISM: Homo sapiens
```

-continued

```
<400> SEQUENCE: 459
cugcaaugua agcacuucuu ac                                              22

<210> SEQ ID NO 460
<211> LENGTH: 22
<212> TYPE: RNA
<213> ORGANISM: Homo sapiens

<400> SEQUENCE: 460
caaaacuggc aauuacuuuu gc                                              22

<210> SEQ ID NO 461
<211> LENGTH: 21
<212> TYPE: RNA
<213> ORGANISM: Homo sapiens

<400> SEQUENCE: 461
ugagaugaag cacuguagcu c                                               21

<210> SEQ ID NO 462
<211> LENGTH: 22
<212> TYPE: RNA
<213> ORGANISM: Homo sapiens

<400> SEQUENCE: 462
aaagugcuuc ucuuuggugg gu                                              22

<210> SEQ ID NO 463
<211> LENGTH: 21
<212> TYPE: RNA
<213> ORGANISM: Homo sapiens

<400> SEQUENCE: 463
uagcagcaca gaaauauugg c                                               21

<210> SEQ ID NO 464
<211> LENGTH: 20
<212> TYPE: RNA
<213> ORGANISM: Homo sapiens

<400> SEQUENCE: 464
ucguuugccu uuucugcuu                                                  20

<210> SEQ ID NO 465
<211> LENGTH: 22
<212> TYPE: RNA
<213> ORGANISM: Homo sapiens

<400> SEQUENCE: 465
uaguaccagu accuuguguu ca                                              22

<210> SEQ ID NO 466
<211> LENGTH: 22
<212> TYPE: RNA
<213> ORGANISM: Homo sapiens

<400> SEQUENCE: 466
ucagugcauc acagaacuuu gu                                              22

<210> SEQ ID NO 467
<211> LENGTH: 22
<212> TYPE: RNA
```

```
<213> ORGANISM: Homo sapiens

<400> SEQUENCE: 467
uugcauaugu aggauguccc au                                             22

<210> SEQ ID NO 468
<211> LENGTH: 22
<212> TYPE: RNA
<213> ORGANISM: Homo sapiens

<400> SEQUENCE: 468
cuagguaugg ucccagggau cc                                             22

<210> SEQ ID NO 469
<211> LENGTH: 22
<212> TYPE: RNA
<213> ORGANISM: Homo sapiens

<400> SEQUENCE: 469
aaagugcauc cuuuuagagg uu                                             22

<210> SEQ ID NO 470
<211> LENGTH: 25
<212> TYPE: RNA
<213> ORGANISM: Homo sapiens

<400> SEQUENCE: 470
ugggaacggg uuccggcaga cgcug                                          25

<210> SEQ ID NO 471
<211> LENGTH: 22
<212> TYPE: RNA
<213> ORGANISM: Homo sapiens

<400> SEQUENCE: 471
ccucugaaau ucaguucuuc ag                                             22

<210> SEQ ID NO 472
<211> LENGTH: 22
<212> TYPE: RNA
<213> ORGANISM: Homo sapiens

<400> SEQUENCE: 472
ugaccgauuu cuccuggugu uc                                             22

<210> SEQ ID NO 473
<211> LENGTH: 22
<212> TYPE: RNA
<213> ORGANISM: Homo sapiens

<400> SEQUENCE: 473
ucggccugac cacccacccc ac                                             22

<210> SEQ ID NO 474
<211> LENGTH: 22
<212> TYPE: RNA
<213> ORGANISM: Homo sapiens

<400> SEQUENCE: 474
cucggcgcgg ggcgcgggcu cc                                             22

<210> SEQ ID NO 475
<211> LENGTH: 22
```

```
<212> TYPE: RNA
<213> ORGANISM: Homo sapiens

<400> SEQUENCE: 475
aaaccguuac cauuacugag uu                                        22

<210> SEQ ID NO 476
<211> LENGTH: 21
<212> TYPE: RNA
<213> ORGANISM: Homo sapiens

<400> SEQUENCE: 476
ugauauguuu gauauugggu u                                         21

<210> SEQ ID NO 477
<211> LENGTH: 17
<212> TYPE: RNA
<213> ORGANISM: Homo sapiens

<400> SEQUENCE: 477
uaagugcuuc caugcuu                                              17

<210> SEQ ID NO 478
<211> LENGTH: 22
<212> TYPE: RNA
<213> ORGANISM: Homo sapiens

<400> SEQUENCE: 478
guucucccaa cguaagccca gc                                        22

<210> SEQ ID NO 479
<211> LENGTH: 22
<212> TYPE: RNA
<213> ORGANISM: Homo sapiens

<400> SEQUENCE: 479
aaaaguauuu gcggguuuug uc                                        22

<210> SEQ ID NO 480
<211> LENGTH: 25
<212> TYPE: RNA
<213> ORGANISM: Homo sapiens

<400> SEQUENCE: 480
agggaucgcg ggcggguggc ggccu                                     25

<210> SEQ ID NO 481
<211> LENGTH: 21
<212> TYPE: RNA
<213> ORGANISM: Homo sapiens

<400> SEQUENCE: 481
ugacaacuau ggaugagcuc u                                         21

<210> SEQ ID NO 482
<211> LENGTH: 22
<212> TYPE: RNA
<213> ORGANISM: Homo sapiens

<400> SEQUENCE: 482
caucaucguc ucaaaugagu cu                                        22

<210> SEQ ID NO 483
```

```
<211> LENGTH: 21
<212> TYPE: RNA
<213> ORGANISM: Homo sapiens

<400> SEQUENCE: 483
gcaggaacuu gugagucucc u                                              21

<210> SEQ ID NO 484
<211> LENGTH: 22
<212> TYPE: RNA
<213> ORGANISM: Homo sapiens

<400> SEQUENCE: 484
ugugagguug gcauuguugu cu                                             22

<210> SEQ ID NO 485
<211> LENGTH: 22
<212> TYPE: RNA
<213> ORGANISM: Homo sapiens

<400> SEQUENCE: 485
ugcggggcua gggcuaacag ca                                             22

<210> SEQ ID NO 486
<211> LENGTH: 22
<212> TYPE: RNA
<213> ORGANISM: Homo sapiens

<400> SEQUENCE: 486
acugcugagc uagcacuucc cg                                             22

<210> SEQ ID NO 487
<211> LENGTH: 22
<212> TYPE: RNA
<213> ORGANISM: Homo sapiens

<400> SEQUENCE: 487
ucaggcucag uccccucccg au                                             22

<210> SEQ ID NO 488
<211> LENGTH: 17
<212> TYPE: RNA
<213> ORGANISM: Homo sapiens

<400> SEQUENCE: 488
ucgccuccuc cucuccc                                                   17

<210> SEQ ID NO 489
<211> LENGTH: 21
<212> TYPE: RNA
<213> ORGANISM: Homo sapiens

<400> SEQUENCE: 489
gcgacccaua cuugguuuca g                                              21

<210> SEQ ID NO 490
<211> LENGTH: 22
<212> TYPE: RNA
<213> ORGANISM: Homo sapiens

<400> SEQUENCE: 490
uggcucaguu cagcaggaac ag                                             22
```

```
<210> SEQ ID NO 491
<211> LENGTH: 22
<212> TYPE: RNA
<213> ORGANISM: Homo sapiens

<400> SEQUENCE: 491
ccucccacac ccaaggcuug ca                                              22

<210> SEQ ID NO 492
<211> LENGTH: 22
<212> TYPE: RNA
<213> ORGANISM: Homo sapiens

<400> SEQUENCE: 492
aaaagcuggg uugagagggc ga                                              22

<210> SEQ ID NO 493
<211> LENGTH: 22
<212> TYPE: RNA
<213> ORGANISM: Homo sapiens

<400> SEQUENCE: 493
ugagguagua gguugugugg uu                                              22

<210> SEQ ID NO 494
<211> LENGTH: 17
<212> TYPE: RNA
<213> ORGANISM: Homo sapiens

<400> SEQUENCE: 494
ucccuguucg ggcgcca                                                    17

<210> SEQ ID NO 495
<211> LENGTH: 22
<212> TYPE: RNA
<213> ORGANISM: Homo sapiens

<400> SEQUENCE: 495
aaaagcuggg uugagagggc aa                                              22

<210> SEQ ID NO 496
<211> LENGTH: 22
<212> TYPE: RNA
<213> ORGANISM: Homo sapiens

<400> SEQUENCE: 496
cugugcgugu gacagcggcu ga                                              22

<210> SEQ ID NO 497
<211> LENGTH: 22
<212> TYPE: RNA
<213> ORGANISM: Homo sapiens

<400> SEQUENCE: 497
uagcagcaca ucaugguuua ca                                              22

<210> SEQ ID NO 498
<211> LENGTH: 23
<212> TYPE: RNA
<213> ORGANISM: Homo sapiens

<400> SEQUENCE: 498
caacggaauc ccaaaagcag cug                                             23
```

```
<210> SEQ ID NO 499
<211> LENGTH: 20
<212> TYPE: RNA
<213> ORGANISM: Homo sapiens

<400> SEQUENCE: 499
aaaagcuggg uugagagggu                                              20

<210> SEQ ID NO 500
<211> LENGTH: 22
<212> TYPE: RNA
<213> ORGANISM: Homo sapiens

<400> SEQUENCE: 500
gacugacacc ucuuugggug aa                                           22

<210> SEQ ID NO 501
<211> LENGTH: 22
<212> TYPE: RNA
<213> ORGANISM: Homo sapiens

<400> SEQUENCE: 501
uagcagcacg uaaauauugg cg                                           22

<210> SEQ ID NO 502
<211> LENGTH: 21
<212> TYPE: RNA
<213> ORGANISM: Homo sapiens

<400> SEQUENCE: 502
uuggccacaa ugggguagaa c                                            21

<210> SEQ ID NO 503
<211> LENGTH: 21
<212> TYPE: RNA
<213> ORGANISM: Homo sapiens

<400> SEQUENCE: 503
gccccugggc cuauccuaga a                                            21

<210> SEQ ID NO 504
<211> LENGTH: 22
<212> TYPE: RNA
<213> ORGANISM: Homo sapiens

<400> SEQUENCE: 504
acucaaaacc cuucagugac uu                                           22

<210> SEQ ID NO 505
<211> LENGTH: 21
<212> TYPE: RNA
<213> ORGANISM: Homo sapiens

<400> SEQUENCE: 505
acuggacuug gagucagaag g                                            21

<210> SEQ ID NO 506
<211> LENGTH: 22
<212> TYPE: RNA
<213> ORGANISM: Homo sapiens

<400> SEQUENCE: 506
uucaaguaau ccaggauagg cu                                           22
```

```
<210> SEQ ID NO 507
<211> LENGTH: 23
<212> TYPE: RNA
<213> ORGANISM: Homo sapiens

<400> SEQUENCE: 507
ucuuugguua ucuagcugua uga                                          23

<210> SEQ ID NO 508
<211> LENGTH: 22
<212> TYPE: RNA
<213> ORGANISM: Homo sapiens

<400> SEQUENCE: 508
aaugcaccug ggcaaggauu ca                                           22

<210> SEQ ID NO 509
<211> LENGTH: 22
<212> TYPE: RNA
<213> ORGANISM: Homo sapiens

<400> SEQUENCE: 509
ugucaguuug ucaaauaccc ca                                           22

<210> SEQ ID NO 510
<211> LENGTH: 22
<212> TYPE: RNA
<213> ORGANISM: Homo sapiens

<400> SEQUENCE: 510
cauugcacuu gucucggucu ga                                           22

<210> SEQ ID NO 511
<211> LENGTH: 23
<212> TYPE: RNA
<213> ORGANISM: Homo sapiens

<400> SEQUENCE: 511
ccugcagcga cuugauggcu ucc                                          23

<210> SEQ ID NO 512
<211> LENGTH: 22
<212> TYPE: RNA
<213> ORGANISM: Homo sapiens

<400> SEQUENCE: 512
caacaaauca cagucugcca ua                                           22

<210> SEQ ID NO 513
<211> LENGTH: 24
<212> TYPE: RNA
<213> ORGANISM: Homo sapiens

<400> SEQUENCE: 513
aaagacauag gauagaguca ccuc                                         24

<210> SEQ ID NO 514
<211> LENGTH: 20
<212> TYPE: RNA
<213> ORGANISM: Homo sapiens

<400> SEQUENCE: 514
```
acugccccag gugcugcugg                                           20

<210> SEQ ID NO 515
<211> LENGTH: 23
<212> TYPE: RNA
<213> ORGANISM: Homo sapiens

<400> SEQUENCE: 515
ucccuguccu ccaggagcuc acg                                       23

<210> SEQ ID NO 516
<211> LENGTH: 22
<212> TYPE: RNA
<213> ORGANISM: Homo sapiens

<400> SEQUENCE: 516
ugagguagua gguuguaugg uu                                        22

<210> SEQ ID NO 517
<211> LENGTH: 22
<212> TYPE: RNA
<213> ORGANISM: Homo sapiens

<400> SEQUENCE: 517
ugcccugugg acucaguucu gg                                        22

<210> SEQ ID NO 518
<211> LENGTH: 22
<212> TYPE: RNA
<213> ORGANISM: Homo sapiens

<400> SEQUENCE: 518
ggcuacaaca caggacccgg gc                                        22

<210> SEQ ID NO 519
<211> LENGTH: 22
<212> TYPE: RNA
<213> ORGANISM: Homo sapiens

<400> SEQUENCE: 519
uguaaacauc cccgacugga ag                                        22

<210> SEQ ID NO 520
<211> LENGTH: 22
<212> TYPE: RNA
<213> ORGANISM: Homo sapiens

<400> SEQUENCE: 520
aggcggggcg ccgcgggacc gc                                        22

<210> SEQ ID NO 521
<211> LENGTH: 22
<212> TYPE: RNA
<213> ORGANISM: Homo sapiens

<400> SEQUENCE: 521
augcugacau auuuacuaga gg                                        22

<210> SEQ ID NO 522
<211> LENGTH: 18
<212> TYPE: RNA
<213> ORGANISM: Homo sapiens

<400> SEQUENCE: 522

```
ucagcuggcc cucauuuc                                          18

<210> SEQ ID NO 523
<211> LENGTH: 20
<212> TYPE: RNA
<213> ORGANISM: Homo sapiens

<400> SEQUENCE: 523
agaccauggg uucucauugu                                        20

<210> SEQ ID NO 524
<211> LENGTH: 23
<212> TYPE: RNA
<213> ORGANISM: Homo sapiens

<400> SEQUENCE: 524
uaagugcuuc cauguuugag ugu                                    23

<210> SEQ ID NO 525
<211> LENGTH: 22
<212> TYPE: RNA
<213> ORGANISM: Homo sapiens

<400> SEQUENCE: 525
cagugccucg gcagugcagc cc                                     22

<210> SEQ ID NO 526
<211> LENGTH: 22
<212> TYPE: RNA
<213> ORGANISM: Homo sapiens

<400> SEQUENCE: 526
ugagccccug ugccgccccc ag                                     22

<210> SEQ ID NO 527
<211> LENGTH: 22
<212> TYPE: RNA
<213> ORGANISM: Homo sapiens

<400> SEQUENCE: 527
auucuaauuu cuccacgucu uu                                     22

<210> SEQ ID NO 528
<211> LENGTH: 22
<212> TYPE: RNA
<213> ORGANISM: Homo sapiens

<400> SEQUENCE: 528
cuccuauaug augccuuucu uc                                     22

<210> SEQ ID NO 529
<211> LENGTH: 27
<212> TYPE: RNA
<213> ORGANISM: Homo sapiens

<400> SEQUENCE: 529
cacuguaggu gauggugaga gugggca                                27

<210> SEQ ID NO 530
<211> LENGTH: 21
<212> TYPE: RNA
<213> ORGANISM: Homo sapiens
```

```
<400> SEQUENCE: 530
uuuugcaccu uuuggaguga a                                        21

<210> SEQ ID NO 531
<211> LENGTH: 20
<212> TYPE: RNA
<213> ORGANISM: Homo sapiens

<400> SEQUENCE: 531
cggcucuggg ucugugggga                                          20

<210> SEQ ID NO 532
<211> LENGTH: 17
<212> TYPE: RNA
<213> ORGANISM: Homo sapiens

<400> SEQUENCE: 532
ucccaccgcu gccaccc                                             17

<210> SEQ ID NO 533
<211> LENGTH: 23
<212> TYPE: RNA
<213> ORGANISM: Homo sapiens

<400> SEQUENCE: 533
ucucacacag aaaucgcacc cgu                                      23

<210> SEQ ID NO 534
<211> LENGTH: 22
<212> TYPE: RNA
<213> ORGANISM: Homo sapiens

<400> SEQUENCE: 534
caaagugccu cccuuuagag ug                                       22

<210> SEQ ID NO 535
<211> LENGTH: 23
<212> TYPE: RNA
<213> ORGANISM: Homo sapiens

<400> SEQUENCE: 535
gcgaggaccc cucggggucu gac                                      23

<210> SEQ ID NO 536
<211> LENGTH: 21
<212> TYPE: RNA
<213> ORGANISM: Homo sapiens

<400> SEQUENCE: 536
guggcugcac ucacuuccuu c                                        21

<210> SEQ ID NO 537
<211> LENGTH: 21
<212> TYPE: RNA
<213> ORGANISM: Homo sapiens

<400> SEQUENCE: 537
cauaaaguag aaagcacuac u                                        21

<210> SEQ ID NO 538
<211> LENGTH: 23
<212> TYPE: RNA
<213> ORGANISM: Homo sapiens
```

```
<400> SEQUENCE: 538
agguuacccg agcaacuuug cau                                       23

<210> SEQ ID NO 539
<211> LENGTH: 22
<212> TYPE: RNA
<213> ORGANISM: Homo sapiens

<400> SEQUENCE: 539
caugccuuga guguaggacc gu                                        22

<210> SEQ ID NO 540
<211> LENGTH: 23
<212> TYPE: RNA
<213> ORGANISM: Homo sapiens

<400> SEQUENCE: 540
ugugcaaauc uaugcaaaac uga                                       23

<210> SEQ ID NO 541
<211> LENGTH: 22
<212> TYPE: RNA
<213> ORGANISM: Homo sapiens

<400> SEQUENCE: 541
uguaaacauc cuacacucag cu                                        22

<210> SEQ ID NO 542
<211> LENGTH: 22
<212> TYPE: RNA
<213> ORGANISM: Homo sapiens

<400> SEQUENCE: 542
gcuacuucac aacaccaggg cc                                        22

<210> SEQ ID NO 543
<211> LENGTH: 23
<212> TYPE: RNA
<213> ORGANISM: Homo sapiens

<400> SEQUENCE: 543
aggaugagca aagaaaguag auu                                       23

<210> SEQ ID NO 544
<211> LENGTH: 22
<212> TYPE: RNA
<213> ORGANISM: Homo sapiens

<400> SEQUENCE: 544
ccaguauuaa cugugcugcu ga                                        22

<210> SEQ ID NO 545
<211> LENGTH: 20
<212> TYPE: RNA
<213> ORGANISM: Homo sapiens

<400> SEQUENCE: 545
cugcaaaggg aagcccuuuc                                           20

<210> SEQ ID NO 546
<211> LENGTH: 21
<212> TYPE: RNA
```

```
<213> ORGANISM: Homo sapiens

<400> SEQUENCE: 546
aguuaggauu aggucgugga a                                              21

<210> SEQ ID NO 547
<211> LENGTH: 22
<212> TYPE: RNA
<213> ORGANISM: Homo sapiens

<400> SEQUENCE: 547
ugagguagua guuugugcug uu                                             22

<210> SEQ ID NO 548
<211> LENGTH: 22
<212> TYPE: RNA
<213> ORGANISM: Homo sapiens

<400> SEQUENCE: 548
uggaauguaa agaaguaugu au                                             22

<210> SEQ ID NO 549
<211> LENGTH: 23
<212> TYPE: RNA
<213> ORGANISM: Homo sapiens

<400> SEQUENCE: 549
uaaaucccau ggugccuucu ccu                                            23

<210> SEQ ID NO 550
<211> LENGTH: 21
<212> TYPE: RNA
<213> ORGANISM: Homo sapiens

<400> SEQUENCE: 550
acucuuuccc uguugcacua c                                              21

<210> SEQ ID NO 551
<211> LENGTH: 22
<212> TYPE: RNA
<213> ORGANISM: Homo sapiens

<400> SEQUENCE: 551
uuguacaugg uaggcuuuca uu                                             22

<210> SEQ ID NO 552
<211> LENGTH: 22
<212> TYPE: RNA
<213> ORGANISM: Homo sapiens

<400> SEQUENCE: 552
aggcauugac uucucacuag cu                                             22

<210> SEQ ID NO 553
<211> LENGTH: 22
<212> TYPE: RNA
<213> ORGANISM: Homo sapiens

<400> SEQUENCE: 553
cuccugagcc auucugagcc uc                                             22

<210> SEQ ID NO 554
<211> LENGTH: 22
```

```
<212> TYPE: RNA
<213> ORGANISM: Homo sapiens

<400> SEQUENCE: 554
aagcccuuac cccaaaaagc au                                              22

<210> SEQ ID NO 555
<211> LENGTH: 21
<212> TYPE: RNA
<213> ORGANISM: Homo sapiens

<400> SEQUENCE: 555
caaaacguga ggcgcugcua u                                               21

<210> SEQ ID NO 556
<211> LENGTH: 20
<212> TYPE: RNA
<213> ORGANISM: Homo sapiens

<400> SEQUENCE: 556
ccccagggcg acgcggcggg                                                 20

<210> SEQ ID NO 557
<211> LENGTH: 23
<212> TYPE: RNA
<213> ORGANISM: Homo sapiens

<400> SEQUENCE: 557
aucccuugca ggggcuguug ggu                                             23

<210> SEQ ID NO 558
<211> LENGTH: 22
<212> TYPE: RNA
<213> ORGANISM: Homo sapiens

<400> SEQUENCE: 558
ugagguagua gauuguauag uu                                              22

<210> SEQ ID NO 559
<211> LENGTH: 22
<212> TYPE: RNA
<213> ORGANISM: Homo sapiens

<400> SEQUENCE: 559
uugagaauga ugaaucauua gg                                              22

<210> SEQ ID NO 560
<211> LENGTH: 22
<212> TYPE: RNA
<213> ORGANISM: Homo sapiens

<400> SEQUENCE: 560
cagugcaaug uuaaagggc au                                               22

<210> SEQ ID NO 561
<211> LENGTH: 21
<212> TYPE: RNA
<213> ORGANISM: Homo sapiens

<400> SEQUENCE: 561
cccggagcca ggaugcagcu c                                               21

<210> SEQ ID NO 562
```

-continued

```
<211> LENGTH: 21
<212> TYPE: RNA
<213> ORGANISM: Homo sapiens

<400> SEQUENCE: 562
uuaggccgca gaucugggug a                                              21

<210> SEQ ID NO 563
<211> LENGTH: 25
<212> TYPE: RNA
<213> ORGANISM: Homo sapiens

<400> SEQUENCE: 563
gggcgacaaa gcaagacucu uucuu                                          25

<210> SEQ ID NO 564
<211> LENGTH: 23
<212> TYPE: RNA
<213> ORGANISM: Homo sapiens

<400> SEQUENCE: 564
gcagcagaga auaggacuac guc                                            23

<210> SEQ ID NO 565
<211> LENGTH: 23
<212> TYPE: RNA
<213> ORGANISM: Homo sapiens

<400> SEQUENCE: 565
aacauucaac gcugucggug agu                                            23

<210> SEQ ID NO 566
<211> LENGTH: 22
<212> TYPE: RNA
<213> ORGANISM: Homo sapiens

<400> SEQUENCE: 566
cguguauuug acaagcugag uu                                             22

<210> SEQ ID NO 567
<211> LENGTH: 22
<212> TYPE: RNA
<213> ORGANISM: Homo sapiens

<400> SEQUENCE: 567
uaacugguug aacaacugaa cc                                             22

<210> SEQ ID NO 568
<211> LENGTH: 20
<212> TYPE: RNA
<213> ORGANISM: Homo sapiens

<400> SEQUENCE: 568
cuacaaaggg aagcccuuuc                                                20

<210> SEQ ID NO 569
<211> LENGTH: 22
<212> TYPE: RNA
<213> ORGANISM: Homo sapiens

<400> SEQUENCE: 569
uacgucaucg uugucaucgu ca                                             22
```

```
<210> SEQ ID NO 570
<211> LENGTH: 22
<212> TYPE: RNA
<213> ORGANISM: Homo sapiens

<400> SEQUENCE: 570
aacuggccua caaagucccca gu                                            22

<210> SEQ ID NO 571
<211> LENGTH: 21
<212> TYPE: RNA
<213> ORGANISM: Homo sapiens

<400> SEQUENCE: 571
gugucuuuug cucugcaguc a                                              21

<210> SEQ ID NO 572
<211> LENGTH: 20
<212> TYPE: RNA
<213> ORGANISM: Homo sapiens

<400> SEQUENCE: 572
caccaggcau uguggucucc                                                20

<210> SEQ ID NO 573
<211> LENGTH: 21
<212> TYPE: RNA
<213> ORGANISM: Homo sapiens

<400> SEQUENCE: 573
caacaccagu cgaugggcug u                                              21

<210> SEQ ID NO 574
<211> LENGTH: 23
<212> TYPE: RNA
<213> ORGANISM: Homo sapiens

<400> SEQUENCE: 574
uggugcggag agggcccaca gug                                            23

<210> SEQ ID NO 575
<211> LENGTH: 22
<212> TYPE: RNA
<213> ORGANISM: Homo sapiens

<400> SEQUENCE: 575
cuacaaaggg aagcacuuuc uc                                             22

<210> SEQ ID NO 576
<211> LENGTH: 21
<212> TYPE: RNA
<213> ORGANISM: Homo sapiens

<400> SEQUENCE: 576
ugguucuaga cuugccaacu a                                              21

<210> SEQ ID NO 577
<211> LENGTH: 21
<212> TYPE: RNA
<213> ORGANISM: Homo sapiens

<400> SEQUENCE: 577
cggggcagcu caguacagga u                                              21
```

```
<210> SEQ ID NO 578
<211> LENGTH: 22
<212> TYPE: RNA
<213> ORGANISM: Homo sapiens

<400> SEQUENCE: 578
aauugcacuu uagcaauggu ga                                              22

<210> SEQ ID NO 579
<211> LENGTH: 22
<212> TYPE: RNA
<213> ORGANISM: Homo sapiens

<400> SEQUENCE: 579
aaauuauugu acaucggaug ag                                              22

<210> SEQ ID NO 580
<211> LENGTH: 22
<212> TYPE: RNA
<213> ORGANISM: Homo sapiens

<400> SEQUENCE: 580
caaaguuuaa gauccuugaa gu                                              22

<210> SEQ ID NO 581
<211> LENGTH: 22
<212> TYPE: RNA
<213> ORGANISM: Homo sapiens

<400> SEQUENCE: 581
uccuguacug agcugccccg ag                                              22

<210> SEQ ID NO 582
<211> LENGTH: 22
<212> TYPE: RNA
<213> ORGANISM: Homo sapiens

<400> SEQUENCE: 582
caggccauau ugugcugccu ca                                              22

<210> SEQ ID NO 583
<211> LENGTH: 21
<212> TYPE: RNA
<213> ORGANISM: Homo sapiens

<400> SEQUENCE: 583
uaaggcaccc uucugaguag a                                               21

<210> SEQ ID NO 584
<211> LENGTH: 22
<212> TYPE: RNA
<213> ORGANISM: Homo sapiens

<400> SEQUENCE: 584
aacgccauua ucacacuaaa ua                                              22

<210> SEQ ID NO 585
<211> LENGTH: 22
<212> TYPE: RNA
<213> ORGANISM: Homo sapiens

<400> SEQUENCE: 585
acaguagucu gcacauuggu ua                                              22
```

```
<210> SEQ ID NO 586
<211> LENGTH: 22
<212> TYPE: RNA
<213> ORGANISM: Homo sapiens

<400> SEQUENCE: 586
caagcuugua ucuauaggua ug                                              22

<210> SEQ ID NO 587
<211> LENGTH: 22
<212> TYPE: RNA
<213> ORGANISM: Homo sapiens

<400> SEQUENCE: 587
aaaaccgucu aguuacaguu gu                                              22

<210> SEQ ID NO 588
<211> LENGTH: 21
<212> TYPE: RNA
<213> ORGANISM: Homo sapiens

<400> SEQUENCE: 588
uuaauaucgg acaaccauug u                                               21
```